US006852761B2

(12) United States Patent
South et al.

(10) Patent No.: US 6,852,761 B2
(45) Date of Patent: Feb. 8, 2005

(54) POLYCYCLIC ARYL AND HETEROARYL SUBSTITUTED BENZENES USEFUL FOR SELECTIVE INHIBITION OF THE COAGULATION CASCADE

(75) Inventors: Michael S. South, St. Louis, MO (US); John J. Parlow, Arnold, MO (US)

(73) Assignee: Pharmacia Corporation, St. Louis, MO (US)

(*) Notice: Subject to any disclaimer, the term of this patent is extended or adjusted under 35 U.S.C. 154(b) by 0 days.

(21) Appl. No.: 10/203,866

(22) PCT Filed: Mar. 13, 2001

(86) PCT No.: PCT/US01/07918

§ 371 (c)(1),
(2), (4) Date: Nov. 13, 2002

(87) PCT Pub. No.: WO01/68605

PCT Pub. Date: Sep. 20, 2001

(65) Prior Publication Data

US 2003/0236231 A1 Dec. 25, 2003

Related U.S. Application Data

(60) Provisional application No. 60/188,943, filed on Mar. 13, 2000, and provisional application No. 60/252,159, filed on Nov. 20, 2000.

(51) Int. Cl.[7] ............... A61K 31/155; C07C 257/14

(52) U.S. Cl. ............... 514/637; 564/92; 564/157; 564/168; 564/244; 564/246

(58) Field of Search ............... 514/318, 357, 514/428, 438, 461, 604, 616, 619, 637; 546/229, 334; 548/565; 549/74, 430; 564/92, 157, 168, 244, 246

(56) References Cited

U.S. PATENT DOCUMENTS

| | | | |
|---|---|---|---|
| 4,489,096 A | 12/1984 | Terao et al. | |
| 4,851,413 A | 7/1989 | Terao et al. | |
| 4,992,469 A | 2/1991 | Ozawa et al. | |
| 5,304,658 A | 4/1994 | Terao et al. | |
| 5,441,960 A | 8/1995 | Bernstein et al. | |
| 5,656,645 A | 8/1997 | Tamura et al. | |
| 5,658,930 A | 8/1997 | Tamura et al. | |
| 5,668,289 A | 9/1997 | Sanderson et al. | |
| 5,741,819 A | * 4/1998 | Illig et al. ........... | 514/602 |
| 5,792,779 A | 8/1998 | Sanderson et al. | |
| 5,861,380 A | 1/1999 | Gyorkos et al. | |
| 5,866,573 A | 2/1999 | Sanderson et al. | |
| 5,869,487 A | 2/1999 | Coburn et al. | |
| 5,872,138 A | 2/1999 | Naylor-Olsen et al. | |
| 6,011,158 A | 1/2000 | Tamura et al. | |
| 6,037,356 A | 3/2000 | Lu et al. | |
| 6,180,627 B1 | 1/2001 | Blagg et al. | |
| 6,660,885 B2 | * 12/2003 | South et al. ........... | 564/157 |

FOREIGN PATENT DOCUMENTS

| | | |
|---|---|---|
| DE | 198 51 421 A1 | 5/2000 |
| EP | 0 354 495 A1 | 2/1990 |
| EP | 0 528 633 B1 | 2/1993 |
| EP | 0 826 671 A1 | 3/1998 |
| EP | 0 936 216 A1 | 8/1999 |
| EP | 0 940 400 A1 | 9/1999 |
| EP | 0 997 474 A1 | 5/2000 |
| WO | WO 93/21214 A1 | 10/1993 |
| WO | WO 96/18644 A1 | 6/1996 |

(List continued on next page.)

OTHER PUBLICATIONS

Coburn, C.A., "Small–molecule direct thrombin inhibitors 1997–2000." Expert Opinions on Therapeutic Patents, 2001, 721–738, vol. 11, No. 5.

XP–002182132—Darvas, et al., "Investigation of the Common Mechanism of Action of Antibacterial Compounds Containing .gamma.–pyridone–.beta.–carboxylic acid Structure by Principal Component." Arzneim.–Forshc., 1979, pp. 1334–1339, vol. 29, 9.

Handin, R., "Bleeding and Thrombosis." Harrison's Principles of Internal Medicine, 12th Edition, 1991, pp. 348–353, McGraw–Hill, Inc., New York.

XP–002172033—Kohama et al., "Preparation of Piperidinyloxyacetylaminobenzoylalanine Derivatives and Analogs as Antithrombotics." JP 07,233, 148.

Majerus, et al. "Anticoagulant, Thrombolytic, and Antiplatlet Drugs." Goodman & Gilman's The Pharmacological Basis of Therapeutics, Ninth Edition, 1996, pp. 1341–1359, McGraw–Hill, New York.

XP–002187583—Moerner, Hoppe–Seyler's Z. Physiol. Chem., 69, 1910; 357.

Patel et al., "Directed Aminomethylation of 3–Hydroxy–3(1H)–pyridinones and 3–hydroxy–4(1H)–pyridinones: Synthesis of iso–Deferiprone." Tetrahedron, 1996, pp. 1835–1840, vol. 52, No. 5.

Rauch et al., "Thrombus Formation on Atherosclreatic Plaques: Pathogenesis and Clinical Consequences." Animals of Internal Medicine, 2001, pp. 224–233, vol. 134, No. 3.

Sanderson et al., "L–373,890, An Achiral, Noncovalent, Subnamomolar Thrombin Inhibitor." Bioorganic & Medicinal Chemistry Letters, vol. 7, No. 12, pp. 1497–1500, 1997.

XP–002182410—Trecourt et al., "First Synthesis of (+–)–harzianopyridone by Metalation of Polysubstituted O–pyridylcarbamates." J. Heterocycl. Chem., 1995, pp. 1117–1114, vol. 32, No. 4.

Tulinsky et al., "Novel Asymmetric of Atropisomeric 6–Aryl Pyrazinones via an Unusual Chirality Transfer Process." J. Org. Chem., 1999, pp. 93–100, vol. 64, No. 1.

Van Aken, et al., "Anticoagulation: The Present and Future." Clin. Appl. Thromiosis/Hemostasis, 2001, vol. 7, No. 3.

Primary Examiner—Celia Chang

(57) ABSTRACT

The invention relates to polycyclic aryl and heteroaryl substituted benzene compounds useful as inhibitors of serine proteases of the coagulation cascade and compounds, compositions and methods for anticoagulant therapy for the treatment and prevention of a variety of thrombotic conditions including coronary artery and cerebrovascular diseases.

14 Claims, No Drawings

FOREIGN PATENT DOCUMENTS

| | | |
|---|---|---|
| WO | WO 96/33974 A1 | 10/1996 |
| WO | WO 96/39380 A1 | 12/1996 |
| WO | WO 96/40100 A1 | 12/1996 |
| WO | WO 97/01338 A1 | 1/1997 |
| WO | WO 97/30708 A1 | 8/1997 |
| WO | WO 97/40024 A1 | 10/1997 |
| WO | WO 97/46207 A2 | 12/1997 |
| WO | WO 98/08840 A1 | 3/1998 |
| WO | WO 98/09949 A1 | 3/1998 |
| WO | WO 98/09987 A1 | 3/1998 |
| WO | WO 98/10763 A1 | 3/1998 |
| WO | WO 98/16525 A1 | 4/1998 |
| WO | WO 98/16547 A1 | 4/1998 |
| WO | WO 98/17274 A1 | 4/1998 |
| WO | WO 98/31670 A1 | 7/1998 |
| WO | WO 98/42342 A1 | 10/1998 |
| WO | WO 98/47876 A1 | 10/1998 |
| WO | WO 98/50420 A1 | 11/1998 |
| WO | WO 99/00121 A1 | 1/1999 |
| WO | WO 99/00126 A1 | 1/1999 |
| WO | WO 99/00128 A1 | 1/1999 |
| WO | WO 99/11267 A1 | 3/1999 |
| WO | WO 99/26920 A1 | 3/1999 |
| WO | WO 99/26926 A1 | 6/1999 |
| WO | WO 99/36426 A1 | 7/1999 |
| WO | WO 99/43660 A1 | 9/1999 |
| WO | WO 99/48892 A1 | 9/1999 |
| WO | WO 99/56591 A1 | 11/1999 |
| WO | WO 99/61442 A1 | 12/1999 |
| WO | WO 99/62538 A1 | 12/1999 |
| WO | WO 99/64446 A1 | 12/1999 |
| WO | WO 00/18762 A1 | 4/2000 |
| WO | WO 00/26210 A1 | 5/2000 |
| WO | WO 00/26211 A1 | 5/2000 |
| WO | WO 00/32574 A1 | 6/2000 |
| WO | WO 00/39102 A1 | 7/2000 |
| WO | WO 00/69826 A1 | 11/2000 |
| WO | WO 00/69832 A1 | 11/2000 |
| WO | WO 00/69833 A1 | 11/2000 |
| WO | WO 01/77097 A1 | 10/2001 |

* cited by examiner

POLYCYCLIC ARYL AND HETEROARYL SUBSTITUTED BENZENES USEFUL FOR SELECTIVE INHIBITION OF THE COAGULATION CASCADE

This application is a 371 of PCT/US01/07918 filed Mar. 13, 2001.

FIELD OF THE INVENTION

This invention is in the field of anticoagulant therapy, and specifically relates to compounds, compositions and methods for preventing and treating thrombotic conditions such as coronary artery and cerebrovascular disease. More particularly, the invention relates to polycyclic aryl and heteroaryl substituted benzene compounds that inhibit serine proteases of the coagulation cascade.

BACKGROUND OF THE INVENTION

Physiological systems control the fluidity of blood in mammals [Majerus, P. W. et al: Anticoagulant, Thrombolytic, and Antiplatelet Drugs. In Hardman, J. G. and Limbird, L. E., editors: Goodman & Gilman's The Pharmacological Basis of Therapeutics. 9th edition. New York, McGraw-Hill Book Co., 1996, pp. 1341–1343]. Blood must remain fluid within the vascular systems and yet be able to undergo hemostasis, cessation of blood loss from a damaged vessel, quickly. Hemostasis or clotting begins when platelets first adhere to macromolecules in subendothelian regions of an injured and/or damaged vessels. These platelets aggregate to form the primary hemostatic plug and stimulate local activation of plasma coagulation factors leading to generation of a fibrin clot that reinforces the aggregated platelets.

Plasma coagulation factors include factors II, V, VII, VIII, IX, X, XI, and XII; these are also called protease zymogens. These coagulation factors or protease zymogens are activated by serine proteases leading to coagulation in a so called "coagulation cascade" or chain reaction [Handin, R. I.: Bleeding and Thrombosis. In Wilson, J., et al. editors: Harrison's Principles of Internal Medicine. 12th Edition, New York, McGraw-Hill Book Co., 1991,p.350]. Coagulation or clotting occurs in two ways through different pathways. An intrinsic or contact pathway leads from XII to XIIa to XIa to IXa and to the conversion of X to Xa. Xa with factor Va converts prothrombin (II) to thrombin (IIa) leading to conversion of fibrinogen to fibrin. Polymerization of fibrin leads to a fibrin clot. An extrinsic pathway is initiated by the conversion of coagulation factor VII to VIIa by Xa. The presence of Tissue Factor and VIIa accelerates formation of Xa in the presence of calcium ion and phospholipids. Formation of Xa leads to thrombin, fibrin, and a fibrin clot as described above. The presence of one or more of these many different coagulation factors and two distinct pathways of clotting could enable the efficacious, selective control and better understanding of parts of the coagulation or clotting process.

While clotting as a result of an injury to a blood vessel is a critical physiological process for mammals such as man, clotting can also lead to disease states. A pathological process called thrombosis results when platelet aggregation and/or a fibrin clot blocks (i.e., occludes) a blood vessel. Arterial thrombosis may result in ischemic necrosis of the tissue supplied by the artery. When the thrombosis occurs in a coronary artery, a myocardial infarction or heart attack can result. A thrombosis occurring in a vein may cause tissues drained by the vein to become edematous and inflamed. Thrombosis of a deep vein may be complicated by a pulmonary embolism. Preventing or treating clots in a blood vessel may be therapeutically useful by inhibiting formation of blood platelet aggregates, inhibiting formation of fibrin, inhibiting thrombus formation, inhibiting embolus formation, and for treating or preventing unstable angina, refractory angina, myocardial infarction, transient ischemic attacks, atrial fibrillation, thrombotic stroke, embolic stroke, deep vein thrombosis, disseminated intravascular coagulation, ocular build up of fibrin, and reocclusion or restenosis of recanalized vessels.

There have been several reports of non-peptidic benzene compounds that act as an inhibitor of a coagulation factor present in the coagulation cascade or clotting process. In PCT Patent Applications WO 99/00121 and WO 99/00128, Beight et al. describe certain aroylamido, aroyloxy, and N-arylamidocarbonyl and certain heteroaroylamido, heteroaroyloxy, and N-heteroarylamidocarbonyl benzenes that may be further substituted at the other benzene ring carbons by other groups and that are reported to have inhibitory activity against factor Xa. In U.S. Pat. No. 5,872,138 and PCT Patent Application WO 98/10763, Naylor-Olsen et al. describe disubstituted benzenes having a group linked through an oxygen, nitrogen or sulfur heteroatom, any one of six basic heterocycles linked to the ring through linker group, and, optionally, an additional alkyl, alkenyl, alkoxy, amino, or arylmethylenesulfonamido group and claimed to inhibit human thrombin. In PCT Patent Application WO 99/26920, Semple et al. disclose 1-oxy-2,3,4,5-tetrasubstituted-phenylacetamides having an acyl function in the group substituting the amide nitrogen and having activity against thrombin. In PCT Patent Application WO 96/39380, Lu and Soll describe bis-(sulfonamido substitutedbenzoyl) derivatives of diamines claimed to have utility as inhibitors of thrombotic disorders. In PCT Patent Application WO 96/40100, Illig et al. describe sulfonamido substitutedbenzoyl and benzyl derivatives of amines directed to non-peptidic factor Xa and claimed to have utility as inhibitors of thrombotic disorders. In PCT Patent Applications WO 00/039102, Wexler et al. describe certain 3-(amino substituted bicyclic heteroaryl)-propoxy, -propylamino, and -propionylamino benzene compounds that may be further substituted at the other two benzene ring carbons by other groups and that are reported to be inhibitors of trysin-like serine protease enzymes, especially factor Xa and thrombin.

SUMMARY OF THE INVENTION

It is an object of the present invention to provide novel compounds that are beneficial in anticoagulant therapy and that have a general structure:

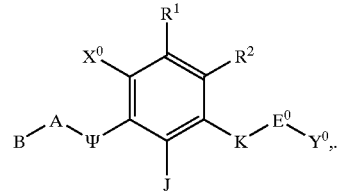

Formula (I)

It is another object of the present invention to provide methods for preventing and treating thrombotic conditions, such as coronary artery disease, cerebrovascular disease, and other coagulation related disorders. Such thrombotic conditions are prevented and treated by administering to a patient in need thereof an effective amount of compounds of Formula (I).

DESCRIPTION OF THE INVENTION

Various other objects and advantages of the present invention will become apparent from the following description of the invention.

The present invention relates to a class of compounds comprising Polycyclic Aryl and Heteroaryl Substituted Benzenes, which are beneficial in anticoagulant therapy for the treatment and prevention of a variety of thrombotic conditions including coronary artery and cerebrovascular disease, as given in Formula (I):

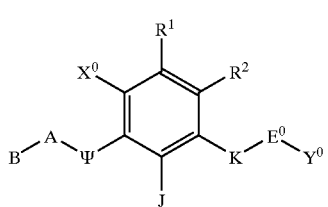

(I)

or a pharmaceutically acceptable salt thereof, wherein;

J is selected from the group consisting of hydrido, halo, hydroxy, hydroxyalkyl, amino, aminoalkyl, cyano, alkyl, alkenyl, haloalkyl, haloalkenyl, carboxy, carboxyalkyl, carboalkoxy, amidocarbonyl, acyl, phosphono, sulfo, O—$R^6$, NH—$R^6$, S—$R^6$, S(O)—$R^6$, and $S(O)_2$—$R^6$, wherein $R^6$ is selected from the group consisting of alkyl, alkenyl, aryl, heteroaryl, aralkyl, heteroaralkyl, haloalkyl, haloalkenyl, acyl, aroyl, and heteroaroyl;

B is formula (V):

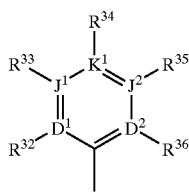

(V)

wherein $D^1$, $D^2$, $J^1$, $J^2$ and $K^1$ are independently selected from the group consisting of C, N, O, S and a covalent bond with the provisos that no more than one can be a covalent bond, no more than one of $D^1$, $D^2$, $J^1$, $J^2$ and $K^1$ can be O, no more than one of $D^1$, $D^2$, $J^1$, $J^2$ and $K^1$ can be S, one of $D^1$, $D^2$, $J^1$, $J^2$ and $K^1$ must be a covalent bond when two of $D^1$, $D^2$, $J^1$, $J^2$ and $K^1$ are O and S, and no more than four of $D^1$, $D^2$, $J^1$, $J^2$ and $K^1$ can be N with the proviso that $R^{32}$, $R^{33}$, $R^{34}$, $R^{35}$, and $R^{36}$ are each independently selected to maintain the tetravalent nature of carbon, trivalent nature of nitrogen, the divalent nature of sulfur, and the divalent nature of oxygen;

$R^{32}$, $R^{33}$, $R^{34}$, $R^{35}$, and $R^{36}$ can independently be $Q^b$;

$R^9$, $R^{10}$, $R^{11}$, $R^{12}$, $R^{13}$, $R^{16}$, $R^{17}$, $R^{18}$, $R^{19}$, $R^{32}$, $R^{33}$, $R^{34}$, $R^{35}$, and $R^{36}$ are independently selected from the group consisting of hydrido, amidino, guanidino, dialkylsulfonium, trialkylphosphonium, dialkylsulfoniumalkyl, carboxy, heteroaralkylthio, heteroaralkoxy, cycloalkylamino, acylalkyl, acyloxy, aryloylaxy, heterocyclyloxy, aralkylaryl, aralkyl, aralkenyl, aralkynyl, heterocyclyl, perhaloaralkyl, aralkylsulfonyl, aralkylsulfonylalkyl, aralkylsulfinyl, aralkylsulfinylalkyl, halocycloalkyl, halocycloalkenyl, cycloalkylsulfinyl, cycloalkylsulfinylalkyl, cycloalkylsulfonyl, cycloalkylsulfonylalkyl, heteroarylamino, N-heteroarylamino-N-alkylamino, heteroarylaminoalkyl, haloalkylthio, alkanoyloxy, alkoxy, alkoxyalkyl, haloalkoxyalkyl, heteroaralkoxy, cycloalkoxy, cycloalkenyloxy, cycloalkoxyalkyl, cycloalkylalkoxy, cycloalkenyloxyalkyl, cycloalkylenedioxy, halocycloalkoxy, halocycloalkoxyalkyl, halocycloalkenyloxy, halocycloalkenyloxyalkyl, hydroxy, amino, alkoxyamino, thio, nitro, lower alkylamino, alkylthio, alkylthioalkyl, arylamino, aralkylamino, arylthio, arylthioalkyl, heteroaralkoxyalkyl, alkylsulfinyl, alkylsulfinylalkyl, arylsulfinylalkyl, arylsulfonylalkyl, heteroarylsulfinylalkyl, heteroarylsulfonylalkyl, alkylsulfonyl, alkylsulfonylalkyl, haloalkylsulfinylalkyl, haloalkylsulfonylalkyl, alkylsulfonamido, alkylaminosulfonyl, amidosulfonyl, monoalkyl amidosulfonyl, dialkyl amidosulfonyl, monoarylamidosulfonyl, arylsulfonamido, diarylamidosulfonyl, monoalkyl monoaryl amidosulfonyl, arylsulfinyl, arylsulfonyl, heteroarylthio, heteroarylsulfinyl, heteroarylsulfonyl, heterocyclylsulfonyl, heterocyclylthio, alkanoyl, alkenoyl, aroyl, heteroaroyl, aralkanoyl, heteroaralkanoyl, haloalkanoyl, alkyl, alkenyl, alkynyl, alkenyloxy, alkenyloxyalky, alkylenedioxy, haloalkylenedioxy, cycloalkyl, cycloalkylalkanoyl, cycloalkenyl, lower cycloalkylalkyl, lower cycloalkenylalkyl, halo, haloalkyl, haloalkenyl, haloalkoxy, hydroxyhaloalkyl, hydroxyaralkyl, hydroxyalkyl, aminoalkyl, hydoxyheteroaralkyl, haloalkoxyalkyl, aryl, aralkyl, aryloxy, aralkoxy, aryloxyalkyl, saturated heterocyclyl, partially saturated heterocyclyl, heteroaryl, heteroaryloxy, heteroaryloxyalkyl, arylalkyl, heteroarylalkyl, arylalkenyl, heteroarylalkenyl, carboxyalkyl, carboalkoxy, alkoxycarboxamido, alkylamidocarbonylamido, arylamidocarbonylamido, carboalkoxyalkyl, carboalkoxyalkenyl, carboaralkoxy, carboxamido, carboxamidoalkyl, cyano, carbohaloalkoxy, phosphono, phosphonoalkyl, diaralkoxyphosphono, and diaralkoxyphosphonoalkyl;

$R^{32}$ and $R^{33}$, $R^{33}$ and $R^{34}$, $R^{34}$ and $R^{35}$, and $R^{35}$ and $R^{36}$ can be independently selected to form a spacer pair wherein a spacer pair is taken together to form a linear moiety having from 3 through 6 contiguous atoms connecting the points of bonding of said spacer pair members to form a ring selected from the group consisting of a cycloalkenyl ring having 5 through 8 contiguous members, a partially saturated heterocyclyl ring having 5 through 8 contiguous members, a heteroaryl ring having 5 through 6 contiguous members, and an aryl with the proviso that no more than one of the group consisting of spacer pairs $R^{32}$ and $R^{33}$, $R^{33}$ and $R^{34}$, $R^{34}$ and $R^{35}$, and $R^{35}$ and $R^{36}$ can be used at the same time;

$R^9$ and $R^{10}$, $R^{10}$ and $R^{11}$, $R^{11}$ and $R^{12}$, and $R^{12}$ and $R^{13}$ can be independently selected to form a spacer pair wherein a spacer pair is taken together to form a linear moiety having from 3 through 6 contiguous atoms connecting the points of bonding of said spacer pair members to form a ring selected from the group consisting of a cycloalkenyl ring having 5 through 8 contiguous members, a partially saturated heterocyclyl ring having 5 through 8 contiguous members, a heteroaryl ring having 5 through 6 contiguous members, and an aryl with the proviso that no more than one of the group consisting of spacer pairs $R^9$ and $R^{10}$, $R^{10}$ and $R^{11}$, $R^{11}$ and $R^{12}$, and $R^{12}$ and $R^{13}$ can be used at the same time;

B can be formula (VI):

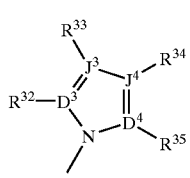

(VI)

wherein $D^3$, $D^4$, $J^3$, and $J^4$ are independently selected from the group consisting of C, N, O, and S, no more than one of $D^3$, $D^4$, $J^3$, and $J^4$ can be O, no more than one of $D^3$, $D^4$, $J^3$, and $J^4$ can be S, and no more than three of $D^1$, $D^2$, $J^1$, and $J^2$ can be N with the proviso that $R^{32}$, $R^{33}$, $R^{34}$, and $R^{35}$ are each independently selected to maintain the tetravalent nature of carbon, trivalent nature of nitrogen, the divalent nature of sulfur, and the divalent nature of oxygen;

B can be selected from the group consisting of C3–C8 alkyl, C3–C8 alkenyl, C3–C8 alkynyl, C3–C8 haloalkyl, and C3–C8 haloalkenyl wherein each member of group B may be optionally substituted at any carbon up to and including 6 atoms from the point of attachment of B to A with one or more of the group consisting of $R_{32}$, $R_{33}$, $R_{34}$, $R_{35}$, and $R_{36}$;

B can be selected from the group consisting of C3–C10 cycloalkyl, C5–C10 cycloalkenyl, C4–C9 saturated heterocyclyl, and C4–C9 partially saturated heterocyclyl, wherein each ring carbon may be optionally substituted with $R_{33}$, a ring carbon other than the ring carbon at the point of attachment of B to A may be optionally substituted with oxo provided that no more than one ring carbon is substituted by oxo at the same time, ring carbon and nitrogen atoms adjacent to the carbon atom at the point of attachment may be optionally substituted with $R_9$ or $R_{13}$, a ring carbon or nitrogen atom adjacent to the $R_9$ position and two atoms from the point of attachment may be substituted with $R_{10}$, a ring carbon or nitrogen atom adjacent to the $R_{13}$ position and two atoms from the point of attachment may be substituted with $R_{12}$, a ring carbon or nitrogen atom three atoms from the point of attachment and adjacent to the $R_{10}$ position may be substituted with $R_{11}$, a ring carbon or nitrogen atom three atoms from the point of attachment and adjacent to the $R_{12}$ position may be substituted with $R_{33}$, and a ring carbon or nitrogen atom four atoms from the point of attachment and adjacent to the $R_{11}$ and $R_{33}$ positions may be substituted with $R_{34}$;

A is selected from the group consisting of single covalent bond, $(W^7)_{rr}$—$(CH(R^{15}))_{pa}$ and $(CH(R^{15}))_{pa}$—$(W^7)_{rr}$ wherein rr is an integer selected from 0 through 1, pa is an integer selected from 0 through 6, and $W^7$ is selected from the group consisting of O, S, C(O), C(S), C(O)S, C(S)O, C(O)N($R^7$), C(S)N($R^7$), ($R^7$)NC(O), ($R^7$)NC(S), S(O), S(O)$_2$, S(O)$_2$N($R^7$), ($R^7$)NS(O)$_2$, Se(O), Se(O)$_2$, Se(O)$_2$N($R^7$), ($R^7$)NSe(O)$_2$, P(O)($R^8$), N($R^7$)P(O)($R^8$), P(O)($R^8$)N($R^7$), C(N$R^7$)N($R^7$), ($R^7$)NC(N$R^7$), and N($R^7$) with the proviso that no more than one of the group consisting of rr and pa can be 0 at the same time;

$R^7$ and $R^8$ are independently selected from the group consisting of hydrido, hydroxy, alkyl, alkenyl, aryl, aralkyl, aryloxy, alkoxy, alkenyloxy, alkylthio, alkylamino, arylthio, arylamino, acyl, aroyl, heteroaroyl, aralkoxyalkyl, heteroaralkoxyalkyl, aryloxyalkyl, alkoxyalkyl, alkenyloxyalkyl, alkylthioalkyl, arylthioalkyl, aralkoxyalkyl, heteroaralkoxyalkyl, alkylsulfinylalkyl, alkylsulfonylalkyl, heteroaryl, heteroaryloxy, heteroarylamino, heteroaralkyl, heteroaralkyloxy, heteroaralkylamino, and heteroaryloxyalkyl;

$R^{14}$, $R^{15}$, $R^{37}$, $R^{38}$, $R^{39}$, $R^{40}$, $R^{41}$ and $R^{42}$ are independently selected from the group consisting of hydrido, hydroxy, halo, cyano, aryloxy, amino, alkylamino, dialkylamino, hydroxyalkyl, aminoalkyl, acyl, aroyl, heteroaroyl, heteroaryloxyalkyl, sulfhydryl, acylamido, alkoxy, alkylthio, arylthio, alkyl, alkenyl, alkynyl, aryl, aralkyl, aryloxyalkyl, aralkoxyalkylalkoxy, alkylsulfinylalkyl, alkylsulfonylalkyl, aralkylthioalkyl, heteroaralkoxythioalkyl, alkoxyalkyl, heteroaryloxyalkyl, alkenyloxyalkyl, alkylthioalkyl, arylthioalkyl, cycloalkyl, cycloalkylalkyl, cycloalkylalkenyl, cycloalkenyl, cycloalkenylalkyl, haloalkyl, haloalkenyl, halocycloalkyl, halocycloalkenyl, haloalkoxy, haloalkoxyalkyl, haloalkenyloxyalkyl, halocycloalkoxy, halocycloalkoxyalkyl, halocycloalkenyloxyalkyl, saturated heterocyclyl, partially saturated heterocyclyl, heteroaryl, heteroarylalkyl, heteroarylthioalkyl, heteroaralkylthioalkyl, monocarboalkoxyalkyl, dicarboalkoxyalkyl, monocyanoalkyl, dicyanoalkyl, carboalkoxycyanoalkyl, alkylsulfinyl, alkylsulfonyl, haloalkylsulfinyl, haloalkylsulfonyl, arylsulfinyl, arylsulfinylalkyl, arylsulfonyl, arylsulfonylalkyl, aralkylsulfinyl, aralkylsulfonyl, cycloalkylsulfinyl, cycloalkylsulfonyl, cycloalkylsulfinylalkyl, cycloalkylsufonylalkyl, heteroarylsulfonylalkyl, heteroarylsulfinyl, heteroarylsulfonyl, heteroarylsulfinylalkyl, aralkylsulfinylalkyl, aralkylsulfonylalkyl, carboxy, carboxyalkyl, carboalkoxy, carboxamide, carboxamidoalkyl, carboaralkoxy, trialkylsilyl, dialkoxyphosphono, diaralkoxyphosphono, dialkoxyphosphonoalkyl, and diaralkoxyphosphonoalkyl with the proviso that $R^{37}$ and $R^{38}$ are independently selected from an acyl other than formyl;

$R^{14}$ and $R^{14}$, when bonded to different carbons, can be taken together to form a group selected from the group consisting of covalent bond, alkylene, haloalkylene, and a linear moiety spacer selected to form a ring selected from the group consisting of cycloalkyl ring having from 5 through 8 contiguous members, cycloalkenyl ring having from 5 through 8 contiguous members, and a heterocyclyl having from 5 through 8 contiguous members;

$R^{14}$ and $R^{15}$, when bonded to different carbons, can be taken together to form a group selected from the group consisting of covalent bond, alkylene, haloalkylene, and a linear moiety spacer selected to form a ring selected from the group consisting of a cycloalkyl ring having from 5 through 8 contiguous members, a cycloalkenyl ring having from 5 through 8 contiguous members, and a heterocyclyl having from 5 through 8 contiguous members;

$R^{15}$ and $R^{15}$, when bonded to different carbons, can be taken together to form a group selected from the group consisting of covalent bond, alkylene, haloalkylene, and a linear moiety spacer selected to form a ring selected from the group consisting of cycloalkyl ring having from 5 through 8 contiguous members, cycloalkenyl ring having from 5 through 8 contiguous members, and a heterocyclyl having from 5 through 8 contiguous members;

Ψ is selected from the group consisting of $NR^5$, O, C(O), C(S), S, S(O), S(O)$_2$, ON($R^5$), P(O)($R^8$), and $CR^{39}R^{40}$ with the provisos that Ψ is selected from other than $NR^5$, O, S, S(O), and S(O)$_2$ unless any two of $X^0$, $R^2$, $R^1$, and J are other than hydrido, or that Ψ is selected from other than O, unless A is selected from other than methylene when B is phenyl, that Ψ is selected from other than C(O), unless A is selected from other than methyleneoxy when B is phenyl, or that Ψ is selected from other than NH unless A is selected from other than a single covalent bond when B is acyl, or that Ψ is selected from other than NH unless A is selected from other than S(O) or S(O)$_2$ when B is phenyl;

$R^5$ is selected from the group consisting of hydrido, alkyl, alkenyl, alkynyl, aryl, aralkyl, aryloxy, alkoxy, alkenyloxy, alkylthio, arylthio, aralkoxyalkyl, heteroaralkoxyalkyl, aryloxyalkyl, alkoxyalkyl, alkenyloxyalkyl, alkylthioalkyl, arylthioalkyl, aralkoxyalkyl, heteroaralkoxyalky, alkylsulfinylalkyl, alkylsulfonylalkyl, cycloalkyl, cycloalkylalkyl, cycloalkylalkenyl, cycloalkenyl, cycloalkenylalkyl, haloalkyl, haloalkenyl, halocycloalkyl, halocycloalkenyl, haloalkoxyalkyl, haloalkenyloxyalkyl, halocycloalkoxyalkyl, halocycloalkenyloxyalkyl, heteroaryl, heteroarylalkyl, monocarboalkoxyalkyl, monocarboalkoxy, dicarboalkoxyalkyl, monocarboxamido, monocyanoalkyl, dicyanoalkyl, carboalkoxycyanoalkyl, acyl, aroyl, heteroaroyl, heteroaryloxyalkyl, and dialkoxyphosphonoalkyl;

$R^{39}$ and $R^{40}$, when bonded to the same carbon, can be taken together to form a group selected from a group consisting of oxo, thiono, $R^5$—N, alkylene, haloalkylene, and a linear moiety spacer having from 2 through 7 contiguous atoms to form a ring selected from the group consisting of a cycloalkyl ring having from 3 through 8 contiguous members, a cycloalkenyl ring having from 3 through 8 contiguous members, and a heterocyclyl ring having from 3 through 8 contiguous members;

$X^0$, $R^2$ and $R^1$ are independently selected from the group consisting of $Z^0$—Q, hydrido, alkyl, alkenyl, and halo;

$X^0$, $R^2$ and $R^1$ can be independently selected from the group consisting of amidino, guanidino, dialkylsulfonium, trialkylphosphonium, dialkylsulfoniumalkyl, heteroarylamino, amino, nitro, alkylamino, arylamino, aralkylamino, alkanoyl, alkenoyl, aroyl, heteroaroyl, aralkanoyl, heteroaralkanoyl, haloalkanoyl, hydroxyhaloalkyl, cyano, and phosphono;

$X^0$ and $R^1$ can be taken together to form a spacer pair wherein the spacer pair forms a linear moiety having from 3 through 6 contiguous atoms connecting the points of bonding of said spacer pair members to form a ring selected from the group consisting of a cycloalkenyl ring having from 5 through 8 contiguous members and a partially saturated heterocyclyl ring having from 5 through 8 contiguous members with the proviso that no more than one of the group consisting of spacer pair $X^0$ and $R^1$ and spacer pair $R^2$ and $R^1$ can be used at the same time;

$X^0$ and $R^5$ can be taken together to form a spacer pair wherein the spacer pair forms a linear spacer moiety having from 2 through 5 contiguous atoms connecting the points of bonding of said spacer pair members to form a heterocyclyl ring having from 5 through 8 contiguous members;

$X^0$ and $R^{39}$ can be taken together to form a spacer pair wherein the spacer pair forms a linear spacer moiety having from 2 through 5 contiguous atoms connecting the points of bonding of said spacer pair members to form a heterocyclyl ring having from 5 through 8 contiguous members;

$X^0$ and $R^{40}$ can be taken together to form a spacer pair wherein the spacer pair forms a linear spacer moiety having from 2 through 5 contiguous atoms connecting the points of bonding of said spacer pair members to form a heterocyclyl ring having from 5 through 8 contiguous members;

$X^0$ can be independently selected to form a linear moiety having from 2 through 5 contiguous atoms linked to the points of bonding of both $R^{39}$ and $R^{40}$ to form a heterocyclyl ring having from 5 through 8 contiguous members;

$R^2$ and $R^1$ can be taken together to form a spacer pair wherein the spacer pair forms a linear moiety having from 3 through 6 contiguous atoms connecting the points of bonding of said spacer pair members to form a ring selected from the group consisting of a cycloalkenyl ring having from 5 through 8 contiguous members and a partially saturated heterocyclyl ring having from 5 through 8 contiguous members with the proviso that no more than one of the group consisting of spacer pair $X^0$ and $R^1$ and spacer pair $R^2$ and $R^1$ can be used at the same time;

$X^0$ and $R^1$ and $R^2$ and $R^1$ spacer pairs are selected independently to be —W=X—Y=Z— forming a ring selected from the group consisting of a heteroaryl ring having from 5 through 6 contiguous members and an aryl with the proviso that no more than one of the group consisting of spacer pair $X^0$ and $R^1$ and spacer pair $R^2$ and $R^1$ is used at the same time;

W, X, Y, and Z are independently selected from the group consisting of C($R^9$), N,N($R^{10}$), O, S and a covalent bond with the provisos that one of W, X, Y, and Z is independently selected to be a covalent bond when one of W, X, Y, and Z is selected from the group consisting of O and S, no more than one of W, X, Y, and Z is selected from the group consisting of O and S, no more than three of W, X, Y, and Z are selected from the group consisting of N and N($R^{10}$), and C($R^9$), N,N($R^{10}$), O, and S are independently selected to maintain the tetravalent nature of carbon, trivalent nature of nitrogen, the divalent nature of sulfur, the divalent nature of oxygen, and the aromaticity of the ring;

$R^2$ and $R^{4a}$, $R^2$ and $R^{4b}$, $R^2$ and $R^{14}$, and $R^2$ and $R^{15}$ can be independently selected to form spacer pairs wherein a spacer pair is taken together to form a linear moiety having from 2 through 5 contiguous atoms connecting the points of bonding of said spacer pair members to form a heterocyclyl ring having from 5 through 8 contiguous members with the proviso that no more than one of the group of spacer pairs consisting of $R^2$ and $R^{4a}$, $R^2$ and $R^{4b}$, $R^2$ and $R^{14}$, and $R^2$ and $R^{15}$ can be used at the same time;

$R^2$ can be independently selected to form a linear moiety having from 2 through 5 contiguous atoms linked to the points of bonding of both $R^{4a}$ and $R^{4b}$ to form a heterocyclyl ring having from 5 through 8 contiguous members;

$Z^0$ is selected from the group consisting of covalent single bond, $(CR^{41}R^{42})_q$ wherein q is an integer selected from 1 through 6, $(CH(R^{41}))_g$—$W^0$—$(CH(R^{42}))_p$ wherein g and p are integers independently selected from 0 through 3 and $W^0$ is selected from the group consisting of O, S, C(O), C(S), C(O)O, C(S)O, C(O)S, C(S)S, C(O)N($R^{41}$), ($R^{41}$)NC(O), C(S)N($R^{41}$), ($R^{41}$)NC(S), OC(O)N($R^{41}$), ($R^{41}$)NC(O)O, SC(S)N($R^{41}$), ($R^{41}$)NC(S)S, SC(O)N($R^{41}$), ($R^{41}$)NC(O)S, OC(S)N($R^{41}$), ($R^{41}$)NC(S)O, N($R^{42}$)C(O)N($R^{41}$), ($R^{41}$)NC(O)N($R^{42}$), N($R^{42}$)C(S)N($R^{41}$), ($R^{41}$)NC(S)N($R^{42}$), S(O), S(O)$_2$, S(O)$_2$N($R^{41}$), N($R^{41}$)S(O)$_2$, Se, Se(O), Se(O)$_2$, Se(O)$_2$N($R^{41}$), N($R^{41}$)Se(O)$_2$, P(O)($R^8$), N($R^7$)P(O)($R^8$), P(O)($R^8$)N($R^7$), N($R^{41}$), ON($R^{41}$), and Si$R^{28}R^{29}$, and $(CH(R^{41}))_e$—$W^2$—$(CH(R^{42}))_h$ wherein e and h are integers independently selected from 0 through 2 and $W^2$ is selected from the group consisting of $CR^{41}$=$CR^{42}$, $CR^{41}R^{42}$=C; vinylidene), and ethynylidene (C≡C; 1,2-ethynyl), with the provisos that $R^{41}$ and $R^{42}$ are selected from other than halo and cyano when directly bonded to N and $Z^0$ is directly bonded to the benzene ring, that $W^0$ is selected, wherein g is 0, from other than NHS(O)$_2$CH$_2$aryl or N($R^{41}$) unless $R^{41}$ is selected from other than hydrido, alkyl, or aralkylsulfonyl, and $Z^0$ is selected from other than OC(O), C(O)N(H), and (H)NC(O), unless Q is selected from other than phenyl, 2-furyl, 2-thienyl, 4-thiazolyl, 2-pyridyl, 2-naphthyl, 1,2-dihydrobenzofuran-5-yl, 1,2-dihydrobenzofuran-6-yl, or 1,2benzisoxazol-6-yl, or $X^O$ is selected from other than hydrido, halo, or methyl, or $R^1$ is selected from other than hydrido, fluoro, hydroxy, acetoxy, propanoyloxy, 2-carboxyacetoxy, 2,3 or 4-carboxypropanoyloxy, benzoyloxy, methyl, or methoxy;

$R^{28}$ and $R^{29}$ are independently selected from the group consisting of hydrido, hydroxyalkyl, alkyl, alkenyl, alkynyl, aryl, aralkyl, aryloxyalkyl, acyl, aroyl, aralkanoyl, heteroaroyl, aralkoxyalkyl, alkylsulfinylalkyl, alkylsulfonylalkyl, aralkylthioalkyl, heteroaralkylthioalkyl, alkoxyalkyl, heteroaryloxyalkyl, alkenyloxyalkyl, alkylthioalkyl, arylthioalkyl, cycloalkyl, cycloalkylalkyl, cycloalkylalkenyl, cycloalkenyl, cycloalkenylalkyl, haloalkyl, haloalkenyl, halocycloalkyl, halocycloalkenyl, haloalkoxyalkyl, haloalkenyloxyalkyl, halocycloalkoxy, halocycloalkoxyalkyl, halocycloalkenyloxyalkyl, perhaloaryl, perhaloaralkyl, perhaloaryloxyalkyl, heteroaryl, heteroarylalkyl, heteroarylthioalkyl, heteroaralkylthioalkyl, cyanoalkyl, dicyanoalkyl, carboxamidoalkyl, dicarboxamidoalkyl, cyanocarboalkoxyalkyl, carboalkoxyalkyl, dicarboalkoxyalkyl, cyanocycloalkyl, dicyanocycloalkyl, carboxamidocycloalkyl, dicarboxamidocycloalkyl, carboalkoxycyanocycloalkyl, carboalkoxycycloalkyl, dicarboalkoxycycloalkyl, formylalkyl, acylalkyl, arylsulfinylalkyl, arylsulfonylalkyl, aralkylsulfinyl, cycloalkylsulfinylalkyl, cycloalkylsufonylalkyl, heteroarylsulfonylalkyl, heteroarylsulfinylalkyl, aralkylsulfinylalkyl, aralkylsulfonylalkyl, carboxy, dialkoxyphosphono, diaralkoxyphosphono, dialkoxyphosphonoalkyl and diaralkoxyphosphonoalkyl;

$R^{28}$ and $R^{29}$ can be taken together to form a linear moiety spacer having from 2 through 7 contiguous atoms and forming a ring selected from the group consisting of a cycloalkyl ring having from 3 through 8 contiguous members, a cycloalkenyl ring having from 3 through 8 contiguous members, and a heterocyclyl ring having from 3 through 8 contiguous members;

Q is formula (II):

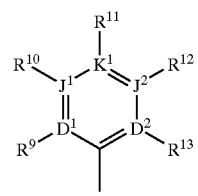

(II)

wherein $D^1$, $D^2$, $J^1$, $J^2$ and $K^1$ are independently selected from the group consisting of C, N, O, S and a covalent bond with the provisos that no more than one can be a covalent bond, no more than one of $D^1$, $D^2$, $J^1$, $J^2$ and $K^1$ can be O, no more than one of $D^1$, $D^2$, $J^1$, $J^2$ and $K^1$ can be S, one of $D^1$, $D^2$, $J^1$, $J^2$ and $K^1$ must be a covalent bond when two of $D^1$, $D^2$, $J^1$, $J^2$ and $K^1$ are O and S, and no more than four of $D^1$, $D^2$, $J^1$, $J^2$ and $K^1$ can be N with the proviso that $R^9$, $R^{10}$, $R^{11}$, $R^{12}$, and $R^{13}$ are each independently selected to maintain the tetravalent nature of carbon, trivalent nature of nitrogen, the divalent nature of sulfur, and the divalent nature of oxygen;

Q can be formula (III):

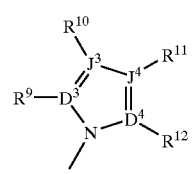

(III)

wherein $D^3$, $D^4$, $J^3$, and $J^4$ are independently selected from the group consisting of C, N, O, and S, no more than one of $D^3$, $D^4$, $J^3$, and $J^4$ can be O, no more than one of $D^3$, $D^4$, $J^3$, and $J^4$ can be S, and no more than three of $D^1$, $D^2$, $J^1$, and $J^2$ can be N with the proviso that $R^9$, $R^{10}$, $R^{11}$, and $R^{12}$ are each independently selected to maintain the tetravalent nature of carbon, trivalent nature of nitrogen, the divalent nature of sulfur, and the divalent nature of oxygen;

Q can be selected from the group consisting of alkyl, alkoxy, alkylamino, alkylthio, haloalkylthio, alkenyl, alkynyl, saturated heterocyclyl, partially saturated heterocyclyl, acyl, aroyl, heteroaroyl, cycloalkyl, cycloalkylalkyl, cycloalkenyl, cycloalkenylalkyl, cycloalkylalkenyl, haloalkyl, haloalkoxy, haloalkenyl, halocycloalkyl, halocycloalkenyl, haloalkoxyalkyl, haloalkenyloxyalkyl, halocycloalkoxyalkyl, and halocycloalkenyloxyalkyl with the proviso that Q is selected from other than than alkyl or alkenyl unless any one of $X^0$, $R^1$, and J are other than hydrido;

K is $(CR^{4a}R^{4b})_n$ wherein n is an integer selected from 1 through 4;

$R^{4a}$ and $R^{4b}$ are independently selected from the group consisting of halo, hydrido, hydroxy, cyano, hydroxyalkyl, allyl, alkenyl, aryl, aralkyl, aralkoxyalkyl, aryloxyalkyl, alkoxyalkyl, heteroaryloxyalkyl, alkenyloxyalkyl, alkylthioalkyl, aralkylthioalkyl, arylthioalkyl, cycloalkyl, cycloalkylalkyl, haloalkyl, haloalkenyl, heteroaryl, heteroarylalkyl, heteroarylthioalkyl, heteroaralkyl-thioalkyl, cyanoalkyl, alkylsulfinylalkyl, alkylsulfonylalkyl, haloalkylsulfinyl, arylsulfinylalkyl, arylsulfonylalkyl, heteroarylsulfonylalkyl, heteroarylsulfinylalkyl, aralkylsulfinylalkyl, and aralkylsulfonylalkyl;

$R^{4a}$ and $R^{4b}$, when bonded to the same carbon, can be taken together to form a group selected from the group consisting of oxo, thiono, and a linear spacer moiety having from 2 through 7 contiguous atoms connected to form a ring selected from the group consisting of a cycloalkyl ring having 3 through 8 contiguous members, a cycloalkenyl ring having 5 through 8 contiguous members, and a heterocyclyl ring having 5 through 8 contiguous members;

$E^0$ is $E^1$, when K is $(CR^{4a}R^{4b})_n$, wherein $E^1$ is selected from the group consisting of a covalent single bond, O, S, C(O), C(S), C(O)O, C(S)O, C(O)S, C(S)S, C(O)N(R$^7$), (R$^7$)NC(O), C(S)N(R$^7$), (R$^7$)NC(S), OC(O)N(R$^7$), (R$^7$)NC(O)O, SC(S)N(R$^7$), (R$^7$)NC(S)S, SC(O)N(R$^7$), (R$^7$)NC(O)S, OC(S)N(R$^7$), (R$^7$)NC(S)O, N(R$^8$)C(O)N(R$^7$), (R$^7$)NC(O)N(R$^8$), N(R$^8$)C(S)N(R$^7$), (R$^7$)NC(S)N(R$^8$), S(O), S(O)$_2$, S(O)$_2$N(R$^7$), N(R$^7$)S(O)$_2$, S(O)$_2$N(R$^7$)C(O), C(O)N(R$^7$)S(O)$_2$, Se, Se(O), Se(O)$_2$, Se(O)$_2$N(R$^7$), N(R$^7$)Se(O)$_2$, P(O)(R$^8$), N(R$^7$)P(O)(R$^8$), P(O)(R$^8$)N(R$^7$), N(R$^7$), ON(R$^7$), SiR$^{28}$R$^{29}$, CR$^{4a}$=CR$^{4b}$, ethynylidene (C≡C; 1,2-ethynyl), and C=CR$^{4a}$R$^{4b}$;

K can be $(CH(R^{14}))_j$—T wherein j is selected from a integer from 0 through 3 and T is selected from the group consisting of single covalent bond, O, S, and N(R$^7$) with the proviso that $(CH(R^{14}))_j$ is bonded to the phenyl ring;

$E^0$ is $E^2$, when K is $(CH(R^{14}))_j$—T, wherein $E^2$ is selected from the group consisting of a covalent single bond, C(O), C(S), C(O)O, C(S)O, C(O)S, C(S)S, C(O)N(R$^7$), (R$^7$)NC(O), C(S)N(R$^7$), (R$^7$)NC(S), (R$^7$)NC(O)O, (R$^7$)NC(S)S, (R$^7$)NC(O)S, (R$^7$)NC(S)O, N(R$^8$)C(O)N(R$^7$), (R$^7$)NC(O)N(R$^8$), N(R$^8$)C(S)N(R$^7$), (R$^7$)NC(S)N(R$^8$), S(O), S(O)$_2$, S(O)$_2$N(R$^7$), N(R$^7$)S(O)$_2$, S(O)$_2$N(H)C(O), C(O)N(H)S(O)$_2$, Se(O), Se(O)$_2$, Se(O)$_2$N(R$^7$), N(R$^7$)Se(O)$_2$, P(O)(R$^8$), N(R$^7$)P(O)(R$^8$), P(O)(R$^8$)N(R$^7$), and N(R$^7$);

K can be G—$(CH(R^{15}))_k$ wherein k is selected from an integer from 1 through 3 and G is selected from the group consisting of O, S, and N(R$^7$) with the proviso that $R^{15}$ is other than hydroxy, cyano, halo, amino, alkylamino, dialkylamino, and sulfhydryl when k is 1;

$E^0$ is $E^3$ when K is G—$(CH(R^{15}))_k$ wherein $E^3$ is selected from the group consisting of a covalent single bond, O, S, C(O), C(S), C(O)O, C(S)O, C(O)S, C(S)S, C(O)N(R$^7$), (R$^7$)NC(O), C(S)N(R$^7$), (R$^7$)NC(S), OC(O)N(R$^7$), (R$^7$)NC(O)O, SC(S)N(R$^7$), (R$^7$)NC(S)S, SC(O)N(R$^7$), (R$^7$)NC(O)S, OC(S)N(R$^7$), (R$^7$)NC(S)O, N(R$^8$)C(O)N(R$^7$), (R$^7$)NC(O)N(R$^8$), N(R$^8$)C(S)N(R$^7$), (R$^7$)NC(S)N(R$^8$), S(O), S(O)$_2$, S(O)$_2$N(R$^7$), N(R$^7$)S(O)$_2$, Se, Se(O), Se(O)$_2$, Se(O)$_2$N(R$^7$), N(R$^7$)Se(O)$_2$, P(O)(R$^8$), N(R$^7$)P(O)(R$^8$), P(O)(R$^8$)N(R$^7$), N(R$^7$), ON(R$^7$), SiR$^{28}$R$^{29}$, CR$^{4a}$=CR$^{4b}$, ethynylidene (C≡C; 1,2-ethynyl), and C=CR$^{4a}$R$^{4b}$;

$Y^0$ is formula (IV):

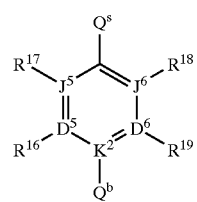

(IV)

wherein $D^5$, $D^6$, $J^5$, and $J^6$ are independently selected from the group consisting of C, N, O, S and a covalent bond with the provisos that no more than one can be a covalent bond, $K^2$ is independently selected from the group consisting of C, and N$^+$, no more than one of $D^5$, $D^6$, $J^5$, and $J^6$ can be O, no more than one of $D^5$, $D^6$, $J^5$, and $J^6$ can be S, one of $D^5$, $D^6$, $J^5$, and $J^6$ must be a covalent bond when two of $D^5$, $D^6$, $J^5$, and $J^6$ are O and S, no more than three of $D^5$, $D^6$, $J^5$, and $J^6$ can be N when $K^2$ is N$^+$, and no more than four of $D^5$, $D^6$, $J^5$, and $J^6$ can be N when $K^2$ is carbon with the provisos that $R^{16}$, $R^{17}$, $R^{18}$, and $R^{19}$ are each independently selected to maintain the tetravalent nature of carbon, trivalent nature of nitrogen, the divalent nature of sulfur, and the divalent nature of oxygen;

$R^{16}$ and $R^{17}$ can be independently taken together to form a linear moiety spacer having from 3 through 6 contiguous atoms connected to form a ring selected from the group consisting of a cycloalkenyl ring having from 5 through 8 contiguous members, a partially saturated heterocyclyl ring having from 5 through 8 contiguous members, a heteroaryl having from 5 through 6 contiguous members, and an aryl;

$R^{18}$ and $R^{19}$ can be independently taken together to form a linear moiety spacer having from 3 through 6 contiguous atoms connected to form a ring selected from the group consisting of a cycloalkenyl ring having from 5 through 8 contiguous members, a partially saturated heterocyclyl ring having from 5 through 8 contiguous members, a heteroaryl having from 5 through 6 contiguous members, and an aryl;

$Q^b$ is selected from the group consisting of NR$^{20}$R$^{21}$, $^+$NR$^{20}$R$^{21}$R$^{22}$, oxy, alkyl, alkylaminoalkyl, aminoalkyl, dialkylsulfoniumalkyl, and acylamino wherein $R^{20}$, $R^{21}$, and $R^{22}$ are independently selected from the group consisting of hydrido, alkyl, hydroxy, alkoxy, alkylamino, dialkylamino, aminoalkyl, and hydroxyalkyl with the provisos that no more than one of $R^{20}$, $R^{21}$, and $R^{22}$ can be hydroxy, alkoxy, alkylamino, amino, and dialkylamino and that $R^{20}$, $R^{21}$, and $R^{22}$ must be other than be hydroxy, alkoxy, alkylamino, amino, and dialkylamino when $K^2$ is N$^+$;

$R^{20}$ and $R^{21}$, $R^{20}$ and $R^{22}$, and $R^{21}$ and $R^{22}$ can be independently selected to form a spacer pair wherein a spacer pair is taken together to form a linear moiety having from 4 through 7 contiguous atoms connecting the points of bonding of said spacer pair members to form a heterocyclyl ring having 5 through 8 contiguous members with the proviso that no more than one of the group consisting of spacer pairs $R^{20}$ and $R^{21}$, $R^{20}$ and $R^{22}$, and $R^{21}$ and $R^{22}$ can be used at the same time;

$Q^b$ can be selected from the group consisting of N(R$^{26}$)SO$_2$N(R$^{23}$)(R$^{24}$), N(R$^{26}$)C(O)OR$^5$, N(R$^{26}$)C(O)SR$^5$, N(R$^{26}$)C(S)OR$^5$ and N(R$^{26}$)C(S)SR$^5$ with the proviso that no more than one of $R^{23}$, $R^{24}$, and $R^{26}$ can be hydroxy, alkoxy, alkylamino, amino, or dialkylamino when two of the group consisting of $R^{23}$, $R^{24}$, and $R^{26}$ are bonded to the same atom;

$Q^b$ can be selected from the group consisting of dialkylsulfonium, trialkylphosphonium, $C(NR^{25})NR^{23}R^{24}$, $N(R^{26})C(NR^{25})N(R^{23})(R^{24})$, $N(R^{26})C(O)N(R^{23})(R^{24})$, $N(R^{26})C(S)N(R^{23})(R^{24})$, $C(NR^{25})OR^5$, $C(O)N(R^{26})C(NR^{25})N(R^{23})(R^{24})$, $C(S)N(R^{26})C(NR^{25})N(R^{23})(R^{24})$, $N(R^{26})N(R^{26})C(NR^{25})N(R^{23})(R^{24})$, $N(R^{26})N(R^{26})SO_2N(R^{23})(R^{24})$, $C(NR^{25})SR^5$, $C(O)NR^{23}R^{24}$, and $C(O)NR^{23}R^{24}$ with the provisos that no more than one of $R^{23}$, $R^{24}$, and $R^{26}$ can be hydroxy, alkoxy, alkylamino, amino, or dialkylamino when two of the group consisting of $R^{23}$, $R^{24}$, and $R^{26}$ are bonded to the same atom and that said $Q^b$ group is bonded directly to a carbon atom;

$R^{23}$, $R^{24}$, $R^{25}$, and $R^{26}$ are independently selected from the group consisting of hydrido, alkyl, hydroxy, alkoxy, alkylamino, dialkylamino, aminoalkyl, and hydroxyalkyl;

$R^{23}$ and $R^{24}$ can be taken together to form a linear spacer moiety having from 4 through 7 contiguous atoms connecting the points of bonding to form a heterocyclyl ring having 5 through 8 contiguous members;

$R^{23}$ and $R^{25}$, $R^{24}$ and $R^{25}$, $R^{25}$ and $R^{26}$, $R^{24}$ and $R^{26}$, and $R^{23}$ and $R^{26}$ can be independently selected to form a spacer pair wherein a spacer pair is taken together from the points of bonding of selected spacer pair members to form the group L—U—V wherein L, U, and V are independently selected from the group consisting of O, S, C(O), C(S), $C(J_H)_2S(O)$, $SO_2$, $OP(OR^{31})R^{30}$, $P(O)R^{30}$, $P(S)R^{30}$, $C(R^{30})R^{31}$, $C=C(R^{30})R^{31}$, $(O)_2POP(O)_2$, $R^{30}(O)POP(O)R^{30}$, $Si(R^{29})R^{28}$, $Si(R^{29})R^{28}Si(R^{29})R^{28}$, $Si(R^{29})R^{28}OSi(R^{29})R^{28}$, $(R^{28})R^{29}COC(R^{28})R^{29}$, $(R^{28})R^{29}CSC(R^{28})R^{29}$, $C(O)C(R^{30})=C(R^{31})$, $C(S)C(R^{30})=C(R^{31})$, $S(O)C(R^{30})=C(R^{31})$, $SO_2C(R^{30})=C(R^{31})$, $PR^{30}C(R^{30})=C(R^{31})$, $P(O)R^{30}C(R^{30})=C(R^{31})$, $P(S)R^{30}C(R^{30})=C(R^{31})$, $DC(R^{30})(R^{31})D$, $OP(OR^{31})R^{30}$, $P(O)R^{30}$, $P(S)R^{30}$, $Si(R^{28})R^{29}$ and $N(R^{30})$, and a covalent bond with the proviso that no more than any two of L, U and V are simultaneously covalent bonds and the heterocyclyl comprised of by L, U, and V has from 5 through 10 contiguous member;

D is selected from the group consisting of oxygen, C=O, C=S, $S(O)_m$ wherein m is an integer selected from 0 through 2;

$J_H$ is independently selected from the group consisting of $OR^{27}$, $SR^{27}$ and $N(R^{20})R^{21}$;

$R^{27}$ is selected from the group consisting of hydrido, alkyl, alkenyl, alkynyl, aralkyl, aryloxyalkyl, aralkoxyalkyl, alkylsulfinylalkyl, alkylsulfonylalkyl, aralkylthioalkyl, heteroaralkylthioalkyl, alkoxyalkyl, heteroaryloxyalkly, alkenyloxyalkyl, alkylthioalkyl, arylthioalkyl, cycloalkyl, cycloalkylalkyl, cycloalkylalkenyl, cycloalkenyl, cycloalkenylalkyl, haloalkyl, haloalkenyl, halocycloalkyl, halocycloalkenyl, haloalkoxyalkyl, haloalkenyloxyalkyl, halocycloalkoxyalkyl, halocycloalkenyloxyalkyl, perhaloaryloxyalkyl, heteroaryl, heteroarylalkyl, heteroarylthioalkyl, heteroaralkylthioalkyl, arylsulfinylalkyl, arylsulfonylalkyl, cycloalkylsulfinylalkyl, cycloalkylsufonylalkyl, heteroarylsulfonylalkyl, heteroarylsulfinylalkyl, aralkylsulfinylalkyl and aralkylsulfonylalkyl;

$R^{30}$ and $R^{31}$ are independently selected from hydrido, hydroxy, thiol, aryloxy, amino, alkylamino, dialkylamino, hydroxyalkyl, heteroaryloxyalkyl, alkoxy, alkylthio, arylthio, alkyl, alkenyl, alkynyl, aryl, aralkyl, aryloxyalkyl, aralkoxyalkyl, alkylsulfinylalkyl, alkylsulfonylalkyl, aralkylthioalkyl, heteroaralkoxythioalkyl, alkoxyalkyl, heteroaryloxyalkyl, alkenyloxyalkyl, alkylthioalkyl, arylthioalkyl, cycloalkyl, cycloalkylalkyl, cycloalkylalkenyl, cycloalkenyl, cycloalkenylalkyl, haloalkyl, haloalkenyl, haloaralkylsulfinylalkyl, aralkylsulfonylalkyl, cyanoalkyl, dicyanoalkyl, carboxamidoalkyl, dicarboxamidoalkyl, cyanocarboalkoxyalkyl, carboalkoxyalkyl, dicarboalkoxyalkyl, cyanocycloalkyl, dicyanocycloalkyl, carboxamidocycloalkyl, dicarboxamidocycloalkyl, carboalkoxycyanocycloalkyl, carboalkoxycycloalkyl, dicarboalkoxycycloalkyl, formylalkyl, acylalkyl, dialkoxyphosphonoalkyl, diaralkoxyphosphonoalkyl, phosphonoalkyl, dialkoxyphosphonoalkoxy, diaralkoxyphosphonoalkoxy, phosphonoalkoxy, dialkoxyphosphonoalkylamino, diaralkoxyphosphonoalkylamino, phosphonoalkylamino, dialkoxyphosphonoalkyl, diaralkoxyphosphonoalkyl, sulfonylalkyl, alkoxysulfonylalkyl, aralkoxysulfonylalkyl, alkoxysulfonylalkoxy, aralkoxysulfonylalkoxy, sulfonylalkoxy, alkoxysulfonylalkylamino, aralkoxysulfonylalkylamino, and sulfonylalkylamino;

$R^{30}$ and $R^{31}$ can be taken to form a linear moiety spacer group having from 2 through 7 contiguous atoms to form a ring selected from the group consisting of a cycloalkyl ring having from 3 through 8 contiguous members, a cycloalkenyl ring having from 3 through 8 contiguous members, and a heterocyclyl ring having from 3 through 8 contiguous members;

$R^{23}$ and $R^{25}$, $R^{24}$ and $R^{25}$, $R^{25}$ and $R^{26}$, $R^{24}$ and $R^{26}$, and $R^{23}$ and $R^{26}$ can be independently selected to form a spacer pair wherein a spacer pair is taken together from the points of bonding of selected spacer pair members to form the group L—U—V wherein L, U, and V are independently selected from the group of 1,2-disubstituted radicals consisting of a cycloalkyl radical, a cycloalkenyl radical wherein cycloalkyl and cycloalkenyl radicals are substituted with one or more groups selected from $R^{30}$ and $R^{31}$, an aryl radical, an heteroaryl radical, a saturated heterocyclic radical and a partially saturated heterocyclic radical wherein said 1,2-substitutents are independently selected from C=O, C=S, $C(R^{28})R^{32}$, S(O), $S(O)_2$, $OP(OR^{31})R^{30}$, $P(O)R^{30}$, $P(S)R^{30}$ and $Si(R^{28})R^{29}$;

$R^{23}$ and $R^{25}$, $R^{24}$ and $R^{25}$, $R^{25}$ and $R^{26}$, $R^{24}$ and $R^{26}$, and $R^{23}$ and $R^{26}$ can be independently selected to form a spacer pair wherein a spacer pair is taken together from the points of bonding of selected spacer pair members to form the group L—U—V wherein L, U, and V are independently selected from the group of radicals consisting of 1,2-disubstituted alkylene radicals and 1,2-disubstituted alkenylene radical wherein said 1,2-substitutents are independently selected from C=O, C=S, $C(R^{28})R^{29}$, S(O), $S(O)_2$, $OP(OR^{31})R^{30}$, $P(O)R^{30}$, $P(S)R^{30}$, and $Si(R^{28})R^{29}$ and said alkylene and alkenylene radical are substituted with one or more $R^{30}$ or $R^{31}$ substituents;

$Q^s$ is selected from the group consisting of a single covalent bond, $(CR^{37}R^{38})_b$—$(W^0)_{az}$ wherein az is an integer selected from 0 through 1, b is an integer selected from 1 through 4, and $W^0$ is selected from the group consisting of O, S, C(O), C(S), C(O)O, C(S)O, C(O)S, C(S)S, C(O)N($R^{14}$), ($R^{14}$)NC(O), C(S)N($R^{14}$), ($R^{14}$)NC(S), OC(O)N($R^{14}$), SC(S)N($R^{14}$), SC(O)N($R^{14}$), OC(S)N($R^{14}$), N($R^{15}$)C(O)N($R^{14}$), ($R^{14}$)NC(O)N($R^{15}$), N($R^{15}$)C(S)N($R^{14}$), ($R^{14}$)NC(S)N($R^{15}$), S(O), S(O)$_2$, S(O)$_2$N($R^{14}$), N($R^{14}$)S(O)$_2$, Se, Se(O), Se(O)$_2$, Se(O)$_2$N($R^{17}$), N($R^{14}$)Se(O)$_2$, P(O)($R^8$), N($R^7$)P(O)($R^8$), P(O)($R^8$)N($R^7$), N($R^{14}$), ON($R^{14}$), and SiR$^{28}$R$^{29}$, (CH($R^{14}$))$_c$—W$^1$—(CH($R^{15}$))$_d$ wherein c and d are integers independently selected from 1 through 4, and W$^1$ is selected from the group consisting of O, S, C(O), C(S), C(O)O, C(S)O, C(O)S, C(S)S, C(O)N($R^{14}$), ($R^{14}$)NC(O), C(S)N($R^{14}$), ($R^{14}$)NC(S), OC(O)N($R^{14}$), ($R^{14}$)NC(O)O, SC(S)N($R^{14}$), ($R^{14}$)NC(S)S, SC(O)N($R^{14}$), ($R^{14}$)NC(O)S, OC(S)N($R^{14}$), ($R^{14}$)NC(S)O, N($R^{15}$)C(O)N($R^{14}$), ($R^{14}$)NC(O)N($R^{15}$), N($R^{15}$)C(S)N($R^{14}$), ($R^{14}$)NC(S)N($R^{15}$), S(O), S(O)$_2$, S(O)$_2$N($R^{14}$), N($R^{14}$)S(O)$_2$, Se, Se(O), Se(O)$_2$, Se(O)$_2$N($R^{14}$), N($R^{14}$)Se(O)$_2$, P(O)($R^8$), N($R^7$)P(O)($R^8$), P(O)($R^8$)N($R^7$), N($R^{14}$), ON($R^{14}$), SiR$^{28}$R$^{29}$, and (CH($R^{14}$))$_e$—W$^2$—(CH($R^{15}$))$_h$ wherein e and h are integers independently selected from 0 through 2 and W$^2$ is selected from the group consisting of CR$^{4a}$=CR$^{4b}$, ethynylidene (C≡C; 1,2-ethynyl), and C=CR$^{4a}$R$^{4b}$ with the provisos that R$^{14}$ and R$^{15}$ are selected from other than halo and cyano when directly bonded to N and that (CR$^{37}$R$^{38}$)$_b$, (CH(R$^{14}$))$_c$, (CH(R$^{14}$))$_e$ and are bonded to E$^0$;

R$^{37}$ and R$^{37}$, when bonded to different carbons, can be taken together to form a linear moiety spacer having from 1 through 7 contiguous atoms to form a ring selected from the group consisting of a cycloalkyl ring having from 3 through 8 contiguous members, a cycloalkenyl ring having from 3 through 8 contiguous members, and a heterocyclyl ring having from 3 through 8 contiguous members;

R$^{37}$ and R$^{38}$, when bonded to different carbons, can be taken together to form a linear moiety spacer having from 1 through 7 contiguous atoms to form a ring selected from the group consisting of a cycloalkyl ring having from 3 through 8 contiguous members, a cycloalkenyl ring having from 3 through 8 contiguous members, and a heterocyclyl ring having from 3 through 8 contiguous members;

R$^{38}$ and R$^{38}$, when bonded to different carbons, can be taken together to form a linear moiety spacer having from 1 through 7 contiguous atoms to form a ring selected from the group consisting of a cycloalkyl ring having from 3 through 8 contiguous members, a cycloalkenyl ring having from 3 through 8 contiguous members, and a heterocyclyl ring having from 3 through 8 contiguous members;

R$^{37}$ and R$^{38}$, when bonded to the same carbon, can be taken together to form a group selected from a group consisting of oxo, thiono, alkylene, haloalkylene, and a linear moiety spacer having from 2 through 7 contiguous atoms to form a ring selected from the group consisting of a cycloalkyl ring having from 3 through 8 contiguous members, a cycloalkenyl ring having from 3 through 8 contiguous members, and a heterocyclyl ring having from 3 through 8 contiguous members;

Y$^0$ can be Q$^b$—Q$^{ss}$ wherein Q$^{ss}$ is selected from the group consisting of (CR$^{37}$R$^{38}$)$_f$ wherein f is an integer selected from 1 through 6, (CH(R$^{14}$))$_c$—W$^1$—(CH(R$^{15}$))$_d$ wherein c and d are integers independently selected from 1 through 4, and W$^1$ is selected from the group consisting of W$^1$ is selected from the group consisting of O, S, C(O), C(S), C(O)O, C(S)O, C(O)S, C(S)S, C(O)N($R^{14}$), ($R^{14}$)NC(O), C(S)N($R^{14}$), ($R^{14}$)NC(S), OC(O)N($R^{14}$), ($R^{14}$)NC(O)O, SC(S)N($R^{14}$), ($R^{14}$)NC(S)S, SC(O)N($R^{14}$), ($R^{14}$)NC(O)S, OC(S)N($R^{14}$), ($R^{14}$)NC(S)O, N($R^{15}$)C(O)N($R^{14}$), ($R^{14}$)NC(O)N($R^{15}$), N($R^{15}$)C(S)N($R^{14}$), ($R^{14}$)NC(S)N($R^{15}$), S(O), S(O)$_2$, S(O)$_2$N($R^{14}$), N($R^{14}$)S(O)$_2$, Se, Se(O), Se(O)$_2$, Se(O)$_2$N($R^{14}$), N($R^{14}$)Se(O)$_2$, P(O)($R^8$), N($R^7$)P(O)($R^8$), P(O)($R^8$)N($R^7$), N($R^{14}$), ON($R^{14}$), SiR$^{28}$R$^{29}$, and (CH($R^{14}$))$_e$—W$^2$—(CH($R^{15}$))$_h$ wherein e and h are integers independently selected from 0 through 2 and W$^2$ is selected from the group consisting of CR$^{4a}$=CR$^{4b}$, ethynylidene (C≡C, 1,2-ethynyl), and C=CR$^{4a}$R$^{4b}$ with the provisos that R$^{14}$ and R$^{15}$ are selected from other than halo and cyano when directly bonded to N and that (CR$^{37}$R$^{38}$)$_p$, (CH(R$^{15}$))$_c$, and (CH(R$^{15}$))$_e$ are bonded to E$^0$;

Y$^0$ can be Q$^b$—Q$^{sss}$ wherein Q$^{sss}$ is (CH(R$^{38}$))$_r$—W$^3$, r is an integer selected from 1 through 3, and W$^3$ is selected from the group consisting of 1,1-cyclopropyl, 1,2-cyclopropyl, 1,1-cyclobutyl, 1,2-cyclobutyl, 1,2-cyclohexyl, 1,3-cyclohexyl, 1,4-cyclohexyl, 1,2-cyclopentyl, 1,3-cyclopentyl, 2,3-morpholinyl, 2,4-morpholinyl, 2,5-morpholinyl, 2,6-morpholinyl, 3,4-morpholinyl, 3,5-morpholinyl, 1,2-piperazinyl, 1,3-piperazinyl, 1,4-piperazinyl, 2,3-piperazinyl, 2,5-piperazinyl, 2,6-piperazinyl, 1,2-piperidinyl, 1,3-piperidinyl, 1,4-piperidinyl, 2,3-piperidinyl, 2,4-piperidinyl, 2,5-piperidinyl, 2,6-piperidinyl, 3,4-piperidinyl, 3,5-piperidinyl, 3,6-piperidinyl, 1,2-pyrrolidinyl, 1,3-pyrrolidinyl, 2,3-pyrrolidinyl, 2,4-pyrrolidinyl, 2,5-pyrrolidinyl, 3,4-pyrrolidinyl, 2H-2,3-pyranyl, 2H-2,4-pyranyl, 2H-2,5-pyranyl, 4H-2,3-pyranyl, 4H-2,4-pyranyl, 4H-2,5-pyranyl, 2H-pyran-2-one-3,4-yl, 2H-pyran-2-one-4,5-yl, 4H-pyran-4-one-2,3-yl, 2,3-tetrahydrofuranyl, 2,4-tetrahydrofuranyl, 2,5-tetrahydrofuranyl, 3,4-tetrahydrofuranyl, 2,3-tetrahydropyranyl, 2,4-tetrahydropyranyl, 2,5-tetrahydropyranyl, 2,6-tetrahydropyranyl, 3,4-tetrahydropyranyl, and 3,5-tetrahydropyranyl with the proviso that (CH(R$^{38}$))$_r$ is bonded to E$^0$ and Q$^b$ is bonded to lowest numbered substituent position of each W$^3$;

Y$^0$ can be Q$^b$—Q$^{sssr}$ wherein Q$^{sssr}$ is (CH(R$^{38}$))$_r$—W$^4$, r is an integer selected from 1 through 3, and W$^4$ is selected from the group consisting of 1,2-cyclobutyl, 1,2-cyclohexyl, 1,3-cyclohexyl, 1,4-cyclohexyl, 1,2-cyclopentyl, 1,3-cyclopentyl, 2,3-morpholinyl, 2,4-morpholinyl, 2,5-morpholinyl, 2,6-morpholinyl, 3,4-morpholinyl, 3,4-morpholinyl, 1,2-piperazinyl, 1,3-piperazinyl, 1,4-piperazinyl, 2,3-piperazinyl, 2,5-piperazinyl, 2,6-piperazinyl, 1,2-piperidinyl, 1,3-piperidinyl, 1,4-piperidinyl, 2,3-piperidinyl, 2,4-piperidinyl, 2,5-piperidinyl, 2,6-piperidinyl, 3,4-piperidinyl, 3,5-piperidinyl, 3,6-piperidinyl, 1,2-pyrrolidinyl, 1,3-pyrrolidinyl, 2,3-pyrrolidinyl, 2,4-pyrrolidinyl, 2,5-pyrrolidinyl, 3,4-pyrrolidinyl, 2H-2,3-pyranyl, 2H-2,4-pyranyl, 2H-2,5-pyranyl, 4H-2,3-pyranyl, 4H-2,4-pyranyl, 4H-2,5-pyranyl, 2H-pyran-2-one-3,4-yl, 2H-pyran-2-one-4,5-yl, 4H-pyran-4-one-2,3-yl, 2,3-tetrahydrofuranyl, 2,4-tetrahydrofuranyl, 2,5-tetrahydrofuranyl, 3,4-tetrahydrofuranyl, 2,3-tetrahydropyranyl, 2,4-tetrahydropyranyl, 2,5-tetrahydropyranyl, 2,6-tetrahydropyranyl, 3,4-tetrahydropyranyl, and 3,5-tetrahydropyranyl with the provisos that $(CH(R^{38}))_r$ is bonded to $E^0$ and $Q^b$ is bonded to highest number substituent position of each $W^4$;

$Y^0$ can be $Q^b$—$Q^{ssss}$ wherein $Q^{ssss}$ is $(CH(R^{38}))_r$—$W^5$, r is an integer selected from 1 through 3, and $W^5$ is selected from the group consisting of 1,4-indenyl, 1,5-indenyl, 1,6-indenyl, 1,7-indenyl, 2,7-indenyl, 2,6-indenyl, 2,5-indenyl, 2,4-indenyl, 3,4-indenyl, 3,5-indenyl, 3,6-indenyl, 3,7-indenyl, 2,4-benzofuranyl, 2,5-benzofuranyl, 2,6-benzofuranyl, 2,7-benzofuranyl, 3,4-benzofuranyl, 3,5-benzofuranyl, 3,6-benzofuranyl, 3,7-benzofuranyl, 2,4-benzothiophenyl, 2,5-benzothiophenyl, 2,6-benzothiophenyl, 2,7-benzothiophenyl, 3,4-benzothiophenyl, 3,5-benzothiophenyl, 3,6-benzothiophenyl, 3,7-benzothiophenyl, 2,4-indolyl, 2,5-indolyl, 2,6-indolyl, 2,7-indolyl, 3,4-indolyl, 3,5-indolyl, 3,6-indolyl, 3,7-indolyl, 1,4-isoindolyl, 1,5-isoindolyl, 1,6-isoindolyl, 2,4-isoindoly, 2,5-isoindolyl, 2,6-isoindolyl, 2,7-isoindolyl, 1,3-isoindolyl, 3,4-indazolyl, 3,5-indazolyl, 3,6-indazolyl, 3,7-indazolyl, 2,4-benzoxazolyl, 2,5-benzoxazolyl, 2,6-benzoxazolyl, 2,7-benzoxazolyl, 3,4-benzisoxazolyl, 3,5-benzisoxazolyl, 3,6-benzisoxazolyl, 3,7-benzisoxazolyl, 1,4-naphthyl, 1,5-naphthyl, 1,6-naphthyl, 1,7-naphthyl, 1,8-naphthyl, 2,4-naphthyl, 2,5-naphthyl, 2,6-naphthyl, 2,7-naphthyl, 2,8-naphthyl, 2,4-quinolinyl, 2,5-quinolinyl, 2,6-quinolinyl, 2,7-quinolinyl, 2,8-quinolinyl, 3,4-quinolinyl, 3,5-quinolinyl, 3,6-quinolinyl, 3,7-quinolinyl, 3,8-quinolinyl, 4,5-quinolinyl, 4,6-quinolinyl, 4,7-quinolinyl, 4,8-quinolinyl, 1,4-isoquinolinyl, 1,5-isoquinolinyl, 1,6-isoquinolinyl, 1,7-isoquinolinyl, 1,8-isoquinolinyl, 3,4-isoquinolinyl, 3,5-isoquinolinyl, 3,6-isoquinolinyl, 3,7-isoquinolinyl, 3,8-isoquinolinyl, 4,5-isoquinolinyl, 4,6-isoquinolinyl, 4,7-isoquinolinyl, 4,8-isoquinolinyl, 3,4-cinnolinyl, 3,5-cinnolinyl, 3,6-cinnolinyl, 3,7-cinnolinyl, 3,8-cinnolinyl, 4,5-cinnolinyl, 4,6-cinnolinyl, 4,7-cinnolinyl, and 4,8-cinnolinyl with the proviso that $Q^b$ is bonded to lowest number substituent position of each $W^5$ and that $(CH(R^{38}))_r$ is bonded to $E^0$;

$Y^0$ can be $Q^b$—$Q^{sssssr}$ wherein $Q^{sssssr}$ is $(CH(R^{38}))_r$—$W^6$, r is an integer selected from 1 through 3, and $W^6$ is selected from the group consisting of 1,4-indenyl, 1,5-indenyl, 1,6-indenyl, 1,7-indenyl, 2,7-indenyl, 2,6-indenyl, 2,5-indenyl, 2,4-indenyl, 3,4-indenyl, 3,5-indenyl, 3,6-indenyl, 3,7-indenyl, 2,4-benzofuranyl, 2,5-benzofuranyl, 2,6-benzofuranyl, 2,7-benzofuranyl, 3,4-benzofuranyl, 3,5-benzofuranyl, 3,6-benzofuranyl, 3,7-benzofuranyl, 2,4-benzothiophenyl, 2,5-benzothiophenyl, 2,6-benzothiophenyl, 2,7-benzothiophenyl, 3,4-benzothiophenyl, 3,5-benzothiophenyl, 3,6-benzothiophenyl, 3,7-benzothiophenyl, 2,4-indolyl, 2,5-indolyl, 2,6-indolyl, 2,7-indolyl, 3,4-indolyl, 3,5-indolyl, 3,6-indolyl, 3,7-indolyl, 1,4-isoindolyl, 1,5-isoindolyl, 1,6-isoindolyl, 2,4-isoindolyl, 2,5-isoindolyl, 2,6-isoindolyl, 2,7-isoindolyl, 1,3-isoindolyl, 3,4-indazolyl, 3,5-indazolyl, 3,6-indazolyl, 3,7-indazolyl, 2,4-benzoxazolyl, 2,5-benzoxazolyl, 2,6-benzoxazolyl, 2,7-benzoxazolyl, 3,4-benzisoxazolyl, 3,5-benzisoxazolyl, 3,6-benzisoxazolyl, 3,7-benzisoxazolyl, 1,4-naphthyl, 1,5-naphthyl, 1,6-naphthyl, 1,7-naphthyl, 1,8-naphthyl, 2,4-naphthyl, 2,5-naphthyl, 2,6-naphthyl, 2,7-naphthyl, 2,8-naphthyl, 2,4-quinolinyl, 2,5-quinolinyl, 2,6-quinolinyl, 2,7-quinolinyl, 2,8-quinolinyl, 3,4-quinolinyl, 3,5-quinolinyl, 3,6-quinolinyl, 3,7-quinolinyl, 3,8-quinolinyl, 4,5-quinolinyl, 4,6-quinolinyl, 4,7-quinolinyl, 4,8-quinolinyl, 1,4-isoquinolinyl, 1,5-isoquinolinyl, 1,6-isoquinolinyl, 1,7-isoquinolinyl, 1,8-isoquinolinyl, 3,4-isoquinolinyl, 3,5-isoquinolinyl, 3,6-isoquinolinyl, 3,7-isoquinolinyl, 3,8-isoquinolinyl, 4,5-isoquinolinyl, 4,6-isoquinolinyl, 4,7-isoquinolinyl, 4,8-isoquinolinyl, 3,4-cinnolinyl, 3,5-cinnolinyl, 3,6-cinnolinyl, 3,7-cinnolinyl, 3,8-cinnolinyl, 4,5-cinnolinyl, 4,6-cinnolinyl, 4,7-cinnolinyl, and 4,8-cinnolinyl with the proviso that $Q^b$ is bonded to highest number substituent position of each $W^6$ and that $(CH(R^{38}))_r$ is bonded to $E^0$.

In an embodiment of compounds of Formula I or a pharmaceutically acceptable salt thereof, J is selected from the group consisting of hydrido, halo, hydroxy, hydroxyalkyl, amino, aminoalkyl, cyano, alkyl, haloalkyl, carboxy, carboxyalkyl, carboalkoxy, amidocarbonyl, acyl, phosphono, sulfo, O—$R^6$, NH—$R^6$, S—$R^6$, S(O)—$R^6$, and S(O)$_2$—$R^6$, wherein $R^6$ is selected from the group consisting of alkyl, and haloalkyl, haloalkenyl;

B is formula (V):

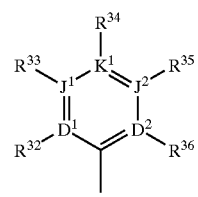

(V)

wherein $D^1$, $D^2$, $J^1$, $J^2$ and $K^1$ are independently selected from the group consisting of C, N, O, S and a covalent bond with the provisos that no more than one can be a covalent bond, no more than one of $D^1$, $D^2$, $J^1$, $J^2$ and $K^1$ can be O, no more than one of $D^1$, $D^2$, $J^1$, $J^2$ and $K^1$ can be S, one of $D^1$, $D^2$, $J^1$, $J^2$ and $K^1$ must be a covalent bond when two of $D^1$, $D^2$, $J^1$, $J^2$ and $K^1$ are O and S, and no more than four of $D^1$, $D^2$, $J^1$, $J^2$ and $K^1$ can be N with the proviso that $R^{32}$, $R^{33}$, $R^{34}$, $R^{35}$, and $R^{36}$ are each independently selected to maintain the tetravalent nature of carbon, trivalent nature of nitrogen, the divalent nature of sulfur, and the divalent nature of oxygen;

$R^{32}$, $R^{33}$, $R^{34}$, $R^{35}$, and $R^{36}$ can independently be $Q^b$;

$R^9$, $R^{10}$, $R^{11}$, $R^{12}$, $R^{13}$, $R^{16}$, $R^{17}$, $R^{18}$, $R^{19}$, $R^{32}$, $R^{33}$, $R^{34}$, $R^{35}$, and $R^{36}$ are independently selected from the group consisting of hydrido, amidino, guanidino, dialkylsulfonium, trialkylphosphonium, dialkylsulfoniumalkyl, carboxy, heteroaralkylthio, heteroaralkoxy, cycloalkylamino, acylalkyl, acylalkoxy, aryloylalkoxy, heterocyclyloxy, aralkylaryl, aralkyl, aralkenyl, aralkynyl, heterocyclyl, perhaloaralkyl, aralkylsulfonyl, aralkylsulfonylalkyl, aralkylsulfinyl, aralkylsulfinylalkyl, halocycloalkyl, halocycloalkenyl, cycloalkylsulfinyl, cycloalkylsulfinylalkyl, cycloalkylsulfonyl, cycloalkylsulfonylalkyl, heteroarylamino, N-heteroarylamino-N-alkylamino, heteroarylaminoalkyl, haloalkylthio, alkanoyloxy, alkoxy, alkoxyalkyl, haloalkoxyalkyl, heteroaralkoxy, cycloalkoxy, cycloalkenyloxy, cycloalkoxyalkyl, cycloalkylalkoxy, cycloalkenyloxyalkyl, cycloalkylenedioxy, halocycloalkoxy, halocycloalkoxyalkyl, halocycloalkenyloxy, halocycloalkenyloxyalkyl, hydroxy, amino, alkoxyamino, thio, nitro, lower alkylamino, alkylthio, alkylthioalkyl, arylamino, aralkylamino, arylthio, arylthioalkyl, heteroaralkoxyalkyl, alkylsulfinyl, alkylsulfinylalkyl, arylsulfinylalkyl, arylsulfonylalkyl, heteroarylsulfinylalkyl, heteroarylsulfonylalkyl, alkylsulfonyl, alkylsulfonylalkyl, haloalkylsulfinylalkyl, haloalkylsulfonylalkyl, alkylsulfonamido, alkylaminosulfonyl, amidosulfonyl, monoalkyl amidosulfonyl, dialkyl amidosulfonyl, monoarylamidosulfonyl, arylsulfonamido, diarylamidosulfonyl, monoalkyl monoaryl amidosulfonyl, arylsulfinyl, arylsulfonyl, heteroarylthio, heteroarylsulfinyl, heteroarylsulfonyl, heterocyclylsulfonyl, heterocyclylthio, alkanoyl, alkenoyl, aroyl, heteroaroyl, aralkanoyl, heteroaralkanoyl, haloalkanoyl, alkyl, alkenyl, alkynyl, alkenyloxy, alkenyloxyalky, alkylenedioxy, haloalkylenedioxy, cycloalkyl, cycloalkylalkanoyl, cycloalkenyl, lower cycloalkylalkyl, lower cycloalkenylalkyl, halo, haloalkyl, haloalkenyl, haloalkoxy, hydroxyhaloalkyl, hydroxyaralkyl, hydroxyalkyl, aminoalkyl, hydoxyheteroaralkyl, haloalkoxyalkyl, aryl, aralkyl, aryloxy, aralkoxy, aryloxyalkyl, saturated heterocyclyl, partially saturated heterocyclyl, heteroaryl, heteroaryloxy, heteroaryloxyalkyl, arylalkyl, heteroarylalkyl, arylalkenyl, heteroarylalkenyl, carboxyalkyl, carboalkoxy, alkoxycarboxamido, alkylamidocarbonylamido, arylamidocarbonylamido, carboalkoxyalkyl, carboalkoxyalkenyl, carboaralkoxy, carboxamido, carboxamidoalkyl, cyano, carbohaloalkoxy, phosphono, phosphonoalkyl, diaralkoxyphosphono, and diaralkoxyphosphonoalkyl;

$R^{32}$ and $R^{33}$, $R^{33}$ and $R^{34}$, $R^{34}$ and $R^{35}$, and $R^{35}$ and $R^{36}$ can be independently selected to form a spacer pair wherein a spacer pair is taken together to form a linear moiety having from 3 through 6 contiguous atoms connecting the points of bonding of said spacer pair members to form a ring selected from the group consisting of a cycloalkenyl ring having 5 through 8 contiguous members, a partially saturated heterocyclyl ring having 5 through 8 contiguous members, a heteroaryl ring having 5 through 6 contiguous members, and an aryl with the proviso that no more than one of the group consisting of spacer pairs $R^{32}$ and $R^{33}$, $R^{33}$ and $R^{34}$, $R^{34}$ and $R^{35}$, and $R^{35}$ and $R^{36}$ can be used at the same time;

$R^9$ and $R^{10}$, $R^{10}$ and $R^{11}$, $R^{11}$ and $R^{12}$, and $R^{12}$ and $R^{13}$ can be independently selected to form a spacer pair wherein a spacer pair is taken together to form a linear moiety having from 3 through 6 contiguous atoms connecting the points of bonding of said spacer pair members to form a ring selected from the group consisting of a cycloalkenyl ring having 5 through 8 contiguous members, a partially saturated heterocyclyl ring having 5 through 8 contiguous members, a heteroaryl ring having 5 through 6 contiguous members, and an aryl with the proviso that no more than one of the group consisting of spacer pairs $R^9$ and $R^{10}$, $R^{10}$ and $R^{11}$, $R^{11}$ and $R^{12}$, and $R^{12}$ and $R^{13}$ can be used at the same time;

B can be selected from the group consisting of C3–C8 alkyl, C3–C8 alkenyl, C3–C8 alkynyl, C3–C8 haloalkyl, and C3–C8 haloalkenyl wherein each member of group B may be optionally substituted at any carbon up to and including 6 atoms from the point of attachment of B to A with one or more of the group consisting of $R_{32}$, $R_{33}$, $R_{34}$, $R_{35}$, and $R_{36}$;

B can be selected from the group consisting of C3–C10 cycloalkyl, C5–C10 cycloalkenyl, C4–C9 saturated heterocyclyl, and C4–C9 partially saturated heterocyclyl, wherein each ring carbon may be optionally substituted with $R_{33}$, a ring carbon other than the ring carbon at the point of attachment of B to A may be optionally substituted with oxo provided that no more than one ring carbon is substituted by oxo at the same time, ring carbon and nitrogen atoms adjacent to the carbon atom at the point of attachment may be optionally substituted with $R_9$ or $R_{13}$, a ring carbon or nitrogen atom adjacent to the $R_9$ position and two atoms from the point of attachment may be substituted with $R_{10}$, a ring carbon or nitrogen atom adjacent to the $R_{13}$ position and two atoms from the point of attachment may be substituted with $R_{12}$, a ring carbon or nitrogen atom three atoms from the point of attachment and adjacent to the $R_{10}$ position may be substituted with $R_{11}$, a ring carbon, or nitrogen atom three atoms from the point of attachment and adjacent to the $R_{12}$ position may be substituted with $R_{33}$, and a ring carbon or nitrogen atom four atoms from the point of attachment and adjacent to the $R_{11}$ and $R_{33}$ positions may be substituted with $R_{34}$;

A is selected from the group consisting of single covalent bond, $(W^7)_{rr}$—$(CH(R^{15}))_{pa}$ and $(CH(R^{15}))_{pa}$—$(W^7)_{rr}$ wherein rr is an integer selected from 0 through 1, pa is an integer selected from 0 through 6, and $W^7$ is selected from the group consisting of O, S, C(O), C(S), C(O)S, C(S)O, C(O)N($R^7$), C(S)N($R^7$), ($R^7$)NC(O), ($R^7$)NC(S), S(O), S(O)$_2$, S(O)$_2$N($R^7$), ($R^7$)NS(O)$_2$, P(O)($R^8$), N($R^7$)P(O)($R^8$), P(O)($R^8$)N($R^7$), C(N$R^7$)N ($R^7$), ($R^7$)NC(N$R^7$), and N($R^7$) with the proviso that no more than one of the group consisting of rr and pa can be 0 at the same time;

$R^7$ and $R^8$ are independently selected from the group consisting of hydrido, hydroxy, alkyl, acyl, aroyl, heteroaroyl, and alkoxyalkyl;

$R^{14}$, $R^{15}$, $R^{37}$, and $R^{38}$ are independently selected from the group consisting of hydrido, hydroxy, halo, cyano, hydroxyalkyl, alkoxy, alkyl, alkoxyalkyl, cycloalkyl, cycloalkylalkyl, cycloalkenyl, cycloalkenylalkyl, haloalkyl, haloalkenyl, haloalkoxy, haloalkoxyalkyl, haloalkenyloxyalkyl, halocycloalkoxy, halocycloalkoxyalkyl, halocycloalkenyloxyalkyl, carboxy, carboxyalkyl, carboalkoxy, carboxamide, and carboxamidoalkyl;

Ψ is selected from the group consisting of N$R^5$, O, C(O), C(S), S, S(O), S(O)$_2$, ON($R^5$), P(O)($R^8$), and C$R^{39}R^{40}$ with the provisos that Ψ is selected from other than N$R^5$, O, S, S(O), and S(O)$_2$ unless any two of $X^0$, $R^2$, $R^1$, and J are other than hydrido, or that Ψ is selected from other than O, unless A is selected from other than methylene when B is phenyl, that Ψ is selected from other than C(O), unless A is selected from other than methyleneoxy when B is phenyl, or that Ψ is selected from other than NH unless A is selected from other than a single covalent bond when B is acyl, or that Ψ is selected from other than NH unless A is selected from other than S(O) or S(O)$_2$ when B is phenyl;

$R^5$ is selected from the group consisting of hydrido, alkyl, alkoxy, alkoxyalkyl, haloalkyl, acyl, aroyl, and heteroaroyl;

$R^{39}$ and $R^{40}$ are independently selected from the group consisting of hydrido, hydroxy, halo, cyano, hydroxyalkyl, acyl, aroyl, heteroaroyl, acylamido, alkoxy, alkyl, alkoxyalkyl, haloalkyl, haloalkoxy, haloalkoxyalkyl, alkylsulfonyl, haloalkylsulfonyl, carboxy, carboxyalkyl, carboalkoxy, carboxamide, and carboxamidoalkyl;

$X^0$, $R^2$ and $R^1$ are independently selected from the group consisting of $Z^0$—Q, hydrido, alkyl, alkenyl, and halo;

$X^0$, $R^2$ and $R^1$ can be independently selected from the group consisting of amidino, guanidino, dialkylsulfonium, trialkylphosphonium, dialkylsulfoniumalkyl, heteroarylamino, amino, nitro, alkylamino, arylamino, aralkylamino, alkanoyl, alkenoyl, aroyl, heteroaroyl, aralkanoyl, heteroaralkanoyl, haloalkanoyl, hydroxyhaloalkyl, cyano, and phosphono;

$X^0$ and $R^1$ can be taken together to form a spacer pair wherein the spacer pair forms a linear moiety having from 3 through 6 contiguous atoms connecting the points of bonding of said spacer pair members to form a ring selected from the group consisting of a cycloalkenyl ring having from 5 through 8 contiguous members and a partially saturated heterocyclyl ring having from 5 through 8 contiguous members with the proviso that no more than one of the group consisting of spacer pair $X^0$ and $R^1$ and spacer pair $R^2$ and $R^1$ can be used at the same time;

$R^2$ and $R^1$ can be taken together to form a spacer pair wherein the spacer pair forms a linear moiety having from 3 through 6 contiguous atoms connecting the points of bonding of said spacer pair members to form a ring selected from the group consisting of a cycloalkenyl ring having from 5 through 8 contiguous members and a partially saturated heterocyclyl ring having from 5 through 8 contiguous members with the proviso that no more than one of the group consisting of spacer pair $X^0$ and $R^1$ and spacer pair $R^2$ and $R^1$ can be used at the same time;

$X^0$ and $R^1$ and $R^2$ and $R^1$ spacer pairs are selected independently to be —W=X—Y=Z— forming a ring selected from the group consisting of a heteroaryl ring having from 5 through 6 contiguous members and an aryl with the proviso that no more than one of the group consisting of spacer pair $X^0$ and $R^1$ and spacer pair $R^2$ and $R^1$ is used at the same time;

W, X, Y, and Z are independently selected from the group consisting of $C(R^9)$, $N,N(R^{10})$, O, S and a covalent bond with the provisos that one of W, X, Y, and Z is independently selected to be a covalent bond when one of W, X, Y, and Z is selected from the group consisting of O and S, no more than one of W, X, Y, and Z is selected from the group consisting of O and S, no more than three of W, X, Y, and Z are selected from the group consisting of N and $N(R^{10})$, and $C(R^9)$, $N,N(R^{10})$, O, and S are independently selected to maintain the tetravalent nature of carbon, trivalent nature of nitrogen, the divalent nature of sulfur, the divalent nature of oxygen, and the aromaticity of the ring;

$Z^0$ is selected from the group consisting of covalent single bond, $(CR^{41}R^{42})_q$ wherein q is an integer selected from 1 through 6, $(CH(R^{41}))_g$—$W^0$—$(CH(R^{42}))_p$ wherein g and p are integers independently selected from 0 through 3 and $W^0$ is selected from the group consisting of O, S, C(O), C(S), C(O)O, C(S)O, C(O)S, C(S)S, C(O)N($R^{41}$), ($R^{41}$)NC(O), C(S)N($R^{41}$), ($R^{41}$)NC(S), OC(O)N($R^{41}$), ($R^{41}$)NC(O)O, SC(S)N($R^{41}$), ($R^{41}$)NC(S)S, SC(O)N($R^{41}$), ($R^{41}$)NC(O)S, OC(S)N($R^{41}$), ($R^{41}$)NC(S)O, N($R^{42}$)C(O)N($R^{41}$), ($R^{41}$)NC(O)N($R^{42}$), N($R^{42}$)C(S)N($R^{41}$), ($R^{41}$)NC(S)N($R^{42}$), S(O), $S(O)_2$, $S(O)_2N(R^{41})$, $N(R^{41})S(O)_2$, $P(O)(R^8)$, $N(R^7)P(O)(R^8)$, $P(O)(R^8)N(R^7)$, N($R^{41}$), ON($R^{41}$), and $(CH(R^{41}))_e$—$W^2$—$(CH(R^{42}))_h$ wherein e and h are integers independently selected from 0 through 2 and $W^2$ is selected from the group consisting of $CR^{41}$=$CR^{42}$, $CR^{41}R^{42}$=C; vinylidene), and ethynylidene (C≡C; 1,2-ethynyl), with the provisos that $R^{41}$ and $R^{42}$ are selected from other than halo and cyano when directly bonded to N and $Z^0$ is directly bonded to the benzene ring, that $W^0$ is selected, wherein g is 0, from other than $NHS(O)_2CH_2$aryl or $N(R^{41})$ unless $R^{41}$ is selected from other than hydrido, alkyl, or aralkylsulfonyl, and $Z^0$ is selected from other than OC(O), C(O)N(H), and (H)NC(O), unless Q is selected from other than phenyl, 2-furyl, 2-thienyl, 4-thiazolyl, 2-pyridyl, 2-naphthyl, 1,2-dihydrobenzofuran-5-yl, 1,2-dihydrobenzofuran-6-yl, or 1,2benzisoxazol-6-yl , or $X^o$ is selected from other than hydrido, halo, or methyl, or $R^1$ is selected from other than hydrido, fluoro, hydroxy, acetoxy, propanoyloxy, 2-carboxyacetoxy, 2,3 or 4-carboxypropanoyloxy, benzoyloxy, methyl, or methoxy;

$R^{41}$ and $R^{42}$ are independently selected from the group consisting of hydrido, hydroxy, halo, cyano, aryloxy, hydroxyalkyl, acyl, aroyl, heteroaroyl, heteroaryloxyalkyl, alkoxy, alkyl, aryl, aralkyl, aryloxyalkyl, aralkoxyalkylalkoxy, alkoxyalkyl, heteroaryloxyalkyl, cycloalkyl, cycloalkylalkyl, cycloalkylalkenyl, cycloalkenyl, cycloalkenylalkyl, haloalkyl, haloalkenyl, halocycloalkyl, halocycloalkenyl, haloalkoxy, haloalkoxyalkyl, haloalkenyloxyalkyl, halocycloalkoxy, halocycloalkoxyalkyl, halocycloalkenyloxyalkyl, saturated heterocyclyl, partially saturated heterocyclyl, heteroaryl, heteroaralkyl, heteroarylthioalkyl, heteroaralkylthioalkyl, alkylsulfonyl, haloalkylsulfonyl, arylsulfonyl, arylsulfonylalkyl, aralkylsulfonyl, cycloalkylsulfonyl, cycloalkylsufonylalkyl, heteroarylsulfonylalkyl, heteroarylsulfonyl, and aralkylsulfonylalkyl;

Q is formula (II):

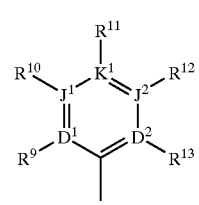

(II)

wherein $D^1$, $D^2$, $J^1$, $J^2$ and $K^1$ are independently selected from the group consisting of C, N, O, S and a covalent bond with the provisos that no more than one can be a covalent bond, no more than one of $D^1$, $D^2$, $J^1$, $J^2$ and $K^1$ can be O, no more than one of $D^1$, $D^2$, $J^1$, $J^2$ and $K^1$ can be S, one of $D^1$, $D^2$, $J^1$, $J^2$ and $K^1$ must be a covalent bond when two of $D^1$, $D^2$, $J^1$, $J^2$ and $K^1$ are O and S, and no more than four of $D^1$, $D^2$, $J^1$, $J^2$ and $K^1$ can be N with the proviso that $R^9$, $R^{10}$, $R^{11}$, $R^{12}$, and $R^{13}$ are each independently selected to maintain the tetravalent nature of carbon, trivalent nature of nitrogen, the divalent nature of sulfur, and the divalent nature of oxygen;

23

Q can be formula (III):

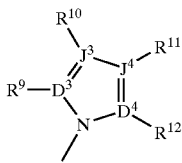

(III)

wherein $D^3$, $D^4$, $J^3$, and $J^4$ are independently selected from the group consisting of C, N, O, and S, no more than one of $D^3$, $D^4$, $J^3$, and $J^4$ can be O, no more than one of $D^3$, $D^4$, $J^3$, and $J^4$ can be S, and no more than three of $D^1$, $D^2$, $J^1$, and $J^2$ can be N with the proviso that $R^9$, $R^{10}$, $R^{11}$, and $R^{12}$ are each independently selected to maintain the tetravalent nature of carbon, trivalent nature of nitrogen, the divalent nature of sulfur, and the divalent nature of oxygen;

Q can be selected from the group consisting of alkyl, alkoxy, alkylamino, alkylthio, haloalkylthio, alkenyl, alkynyl, saturated heterocyclyl, partially saturated heterocyclyl, acyl, aroyl, heteroaroyl, cycloalkyl, cycloalkylalkyl, cycloalkenyl, cycloalkenylalkyl, cycloalkylalkenyl, haloalkyl, haloalkoxy, haloalkenyl, halocycloalkyl, halocycloalkenyl, haloalkoxyalkyl, haloalkenyloxyalkyl, halocycloalkoxyalkyl, and halocycloalkenyloxyalkyl with the proviso that Q is selected from other than than alkyl or alkenyl unless any one of $X^0$, $R^1$, and J are other than hydrido;

K is $(CR^{4a}R^{4b})_n$ wherein n is an integer selected from 1 through 2;

$R^{4a}$ and $R^{4b}$ are independently selected from the group consisting of halo, hydrido, hydroxy, cyano, hydroxyalkyl, alkyl, alkenyl, alkoxyalkyl, haloalkyl, haloalkenyl, and cyanoalkyl;

$R^{4a}$ and $R^{4b}$, when bonded to the same carbon, can be taken together to form a group selected from the group consisting of oxo, and a linear spacer moiety having from 2 through 7 contiguous atoms connected to form a ring selected from the group consisting of a cycloalkyl ring having 3 through 8 contiguous members, a cycloalkenyl ring having 5 through 8 contiguous members, and a heterocyclyl ring having 5 through 8 contiguous members;

$E^0$ is $E^1$, when K is $(CR^{4a}R^{4b})_n$, wherein $E^1$ is selected from the group consisting of a covalent single bond, O, S, C(O), C(S), C(O)O, C(S)O, C(O)S, C(S)S, C(O)N(R^7), (R^7)NC(O), C(S)N(R^7), (R^7)NC(S), OC(O)N(R^7), (R^7)NC(O)O, SC(S)N(R^7), (R^7)NC(S)S, SC(O)N(R^7), (R^7)NC(O)S, OC(S)N(R^7), (R^7)NC(S)O, N(R^8)C(O)N(R^7), (R^7)NC(O)N(R^8), N(R^8)C(S)N(R^7), (R^7)NC(S)N(R^8), S(O), S(O)_2, S(O)_2N(R^7), N(R^7)S(O)_2, S(O)_2N(R^7)C(O), C(O)N(R^7)S(O)_2, P(O)(R^8), N(R^7)P(O)(R^8), P(O)(R^8)N(R^7), N(R^7), ON(R^7), CR^{4a}=CR^{4b}$, ethynylidene (C≡C; 1,2-ethynyl), and $C=CR^{4a}R^{4b}$;

K can be $(CH(R^{14}))_j$—T wherein j is selected from a integer from 0 through 2 and T is selected from the group consisting of single covalent bond, O, S, and $N(R^7)$ with the proviso that $(CH(R^{14}))_j$ is bonded to the phenyl ring;

$E^0$ is $E^2$, when K is $(CH(R^{14}))_j$—T, wherein $E^2$ is selected from the group consisting of a covalent single bond, C(O), C(S), C(O)O, C(S)O, C(O)S, C(S)S, C(O)N(R^7), (R^7)NC(O), C(S)N(R^7), (R^7)NC(S), (R^7)NC(O)O, (R^7)

24

NC(S)S, (R^7)NC(O)S, (R^7)NC(S)O, N(R^8)C(O)N(R^7), (R^7)NC(O)N(R^8), N(R^8)C(S)N(R^7), (R^7)NC(S)N(R^8), S(O), S(O)_2, S(O)_2N(R^7), N(R^7)S(O)_2, S(O)_2N(H)C(O), C(O)N(H)S(O)_2, P(O)(R^8), N(R^7)P(O)(R^8), P(O)(R^8)N(R^7)$, and $N(R^7)$;

K can be $G—(CH(R^{15}))_k$ wherein k is selected from an integer from 1 through 2 and G is selected from the group consisting of O, S, and $N(R^7)$ with the proviso that $R^{15}$ is other than hydroxy, cyano, halo, amino, alkylamino, dialkylamino, and sulfhydryl when k is 1;

$E^0$ is $E^3$ when K is $G—(CH(R^{15}))_k$ wherein $E^3$ is selected from the group consisting of a covalent single bond, O, S, C(O), C(S), C(O)O, C(S)O, C(O)S, C(S)S, C(O)N(R^7), (R^7)NC(O), C(S)N(R^7), (R^7)NC(S), OC(O)N(R^7), (R^7)NC(O)O, SC(S)N(R^7), (R^7)NC(S)S, SC(O)N(R^7), (R^7)NC(O)S, OC(S)N(R^7), (R^7)NC(S)O, N(R^8)C(O)N(R^7), (R^7)NC(O)N(R^8), N(R^8)C(S)N(R^7), (R^7)NC(S)N(R^8), S(O), S(O)_2, S(O)_2N(R^7), N(R^7)S(O)_2, P(O)(R^8), N(R^7)P(O)(R^8), P(O)(R^8)N(R^7), N(R^7), ON(R^7), CR^{4a}=CR^{4b}$, ethynylidene (C≡C; 1,2-ethynyl), and $C=CR^{4a}R^{4b}$;

$Y^0$ is formula (IV):

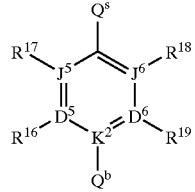

(IV)

wherein $D^5$, $D^6$, $J^5$, and $J^6$ are independently selected from the group consisting of C, N, O, S and a covalent bond with the provisos that no more than one can be a covalent bond, $K^2$ is independently selected from the group consisting of C, and $N^+$, no more than one of $D^5$, $D^6$, $J^5$, and $J^6$ can be O, no more than one of $D^5$, $D^6$, $J^5$, and $J^6$ can be S, one of $D^5$, $D^6$, $J^5$, and $J^6$ must be a covalent bond when two of $D^5$, $D^6$, $J^5$, and $J^6$ are O and S, no more than three of $D^5$, $D^6$, $J^5$, and $J^6$ can be N when $K^2$ is $N^+$, and no more than four of $D^5$, $D^6$, $J^5$, and $J^6$ can be N when $K^2$ is carbon with the provisos that $R^{16}$, $R^{17}$, $R^{18}$, and $R^{19}$ are each independently selected to maintain the tetravalent nature of carbon, trivalent nature of nitrogen, the divalent nature of sulfur, and the divalent nature of oxygen;

$R^{16}$ and $R^{17}$ can be independently taken together to form a linear moiety spacer having from 3 through 6 contiguous atoms connected to form a ring selected from the group consisting of a cycloalkenyl ring having from 5 through 8 contiguous members, a partially saturated heterocyclyl ring having from 5 through 8 contiguous members, a heteroaryl having from 5 through 6 contiguous members, and an aryl;

$Q^b$ is selected from the group consisting of $NR^{20}R^{21}$, $^+NR^{20}R^{21}R^{22}$, oxy, alkyl, alkylaminoalkyl, aminoalkyl, dialkylsulfoniumalkyl, and acylamino wherein $R^{20}$, $R^{21}$, and $R^{22}$ are independently selected from the group consisting of hydrido, alkyl, hydroxy, alkoxy, alkylamino, dialkylamino, aminoalkyl, and hydroxyalkyl with the provisos that no more than one of $R^{20}$, $R^{21}$, and $R^{22}$ can be hydroxy, alkoxy, alkylamino, amino, and dialkylamino and that $R^{20}$, $R^{21}$, and $R^{22}$ must be other than be hydroxy, alkoxy, alkylamino, amino, and dialkylamino when $K^2$ is $N^+$;

$R^{20}$ and $R^{21}$, $R^{20}$ and $R^{22}$, and $R^{21}$ and $R^{22}$ can be independently selected to form a spacer pair wherein a spacer pair is taken together to form a linear moiety having from 4 through 7 contiguous atoms connecting the points of bonding of said spacer pair members to form a heterocyclyl ring having 5 through 8 contiguous members with the proviso that no more than one of the group consisting of spacer pairs $R^{20}$ and $R^{21}$, $R^{20}$ and $R^{22}$, and $R^{21}$ and $R^{22}$ can be used at the same time;

$Q^b$ can be selected from the group consisting of $N(R^{26})$ $SO_2N(R^{23})(R^{24})$, $N(R^{26})C(O)OR^5$, $N(R^{26})C(O)SR^5$, $N(R^{26})C(S)OR^5$ and $N(R^{26})C(S)SR^5$ with the proviso that no more than one of $R^{23}$, $R^{24}$, and $R^{26}$ can be hydroxy, alkoxy, alkylamino, amino, or dialkylamino when two of the group consisting of $R^{23}$, $R^{24}$, and $R^{26}$ are bonded to the same atom;

$Q^b$ can be selected from the group consisting of dialkylsulfonium, trialkylphosphonium, $C(NR^{25})$ $NR^{23}R^{24}$, $N(R^{26})C(NR^{25})N(R^{23})(R^{24})$, $N(R^{26})C(O)N$ $(R^{23})(R^{24})$, $N(R^{26})C(S)N(R^{23})(R^{24})$, $C(NR^{25})OR^5$, $C(O)N(R^{26})C(NR^{25})N(R^{23})(R^{24})$, $C(S)N(R^{26})C(NR^{25})$ $N(R^{23})(R^{24})$, $N(R^{26})N(R^{26})C(NR^{25})N(R^{23})(R^{24})$, $N(R^{26})N(R^{26})SO_2N(R^{23})(R^{24})$, $C(NR^{25})SR^5$, $C(O)$ $NR^{23}R^{24}$, and $C(O)NR^{23}R^{24}$ with the provisos that no more than one of $R^{23}$, $R^{24}$, and $R^{26}$ can be hydroxy, alkoxy, alkylamino, amino, or dialkylamino when two of the group consisting of $R^{23}$, $R^{24}$, and $R^{26}$ are bonded to the same atom and that said $Q^b$ group is bonded directly to a carbon atom;

$R^{23}$, $R^{24}$, $R^{25}$, and $R^{26}$ are independently selected from the group consisting of hydrido, alkyl, hydroxy, alkoxy, alkylamino, dialkylamino, aminoalkyl, and hydroxyalkyl;

$R^{23}$ and $R^{24}$ can be taken together to form a linear spacer moiety having from 4 through 7 contiguous atoms connecting the points of bonding to form a heterocyclyl ring having 5 through 8 contiguous members;

$Q^s$ is selected from the group consisting of a single covalent bond, $(CR^{37}R^{38})_b$—$(W^0)_{az}$ wherein az is an integer selected from 0 through 1, b is an integer selected from 1 through 4, and $W^0$ is selected from the group consisting of O, S, C(O), C(S), C(O)O, C(S)O, C(O)S, C(S)S, C(O)N($R^{14}$), ($R^{14}$)NC(O), C(S)N($R^{14}$), ($R^{14}$)NC(S), OC(O)N($R^{14}$), SC(S)N($R^{14}$), SC(O)N ($R^{14}$), OC(S)N($R^{14}$), N($R^{15}$)C(O)N($R^{14}$), ($R^{14}$)NC(O) N($R^{15}$), N($R^{15}$)C(S)N($R^{14}$), ($R^{14}$)NC(S)N($R^{15}$), S(O), S(O)$_2$, S(O)$_2$N($R^{14}$), N($R^{14}$)S(O)$_2$, P(O)($R^8$), N($R^7$)P (O)($R^8$), P(O)($R^8$)N($R^7$), N($R^{14}$), ON($R^{14}$), (CH($R^{14}$))$_c$—$W^1$—(CH($R^{15}$))$_d$ wherein c and d are integers independently selected from 1 through 4, and $W^1$ is selected from the group consisting of O, S, C(O), C(S), C(O)O, C(S)O, C(O)S, C(S)S, C(O)N($R^{14}$), ($R^{14}$)NC(O), C(S)N($R^{14}$), ($R^{14}$)NC(S), OC(O)N($R^{14}$), ($R^{14}$)NC(O)O, SC(S)N($R^{14}$), ($R^{14}$)NC(S)S, SC(O)N ($R^{14}$), ($R^{14}$)NC(O)S, OC(S)N($R^{14}$), ($R^{14}$)NC(S)O, N($R^{15}$)C(O)N($R^{14}$), ($R^{14}$)NC(O)N($R^{15}$), N($R^{15}$)C(S)N ($R^{14}$), ($R^{14}$)NC(S)N($R^{15}$), S(O), S(O)$_2$, S(O)$_2$N($R^{14}$), N($R^{14}$)S(O)$_2$, P(O)($R^8$), N($R^7$)P(O)($R^8$), P(O)($R^8$)N ($R^7$), N($R^{14}$), ON($R^{14}$), and (CH($R^{14}$))$_e$—$W^2$—(CH ($R^{15}$))$_h$ wherein e and h are integers independently selected from 0 through 2 and $W^2$ is selected from the group consisting of $CR^{4a}$=$CR^{4b}$, ethynylidene (C≡C; 1,2-ethynyl), and C=$CR^{4a}R^{4b}$ with the provisos that $R^{14}$ and $R^{15}$ are selected from other than halo and cyano when directly bonded to N and that $(CR^{37}R^{38})_b$, $(CH(R^{14}))_c$, $(CH(R^{14}))_e$ are bound to $E^0$;

$Y^0$ can be $Q^b$—$Q^{ss}$ wherein $Q^{ss}$ is selected from the group consisting of $(CR^{37}R^{38})_f$ wherein f is an integer selected from 1 through 6, $(CH(R^{14}))_c$—$W^1$—(CH $(R^{15}))_d$ wherein c and d are integers independently selected from 1 through 4, and $W^1$ is selected from the group consisting of $W^1$ is selected from the group consisting of O, S, C(O), C(S), C(O)O, C(S)O, C(O)S, C(S)S, C(O)N($R^{14}$), ($R^{14}$)NC(O), C(S)N($R^{14}$), ($R^{14}$) NC(S), OC(O)N($R^{14}$), ($R^{14}$)NC(O)O, SC(S)N($R^{14}$), ($R^{14}$)NC(S)S, SC(O)N($R^{14}$), ($R^{14}$)NC(O)S, OC(S)N ($R^{14}$), ($R^{14}$)NC(S)O, N($R^{15}$)C(O)N($R^{14}$), ($R^{14}$)NC(O) N($R^{15}$), N($R^{15}$)C(S)N($R^{14}$), ($R^{14}$)NC(S)N($R^{15}$), S(O), S(O)$_2$, S(O)$_2$N($R^{14}$), N($R^{14}$)S(O)$_2$, P(O)($R^8$), N($R^7$)P (O)($R^8$), P(O)($R^8$)N($R^7$), N($R^{14}$), ON($R^{14}$), and (CH ($R^{14}$))$_e$—$W^2$—(CH($R^{15}$))$_h$ wherein e and h are integers independently selected from 0 through 2 and $W^2$ is selected from the group consisting of $CR^{4a}$=$CR^{4b}$, ethynylidene (C≡C, 1,2-ethynyl), and C=$CR^{4a}R^{4b}$ with the provisos that $R^{14}$ and $R^{15}$ are selected from other than halo and cyano when directly bonded to N and that $(CR^{37}R^{38})_f$, $(CH(R^{15}))_c$, and $(CH(R^{15}))_e$ are bonded to $E^0$;

$Y^0$ can be $Q^b$—$Q^{sss}$ wherein $Q^{sss}$ is $(CH(R^{38}))_r$—$W^3$, r is an integer selected from 1 through 3, and $W^3$ is selected from the group consisting of 1,1-cyclopropyl, 1,2-cyclopropyl, 1,1-cyclobutyl, 1,2-cyclobutyl, 1,2-cyclohexyl, 1,3-cyclohexyl, 1,4-cyclohexyl, 1,2-cyclopentyl, 1,3-cyclopentyl, 2,3-morpholinyl, 2,4-morpholinyl, 2,5-morpholinyl, 2,6-morpholinyl, 3,4-morpholinyl, 3,5-morpholinyl, 1,2-piperazinyl, 1,3-piperazinyl, 1,4-piperazinyl, 2,3-piperazinyl, 2,5-piperazinyl, 2,6-piperazinyl, 1,2-piperidinyl, 1,3-piperidinyl, 1,4-piperidinyl, 2,3-piperidinyl, 2,4-piperidinyl, 2,5-piperidinyl, 2,6-piperidinyl, 3,4-piperidinyl, 3,5-piperidinyl, 3,6-piperidinyl, 1,2-pyrrolidinyl, 1,3-pyrrolidinyl, 2,3-pyrrolidinyl, 2,4-pyrrolidinyl, 2,5-pyrrolidinyl, 3,4-pyrrolidinyl, 2H-2,3-pyranyl, 2H-2,4-pyranyl, 2H-2,5-pyranyl, 4H-2,3-pyranyl, 4H-2,4-pyranyl, 4H-2,5-pyranyl, 2H-pyran-2-one-3,4-yl, 2H-pyran-2-one-4,5-yl, 4H-pyran-4-one-2, 3-yl, 2,3-tetrahydrofuranyl, 2,4-tetrahydrofuranyl, 2,5-tetrahydrofuranyl, 3,4-tetrahydrofuranyl, 2,3-tetrahydropyranyl, 2,4-tetrahydropyranyl, 2,5-tetrahydropyranyl, 2,6-tetrahydropyranyl, 3,4-tetrahydropyranyl, and 3,5-tetrahydropyranyl with the proviso that $(CH(R^{38}))_r$ is bonded to $E^0$ and $Q^b$ is bonded to lowest numbered substituent position of each $W^3$;

$Y^0$ can be $Q^b$—$Q^{sssr}$ wherein $Q^{sssr}$ is $(CH(R^{38}))_r$—$W^4$, r is an integer selected from 1 through 3, and $W^4$ is selected from the group consisting of 1,2-cyclobutyl, 1,2-cyclohexyl, 1,3-cyclohexyl, 1,4-cyclohexyl, 1,2-cyclopentyl, 1,3-cyclopentyl, 2,3-morpholinyl, 2,4-morpholinyl, 2,5-morpholinyl, 2,6-morpholinyl, 3,4-morpholinyl, 3,5-morpholinyl, 1,2-piperazinyl, 1,3-piperazinyl, 1,4-piperazinyl, 2,3-piperazinyl, 2,4-piperazinyl, 2,6-piperazinyl, 1,2-piperidinyl, 1,3-piperidinyl, 1,4-piperidinyl, 2,3-piperidinyl, 2,4-piperidinyl, 2,5-piperidinyl, 2,6-piperidinyl, 3,4-piperidinyl, 3,5-piperidinyl, 3,6-piperidinyl, 1,2-pyrrolidinyl, 1,3-pyrrolidinyl, 2,3-pyrrolidinyl, 2,4-pyrrolidinyl, 2,5-pyrrolidinyl, 3,4-pyrrolidinyl, 2H-2,3-pyranyl, 2H-2,4-pyranyl, 2H-2,5-pyranyl, 4H-2,3-pyranyl, 4H-2,4-pyranyl, 4H-2,5-pyranyl, 2H-pyran-2-one-3,4-yl, 2H-pyran-2-one-4,5-yl, 4H-pyran-4-one-2, 3-yl, 2,3-tetrahydrofuranyl, 2,4-tetrahydrofuranyl, 2,5-tetrahydrofuranyl, 3,4-tetrahydrofuranyl, 2,3- tetrahydropyranyl, 2,4-tetrahydropyranyl, 2,5-tetrahydropyranyl, 2,6-tetrahydropyranyl, 3,4-tetrahydropyranyl, and 3,5-tetrahydropyranyl with the provisos that $(CH(R^{38}))_r$ is bonded to $E^0$ and $Q^b$ is bonded to highest number substituent position of each $W^4$;

$Y^0$ can be $Q^b$—$Q^{ssss}$ wherein $Q^{ssss}$ is $(CH(R^{38}))_r$—$W^5$, r is an integer selected from 1 through 3, and $W^5$ is selected from the group consisting of 1,4-indenyl, 1,5-indenyl, 1,6-indenyl, 1,7-indenyl, 2,7-indenyl, 2,6-indenyl, 2,5-indenyl, 2,4-indenyl, 3,4-indenyl, 3,5-indenyl, 3,6-indenyl, 3,7-indenyl, 2,4-benzofuranyl, 2,5-benzofuranyl, 2,6-benzofuranyl, 2,7-benzofuranyl, 3,4-benzofuranyl, 3,5-benzofuranyl, 3,6-benzofuranyl, 3,7-benzofuranyl, 2,4-benzothiophenyl, 2,5-benzothiophenyl, 2,6-benzothiophenyl, 2,7-benzothiophenyl, 3,4-benzothiophenyl, 3,5-benzothiophenyl, 3,6-benzothiophenyl, 3,7-benzothiophenyl, 2,4-indolyl, 2,5-indolyl, 2,6-indolyl, 2,7-indolyl, 3,4-indolyl, 3,5-indolyl, 3,6-indolyl, 3,7-indoly 1,4-isoindolyl, 1,5-isoindolyl, 1,6-isoindolyl, 2,4-isoindoly, 2,5-isoindolyl, 2,6-isoindolyl, 2,7-isoindolyl, 1,3-isoindolyl, 3,4-indazolyl, 3,5-indazolyl, 3,6-indazolyl, 3,7-indazolyl, 2,4-benzoxazolyl, 2,5-benzoxazolyl, 2,6-benzoxazolyl, 2,7-benzoxazolyl, 3,4-benzisoxazolyl, 3,5-benzisoxazolyl, 3,6-benzisoxazolyl, 3,7-benzisoxazolyl, 1,4-naphthyl, 1,5-naphthyl, 1,6-naphthyl, 1,7-naphthyl, 1,8-naphthyl, 2,4-naphthyl, 2,5-naphthyl, 2,6-naphthyl, 2,7-naphthyl, 2,8-naphthyl, 2,4-quinolinyl, 2,5-quinolinyl, 2,6-quinolinyl, 2,7-quinolinyl, 2,8-quinolinyl, 3,4-quinolinyl, 3,5-quinolinyl, 3,6-quinolinyl, 3,7-quinolinyl, 3,8-quinolinyl, 4,5-quinolinyl, 4,6-quinolinyl, 4,7-quinolinyl, 4,8-quinolinyl, 1,4-isoquinolinyl, 1,5-isoquinolinyl, 1,6-isoquinolinyl, 1,7-isoquinolinyl, 1,8-isoquinolinyl, 3,4-isoquinolinyl, 3,5-isoquinolinyl, 3,6-isoquinolinyl, 3,7-isoquinolinyl, 3,8-isoquinolinyl, 4,5-isoquinolinyl, 4,6-isoquinolinyl, 4,7-isoquinolinyl, 4,8-isoquinolinyl, 3,4-cinnolinyl, 3,5-cinnolinyl, 3,6-cinnolinyl, 3,7-cinnolinyl, 3,8-cinnolinyl, 4,5-cinnolinyl, 4,6-cinnolinyl, 4,7-cinnolinyl, and 4,8-cinnolinyl with the proviso that $Q^b$ is bonded to lowest number substituent position of each $W^5$ and that $(CH(R^{38}))_r$ is bonded to $E^0$;

$Y^0$ can be $Q^b$—$Q^{ssssr}$ wherein $Q^{ssssr}$ is $(CH(R^{38}))_r$—$W^6$, r is an integer selected from 1 through 3, and $W^6$ is selected from the group consisting of 1,4-indenyl, 1,5-indenyl, 1,6-indenyl, 1,7-indenyl, 2,7-indenyl, 2,6-indenyl, 2,5-indenyl, 2,4-indenyl, 3,4-indenyl, 3,5-indenyl, 3,6-indenyl, 3,7-indenyl, 2,4-benzofuranyl, 2,5-benzofuranyl, 2,6-benzofuranyl, 2,7-benzofuranyl, 3,4-benzofuranyl, 3,5-benzofuranyl, 3,6-benzofuranyl, 3,7-benzofuranyl, 2,4-benzothiophenyl, 2,5-benzothiophenyl, 2,6-benzothiophenyl, 2,7-benzothiophenyl, 3,4-benzothiophenyl, 3,5-benzothiophenyl, 3,6-benzothiophenyl, 3,7-benzothiophenyl, 2,4-indolyl, 2,5-indolyl, 2,6-indolyl, 2,7-indolyl, 3,4-indolyl, 3,5-indolyl, 3,6-indolyl, 3,7-indolyl, 1,4-isoindolyl, 1,5-isoindolyl, 1,6-isoindolyl, 2,4-isoindolyl, 2,5-isoindolyl, 2,6-isoindolyl, 2,7-isoindolyl, 1,3-isoindolyl, 3,4-indazolyl, 3,5-indazolyl, 3,6-indazolyl, 3,7-indazolyl, 2,4-benzoxazolyl, 2,5-benzoxazolyl, 2,6-benzoxazolyl, 2,7-benzoxazolyl, 3,4-benzisoxazolyl, 3,5-benzisoxazolyl, 3,6-benzisoxazolyl, 3,7-benzisoxazolyl, 1,4-naphthyl, 1,5-naphthyl, 1,6-naphthyl, 1,7-naphthyl, 1,8-naphthyl, 2,4-naphthyl, 2,5-naphthyl, 2,6-naphthyl, 2,7-naphthyl, 2,8-naphthyl, 2,4-quinolinyl, 2,5-quinolinyl, 2,6-quinolinyl, 2,7-quinolinyl, 2,8-quinolinyl, 3,4-quinolinyl, 3,5-quinolinyl, 3,6-quinolinyl, 3,7-quinolinyl, 3,8-quinolinyl, 4,5-quinolinyl, 4,6-quinolinyl, 4,7-quinolinyl, 4,8-quinolinyl, 1,4-isoquinolinyl, 1,5-isoquinolinyl, 1,6-isoquinolinyl, 1,7-isoquinolinyl, 1,8-isoquinolinyl, 3,4-isoquinolinyl, 3,5-isoquinolinyl, 3,6-isoquinolinyl, 3,7-isoquinolinyl, 3,8-isoquinolinyl, 4,5-isoquinolinyl, 4,6-isoquinolinyl, 4,7-isoquinolinyl, 4,8-isoquinolinyl, 3,4-cinnolinyl, 3,5-cinnolinyl, 3,6-cinnolinyl, 3,7-cinnolinyl, 3,8-cinnolinyl, 4,5-cinnolinyl, 4,6-cinnolinyl, 4,7-cinnolinyl, and 4,8-cinnolinyl with the proviso that $Q^b$ is bonded to highest number substituent position of each $W^6$ and that $(CH(R^{38}))_r$ is bonded to $E^0$.

In another embodiment of compounds of Formula I or a pharmaceutically acceptable salt thereof, J is selected from the group consisting of hydrido, halo, hydroxy, hydroxyalkyl, amino, aminoalkyl, cyano, haloalkyl, carboxy, carboxyalkyl, amidocarbonyl, acyl, O—$R^6$, NH—$R^6$, and S—$R^6$, wherein $R^6$ is selected from the group consisting of alkyl and haloalkyl;

B is formula (V):

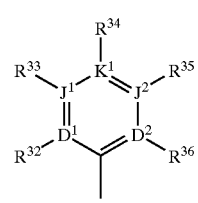

(V)

wherein $D^1$, $D^2$, $J^1$, $J^2$ and $K^1$ are independently selected from the group consisting of C, N, O, S and a covalent bond with the provisos that no more than one can be a covalent bond, no more than one of $D^1$, $D^2$, $J^1$, $J^2$ and $K^1$ can be O, no more than one of $D^1$, $D^2$, $J^1$, $J^2$ and $K^1$ can be S, one of $D^1$, $D^2$, $J^1$, $J^2$ and $K^1$ must be a covalent bond when two of $D^1$, $D^2$, $J^1$, $J^2$ and $K^1$ are O and S, and no more than four of $D^1$, $D^2$, $J^1$, $J^2$ and $K^1$ can be N;

$R^{32}$, $R^{33}$, $R^{34}$, $R^{35}$, and $R^{36}$ can independently be $Q^b$;

$R^9$, $R^{10}$, $R^{11}$, $R^{12}$, $R^{13}$, $R^{16}$, $R^{17}$, $R^{18}$, $R^{19}$, $R^{32}$, $R^{33}$, $R^{34}$, $R^{35}$, and $R^{36}$ are independently selected from the group consisting of hydrido, amidino, guanidino, dialkylsulfonium, trialkylphosphonium, dialkylsulfoniumalkyl, carboxy, heteroaralkylthio, heteroaralkoxy, cycloalkylamino, acylalkyl, acylalkoxy, aryloylalkoxy, heterocyclyloxy, aralkylaryl, aralkyl, aralkenyl, aralkynyl, heterocyclyl, perhaloaralkyl, aralkylsulfonyl, aralkylsulfonylalkyl, aralkylsulfinyl, aralkylsulfinylalkyl, halocycloalkyl, halocycloalkenyl, cycloalkylsulfinyl, cycloalkylsulfinylalkyl, cycloalkylsulfonyl, cycloalkylsulfonylalkyl, heteroarylamino, N-heteroarylamino-N-alkylamino, heteroarylaminoalkyl, haloalkylthio, alkanoyloxy, alkoxy, alkoxyalkyl, haloalkoxyalkyl, heteroaralkoxy, cycloalkoxy, cycloalkenyloxy, cycloalkoxyalkyl, cycloalkylalkoxy, cycloalkenyloxyalkyl, cycloalkylenedioxy, halocycloalkoxy, halocycloalkoxyalkyl, halocycloalkenyloxy, halocycloalkenyloxyalkyl, hydroxy, amino, alkoxyamino, thio, nitro, lower alkylamino, alkylthio, alkylthioalkyl, arylamino, aralkylamino, arylthio, arylthioalkyl, heteroaralkoxyalkyl, alkylsulfinyl, alkylsulfinylalkyl, arylsulfinylalkyl, arylsulfonylalkyl, heteroarylsulfinylalkyl, heteroarylsulfonylalkyl, alkylsulfonyl, alkylsulfonylalkyl, haloalkylsulfinylalkyl, haloalkylsulfonylalkyl, alkylsulfonamido, alkylaminosulfonyl, amidosulfonyl, monoalkyl amidosulfonyl, dialkyl amidosulfonyl, monoarylamidosulfonyl, arylsulfonamido, diarylamidosulfonyl, monoalkyl monoaryl amidosulfonyl, arylsulfinyl, arylsulfonyl, heteroarylthio, heteroarylsulfinyl, heteroarylsulfonyl, heterocyclylsulfonyl, heterocyclylthio, alkanoyl, alkenoyl, aroyl, heteroaroyl, aralkanoyl, heteroaralkanoyl, haloalkanoyl, alkyl, alkenyl, alkynyl, alkenyloxy, alkenyloxyalky, alkylenedioxy, haloalkylenedioxy, cycloalkyl, cycloalkylalkanoyl, cycloalkenyl, lower cycloalkylalkyl, lower cycloalkenylalkyl, halo, haloalkyl, haloalkenyl, haloalkoxy, hydroxyhaloalkyl, hydroxyaralkyl, hydroxyalkyl, aminoalkyl, hydoxyheteroaralkyl, haloalkoxyalkyl, aryl, aralkyl, aryloxy, aralkoxy, aryloxyalkyl, saturated heterocyclyl, partially saturated heterocyclyl, heteroaryl, heteroaryloxy, heteroaryloxyalkyl, arylalkyl, heteroarylalkyl, arylalkenyl, heteroarylalkenyl, carboxyalkyl, carboalkoxy, alkoxycarboxamido, alkylamidocarbonylamido, arylamidocarbonylamido, carboalkoxyalkyl, carboalkoxyalkenyl, carboaralkoxy, carboxamido, carboxamidoalkyl, cyano, carbohaloalkoxy, phosphono, phosphonoalkyl, diaralkoxyphosphono, and diaralkoxyphosphonoalkyl;

B can be selected from the group consisting of C3–C8 alkyl, C3–C8 alkenyl, C3–C8 alkynyl, C3–C8 haloalkyl, and C3–C8 haloalkenyl wherein each member of group B may be optionally substituted at any carbon up to and including 6 atoms from the point of attachment of B to A with one or more of the group consisting of $R_{32}$, $R_{33}$, $R_{34}$, $R_{35}$, and $R_{36}$;

B can be selected from the group consisting of C3–C10 cycloalkyl, C5–C10 cycloalkenyl, C4–C9 saturated heterocyclyl, and C4–C9 partially saturated heterocyclyl, wherein each ring carbon may be optionally substituted with $R_{33}$, a ring carbon other than the ring carbon at the point of attachment of B to A may be optionally substituted with oxo provided that no more than one ring carbon is substituted by oxo at the same time, ring carbon and nitrogen atoms adjacent to the carbon atom at the point of attachment may be optionally substituted with $R_9$ or $R_{13}$, a ring carbon or nitrogen atom adjacent to the $R_9$ position and two atoms from the point of attachment may be substituted with $R_{10}$, a ring carbon or nitrogen atom adjacent to the $R_{13}$ position and two atoms from the point of attachment may be substituted with $R_{12}$, a ring carbon or nitrogen atom three atoms from the point of attachment and adjacent to the $R_{10}$ position may be substituted with $R_{11}$, a ring carbon or nitrogen atom three atoms from the point of attachment and adjacent to the $R_{12}$ position may be substituted with $R_{33}$, and a ring carbon or nitrogen atom four atoms from the point of attachment and adjacent to the $R_{11}$ and $R_{33}$ positions may be substituted with $R_{34}$;

A is selected from the group consisting of single covalent bond, $(W^7)_{rr}$—$(CH(R^{15}))_{pa}$ and $(CH(R^{15}))_{pa}$—$(W^7)_{rr}$ wherein rr is an integer selected from 0 through 1, pa is an integer selected from 0 through 6, and $W^7$ is selected from the group consisting of O, S, C(O), C(S), C(O)S, C(S)O, C(O)N($R^7$), C(S)N($R^7$), ($R^7$)NC(O), ($R^7$)NC(S), S(O), S(O)$_2$, S(O)$_2$N($R^7$), ($R^7$)NS(O)$_2$, C(N$R^7$)N($R^7$), ($R^7$)NC(N$R^7$), and N($R^7$) with the proviso that no more than one of the group consisting of rr and pa can be 0 at the same time;

$R^7$ and $R^8$ are independently selected from the group consisting of hydrido, hydroxy, alkyl, and alkoxyalkyl;

$R^{14}$, $R^{15}$, $R^{37}$, and $R^{38}$ are independently selected from the group consisting of hydrido, hydroxy, halo, alkyl, alkoxyalkyl, haloalkyl, haloalkoxy, and haloalkoxyalkyl;

Ψ is selected from the group consisting of N$R^5$, O, C(O), C(S), S, S(O), S(O)$_2$, and CR$^{39}$R$^{40}$ with the provisos that Ψ is selected from other than N$R^5$, O, S, S(O), and S(O)$_2$ unless any two of $X^0$, $R^2$, $R^1$, and J are other than hydrido, or that Ψ is selected from other than O, unless A is selected from other than methylene when B is phenyl, that Ψ is selected from other than C(O), unless A is selected from other than methyleneoxy when B is phenyl, or that Ψ is selected from other than NH unless A is selected from other than a single covalent bond when B is acyl, or that Ψ is selected from other than NH unless A is selected from other than S(O) or S(O)$_2$ when B is phenyl;

$R^5$ is selected from the group consisting of hydrido, alkyl, and alkoxy;

$R^{39}$ and $R^{40}$ are independently selected from the group consisting of hydrido, hydroxy, halo, hydroxyalkyl, alkyl, alkoxyalkyl, haloalkyl, haloalkoxy, and haloalkoxyalkyl;

$X^0$, $R^2$ and $R^1$ are independently selected from the group consisting of $Z^0$—Q, hydrido, alkyl, alkenyl, and halo;

$X^0$, $R^2$ and $R^1$ can be independently selected from the group consisting of amidino, guanidino, dialkylsulfonium, trialkylphosphonium, dialkylsulfoniumalkyl, heteroarylamino, amino, nitro, alkylamino, arylamino, aralkylamino, alkanoyl, alkenoyl, aroyl, heteroaroyl, aralkanoyl, heteroaralkanoyl, haloalkanoyl, hydroxyhaloalkyl, cyano, and phosphono; $Z^0$ is selected from the group consisting of covalent single bond, $(CR^{41}R^{42})_q$ wherein q is an integer selected from 1 through 2, $(CH(R^{41}))_g$—$W^0$—$(CH(R^{42}))_p$ wherein g and p are integers independently selected from 0 through 2 and $W^0$ is selected from the group consisting of O, S, C(O), C(S), C(O)O, C(S)O, C(O)S, C(S)S, C(O)N($R^{41}$), ($R^{41}$)NC(O), C(S)N($R^{41}$), ($R^{41}$)NC(S), OC(O)N($R^{41}$), ($R^{41}$)NC(O)O, SC(S)N($R^{41}$), ($R^{41}$)NC(S)S, SC(O)N($R^{41}$), ($R^{41}$)NC(O)S, OC(S)N($R^{41}$), ($R^{41}$)NC(S)O, N($R^{42}$)C(O)N($R^{41}$), ($R^{41}$)NC(O)N($R^{42}$), N($R^{42}$)C(S)N($R^{41}$), ($R^{41}$)NC(S)N($R^{42}$), S(O), S(O)$_2$, S(O)$_2$N($R^{41}$), N($R^{41}$)S(O)$_2$, N($R^{41}$), ON($R^{41}$), and $(CH(R^{41}))_e$—$W^2$—$(CH(R^{42}))_h$ wherein e and h are integers independently selected from 0 through 2 and $W^2$ is selected from the group consisting of CR$^{41}$=CR$^{42}$, CR$^{41}$R$^{42}$=C; vinylidene), and ethynylidene (C≡C; 1,2-ethynyl), with the provisos that $R^{41}$ and $R^{42}$ are selected from other than halo and cyano when directly bonded to N and $Z^0$ is directly bonded to the benzene ring, that $W^0$ is selected, wherein g is 0, from other than NHS(O)$_2$CH$_2$aryl or N($R^{41}$) unless $R^{41}$ is selected from other than hydrido, alkyl, or aralkylsulfonyl, and $Z^0$ is selected from other than OC(O), C(O)N(H), and (H)NC (O), unless Q is selected from other than phenyl, 2-furyl, 2-thienyl, 4-thiazolyl, 2-pyridyl, 2-naphthyl, 1,2-dihydrobenzofuran-5-yl, 1,2-dihydrobenzofuran-6- yl, or 1,2benzisoxazol-6-yl , or $X^o$ is selected from other than hydrido, halo, or methyl, or $R^1$ is selected from other than hydrido, fluoro, hydroxy, acetoxy, propanoyloxy, 2-carboxyacetoxy, 2,3 or 4-carboxypropanoyloxy, benzoyloxy, methyl, or methoxy;

$R^{41}$ and $R^{42}$ are independently selected from the group consisting of hydrido, hydroxy, halo, cyano, aryloxy, hydroxyalkyl, acyl, aroyl, heteroaroyl, heteroaryloxyalkyl, alkoxy, alkyl, aryl, aralkyl, aryloxyalkyl, aralkoxyalkylalkoxy, alkoxyalkyl, heteroaryloxyalkyl, cycloalkyl, cycloalkylalkyl, cycloalkylalkenyl, cycloalkenyl, cycloalkenylalkyl, haloalkyl, haloalkenyl, halocycloalkyl, halocycloalkenyl, haloalkoxy, haloalkoxyalkyl, haloalkenyloxyalkyl, halocycloalkoxy, halocycloalkoxyalkyl, halocycloalkenyloxyalkyl, saturated heterocyclyl, partially saturated heterocyclyl, heteroaryl, and heteroaralkyl;

Q is formula (II):

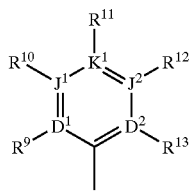

(II)

wherein $D^1$, $D^2$, $J^1$, $J^2$ and $K^1$ are independently selected from the group consisting of C, N, O, S and a covalent bond with the provisos that no more than one can be a covalent bond, no more than one of $D^1$, $D^2$, $J^1$, $J^2$ and $K^1$ can be O, no more than one of $D^1$, $D^2$, $J^1$, $J^2$ and $K^1$ can be S, one of $D^1$, $D^2$, $J^1$, $J^2$ and $K^1$ must be a covalent bond when two of $D^1$, $D^2$, $J^1$, $J^2$ and $K^1$ are O and S, and no more than four of $D^1$, $D^2$, $J^1$, $J^2$ and $K^1$ can be N with the proviso that $R^9$, $R^{10}$, $R^{11}$, $R^{12}$, and $R^{13}$ are each independently selected to maintain the tetravalent nature of carbon, trivalent nature of nitrogen, the divalent nature of sulfur, and the divalent nature of oxygen;

Q can be selected from the group consisting of alkyl, alkoxy, alkylamino, alkylthio, haloalkylthio, saturated heterocyclyl, alkyl, partially saturated heterocyclyl, acyl, aroyl, heteroaroyl, cycloalkyl, cycloalkylalkyl, cycloalkenyl, cycloalkenylalkyl, cycloalkylalkenyl, haloalkyl, haloalkoxy, haloalkenyl, halocycloalkyl, halocycloalkenyl, haloalkoxyalkyl, haloalkenyloxyalkyl, halocycloalkoxyalkyl, and halocycloalkenyloxyalkyl;

K is $(CR^{4a}R^{4b})_n$ wherein n is an integer 1;

$R^{4a}$ and $R^{4b}$ are independently selected from the group consisting of halo, hydrido, hydroxy, hydroxyalkyl, alkyl, alkoxyalkyl, and haloalkyl;

$E^0$ is $E^1$, when K is $(CR^{4a}R^{4b})_n$, wherein $E^1$ is selected from the group consisting of a covalent single bond, O, S, C(O), C(S), C(O)O, C(S)O, C(O)S, C(S)S, C(O)N($R^7$), ($R^7$)NC(O), C(S)N($R^7$), ($R^7$)NC(S), OC(O)N($R^7$), ($R^7$)NC(O)O, SC(S)N($R^7$), ($R^7$)NC(S)S, SC(O)N($R^7$), ($R^7$)NC(O)S, OC(S)N($R^7$), ($R^7$)NC(S)O, N($R^8$)C(O)N($R^7$), ($R^7$)NC(O)N($R^8$), N($R^8$)C(S)N($R^7$), ($R^7$)NC(S)N($R^8$), S(O), S(O)$_2$, S(O)$_2$N($R^7$), N($R^7$)S(O)$_2$, S(O)$_2$N($R^7$)C(O), C(O)N($R^7$)S(O)$_2$, N($R^7$), ON($R^7$), $CR^{4a}$=$CR^{4b}$, ethynylidene (C≡C; 1,2-ethynyl), and C=$CR^{4a}R^{4b}$;

K can be $(CH(R^{14}))_j$—T wherein j is selected from a integer from 0 through 1 and T is selected from the group consisting of single covalent bond, O, S, and N($R^7$) with the proviso that $(CH(R^{14}))_j$ is bonded to the phenyl ring;

$E^0$ is $E^2$, when K is $(CH(R^{14}))_j$—T, wherein $E^2$ is selected from the group consisting of a covalent single bond, C(O), C(S), C(O)O, C(S)O, C(O)S, C(S)S, C(O)N($R^7$), ($R^7$)NC(O), C(S)N($R^7$), ($R^7$)NC(S), ($R^7$)NC(O)O, ($R^7$)NC(S)S, ($R^7$)NC(O)S, ($R^7$)NC(S)O, N($R^8$)C(O)N($R^7$), ($R^7$)NC(O)N($R^8$), N($R^8$)C(S)N($R^7$), ($R^7$)NC(S)N($R^8$), S(O), S(O)$_2$, S(O)$_2$N($R^7$), N($R^7$)S(O)$_2$, S(O)$_2$N(H)C(O), C(O)N(H)S(O)$_2$, and N($R^7$);

K can be G—$(CH(R^{15}))_k$ wherein k is selected from an integer from 1 and G is selected from the group consisting of O, S, and N($R^7$);

$E^0$ is $E^3$ when K is G—$(CH(R^{15}))_k$ wherein $E^3$ is selected from the group consisting of a covalent single bond, O, S, C(O), C(S), C(O)O, C(S)O, C(O)S, C(S)S, C(O)N($R^7$), ($R^7$)NC(O), C(S)N($R^7$), ($R^7$)NC(S), OC(O)N($R^7$), ($R^7$)NC(O)O, SC(S)N($R^7$), ($R^7$)NC(S)S, SC(O)N($R^7$), ($R^7$)NC(O)S, OC(S)N($R^7$), ($R^7$)NC(S)O, N($R^8$)C(O)N($R^7$), ($R^7$)NC(O)N($R^8$), N($R^8$)C(S)N($R^7$), ($R^7$)NC(S)N($R^8$), S(O), S(O)$_2$, S(O)$_2$N($R^7$), N($R^7$)S(O)$_2$, N($R^7$), ON($R^7$), $CR^{4a}$=$CR^{4b}$, ethynylidene (C≡C; 1,2-ethynyl), and C=$CR^{4a}R^{4b}$;

$Y^o$ is formula (IV):

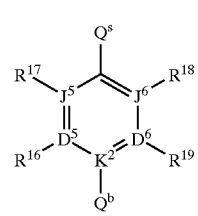

(IV)

wherein $D^5$, $D^6$, $J^5$, and $J^6$ are independently selected from the group consisting of C, N, O, S and a covalent bond with the provisos that no more than one can be a covalent bond, $K^2$ is independently selected from the group consisting of C, and N$^+$, no more than one of $D^5$, $D^6$, $J^5$, and $J^6$ can be O, no more than one of $D^5$, $D^6$, $J^5$, and $J^6$ can be S, one of $D^5$, $D^6$, $J^5$, and $J^6$ must be a covalent bond when two of $D^5$, $D^6$, $J^5$, and $J^6$ are O and S, no more than three of $D^5$, $D^6$, $J^5$, and $J^6$ can be N when $K^2$ is N$^+$, and no more than four of $D^5$, $D^6$, $J^5$, and $J^6$ can be N when $K^2$ is carbon with the provisos that $R^{16}$, $R^{17}$, $R^{18}$, and $R^{19}$ are each independently selected to maintain the tetravalent nature of carbon, trivalent nature of nitrogen, the divalent nature of sulfur, and the divalent nature of oxygen;

$Q^b$ is selected from the group consisting of $NR^{20}R^{21}$, $^+NR^{20}R^{21}R^{22}$, oxy, alkyl, alkylaminoalkyl, aminoalkyl, dialkylsulfoniumalkyl, and acylamino wherein $R^{20}$, $R^{21}$, and $R^{22}$ are independently selected from the group consisting of hydrido, alkyl, hydroxy, alkoxy, alkylamino, dialkylamino, aminoalkyl, and hydroxyalkyl with the provisos that no more than one of $R^{20}$, $R^{21}$, and $R^{22}$ can be hydroxy, alkoxy, alkylamino, amino, and dialkylamino and that $R^{20}$, $R^{21}$, and $R^{22}$ must be other than be hydroxy, alkoxy, alkylamino, amino, and dialkylamino when $K^2$ is N$^+$;

$Q^b$ can be selected from the group consisting of N($R^{26}$)SO$_2$N($R^{23}$)($R^{24}$), N($R^{26}$)C(O)O$R^5$, N($R^{26}$)C(O)S$R^5$, $N(R^{26})C(S)OR^5$ and $N(R^{26})C(S)SR^5$ with the proviso that no more than one of $R^{23}$, $R^{24}$, and $R^{26}$ can be hydroxy, alkoxy, alkylamino, amino, or dialkylamino when two of the group consisting of $R^{23}$, $R^{24}$, and $R^{26}$ are bonded to the same atom;

$Q^b$ can be selected from the group consisting of dialkylsulfonium, trialkylphosphonium, $C(NR^{25})NR^{23}R^{24}$, $N(R^{26})C(NR^{25})N(R^{23})(R^{24})$, $N(R^{26})C(O)N(R^{23})(R^{24})$, $N(R^{26})C(S)N(R^{23})(R^{24})$, $C(NR^{25})OR^5$, $C(O)N(R^{26})C(NR^{25})N(R^{23})(R^{24})$, $C(S)N(R^{26})C(NR^{25})N(R^{23})(R^{24})$, $N(R^{26})N(R^{26})C(NR^{25})N(R^{23})(R^{24})$, $N(R^{26})N(R^{26})SO_2N(R^{23})(R^{24})$, $C(NR^{25})SR^5$, $C(O)NR^{23}R^{24}$, and $C(O)NR^{23}R^{24}$ with the provisos that no more than one of $R^{23}$, $R^{24}$, and $R^{26}$ can be hydroxy, alkoxy, alkylamino, amino, or dialkylamino when two of the group consisting of $R^{23}$, $R^{24}$, and $R^{26}$ are bonded to the same atom and that said $Q^b$ group is bonded directly to a carbon atom;

$R^{23}$, $R^{24}$, $R^{25}$, and $R^{26}$ are independently selected from the group consisting of hydrido, alkyl, hydroxy, alkoxy, alkylamino, dialkylamino, aminoalkyl, and hydroxyalkyl;

$Q^s$ is selected from the group consisting of a single covalent bond, $(CR^{37}R^{38})_b$—$(W^0)_{az}$ wherein az is an integer selected from 0 through 1, b is an integer selected from 1 through 2, and $W^0$ is selected from the group consisting of O, S, C(O), C(S), C(O)O, C(S)O, C(O)S, C(S)S, $C(O)N(R^{14})$, $(R^{14})NC(O)$, $C(S)N(R^{14})$, $(R^{14})NC(S)$, $OC(O)N(R^{14})$, $SC(S)N(R^{14})$, $SC(O)N(R^{14})$, $OC(S)N(R^{14})$, $N(R^{15})C(O)N(R^{14})$, $(R^{14})NC(O)N(R^{15})$, $N(R^{15})C(S)N(R^{14})$, $(R^{14})NC(S)N(R^{15})$, S(O), $S(O)_2$, $S(O)_2N(R^{14})$, $N(R^{14})S(O)_2$, $N(R^{14})$, $ON(R^{14})$, and $(CH(R^{14}))_c$—$W^1$—$(CH(R^{15}))_d$ wherein c and d are integers independently selected from 1 through 2, and $W^1$ is selected from the group consisting of O, S, C(O), C(S), C(O)O, C(S)O, C(O)S, C(S)S, $C(O)N(R^{14})$, $(R^{14})NC(O)$, $C(S)N(R^{14})$, $(R^{14})NC(S)$, $OC(O)N(R^{14})$, $(R^{14})NC(O)O$, $SC(S)N(R^{14})$, $(R^{14})NC(S)S$, $SC(O)N(R^{14})$, $(R^{14})NC(O)S$, $OC(S)N(R^{14})$, $(R^{14})NC(S)O$, $N(R^{15})C(O)N(R^{14})$, $(R^{14})NC(O)N(R^{15})$, $N(R^{15})C(S)N(R^{14})$, $(R^{14})NC(S)N(R^{15})$, S(O), $S(O)_2$, $S(O)_2N(R^{14})$, $N(R^{14})S(O)_2$, $N(R^{14})$, $ON(R^{14})$, and $(CH(R^{14}))_e$—$W^2$—$(CH(R^{15}))_h$ wherein e and h are integers independently selected from 0 through 2 and $W^2$ is selected from the group consisting of $CR^{4a}$=$CR^{4b}$, ethynylidene (C≡C; 1,2-ethynyl), and C=$CR^{4a}R^{4b}$ with the provisos that $R^{14}$ and $R^{15}$ are selected from other than halo and cyano when directly bonded to N and that $(CR^{37}R^{38})_b$, $(CH(R^{14}))_c$, $(CH(R^{14}))_e$ and are bonded to $E^0$;

$Y^0$ can be $Q^b$—$Q^{ss}$ wherein $Q^{ss}$ is selected from the group consisting of $(CR^{37}R^{38})_f$ wherein f is an integer selected from 1 through 4, $(CH(R^{14}))_c$—$W^1$—$(CH(R^{15}))_d$ wherein c and d are integers independently selected from 1 through 2, and $W^1$ is selected from the group consisting of $W^1$ is selected from the group consisting of O, S, C(O), C(S), C(O)O, C(S)O, C(O)S, C(S)S, $C(O)N(R^{14})$, $(R^{14})NC(O)$, $C(S)N(R^{14})$, $(R^{14})NC(S)$, $OC(O)N(R^{14})$, $(R^{14})NC(O)O$, $SC(S)N(R^{14})$, $(R^{14})NC(S)S$, $SC(O)N(R^{14})$, $(R^{14})NC(O)S$, $OC(S)N(R^{14})$, $N(R^{15})C(O)N(R^{14})$, $(R^{14})NC(O)N(R^{15})$, $N(R^{15})C(S)N(R^{14})$, $(R^{14})NC(S)N(R^{15})$, S(O), $S(O)_2$, $S(O)_2N(R^{14})$, $N(R^{14})S(O)_2$, $N(R^{14})$, $ON(R^{14})$, and $(CH(R^{14}))_e$—$W^2$—$(CH(R^{15}))_h$ wherein e and h are integers independently selected from 0 through 2 and $W^2$ is selected from the group consisting of $CR^{4a}$=$CR^{4b}$, ethynylidene (C≡C, 1,2-ethynyl), and C=$CR^{4a}R^{4b}$ with the provisos that $R^{14}$ and $R^{15}$ are selected from other than halo when directly bonded to N and that $(CR^{37}R^{38})_f$, $(CH(R^{15}))_c$, and $(CH(R^{15}))_e$ are bonded to $E^0$;

$Y^0$ can be $Q^b$—$Q^{sss}$ wherein $Q^{sss}$ is $(CH(R^{38}))_r$—$W^3$, r is an integer selected from 1 through 2, and $W^3$ is selected from the group consisting of 1,1-cyclopropyl, 1,2-cyclopropyl, 1,1-cyclobutyl, 1,2-cyclobutyl, 1,2-cyclohexyl, 1,3-cyclohexyl, 1,4-cyclohexyl, 1,2-cyclopentyl, 1,3-cyclopentyl, 2,3-morpholinyl, 2,4-morpholinyl, 2,5-morpholinyl, 2,6-morpholinyl, 3,4-morpholinyl, 3,5-morpholinyl, 1,2-piperazinyl, 1,3-piperazinyl, 1,4-piperazinyl, 2,3-piperazinyl, 2,5-piperazinyl, 2,6-piperazinyl, 1,2-piperidinyl, 1,3-piperidinyl, 1,4-piperidinyl, 2,3-piperidinyl, 2,4-piperidinyl, 2,5-piperidinyl, 2,6-piperidinyl, 3,4-piperidinyl, 3,5-piperidinyl, 3,6-piperidinyl, 1,2-pyrrolidinyl, 1,3-pyrrolidinyl, 2,3-pyrrolidinyl, 2,4-pyrrolidinyl, 2,5-pyrrolidinyl, 3,4-pyrrolidinyl, 2H-2,3-pyranyl, 2H-2,4-pyranyl, 2H-2,5-pyranyl, 4H-2,3-pyranyl, 4H-2,4-pyranyl, 4H-2,5-pyranyl, 2H-pyran-2-one-3,4-yl, 2H-pyran-2-one-4,5-yl, 4H-pyran-4-one-2,3-yl, 2,3-tetrahydrofuranyl, 2,4-tetrahydrofuranyl, 2,5-tetrahydrofuranyl, 3,4-tetrahydrofuranyl, 2,3-tetrahydropyranyl, 2,4-tetrahydropyranyl, 2,5-tetrahydropyranyl, 2,6-tetrahydropyranyl, 3,4-tetrahydropyranyl, and 3,5-tetrahydropyranyl with the proviso that $(CH(R^{38}))_r$ is bonded to $E^0$ and $Q^b$ is bonded to lowest numbered substituent position of each $W^3$;

$Y^0$ can be $Q^b$—$Q^{sssr}$ wherein $Q^{sssr}$ is $(CH(R^{38}))_r$—$W^4$, r is an integer selected from 1 through 2, and $W^4$ is selected from the group consisting of 1,2-cyclobutyl, 1,2-cyclohexyl, 1,3-cyclohexyl, 1,4-cyclohexyl, 1,2-cyclopentyl, 1,3-cyclopentyl, 2,3-morpholinyl, 2,4-morpholinyl, 2,5-morpholinyl, 2,6-morpholinyl, 3,4-morpholinyl, 3,5-morpholinyl, 1,2-piperazinyl, 1,3-piperazinyl, 1,4-piperazinyl, 2,3-piperazinyl, 2,5-piperazinyl, 2,6-piperazinyl, 1,2-piperidinyl, 1,3-piperidinyl, 1,4-piperidinyl, 2,3-piperidinyl, 2,4-piperidinyl, 2,5-piperidinyl, 2,6-piperidinyl, 3,4-piperidinyl, 3,5-piperidinyl, 3,6-piperidinyl, 1,2-pyrrolidinyl, 1,3-pyrrolidinyl, 2,3-pyrrolidinyl, 2,4-pyrrolidinyl, 2,5-pyrrolidinyl, 3,4-pyrrolidinyl, 2H-2,3-pyranyl, 2H-2,4-pyranyl, 2H-2,5-pyranyl, 4H-2,3-pyranyl, 4H-2,4-pyranyl, 4H-2,5-pyranyl, 2H-pyran-2-one-3,4-yl, 2H-pyran-2-one-4,5-yl, 4H-pyran-4-one-2,3-yl, 2,3-tetrahydrofuranyl, 2,4-tetrahydrofuranyl, 2,5-tetrahydrofuranyl, 3,4-tetrahydrofuranyl, 2,3-tetrahydropyranyl, 2,4-tetrahydropyranyl, 2,5-tetrahydropyranyl, 2,6-tetrahydropyranyl, 3,4-tetrahydropyranyl, and 3,5-tetrahydropyranyl with the provisos that $(CH(R^{38}))_r$ is bonded to $E^0$ and $Q^b$ is bonded to highest number substituent position of each $W^4$;

$Y^0$ can be $Q^b$—$Q^{ssss}$ wherein $Q^{ssss}$ is $(CH(R^{38}))_r$—$W^5$, r is an integer selected from 1 through 3, and $W^5$ is selected from the group consisting of 1,4-indenyl, 1,5-indenyl, 1,6-indenyl, 1,7-indenyl, 2,7-indenyl, 2,6-indenyl, 2,5-indenyl, 2,4-indenyl, 3,4-indenyl, 3,5-indenyl, 3,6-indenyl, 3,7-indenyl, 2,4-benzofuranyl, 2,5-benzofuranyl, 2,6-benzofuranyl, 2,7-benzofuranyl, 3,4-benzofuranyl, 3,5-benzofuranyl, 3,6-benzofuranyl, 3,7-benzofuranyl, 2,4-benzothiophenyl, 2,5-benzothiophenyl, 2,6-benzothiophenyl, 2,7-benzothiophenyl, 3,4-benzothiophenyl, 3,5-benzothiophenyl, 3,6-benzothiophenyl, 3,7- benzothiophenyl, 2,4-indolyl, 2,5-indolyl, 2,6-indolyl, 2,7-indolyl, 3,4-indolyl, 3,5-indolyl, 3,6-indolyl, 3,7-indoly, 1,4-isoindolyl, 1,5-isoindolyl, 1,6-isoindolyl, 2,4-isoindoly, 2,5-isoindolyl, 2,6-isoindolyl, 2,7-isoindolyl, 1,3-isoindolyl, 3,4-indazolyl, 3,5-indazolyl, 3,6-indazolyl, 3,7-indazolyl, 2,4-benzisoxazolyl, 2,5-benzisoxazolyl, 2,6-benzisoxazolyl, 2,7-benzisoxazolyl, 3,4-benzisoxazolyl, 3,5-benzisoxazolyl, 3,6-benzisoxazolyl, 3,7-benzisoxazolyl, 1,4-naphthyl, 1,5-naphthyl, 1,6-naphthyl, 1,7-naphthyl, 1,8-naphthyl, 2,4-naphthyl, 2,5-naphthyl, 2,6-naphthyl, 2,7-naphthyl, 2,8-naphthyl, 2,4-quinolinyl, 2,5-quinolinyl, 2,6-quinolinyl, 2,7-quinolinyl, 2,8-quinolinyl, 3,4-quinolinyl, 3,5-quinolinyl, 3,6-quinolinyl, 3,7-quinolinyl, 3,8-quinolinyl, 4,5-quinolinyl, 4,6-quinolinyl, 4,7-quinolinyl, 4,8-quinolinyl, 1,4-isoquinolinyl, 1,5-isoquinolinyl, 1,6-isoquinolinyl, 1,7-isoquinolinyl, 1,8-isoquinolinyl, 3,4-isoquinolinyl, 3,5-isoquinolinyl, 3,6-isoquinolinyl, 3,7-isoquinolinyl, 3,8-isoquinolinyl, 4,5-isoquinolinyl, 4,6-isoquinolinyl, 4,7-isoquinolinyl, 4,8-isoquinolinyl, 3,4-cinnolinyl, 3,5-cinnolinyl, 3,6-cinnolinyl, 3,7-cinnolinyl, 3,8-cinnolinyl, 4,5-cinnolinyl, 4,6-cinnolinyl, 4,7-cinnolinyl, and 4,8-cinnolinyl with the proviso that $Q^b$ is bonded to lowest number substituent position of each $W^5$ and that $(CH(R^{38}))_r$ is bonded to $E^0$;

$Y^0$ can be $Q^b$—$Q^{ssssr}$ wherein $Q^{ssssr}$ is $(CH(R^{38}))_r$—$W^6$, r is an integer selected from 1 through 3, and $W^6$ is selected from the group consisting of 1,4-indenyl, 1,5-indenyl, 1,6-indenyl, 1,7-indenyl, 2,7-indenyl, 2,6-indenyl, 2,5-indenyl, 2,4-indenyl, 3,4-indenyl, 3,5-indenyl, 3,6-indenyl, 3,7-indenyl, 2,4-benzofuranyl, 2,5-benzofuranyl, 2,6-benzofuranyl, 2,7-benzofuranyl, 3,4-benzofuranyl, 3,5-benzofuranyl, 3,6-benzofuranyl, 3,7-benzofuranyl, 2,4-benzothiophenyl, 2,5-benzothiophenyl, 2,6-benzothiophenyl, 2,7-benzothiophenyl, 3,4-benzothiophenyl, 3,5-benzothiophenyl, 3,6-benzothiophenyl, 3,7-benzothiophenyl, 2,4-indolyl, 2,5-indolyl, 2,6-indolyl, 2,7-indolyl, 3,4-indolyl, 3,5-indolyl, 3,6-indolyl, 3,7-indolyl, 1,4-isoindolyl, 1,5-isoindolyl, 1,6-isoindolyl, 2,4-isoindolyl, 2,5-isoindolyl, 2,6-isoindolyl, 2,7-isoindolyl, 1,3-isoindolyl, 3,4-indazolyl, 3,5-indazolyl, 3,6-indazolyl, 3,7-indazolyl, 2,4-benzoxazolyl, 2,5-benzoxazolyl, 2,6-benzoxazolyl, 2,7-benzoxazolyl, 3,4-benzisoxazolyl, 3,5-benzisoxazolyl, 3,6-benzisoxazolyl, 3,7-benzisoxazolyl, 1,4-naphthyl, 1,5-naphthyl, 1,6-naphthyl, 1,7-naphthyl, 1,8-naphthyl, 2,4-naphthyl, 2,5-naphthyl, 2,6-naphthyl, 2,7-naphthyl, 2,8-naphthyl, 2,4-quinolinyl, 2,5-quinolinyl, 2,6-quinolinyl, 2,7-quinolinyl, 2,8-quinolinyl, 3,4-quinolinyl, 3,5-quinolinyl, 3,6-quinolinyl, 3,7-quinolinyl, 3,8-quinolinyl, 4,5-quinolinyl, 4,6-quinolinyl, 4,7-quinolinyl, 4,8-quinolinyl, 1,4-isoquinolinyl, 1,5-isoquinolinyl, 1,6-isoquinolinyl, 1,7-isoquinolinyl, 1,8-isoquinolinyl, 3,4-isoquinolinyl, 3,5-isoquinolinyl, 3,6-isoquinolinyl, 3,7-isoquinolinyl, 3,8-isoquinolinyl, 4,5-isoquinolinyl, 4,6-isoquinolinyl, 4,7-isoquinolinyl, 4,8-isoquinolinyl, 3,4-cinnolinyl, 3,5-cinnolinyl, 3,6-cinnolinyl, 3,7-cinnolinyl, 3,8-cinnolinyl, 4,5-cinnolinyl, 4,6-cinnolinyl, 4,7-cinnolinyl, and 4,8-cinnolinyl with the proviso that $Q^b$ is bonded to highest number substituent position of each $W^6$ and that $(CH(R^{38}))_r$ is bonded to $E^0$.

In a preferred embodiment of compounds of Formula I or a pharmaceutically acceptable salt thereof, J is selected from the group consisting of hydrido, halo, hydroxy, hydroxyalkyl, amino, aminoalkyl, O—$R^6$, NH—$R^6$, S—$R^6$, wherein $R^6$ is selected from the group consisting of alkyl and haloalkyl;

B is formula (V):

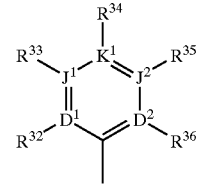

(V)

wherein $D^1$, $D^2$, $J^1$, $J^2$ and $K^1$ are independently selected from the group consisting of C, N, O, S and a covalent bond with the provisos that no more than one can be a covalent bond, no more than one of $D^1$, $D^2$, $J^1$, $J^2$ and $K^1$ can be O, no more than one of $D^1$, $D^2$, $J^1$, $J^2$ and $K^1$ can be S, one of $D^1$, $D^2$, $J^1$, $J^2$ and $K^1$ must be a covalent bond when two of $D^1$, $D^2$, $J^1$, $J^2$ and $K^1$ are O and S, and no more than four of $D^1$, $D^2$, $J^1$, $J^2$ and $K^1$ can be N;

$R^9$, $R^{10}$, $R^{11}$, $R^{12}$, $R^{13}$, $R^{32}$, $R^{33}$, $R^{34}$, $R^{35}$, and $R^{36}$ are independently selected from the group consisting of hydrido, amidino, guanidino, dialkylsulfonium, carboxy, haloalkylthio, alkanoyloxy, alkoxy, alkoxyalkyl, haloalkoxylalkyl, hydroxy, amino, alkoxyamino, thio, nitro, lower alkylamine, alkylthio, alkylthioalkyl, alkylsulfinyl, alkylsulfinylalkyl, alkylsulfonyl, alkylsulfonylalkyl, haloakylsulfinyl-alkyl, haloalkylsulfonylalkyl, alkylsulfonamido, alkylaminosulfonyl, amidosulfonyl, monoalkyl amidosulfonyl, dialkyl amidosulfonyl, alkanoyl, alkenoyl, haloalkanoyl, alkyl, alkenyl, alkenyloxy, alkenyloxyalkyl, halo haloalkyl, haloalkenyl, haloalkoxy, hydroxyhaloalkyl, hydroxyalkyl, aminoalkyl, haloalkoxyalkyl, carboxyalkyl, carboalkoxy, alkoxycarboxamido, alkylamidocarbonylamido, carboalkoxyalkyl, carboalkoxyalkenyl, carboxamido, carboxamidoalkyl, and cyano;

$R^{32}$, $R^{33}$, $R^{34}$, $R^{35}$, and $R^{36}$ can independently be $Q^b$;

B can be selected from the group consisting of C3–C8 alkyl, C3–C8 alkenyl, C3–C8 alkynyl, C3–C8 haloalkyl, and C3–C8 haloalkenyl wherein each member of group B may be optionally substituted at any carbon up to and including 6 atoms from the point of attachment of B to A with one or more of the group consisting of $R_{32}$, $R_{33}$, $R_{34}$, $R_{35}$, and $R_{36}$;

B can be selected from the group consisting of C3–C10 cycloalkyl, C5–C10 cycloalkenyl, C4–C9 saturated heterocyclyl, and C4–C9 partially saturated heterocyclyl, wherein each ring carbon may be optionally substituted with $R_{33}$, a ring carbon other than the ring carbon at the point of attachment of B to A may be optionally substituted with oxo provided that no more than one ring carbon is substituted by oxo at the same time, ring carbon and nitrogen atoms adjacent to the carbon atom at the point of attachment may be optionally substituted with $R_9$ or $R_{13}$, a ring carbon or nitrogen atom adjacent to the $R_9$ position and two atoms from the point of attachment may be substituted with $R_{10}$, a ring carbon or nitrogen atom adjacent to the $R_{13}$ position and two atoms from the point of attachment may be substituted with $R_{12}$, a ring carbon or nitrogen atom three atoms from the point of attachment and adjacent to the $R_{10}$ position may be substituted with $R_{11}$, a ring carbon or nitrogen atom three atoms from the point of attachment and adjacent to the $R_{12}$ position may be substituted with $R_{33}$, and a ring carbon or nitrogen atom four atoms from the point of attachment and adjacent to the $R_{11}$ and $R_{33}$ positions may be substituted with $R_{34}$;

A is selected from the group consisting of single covalent bond, $(W^7)_{rr}$—$(CH(R^{15}))_{pa}$ and $(CH(R^{15}))_{pa}$—$(W^7)_{rr}$ wherein rr is an integer selected from 0 through 1, pa is an integer selected from 0 through 6, and $W^7$ is selected from the group consisting of O, S, C(O), C(S), C(O)S, C(S)O, C(O)N($R^7$), C(S)N($R^7$), ($R^7$)NC(O), ($R^7$)NC(S), S(O), S(O)$_2$, S(O)$_2$N($R^7$), ($R^7$)NS(O)$_2$, C(N$R^7$)N($R^7$), ($R^7$)NC(N$R^7$), and N($R^7$) with the proviso that no more than one of the group consisting of rr and pa can be 0 at the same time;

$R^7$ and $R^8$ are independently selected from the group consisting of hydrido, hydroxy, alkyl, and alkoxyalkyl;

$R^{15}$ is selected from the group consisting of hydrido, hydroxy, halo, alkyl, and haloalkyl;

Ψ is NH with the provisos that Ψ is selected from other than NH unless any two of $X^0$, $R^2$, $R^1$, and J are other than hydrido or that Ψ is selected from other than NH unless A is selected from other than a single covalent bond when B is acyl, or that Ψ is selected from other than NH unless A is selected from other than S(O) or S(O)$_2$ when B is phenyl;

$X^0$ is hydrido;

$R^1$ is selected from the group consisting of hydrido, alkyl, alkoxy, alkylamino, alkylthio, haloalkylthio, haloalkyl, haloalkoxy, and halo;

$R^2$ is selected from the group consisting of $Z^0$—Q, hydrido, alkyl, alkenyl, and halo;

$Z^0$ is a covalent single bond;

Q is formula (II):

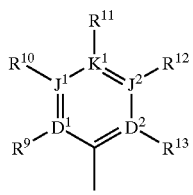

(II)

wherein $D^1$, $D^2$, $J^1$, $J^2$ and $K^1$ are independently selected from the group consisting of C, N, O, S and a covalent bond with the provisos that no more than one can be a covalent bond, no more than one of $D^1$, $D^2$, $J^1$, $J^2$ and $K^1$ can be O, no more than one of $D^1$, $D^2$, $J^1$, $J^2$ and $K^1$ can be S, one of $D^1$, $D^2$, $J^1$, $J^2$ and $K^1$ must be a covalent bond when two of $D^1$, $D^2$, $J^1$, $J^2$ and $K^1$ are O and S, and no more than four of $D^1$, $D^2$, $J^1$, $J^2$ and $K^1$ can be N, with the proviso that $R^9$, $R^{10}$, $R^{11}$, $R^{12}$, and $R^{13}$ are each independently selected to maintain the tetravalent nature of carbon, trivalent nature of nitrogen, the divalent nature of sulfur, and the divalent nature of oxygen;

K is $CR^{4a}R^{4b}$;

$R^{4a}$ and $R^{4b}$ are independently selected from the group consisting of halo, hydrido, hydroxy, alkyl, and haloalkyl;

$E^0$ is $E^1$, when K is $CR^{4a}R^{4b}$, wherein $E^1$ is selected from the group consisting of a covalent single bond, C(O)N(H), (H)NC(O), C(S)N(H), (H)NC(S), S(O)$_2$N(H), N(H)S(O)$_2$, S(O)$_2$N(H)C(O), and C(O)N(H)S(O)$_2$;

K can be $(CH(R^{14}))_j$—T wherein j is selected from an integer from 0 through 1 and T is selected from the group consisting of single covalent bond and N($R^7$) with the proviso that $(CH(R^{14}))_j$ is bonded to the phenyl ring;

$E^0$ is $E^2$, when K is $(CH(R^{14}))_j$—T, wherein $E^2$ is selected from the group consisting of C(O)N(H), (H)NC(O), C(S)N(H), (H)NC(S), S(O)$_2$N(H), N(H)S(O)$_2$, S(O)$_2$N(H)C(O), and C(O)N(H)S(O)$_2$;

$R^{14}$ is selected from the group consisting of hydrido, halo, alkyl, and haloalkyl;

$Y^0$ is formula (IV):

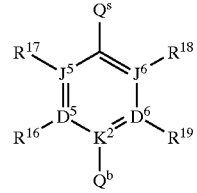

(IV)

wherein $D^5$, $D^6$, $J^5$, and $J^6$ are independently selected from the group consisting of C, N, O, S and a covalent bond with the provisos that no more than one can be a covalent bond, $K^2$ is independently selected from the group consisting of C, and $N^+$, no more than one of $D^5$, $D^6$, $J^5$, and $J^6$ can be O, no more than one of $D^5$, $D^6$, $J^5$, and $J^6$ can be S, one of $D^5$, $D^6$, $J^5$, and $J^6$ must be a covalent bond when two of $D^5$, $D^6$, $J^5$, and $J^6$ are O and S, no more than three of $D^5$, $D^6$, $J^5$, and $J^6$ can be N when $K^2$ is $N^+$, and no more than four of $D^5$, $D^6$, $J^5$, and $J^6$ can be N when $K^2$ is carbon with the provisos that $R^{16}$, $R^{17}$, $R^{18}$, and $R^{19}$ are each independently selected to maintain the tetravalent nature of carbon, trivalent nature of nitrogen, the divalent nature of sulfur, and the divalent nature of oxygen;

$R^{16}$, $R^{17}$, $R^{18}$, and $R^{19}$ are independently selected from the group consisting of hydrido, amidino, guanidino, dialkylsulfonium, carboxy, haloalkylthio, alkoxy, hydroxy, amino, thio, nitro, lower alkylamino, alkylthio, alkylsulfinyl, alkylsulfonyl, alkanoyl, alkenoyl, haloalkanoyl, alkyl, alkenyl, halo, haloalkyl, haloalkenyl, haloalkoxy, hydroxyalkyl, aminoalkyl, haloalkoxyalkyl, carboalkoxy, carboalkoxyalkyl, and cyano;

$Q^b$ is selected from the group consisting of $NR^{20}R^{21}$, $^+NR^{20}R^{21}R^{22}$, oxy, alkyl, alkylaminoalkyl, aminoalkyl, dialkylsulfoniumalkyl, and acylamino wherein $R^{20}$, $R^{21}$, and $R^{22}$ are independently selected from the group consisting of hydrido, alkyl, hydroxy, alkoxy, alkylamino, dialkylamino, aminoalkyl, and hydroxyalkyl with the provisos that no more than one of $R^{20}$, $R^{21}$, and $R^{22}$ can be hydroxy, alkoxy, alkylamino, amino, and dialkylamino and that $R^{20}$, $R^{21}$, and $R^{22}$ must be other than be hydroxy, alkoxy, alkylamino, amino, and dialkylamino when $K^2$ is $N^+$;

$Q^b$ can be $N(R^{26})SO_2N(R^{23})(R^{24})$ with the proviso that no more than one of $R^{23}$, $R^{24}$, and $R^{26}$ can be hydroxy, alkoxy, alkylamino, amino, or dialkylamino when two of the group consisting of $R^{23}$, $R^{24}$, and $R^{26}$ are bonded to the same atom;

$Q^b$ can be selected from the group consisting of dialkylsulfonium, trialkylphosphonium, $C(NR^{25})$ NR²³R²⁴, N(R²⁶)C(NR²⁵)N(R²³)(R²⁴), N(R²⁶)C(O)N(R²³)(R²⁴), N(R²⁶)C(S)N(R²³)(R²⁴), C(O)N(R²⁶)C(NR²⁵)N(R²³)(R²⁴), C(S)N(R²⁶)C(NR²⁵)N(R²³)(R²⁴), N(R²⁶)N(R²⁶)C(NR²⁵)N(R²³)(R²⁴), N(R²⁶)N(R²⁶)SO₂N(R²³)(R²⁴), C(O)NR²³R²⁴, and C(O)NR²³R²⁴ with the provisos that no more than one of R²³, R²⁴, and R²⁶ can be hydroxy, alkoxy, alkylamino, amino, or dialkylamino when two of the group consisting of R²³, R²⁴, and R²⁶ are bonded to the same atom and that said $Q^b$ group is bonded directly to a carbon atom;

R²³, R²⁴, R²⁵, and R²⁶ are independently selected from the group consisting of hydrido, alkyl, hydroxy, alkoxy, alkylamino, dialkylamino, aminoalkyl, and hydroxyalkyl;

$Q^s$ is selected from the group consisting of a single covalent bond and $(CR^{37}R^{38})_b$—$(W^0)_{az}$ wherein az is an integer selected from 0 through 1, b is an integer selected from 1 through 2, and $W^0$ is selected from the group consisting of O, S, C(O), S(O)₂, N(R¹⁴), and ON(R¹⁴) with the proviso that R¹⁴ is selected from other than halo when directly bonded to N and that $(CR^{37}R^{38})_b$ is bonded to $E^0$;

R³⁷ and R³⁸ are independently selected from the group consisting of hydrido, halo, alkyl, and haloalkyl;

$Y^0$ can be $Q^b$—$Q^{ssss}$ wherein $Q^{ssss}$ is $(CH(R^{38}))_r$—$W^5$, r is an integer selected from 1 through 3, and $W^5$ is selected from the group consisting of 1,4-indenyl, 1,5-indenyl, 1,6-indenyl, 1,7-indenyl, 2,7-indenyl, 2,6-indenyl, 2,5-indenyl, 2,4-indenyl, 3,4-indenyl, 3,5-indenyl, 3,6-indenyl, 3,7-indenyl, 2,4-benzofuranyl, 2,5-benzofuranyl, 2,6-benzofuranyl, 2,7-benzofuranyl, 3,4-benzofuranyl, 3,5-benzofuranyl, 3,6-benzofuranyl, 3,7-benzofuranyl, 2,4-benzothiophenyl, 2,5-benzothiophenyl, 2,6-benzothiophenyl, 2,7-benzothiophenyl, 3,4-benzothiophenyl, 3,5-benzothiophenyl, 3,6-benzothiophenyl, 3,7-benzothiophenyl, 2,4-indolyl, 2,5-indolyl, 2,6-indolyl, 2,7-indolyl, 3,4-indolyl, 3,5-indolyl, 3,6-indolyl, 3,7-indoly, 1,4-isoindolyl, 1,5-isoindolyl, 1,6-isoindolyl, 2,4-isoindoly, 2,5-isoindolyl, 2,6-isoindolyl, 2,7-isoindolyl, 1,3-isoindolyl, 3,4-indazolyl, 3,5-indazolyl, 3,6-indazolyl, 3,7-indazolyl, 2,4-benzoxazolyl, 2,5-benzoxazolyl, 2,6-benzoxazolyl, 2,7-benzoxazolyl, 3,4-benzisoxazolyl, 3,5-benzisoxazolyl, 3,6-benzisoxazolyl, 3,7-benzisoxazolyl, 1,4-naphthyl, 1,5-naphthyl, 1,6-naphthyl, 1,7-naphthyl, 1,8-naphthyl, 2,4-naphthyl, 2,5-naphthyl, 2,6-naphthyl, 2,7-naphthyl, 2,8-naphthyl, 2,4-quinolinyl, 2,5-quinolinyl, 2,6-quinolinyl, 2,7-quinolinyl, 2,8-quinolinyl, 3,4-quinolinyl, 3,5-quinolinyl, 3,6-quinolinyl, 3,7-quinolinyl, 3,8-quinolinyl, 4,5-quinolinyl, 4,6-quinolinyl, 4,7-quinolinyl, 4,8-quinolinyl, 1,4-isoquinolinyl, 1,5-isoquinolinyl, 1,6-isoquinolinyl, 1,7-isoquinolinyl, 1,8-isoquinolinyl, 3,4-isoquinolinyl, 3,5-isoquinolinyl, 3,6-isoquinolinyl, 3,7-isoquinolinyl, 3,8-isoquinolinyl, 4,5-isoquinolinyl, 4,6-isoquinolinyl, 4,7-isoquinolinyl, 4,8-isoquinolinyl, 3,4-cinnolinyl, 3,5-cinnolinyl, 3,6-cinnolinyl, 3,7-cinnolinyl, 3,8-cinnolinyl, 4,5-cinnolinyl, 4,6-cinnolinyl, 4,7-cinnolinyl, and 4,8-cinnolinyl with the proviso that $Q^b$ is bonded to lowest number substituent position of each $W^5$ and that $(CH(R^{38}))_r$ is bonded to $E^0$;

$Y^0$ can be $Q^b$—$Q^{ssssr}$ wherein $Q^{ssssr}$ is $(CH(R^{38}))_r$—$W^6$, r is an integer selected from 1 through 3, and $W^6$ is selected from the group consisting of 1,4-indenyl, 1,5-indenyl, 1,6-indenyl, 1,7-indenyl, 2,7-indenyl, 2,6-indenyl, 2,5-indenyl, 2,4-indenyl, 3,4-indenyl, 3,5-indenyl, 3,6-indenyl, 3,7-indenyl, 2,4-benzofuranyl, 2,5-benzofuranyl, 2,6-benzofuranyl, 2,7-benzofuranyl, 3,4-benzofuranyl, 3,5-benzofuranyl, 3,6-benzofuranyl, 3,7-benzofuranyl, 2,4-benzothiophenyl, 2,5-benzothiophenyl, 2,6-benzothiophenyl, 2,7-benzothiophenyl, 3,4-benzothiophenyl, 3,5-benzothiophenyl, 3,6-benzothiophenyl, 3,7-benzothiophenyl, 2,4-indolyl, 2,5-indolyl, 2,6-indolyl, 2,7-indolyl, 3,4-indolyl, 3,5-indolyl, 3,6-indolyl, 3,7-indolyl, 1,4-isoindolyl, 1,5-isoindolyl, 1,6-isoindolyl, 2,4-isoindolyl, 2,5-isoindolyl, 2,6-isoindolyl, 2,7-isoindolyl, 1,3-isoindolyl, 3,4-indazolyl, 3,5-indazolyl, 3,6-indazolyl, 3,7-indazolyl, 2,4-benzoxazolyl, 2,5-benzoxazolyl, 2,6-benzoxazolyl, 2,7-benzoxazolyl, 3,4-benzisoxazolyl, 3,5-benzisoxazolyl, 3,6-benzisoxazolyl, 3,7-benzisoxazolyl, 1,4-naphthyl, 1,5-naphthyl, 1,6-naphthyl, 1,7-naphthyl, 1,8-naphthyl, 2,4-naphthyl, 2,5-naphthyl, 2,6-naphthyl, 2,7-naphthyl, 2,8-naphthyl, 2,4-quinolinyl, 2,5-quinolinyl, 2,6-quinolinyl, 2,7-quinolinyl, 2,8-quinolinyl, 3,4-quinolinyl, 3,5-quinolinyl, 3,6-quinolinyl, 3,7-quinolinyl, 3,8-quinolinyl, 4,5-quinolinyl, 4,6-quinolinyl, 4,7-quinolinyl, 4,8-quinolinyl, 1,4-isoquinolinyl, 1,5-isoquinolinyl, 1,6-isoquinolinyl, 1,7-isoquinolinyl, 1,8-isoquinolinyl, 3,4-isoquinolinyl, 3,5-isoquinolinyl, 3,6-isoquinolinyl, 3,7-isoquinolinyl, 3,8-isoquinolinyl, 4,5-isoquinolinyl, 4,6-isoquinolinyl, 4,7-isoquinolinyl, 4,8-isoquinolinyl, 3,4-cinnolinyl, 3,5-cinnolinyl, 3,6-cinnolinyl, 3,7-cinnolinyl, 3,8-cinnolinyl, 4,5-cinnolinyl, 4,6-cinnolinyl, 4,7-cinnolinyl, and 4,8-cinnolinyl with the proviso that $Q^b$ is bonded to highest number substituent position of each $W^6$ and that $(CH(R^{38}))_r$ is bonded to $E^0$.

In a more preferred embodiment of compounds of Formula I or a pharmaceutically acceptable salt thereof, J is selected from the group consisting of halo, hydroxy, hydroxyalkyl, amino aminoalkyl, O—R⁶, NH—R⁶, and S—R⁶, wherein R⁶ is selected from the group consisting of alkyl and haloalkyl;

B is selected from the group consisting of aryl and heteroaryl wherein a carbon adjacent to the carbon at the point of attachment may be substituted by R³², the other carbon adjacent to the carbon at the point of attachment may be substituted by R³⁶, a carbon adjacent to R³² and two atoms from the carbon at the point of attachment may be substituted by R³³, a carbon adjacent to R³⁶ and two atoms from the carbon at the point of attachment may be substituted by R³⁵, and any carbon adjacent to both R³³ and R³⁵ may be substituted by R³⁴;

R³², R³³, R³⁴, R³⁵, and R³⁶ are independently selected from the group consisting of hydrido, amidino, guanidino, dialkylsulfonium, carboxy, haloalkylthio, alkoxy, hydroxy, amino, alkoxyamino, thio, nitro, lower alkylamino, alkylthio, alkylsulfinyl, alkylsulfonyl, amidosulfonyl, alkanoyl, haloalkanoyl, alkyl, halo, haloalkyl, haloalkenyl, haloalkoxy, hydroxyhaloalkyl, hydroxyalkyl, aminoalkyl, carboxyalkyl, carboalkoxy, carboxamido, and cyano;

R³², R³³, R³⁴, R³⁵, and R³⁶ can independently be $Q^b$;

B can be selected from the group consisting of C3–C8 alkyl, C3–C8 alkenyl, C3–C8 haloalkyl, and C3–C8 haloalkenyl wherein each member of group B may be optionally substituted at any carbon up to and including 6 atoms from the point of attachment of B to A with one or more of the group consisting of R₃₂, R₃₃, R₃₄, R₃₅, and R₃₆;

B can be selected from the group consisting of C3–C10 cycloalkyl, C5–C10 cycloalkenyl, C4–C9 saturated heterocyclyl, and C4–C9 partially saturated heterocyclyl, wherein each ring carbon may be optionally substituted with $R_{33}$, a ring carbon other than the ring carbon at the point of attachment of B to A may be optionally substituted with oxo provided that no more than one ring carbon is substituted by oxo at the same time, ring carbon and nitrogen atoms adjacent to the carbon atom at the point of attachment may be optionally substituted with $R_9$ or $R_{13}$, a ring carbon or nitrogen atom adjacent to the $R_9$ position and two atoms from the point of attachment may be substituted with $R_{10}$, a ring carbon or nitrogen atom adjacent to the $R_{13}$ position and two atoms from the point of attachment may be substituted with $R_{12}$, a ring carbon or nitrogen atom three atoms from the point of attachment and adjacent to the $R_{10}$ position may be substituted with $R_{11}$, a ring carbon or nitrogen atom three atoms from the point of attachment and adjacent to the $R_{12}$ position may be substituted with $R_{33}$, and a ring carbon or nitrogen atom four atoms from the point of attachment and adjacent to the $R_{11}$ and $R_{33}$ positions may be substituted with $R_{34}$;

$R^9$, $R^{10}$, $R^{11}$, $R^{12}$, and $R^{13}$ are independently selected from the group consisting of hydrido, amidino, guanidino, dialkylsulfonium, carboxy, haloalkylthio, alkoxy, hydroxy, amino, alkoxyamino, thio, nitro, lower alkylamino, alkylthio, alkylsulfinyl, alkylsulfonyl, amidosulfonyl, alkanoyl, haloalkanoyl, alkyl, halo, haloalkyl, haloalkenyl, haloalkoxy, hydroxyhaloalkyl, hydroxyalkyl, aminoalkyl, carboxyalkyl, carboalkoxy, carboxamido, and cyano;

A is selected from the group consisting of single covalent bond, $(W^7)_{rr}$—$(CH(R^{15}))_{pa}$ and $(CH(R^{15}))_{pa}$—$(W^7)_{rr}$ wherein rr is an integer selected from 0 through 1, pa is an integer selected from 0 through 6, and $W^7$ is selected from the group consisting of O, S, and C(O) with the proviso that no more than one of the group consisting of rr and pa can be 0 at the same time;

$R^{15}$ is selected from the group consisting of hydrido, hydroxy, halo, alkyl, and haloalkyl;

Ψ is NH;

$X^0$ is hydrido;

$R^1$ is selected from the group consisting of hydrido, alkyl, alkoxy, alkylamino, alkylthio, haloalkylthio, haloalkyl, haloalkoxy, and halo;

$R^2$ is Q, wherein Q is selected from the group consisting of aryl and heteroaryl wherein a carbon adjacent to the carbon at the point of attachment may be substituted by $R^9$, the other carbon adjacent to the carbon at the point of attachment may be substituted by $R^{13}$, a carbon adjacent to $R^9$ and two atoms from the carbon at the point of attachment may be substituted by $R^{10}$, a carbon adjacent to $R^{13}$ and two atoms from the carbon at the point of attachment may be substituted by $R^{12}$, and any carbon adjacent to both $R^{10}$ and $R^{12}$ may be substituted by $R^{11}$;

K is $CR^{4a}R^{4b}$ wherein $R^{4a}$ and $R^{4b}$ are independently selected from the group consisting of halo and hydrido;

$E^0$ is $E^1$, when K is $CR^{4a}R^{4b}$, wherein $E^1$ is selected from the group consisting of a covalent single bond, C(O)N(H), (H)NC(O), S(O)$_2$N(H), N(H)S(O)$_2$, S(O)$_2$N(H)C(O), and C(O)N(H)S(O)$_2$;

K can be $(CH(R^{14}))_j$—T wherein j is selected from an integer from 0 through 1 and T is selected from the group consisting of single covalent bond and $N(R^7)$ with the proviso that $(CH(R^{14}))_j$ is bonded to the phenyl ring;

$R^7$ is selected from the group consisting of hydrido, hydroxy, alkyl, and alkoxyalkyl;

$R^{14}$ is selected from the group consisting of hydrido and halo;

$E^0$ is $E^2$, when K is $(CH(R^{14}))_j$—T, wherein $E^2$ is selected from the group consisting of C(O)N(H), (H)NC(O), S(O)$_2$N(H), N(H)S(O)$_2$, S(O)$_2$N(H)C(O), and C(O)N(H)S(O)$_2$;

$Y^0$ is formula (IV):

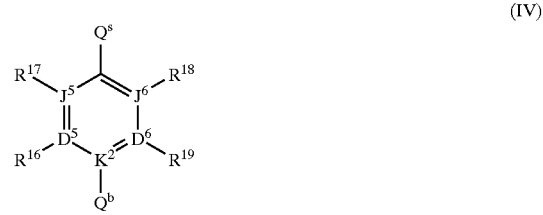

(IV)

wherein $D^5$, $D^6$, $J^5$, and $J^6$ are independently selected from the group consisting of C, N, O, S and a covalent bond with the provisos that no more than one can be a covalent bond, $K^2$ is independently selected from the group consisting of C, and $N^+$, no more than one of $D^5$, $D^6$, $J^5$, and $J^6$ can be O, no more than one of $D^5$, $D^6$, $J^5$, and $J^6$ can be S, one of $D^5$, $D^6$, $J^5$, and $J^6$ must be a covalent bond when two of $D^5$, $D^6$, $J^5$, and $J^6$ are O and S, no more than three of $D^5$, $D^6$, $J^5$, and $J^6$ can be N when $K^2$ is $N^+$, and no more than four of $D^5$, $D^6$, $J^5$, and $J^6$ can be N when $K^2$ is carbon with the provisos that $R^{16}$, $R^{17}$, $R^{18}$, and $R^{19}$ are each independently selected to maintain the tetravalent nature of carbon, trivalent nature of nitrogen, the divalent nature of sulfur, and the divalent nature of oxygen;

$R^{16}$, $R^{17}$, $R^{18}$, and $R^{19}$ are independently selected from the group consisting of hydrido, amidino, guanidino, dialkylsulfonium, carboxy, haloalkylthio, alkoxy, hydroxy, amino, thio, nitro, lower alkylamino, alkylthio, alkylsulfinyl, alkylsulfonyl, alkanoyl, alkenoyl, haloalkanoyl, alkyl, alkenyl, halo, haloalkyl, haloalkenyl, haloalkoxy, hydroxyalkyl, aminoalkyl, haloalkoxyalkyl, carboalkoxy, carboalkoxyalkyl, and cyano;

$Q^b$ is selected from the group consisting of $NR^{20}R^{21}$, $^+NR^{20}R^{21}R^{22}$, oxy, alkyl, alkylaminoalkyl, aminoalkyl, dialkylsulfoniumalkyl, and acylamino wherein $R^{20}$, $R^{21}$, and $R^{22}$ are independently selected from the group consisting of hydrido, alkyl, hydroxy, alkoxy, alkylamino, dialkylamino, aminoalkyl, and hydroxyalkyl with the provisos that no more than one of $R^{20}$, $R^{21}$, and $R^{22}$ can be hydroxy, alkoxy, alkylamino, amino, and dialkylamino and that $R^{20}$, $R^{21}$, and $R^{22}$ must be other than be hydroxy, alkoxy, alkylamino, amino, and dialkylamino when $K^2$ is $N^+$;

$Q^b$ can be selected from the group consisting of dialkylsulfonium, trialkylphosphonium, $C(NR^{25})NR^{23}R^{24}$, $N(R^{26})C(NR^{25})N(R^{23})(R^{24})$, $C(O)N(R^{26})C(NR^{25})N(R^{23})(R^{24})$, $N(R^{26})N(R^{26})C(NR^{25})N(R^{23})(R^{24})$, $N(R^{26})N(R^{26})SO_2N(R^{23})(R^{24})$, $C(O)NR^{23}R^{24}$, and $C(O)NR^{23}R^{24}$ with the provisos that no more than one of $R^{23}$, $R^{24}$, and $R^{26}$ can be hydroxy, alkoxy, alkylamino, amino, or dialkylamino when two of the group consisting of $R^{23}$, $R^{24}$, and $R^{26}$ are bonded to the same atom and that said $Q^b$ group is bonded directly to a carbon atom;

$R^{23}$, $R^{24}$, $R^{25}$, and $R^{26}$ are independently selected from the group consisting of hydrido, alkyl, hydroxy, alkoxy, alkylamino, dialkylamino, aminoalkyl, and hydroxyalkyl;

$Q^s$ is selected from the group consisting of a single covalent bond and $(CR^{37}R^{38})_b$—$(W^0)_{az}$ wherein az is an integer selected from 0 through 1, b is the integer 1, and $W^0$ is selected from the group consisting of O, S, and C(O) with the proviso that $(CR^{37}R^{38})_b$ is bonded to $E^0$;

$R^{37}$ and $R^{38}$ are independently selected from the group consisting of hydrido, halo, alkyl, and haloalkyl.

In a specific embodiment of Formula I, compounds have the Formula I-S:

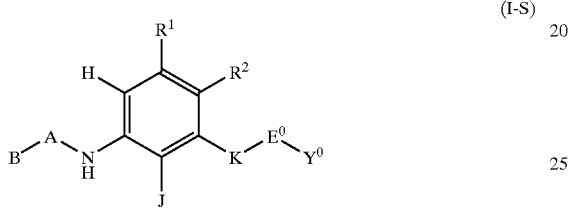

(I-S)

or a pharmaceutically acceptable salt thereof, wherein;

J is selected from the group consisting of fluoro, chloro, bromo, hydroxy, hydroxymethyl, 1-hydroxyethyl, 2-hydroxyethyl, amino, aminomethyl, 1-aminoethyl, 2-aminoethyl, methoxy, ethoxy, trifluoromethoxy, N-methylamino, N-ethylamino, methythio, ethylthio, and trifluoromethylthio;

B is selected from the group consisting of phenyl, 2-thienyl, 3-thienyl, 2-furyl, 3-furyl, 2-pyrrolyl, 3-pyrrolyl, 2-imidazolyl, 4-imidazolyl, 3-pyrazolyl, 4-pyrazolyl, 1,2,4-triazol-3-yl, 1,2,4-triazol-5-yl, 1,2,4-oxadiazol-3-yl, 1,2,4-oxadiazol-5-yl, 1,3,4-oxadiazol-3-yl, 1,3,4-oxadiazol-5-yl, 3-isothiazolyl, 5-isothiazolyl, 2-oxazolyl, 2-thiazolyl, 3-isoxazolyl, 5-isoxazolyl, 2-pyridyl, 3-pyridyl, 4-pyridyl, 2-pyrazinyl, 2-pyrimidinyl, 4-pyridinyl, 5-pyrimidinyl, 3-pyridazinyl, 4-pyridazinyl, 1,3,5-triazin-2-yl, 1,2,4-triazin-3-yl, 1,2,4-triazin-5-yl, 1,2,4-triazin-6-yl, and 1,2,3-triazin-4-yl, wherein a carbon adjacent to the carbon at the point of attachment may be substituted by $R^{32}$, the other carbon adjacent to the carbon at the point of attachment may be substituted by $R^{36}$, a carbon adjacent to $R^{32}$ and two atoms from the carbon at the point of attachment may be substituted by $R^{33}$, a carbon adjacent to $R^{36}$ and two atoms from the carbon at the point of attachment may be substituted by $R^{35}$, and any carbon adjacent to both $R^{33}$ and $R^{35}$ may be substituted by $R^{34}$;

$R^{32}$, $R^{33}$, $R^{34}$, $R^{35}$, and $R^{36}$ are independently selected from the group consisting of hydrido, amidino, guanidino, dimethylsulfonium, carboxy, methoxy, ethyoxy, isopropoxy, propoxy, hydroxy, amino, methoxyamino, ethoxyamino, thio, nitro, aminomethyl, 1-aminoethyl, 2-aminoethyl, N-N-methylamino, dimethylamino, N-ethylamino, methylthio, ethylthio, isopropylthio, trifluoromethylthio, methylsulfinyl, ethylsulfinyl, methylsulfonyl, ethylsulfonyl, trifluoromethyl, pentafluoroethyl, 2,2,2-trifluoroethyl, 2,2,3,3,3-pentafluoropropyl, trifluoromethoxy, 1,1,2,2-tetrafluoroethoxy, fluoro, chloro, bromo, amidosulfonyl, N-methylamidosulfonyl, N,N-dimethylamidosulfonyl, acetyl, propanoyl, trifluoroacetyl, pentafluoropropanoyl, hydroxymethyl, 1-hydroxyethyl, 2-hydroxyethyl, 2,2,2-trifluoro-1-hydroxyethyl, 2,2,2-trifluoro-1-trifluoromethyl-1-hydroxyethyl, carboxymethyl, methoxycarbonyl, ethoxycarbonyl, amidocarbonyl, N-methylamidocarbonyl, N,N-dimethylamidocarbonyl, cyano, and $Q^b$;

B can be selected from the group consisting of 1-propenyl, propyl, isopropyl, butyl, 2-butenyl, 3-butenyl, 2-butynyl, sec-butyl, isobutyl, 2-methylpropenyl, 1-pentyl, 2-pentenyl, 3-pentenyl, 4-pentenyl, 2-pentynyl, 3-pentynyl, 2-pentyl, 1-methyl-2-butenyl, 1-methyl-3-butenyl, 1-methyl-2-butynyl, 3-pentyl, 1-ethyl-2-propenyl, 2-methylbutyl, 2-methyl,-2-butenyl, 2-methyl-3-butenyl, 2-methyl-3-butynyl, 3-methylbutyl, 3-methyl-2-butenyl, 3-methyl-3-butenyl, 1-hexyl, 2-hexenyl, 3-hexenyl, 4-hexenyl, 5-hexenyl, 2-hexynyl, 3-hexynyl, 4-hexynyl, 2-hexyl, 1-methyl-2-pentenyl, 1-methyl-3-pentenyl, 1-methyl-4-pentenyl, 1-methyl-2-pentynyl, 1-methyl-3-pentynyl, 3-hexyl, 1-ethyl-2-butenyl, 1-ethyl-3-butenyl, 1-propyl-2-propenyl, 1-ethyl-2-butynyl, 1-heptyl, 2-heptenyl, 3-heptenyl, 4-heptenyl, 5-heptenyl, 6-heptenyl, 2-heptynyl, 3-heptynyl, 4-heptynyl, 5-heptynyl, 2-heptyl, 1-methyl-2-hexenyl, 1-methyl-3-hexenyl, 1-methyl-4-hexenyl, 1-methyl-5-hexenyl, 1-methyl-2-hexynyl, 1-methyl-3-hexynyl, 1-methyl-4-hexynyl, 3-heptyl, 1-ethyl-2-pentenyl, 1-ethyl-3-pentenyl, 1-ethyl-4-pentenyl, 1-butyl-2-propenyl, 1-ethyl-2-pentynyl, 1-ethyl-3-pentynyl, 1-octyl, 2-octenyl, 3-octenyl, 4-octenyl, 5-octenyl, 6-octenyl, 7-octenyl, 2-octynyl, 3-octynyl, 4-octynyl, 5-octynyl, 6-octynyl, 2-octyl, 1-methyl-2-heptenyl, 1-methyl-3-heptenyl, 1-methyl-4-heptenyl, 1-methyl-5-heptenyl, 1-methyl-6-heptenyl, 1-methyl-2-heptynyl, 1-methyl-3-heptynyl, 1-methyl-4-heptynyl, 1-methyl-5-heptynyl, 1-methyl-6-heptynyl, 1-methyl-2-heptenyl, 1-methyl-3-heptynyl, 1-methyl-4-heptynyl, 1-methyl-5-heptynyl, 3-octyl, 1-ethyl-2-hexenyl, 1-ethyl-3-hexenyl, 1-ethyl-4-hexenyl, 1-ethyl-2-hexynyl, 1-ethyl-3-hexynyl, 1-ethyl-4-hexynyl, 1-ethyl-5-hexenyl, 1-pentyl-2-propenyl, 4-octyl, 1-propyl-2-pentenyl, 1-propyl-3-pentenyl, 1-propyl-4-pentenyl, 1-butyl-2-butenyl, 1-propyl-2-pentynyl, 1-propyl-3-pentynyl, 1-butyl-2-butynyl, 1-butyl-3-butenyl, 2,2-difluoropropyl, 4-trifluoromethyl-5,5,5-trifluoropentyl, 4-trifluoromethylpentyl, 5,5,6,6,6-pentafluorohexyl, and 3,3,3-trifluoropropyl, wherein each member of group B may be optionally substituted at any carbon up to and including 5 atoms from the point of attachment of B to A with one or more of the group consisting of $R_{32}$, $R_{33}$, $R_{34}$, $R_{35}$, and $R_{36}$;

B can be selected from the group consisting of cyclopropyl, cyclobutyl, oxetan-2-yl, oxetan-3-yl, azetidin-1-yl, azetidin-2-yl, azetidin-3-yl, thiaetan-2-yl, thiaetan-3-yl, cyclopentyl, cyclopent-2-enyl, cyclopent-3-enyl, cyclohexyl, 4-methylcyclohexyl, 4-chloro-3-ethylphenoxycyclohexyl, 3-trifluoromethoxyphenoxycyclohexyl, 3-trifluoromethylcyclohexyl, 4-trifluoromethylcyclohexyl, 3,5bis-trifluoromethylcyclohexyl, adamantyl, 3-trifluoromethyladamantyl, norbornyl, 3-trifluoromethylnorbornyl, norbornenyl, 7-oxabicyclo

[2.2.1]heptan-2-yl, bicyclo[3.1.0]hexan-6-yl, cyclohex-2-enyl, cyclohex-3-enyl, cycloheptyl, cyclohept-2-enyl, cyclohept-3-enyl, cyclooctyl, cyclooct-2-enyl, cyclooct-3-enyl, cyclooct-4-enyl, 2-morpholinyl, 3-morpholinyl, 4-morpholinyl, 1-piperazinyl, 2-piperazinyl, 1-piperidinyl, 2-piperidinyl, 3-piperidinyl, 4-piperidinyl, 1-pyrrolidinyl, 2-pyrrolidinyl, 3-pyrrolidinyl, 2-dioxanyl, 2H-2-pyranyl, 2H-3-pyranyl, 2H-4-pyranyl, 4H-2-pyranyl, 4H-3-pyranyl, 4H-4-pyranyl, 2H-pyran-2-one-3-yl, 2H-pyran-2-one-4-yl, 2H-pyran-2-one-5-yl, 4H-pyran-4-one-2-yl, 4H-pyran-4-one-3-yl, 2-tetrahydrofuranyl, 3-tetrahydrofuranyl, 2-tetrahydropyranyl, 3-tetrahydropyranyl, 4-tetrahydropyranyl, 2-tetrahydrothienyl, and 3-tetrahydrothienyl, wherein each ring carbon may be optionally substituted with $R_{33}$, a ring carbon and nitrogen atoms adjacent to the carbon atom at the point of attachment may be optionally substituted with $R_9$ or $R_{13}$, a ring carbon or nitrogen atom adjacent to the $R_9$ position and two atoms from the point of attachment may be substituted with $R_{10}$, and a ring carbon or nitrogen atom adjacent to the $R_{13}$ position and two atoms from the point of attachment may be substituted with $R_{12}$;

$R^9$, $R^{10}$, $R^{11}$, $R^{12}$, and $R^{13}$ are independently selected from the group consisting of amidino, guanidino, dimethylsulfonium, methylethylsulfonium, carboxy, methoxy, ethoxy, isopropoxy, propoxy, butoxy, hydroxy, amino, methoxyamino, ethoxyamino, aminomethyl, 1-aminoethyl, 2-aminoethyl, N-N-dimethylamino, N-methylamino, N-ethylamino, methylsulfinyl, ethylsulfinyl, methylsulfonyl, ethylsulfonyl, amidosulfonyl, N-methylamidosulfonyl, N,N-dimethylamidosulfonyl, acetyl, propanoyl, butanoyl, trifluoroacetyl, pentafluoropropanoyl, hydroxymethyl, 1-hydroxyethyl, 2-hydroxyethyl, 2,2,2-trifluoro-1-hydroxyethyl, 2,2,2-trifluoro-1-trifluoromethyl-1-hydroxyethyl, carboxymethyl, 2-carboxyethyl, methoxycarbonyl, ethoxycarbonyl, amidocarbonyl, N-methylamidocarbonyl, N,N-dimethylamidocarbonyl, and cyano;

A is selected from the group consisting of single covalent bond, O, C(O), $CH_2$, $CH_3CH$, $CF_3CH$, $CH_3CC(O)$, $CF_3CC(O)$, $C(O)CCH_3$, $C(O)CCF_3$, $CH_2C(O)$, $(O)CCH_2$, $CH_2CH_2$, $CH_2CH_2CH_2$, $CH_3CCH_2$, $CF_3CCH_2$, $CH_3CC(O)CH_2$, $CF_3CC(O)CH_2$, $CH_2C(O)CCH_3$, $CH_2C(O)CCF_3$, $CH_2CH_2C(O)$, and $CH_2(O)CCH_2$;

$R^1$ is selected from the group consisting of hydrido, methyl, ethyl, propyl, butyl, methoxy, ethoxy, propoxy, isopropoxy, butoxy, sec-butoxy, N-methylamino, N,N-dimethylamino, N-ethylamino, N,N-diethylamino, methylthio, ethylthio, isopropylthio, trifluoromethylthio, trifluoromethyl, pentafluoroethyl, 2,2,2-trifluoroethyl, 2,2,3,3,3-pentafluoropropyl, trifluoromethoxy, 1,1,2,2-tetrafluoroethoxy, fluoro, chloro, and bromo;

$R^2$ is selected from the group consisting of phenyl, 2-thienyl, 3-thienyl, 2-furyl, 3-furyl, 2-pyrrolyl, 3-pyrrolyl, 2-imidazolyl, 4-imidazolyl, 3-pyrazolyl, 4-pyrazolyl, 1,2,4-triazol-3-yl, 1,2,4-triazol-5-yl, 1,2,4-oxadiazol-3-yl, 1,2,4-oxadiazol-5-yl, 1,3,4-oxadiazol-3-yl, 1,3,4-oxadiazol-5-yl, 3-isothiazolyl, 5-isothiazolyl, 2-oxazolyl, 2-thiazolyl, 3-isoxazolyl, 5-isoxazolyl, 2-pyridyl, 3-pyridyl, 4-pyridyl, 2-pyrazinyl, 2-pyrimidinyl, 4-pyrimidinyl, 5-pyrimidinyl, 3-pyridazinyl, 4-pyridazinyl, 1,3,5-triazin-2-yl, 1,2,4-triazin-3-yl, 1,2,4-triazin-5-yl, 1,2,4-triazin-6-yl, and 1,2,3-triazin-4-yl, wherein a carbon adjacent to the carbon at the point of attachment may be substituted by $R^9$, the other carbon adjacent to the carbon at the point of attachment may be substituted by $R^{13}$, a carbon adjacent to $R^9$ and two atoms from the carbon at the point of attachment may be substituted by $R^{10}$, a carbon adjacent to $R^{13}$ and two atoms from the carbon at the point of attachment may be substituted by $R^{12}$, and any carbon adjacent to both $R^{10}$ and $R^{12}$ may be substituted by $R^{11}$;

K is $CR^{4a}R^{4b}$ wherein $R^{4a}$ and $R^{4b}$ are independently selected from the group consisting of chloro, fluoro, and hydrido;

$E^0$ is $E^1$, when K is $CR^{4a}R^{4b}$, wherein $E^1$ is selected from the group consisting of a covalent single bond, C(O)N(H), (H)NC(O), $S(O)_2N(H)$, $N(H)S(O)_2$, $S(O)_2N(H)C(O)$, and $C(O)N(H)S(O)_2$;

K can be N(H) and $CH_2N(H)$;

$E^0$ is $E^2$, when K is N(H) and $CH_2N(H)$, wherein $E^2$ is selected from the group consisting of C(O)N(H), (H)NC(O), $S(O)_2N(H)$, $N(H)S(O)_2$, $S(O)_2N(H)C(O)$, and $C(O)N(H)S(O)_2$;

$Y^0$ is selected from the group of formulas consisting of:

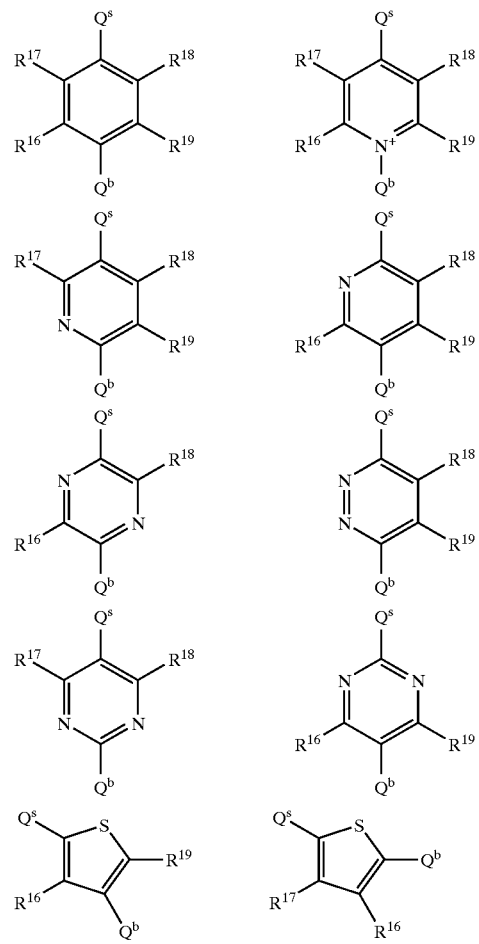

-continued

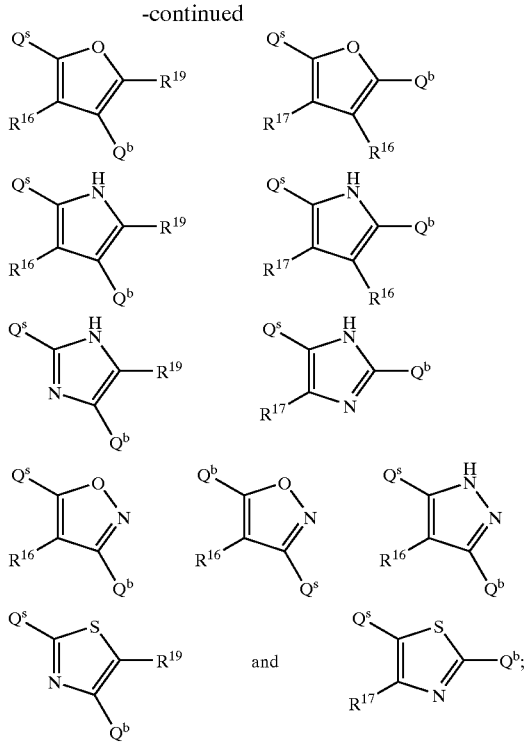

R$^{16}$, R$^{17}$, R$^{18}$, and R$^{19}$ are independently selected from the group consisting of hydrido, amidino, guanidino, dimethylsulfonium, carboxy, methoxy, ethoxy, isopropoxy, propoxy, hydroxy, amino, methoxyamino, ethoxyamino, thio, nitro, aminomethyl, 1-aminoethyl, 2-aminoethyl, N-N-methylamino, dimethylamino, N-ethylamino, methylthio, ethylthio, isopropylthio, trifluoromethylthio, methylsulfinyl, ethylsulfinyl, methylsulfonyl, ethylsulfonyl, trifluoromethyl, pentafluoroethyl, 2,2,2-trifluoroethyl, 2,2,3,3,3-pentafluoropropyl, trifluoromethoxy, 1,1,2,2-tetrafluoroethoxy, fluoro, chloro, bromo, amidosulfonyl, N-methylamidosulfonyl, N,N-dimethylamidosulfonyl, acetyl, propanoyl, trifluoroacetyl, pentafluoropropanoyl, hydroxymethyl, 1-hydroxyethyl, 2-hydroxyethyl, 2,2,2-trifluoro-1-hydroxyethyl, 2,2,2-trifluoro-1-trifluoromethyl-1-hydroxyethyl, carboxymethyl, methoxycarbonyl, ethoxycarbonyl, amidocarbonyl, N-methylamidocarbonyl, N,N-dimethylamidocarbonyl, and cyano;

Q$^b$ is selected, when bonded to a carbon, from the group consisting of NR$^{20}$R$^{21}$, $^+$NR$^{20}$R$^{21}$R$^{22}$, dimethylsulfonium, methylethylsulfonium, diethylsulfonium, trimethylphosphonium, C(NR$^{25}$)NR$^{23}$R$^{24}$, N(R$^{26}$)C(NR$^{25}$)N(R$^{23}$)(R$^{24}$), C(O)N(R$^{26}$)C(NR$^{25}$)N(R$^{23}$)(R$^{24}$), N(R$^{26}$)N(R$^{26}$)C(NR$^{25}$)N(R$^{23}$)(R$^{24}$), N(R$^{26}$)N(R$^{26}$)SO$_2$N(R$^{23}$)(R$^{24}$), C(O)NR$^{23}$R$^{24}$, and C(O)NR$^{23}$R$^{24}$ with the provisos that no more than one of R$^{20}$, R$^{21}$, and R$^{22}$ can be hydroxy, methoxy, ethoxy, N-methylamino, N,N-dimethylamino, and N,N,N-trimethylamino, and amino and that no more than one of R$^{23}$, R$^{24}$, and R$^{26}$ can be hydroxy, methoxy, ethoxy, N-methylamino, N,N-dimethylamino, N,N,N-trimethylamino, or amino when two of the group consisting of R$^{23}$, R$^{24}$, and R$^{26}$ are bonded to the same atom and that said Q$^b$ group is bonded directly to a carbon atom;

R$^{20}$, R$^{21}$, R$^{22}$, R$^{23}$, R$^{24}$, R$^{25}$, and R$^{26}$ are independently selected from the group consisting of hydrido, methyl, ethyl, propyl, butyl, isopropyl, hydroxy, methoxy, ethoxy, isopropoxy, propoxy, 2-aminoethyl, 2-(N-methylamino)ethyl, 2-(N,N-dimethylamino)ethyl, 2-(N,N,N-trimethylamino)ethyl, N-(2-hydroxyethyl)amino, N,N-bis-(2-hydroxyethyl)amino, N-(2-hydroxyethyl)-N-(2-aminoethyl)amino, N-methylamino, N-ethylamino, N,N-dimethylamino, N,N-diethylamino, and N,N,N-trimethylamino;

Q$^b$ is selected, when bonded to a nitrogen, from the group consisting of oxy, methyl, ethyl, 2-aminoethyl, 2-(N-methylamino)ethyl, 2-(N,N-dimethylamino)ethyl, 2-(N,N,N-trimethylamino)ethyl, N-(2-hydroxyethyl)amino, N,N-bis-(2-hydroxyethyl)amino, amino, hydroxylamino, N-methoxyamino, N-methylamino, N,N-dimethylamino, and N,N,N-trimethylamino;

Q$^s$ is selected from the group consisting of a single covalent bond, CH$_2$, CH$_3$CH, CF$_2$, CF$_3$CH, CH$_2$O, CH$_3$C(H)O, CF$_3$C(H)O, CH$_2$S, CH$_3$C(H)S, CF$_3$C(H)S, CH$_2$C(O), CH$_3$C(H)C(O), CF$_3$C(H)C(O), and CF$_2$C(O) with the proviso that Q$^s$ is bonded to E$^0$ through a carbon atom.

In a more preferred specific embodiment of Formula I, compounds have the Formula I-MPS:

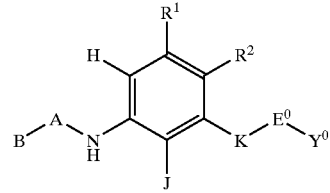

(I-MPS)

or a pharmaceutically acceptable salt thereof, wherein;

J is selected from the group consisting of fluoro, chloro, hydroxy, hydroxymethyl, amino, aminomethyl, methoxy, trifluoromethoxy, N-methylamino, methythio, and trifluoromethylthio;

B is selected from the group consisting of phenyl, 2-thienyl, 3-thienyl, 2-furyl, 3-furyl, 2-pyrrolyl, 3-pyrrolyl, 2-imidazolyl, 4-imidazolyl, 3-pyrazolyl, 4-pyrazolyl, 2-thiazolyl, 3-isoxazolyl, 5-isoxazolyl, 2-pyridyl, 3-pyridyl, 4-pyridyl, 2-pyrazinyl, 2-pyrimidinyl, 4-pyrimidinyl, 5-pyrimidinyl, 3-pyridazinyl, 4-pyridazinyl, and 1,3,5-triazin-2-yl, wherein a carbon adjacent to the carbon at the point of attachment may be substituted by R$^{32}$, the other carbon adjacent to the carbon at the point of attachment may be substituted by R$^{36}$, a carbon adjacent to R$^{32}$ and two atoms from the carbon at the point of attachment may be substituted by R$^{33}$, a carbon adjacent to R$^{36}$ and two atoms from the carbon at the point of attachment may be substituted by R$^{35}$, and any carbon adjacent to both R$^{33}$ and R$^{35}$ may be substituted by R$^{34}$;

R$^{32}$, R$^{33}$, R$^{34}$, R$^{35}$, and R$^{36}$ are independently selected from the group consisting of hydrido, amidino, guanidino, dimethylsulfonium, carboxy, methoxy, ethyoxy, isopropoxy, propoxy, hydroxy, amino, methoxyamino, ethoxyamino, thio, nitro, aminomethyl, 1-aminoethyl, 2-aminoethyl, N-N-methylamino, dimethylamino, N-ethylamino, methylthio, ethylthio, trifluoromethylthio, methylsulfinyl, ethylsulfinyl, methylsulfonyl, ethylsulfonyl, trifluoromethyl, pentafluoroethyl, 2,2,2-trifluoroethyl, 2,2,3,3,3- pentafluoropropyl, trifluoromethoxy, 1,1,2,2-tetrafluoroethoxy, fluoro, chloro, bromo, amidosulfonyl, N-methylamidosulfonyl, N,N-dimethylamidosulfonyl, acetyl, propanoyl, trifluoroacetyl, pentafluoropropanoyl, hydroxymethyl, 1-hydroxyethyl, 2-hydroxyethyl, 2,2,2-trifluoro-1-hydroxyethyl, 2,2,2-trifluoro-1-trifluoromethyl-1-hydroxyethyl, carboxymethyl, methoxycarbonyl, ethoxycarbonyl, amidocarbonyl, N-methylamidocarbonyl, N,N-dimethylamidocarbonyl, cyano, and $Q^b$;

B can be selected from the group consisting of 1-propenyl, propyl, isopropyl, butyl, 2-butenyl, 3-butenyl, sec-butyl, isobutyl, 2-methylpropenyl, 1-pentyl, 2-pentenyl, 3-pentenyl, 4-pentenyl, 2-pentynyl, 1-methyl-2-butenyl, 1-methyl-3-butenyl, 3-pentyl, 1-ethyl-2-propenyl, 2-methylbutyl, 2-methyl-2-butenyl, 2-methyl-3-butenyl, 3-methylbutyl, 3-methyl-2-butenyl, 3-methyl-3-butenyl, 2,2-difluoropropyl, 2-trifluoromethyl-3,3,3-trifluoropropyl, 1,1,1,2,2,2-hexafluoropropyl, 3,3,3-trifluoroprop-1-yl, and 3,3,3-trifluoroprop-2-yl, wherein each member of group B may be optionally substituted at any carbon up to and including 5 atoms from the point of attachment of B to A with one or more of the group consisting of $R_{32}$, $R_{33}$, $R_{34}$, $R_{35}$, and $R_{36}$;

B can be selected from the group consisting of cyclopropyl, cyclobutyl, oxetan-2-yl, oxetan-3-yl, azetidin-1-yl, azetidin-2-yl, azetidin-3-yl, thiaetan-2-yl, thiaetan-3-yl, wherein each ring carbon may be optionally substituted with $R_{33}$, a ring carbon and nitrogen atoms adjacent to the carbon atom at the point of attachment may be optionally substituted with $R_9$ or $R_{13}$, a ring carbon or nitrogen atom adjacent to the $R_9$ position and two atoms from the point of attachment may be substituted with $R_{10}$, and a ring carbon or nitrogen atom adjacent to the $R_{13}$ position and two atoms from the point of attachment may be substituted with $R_{12}$;

$R^9$, $R^{10}$, $R^{11}$, $R^{12}$, and $R^{13}$ are independently selected from the group consisting of amidino, guanidino, dimethylsulfonium, carboxy, methoxy, ethoxy, isopropoxy, propoxy, amino, methoxyamino, ethoxyamino, aminomethyl, 1-aminoethyl, 2-aminoethyl, N-N-methylamino, dimethylamino, N-ethylamino, methylsulfinyl, ethylsulfinyl, methylsulfonyl, ethylsulfonyl, amidosulfonyl, N-methylamidosulfonyl, N,N-dimethylamidosulfonyl, acetyl, propanoyl, trifluoroacetyl, pentafluoropropanoyl, hydroxymethyl, 1-hydroxyethyl, 2-hydroxyethyl, 2,2,2-trifluoro-1-hydroxyethyl, 2,2,2-trifluoro-1-trifluoromethyl-1-hydroxyethyl, carboxymethyl, 2-carboxyethyl, methoxycarbonyl, ethoxycarbonyl, amidocarbonyl, N-methylamidocarbonyl, N,N-dimethylamidocarbonyl, and dimethylamidocarbonyl, and cyano;

A is selected from the group consisting of single covalent bond, O, C(O), $CH_2$, $CH_3CH$, $CF_3CH$, $CH_3CC(O)$, $CF_3CC(O)$, C C(O)$CCH_3$, C(O)$CCF_3$, $CH_2C(O)$, and (O)$CCH_2$;

$R^1$ is selected from the group consisting of hydrido, methyl, ethyl, propyl, methoxy, ethoxy, N-methylamino, dimethylamino, N-ethylamino, methylthio, ethylthio, trifluoromethylthio, trifluoromethyl, pentafluoroethyl, 2,2,2-trifluoroethyl, 2,2,3,3,3-pentafluoropropyl, trifluoromethoxy, 1,1,2,2-tetrafluoroethoxy, fluoro, chloro, and bromo;

$R^2$ is selected from the group consisting of phenyl, 2-thienyl, 3-thienyl, 2-furyl, 3-furyl, 2-pyrrolyl, 3-pyrrolyl, 2-imidazolyl, 4-imidazolyl, 3-pyrazolyl, 4-pyrazolyl, 2-thiazolyl, 3-isoxazolyl, 5-isoxazolyl, 2-pyridyl, 3-pyridyl, 4-pyridyl, 2-pyrazinyl, 2-pyrimidinyl, 4-pyrimidinyl, 5-pyrimidinyl, 3-pyridazinyl, 4-pyridazinyl, and 1,3,5-triazin-2-yl, wherein a carbon adjacent to the carbon at the point of attachment may be substituted by $R^9$, the other carbon adjacent to the carbon at the point of attachment may be substituted by $R^{13}$, a carbon adjacent to $R^9$ and two atoms from the carbon at the point of attachment may be substituted by $R^{10}$, a carbon adjacent to $R^{13}$ and two atoms from the carbon at the point of attachment may be substituted by $R^{12}$, and any carbon adjacent to both $R^{10}$ and $R^{12}$ may be substituted by $R^{11}$;

K is $CR^{4a}R^{4b}$ wherein $R^{4a}$ and $R^{4b}$ are independently selected from the group consisting of chloro, fluoro, and hydrido;

$E^0$ is $E^1$, when K is $CR^{4a}R^{4b}$, wherein $E^1$ is selected from the group consisting of a covalent single bond, C(O)N(H), (H)NC(O), $S(O)_2N(H)$, $N(H)S(O)_2$, $S(O)_2N(H)C(O)$, and $C(O)N(H)S(O)_2$;

K can be N(H) and $CH_2N(H)$;

$E^0$ is $E^2$, when K is N(H) and $CH_2N(H)$, wherein $E^2$ is selected from the group consisting of C(O)N(H), (H)NC(O), $S(O)_2N(H)$, $N(H)S(O)_2$, $S(O)_2N(H)C(O)$, and $C(O)N(H)S(O)_2$;

$Y^0$ is selected from the group of formulas consisting of:

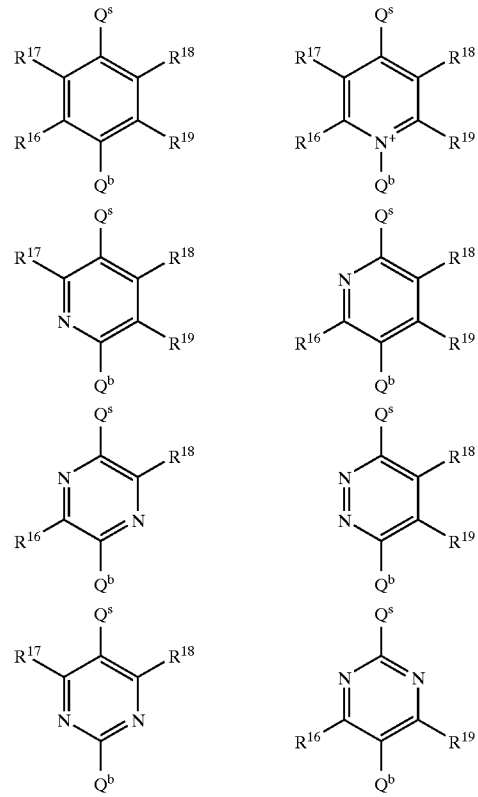

-continued

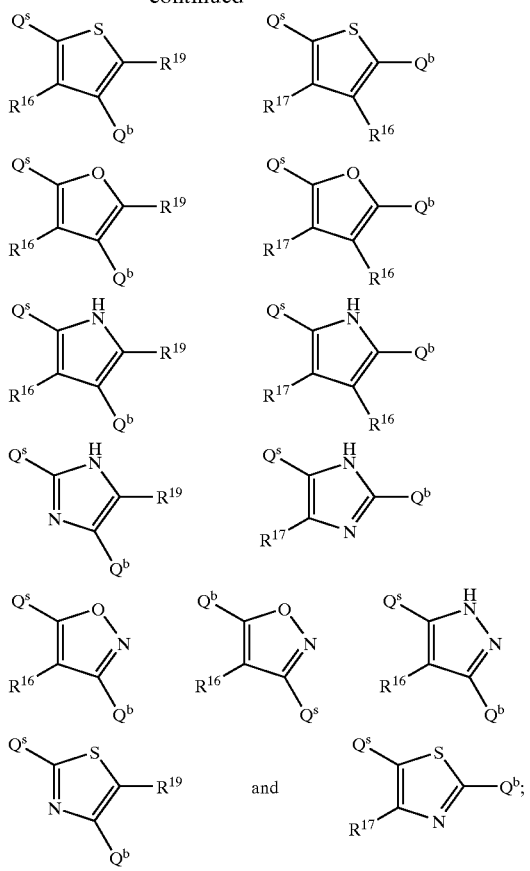

R¹⁶, R¹⁷, R¹⁸, and R¹⁹ are independently selected from the group consisting of hydrido, amidino, guanidino, methoxy, ethoxy, isopropoxy, methylthio, ethylthio, trifluoromethylthio, trifluoromethyl, pentafluoroethyl, 2,2,2-trifluoroethyl, 2,2,3,3,3-pentafluoropropyl, trifluoromethoxy, 1,1,2,2-tetrafluoroethoxy, fluoro, chloro, bromo, acetyl, propanoyl, trifluoroacetyl, pentafluoropropanoyl, methoxycarbonyl, ethoxycarbonyl, and cyano;

$Q^b$ is selected, when bonded to a carbon, from the group consisting of $NR^{20}R^{21}$, $^+NR^{20}R^{21}R^{22}$, dimethylsulfonium, methylethylsulfonium, diethylsulfonium, trimethylphosphonium, $C(NR^{25})NR^{23}R^{24}$, $N(R^{26})C(NR^{25})N(R^{23})(R^{24})$, $C(O)N(R^{26})C(NR^{25})N(R^{23})(R^{24})$, $N(R^{26})N(R^{26})C(NR^{25})N(R^{23})(R^{24})$, $N(R^{26})N(R^{26})SO_2N(R^{23})(R^{24})$, $C(O)NR^{23}R^{24}$, and $C(O)NR^{23}R^{24}$ with the provisos that no more than one of $R^{20}$, $R^{21}$, and $R^{22}$ can be hydroxy, methoxy, ethoxy, N-methylamino, N,N-dimethylamino, N,N,N-trimethylamino, or amino and that no more than one of $R^{23}$, $R^{24}$, and $R^{26}$ can be hydroxy, methoxy, ethoxy, N-methylamino, N,N-dimethylamino, N,N,N-trimethylamino, or amino when two of the group consisting of $R^{23}$, $R^{24}$, and $R^{26}$ are bonded to the same atom and tat said $Q^b$ group is bonded directly to a carbon atom;

$R^{20}$, $R^{21}$, $R^{22}$, $R^{23}$, $R^{24}$, $R^{25}$, and $R^{26}$ are independently selected from the group consisting of hydrido, methyl, ethyl, hydroxy, methoxy, ethoxy, 2-aminoethyl, 2-(N-methylamino)ethyl, 2-(N,N-dimethylamino)ethyl, 2-(N,N,N-trimethylamino)ethyl, N-(2-hydroxyethyl)amino, N,N-bis-(2-hydroxyethyl)amino, N-(2-hydroxyethyl)-N-(2-aminoethyl)amino, N-methylamino, N,N-dimethylamino, and N,N,N-trimethylamino;

$Q^b$ is selected, when bonded to a nitrogen, from the group consisting of oxy, methyl, ethyl, 2-aminoethyl, 2-(N-methylamino)ethyl, 2-(N,N-dimethylamino)ethyl, 2-(N,N,N-trimethylamino)ethyl, N-(2-hydroxyethyl)amino, N,N-bis-(2-hydroxyethyl)amino, amino, hydroxylamino, N-methoxyamino, N-methylamino, N,N-dimethylamino, and N,N,N-trimethylamino;

$Q^s$ is selected from the group consisting of a single covalent bond, $CH_2$, $CH_3CH$, $CF_2$, $CF_3CH$, $CH_2O$, $CH_3C(H)O$, $CF_3C(H)O$, $CH_2S$, $CH_3C(H)S$, $CF_3C(H)S$, $CH_2C(O)$, $CH_3C(H)C(O)$, $CF_3C(H)C(O)$, and $CF_2C(O)$ with the proviso that $Q^s$ is bonded to $E^0$ through a carbon atom.

In an even more preferred specific embodiment of compounds of Formula I, compounds have the Formula I-EMPS:

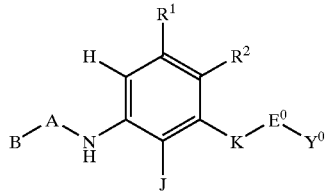

(I-EMPS)

or a pharmaceutically acceptable salt thereof, wherein;

J is selected from the group consisting of fluoro, chloro, hydroxy, hydroxymethyl, amino, aminomethyl, methoxy, trifluoromethoxy, and N-methylamino;

B is selected from the group consisting of phenyl, 2-thienyl, 3-thienyl, 2-furyl, 3-furyl, 2-pyrrolyl, 3-pyrrolyl, 2-imidazolyl, 4-imidazolyl, 3-pyrazolyl, 4-pyrazolyl, 2-thiazolyl, 3-isoxazolyl, 5-isoxazolyl, 2-pyridyl, 3-pyridyl, 4-pyridyl, wherein a carbon adjacent to the carbon at the point of attachment may be substituted by $R^{32}$, the other carbon adjacent to the carbon at the point of attachment may be substituted by $R^{36}$, a carbon adjacent to $R^{32}$ and two atoms from the carbon at the point of attachment may be substituted by $R^{33}$, a carbon adjacent to $R^{36}$ and two atoms from the carbon at the point of attachment may be substituted by $R^{35}$, and any carbon adjacent to both $R^{33}$ and $R^{35}$ may be substituted by $R^{34}$;

$R^{32}$, $R^{33}$, $R^{34}$, $R^{35}$, and $R^{36}$ are independently selected from the group consisting of hydrido, amidino, guanidino, methoxy, ethyoxy, hydroxy, amino, methoxyamino, ethoxyamino, aminomethyl, 1-aminoethyl, 2-aminoethyl, N-N-methylamino, dimethylamino, N-ethylamino, trifluoromethyl, pentafluoroethyl, 2,2,2-trifluoroethyl, 2,2,3,3,3-pentafluoropropyl, fluoro, chloro, bromo, hydroxymethyl, 1-hydroxyethyl, 2-hydroxyethyl, 2,2,2-trifluoro-1-hydroxyethyl, 2,2,2-trifluoro-1-trifluoromethyl-1-hydroxyethyl, methoxycarbonyl, ethoxycarbonyl, cyano, and $Q^b$;

B can be selected from the group consisting of propyl, isopropyl, butyl, sec-butyl, isobutyl, 1-pentyl, 2-pentenyl, 3-pentenyl, 2-methylbutyl, 3-methylbutyl, 2,2-difluoropropyl, 2-trifluoromethyl-3,3,3-trifluoropropyl, 1,1,1,2,2,2-hexafluoropropyl, 3,3,3-trifluoroprop-1-yl, and 3,3,3-trifluoroprop-2-yl, wherein each member of group B may be optionally substituted at any carbon up to and including 5 atoms from the point of attachment of B to A with one or more of the group consisting of $R_{32}$, $R_{33}$, $R_{34}$, $R_{35}$, and $R_{36}$;

B can be selected from the group consisting of cyclopropyl, cyclobutyl, oxetan-2-yl, oxetan-3-yl, azetidin-1-yl, azetidin-2-yl, azetidin-3-yl, thiaetan-2-yl, thiaetan-3-yl, wherein each ring carbon may be optionally substituted with $R_{33}$, a ring carbon and nitrogen atoms adjacent to the carbon atom at the point of attachment may be optionally substituted with $R_9$ or $R_{13}$, a ring carbon or nitrogen atom adjacent to the $R_9$ position and two atoms from the point of attachment may be substituted with $R_{10}$, and a ring carbon or nitrogen atom adjacent to the $R_{13}$ position and two atoms from the point of attachment may be substituted with $R_{12}$;

$R^9$, $R^{10}$, $R^{11}$, $R^{12}$, and $R^{13}$ are independently selected from the group consisting of amidino, guanidino, carboxy, methoxy, ethoxy, hydroxy, amino, methoxyamino, ethoxyamino, aminomethyl, 1-aminoethyl, 2-aminoethyl, N-N-methylamino, dimethylamino, N-ethylamino, acetyl, propanoyl, trifluoroacetyl, pentafluoropropanoyl, hydroxymethyl, 1-hydroxyethyl, 2-hydroxyethyl, carboxymethyl, methoxycarbonyl, ethoxycarbonyl, amidocarbonyl, N-methylamidocarbonyl, N,N-dimethylamidocarbonyl, and cyano;

A is selected from the group consisting of single covalent bond, O, C(O), $CH_2$, $CH_2C(O)$, and $(O)CCH_2$;

$R^1$ is selected from the group consisting of hydrido, methyl, ethyl, methoxy, ethoxy, N-methylamino, dimethylamino, N-ethylamino, trifluoromethylthio, pentafluoroethyl, 2,2,2-trifluoroethyl, fluoro, chloro, and bromo;

$R^2$ is selected from the group consisting of phenyl, 2-thienyl, 3-thienyl, 2-furyl, 3-furyl, 2-pyrrolyl, 3-pyrrolyl, 2-imidazolyl, 4-imidazolyl, 3-pyrazolyl, 4-pyrazolyl, 2-thiazolyl, 3-isoxazolyl, 5-isoxazolyl, 2-pyridyl, 3-pyridyl, 4-pyridyl, 2-pyrazinyl, 2-pyrimidinyl, 4-pyrimidinyl, 5-pyrimidinyl, 3-pyridazinyl, 4-pyridazinyl, and 1,3,5-triazin-2-yl, wherein a carbon adjacent to the carbon at the point of attachment may be substituted by $R^9$, the other carbon adjacent to the carbon at the point of attachment may be substituted by $R^{13}$, a carbon adjacent to $R^9$ and two atoms from the carbon at the point of attachment may be substituted by $R^{10}$, a carbon adjacent to $R^{13}$ and two atoms from the carbon at the point of attachment may be substituted by $R^{12}$, and any carbon adjacent to both $R^{10}$ and $R^{12}$ may be substituted by $R^{11}$;

K is $CR^{4a}R^{4b}$ wherein $R^{4a}$ and $R^{4b}$ are independently selected from the group consisting of chloro, fluoro, and hydrido;

$E^0$ is $E^1$, when K is $CR^{4a}R^{4b}$, wherein $E^1$ is selected from the group consisting of a covalent single bond, C(O)N(H), (H)NC(O), $S(O)_2N(H)$, $N(H)S(O)_2$, $S(O)_2N(H)C(O)$, and $C(O)N(H)S(O)_2$;

K can be N(H) and $CH_2N(H)$;

$E^0$ is $E^2$, when K is N(H) and $CH_2N(H)$, wherein $E^2$ is selected from the group consisting of C(O)N(H), (H)NC(O), $S(O)_2N(H)$, $N(H)S(O)_2$, $S(O)_2N(H)C(O)$, and $C(O)N(H)S(O)_2$;

$Y^0$ is selected from the group of formulas consisting of:

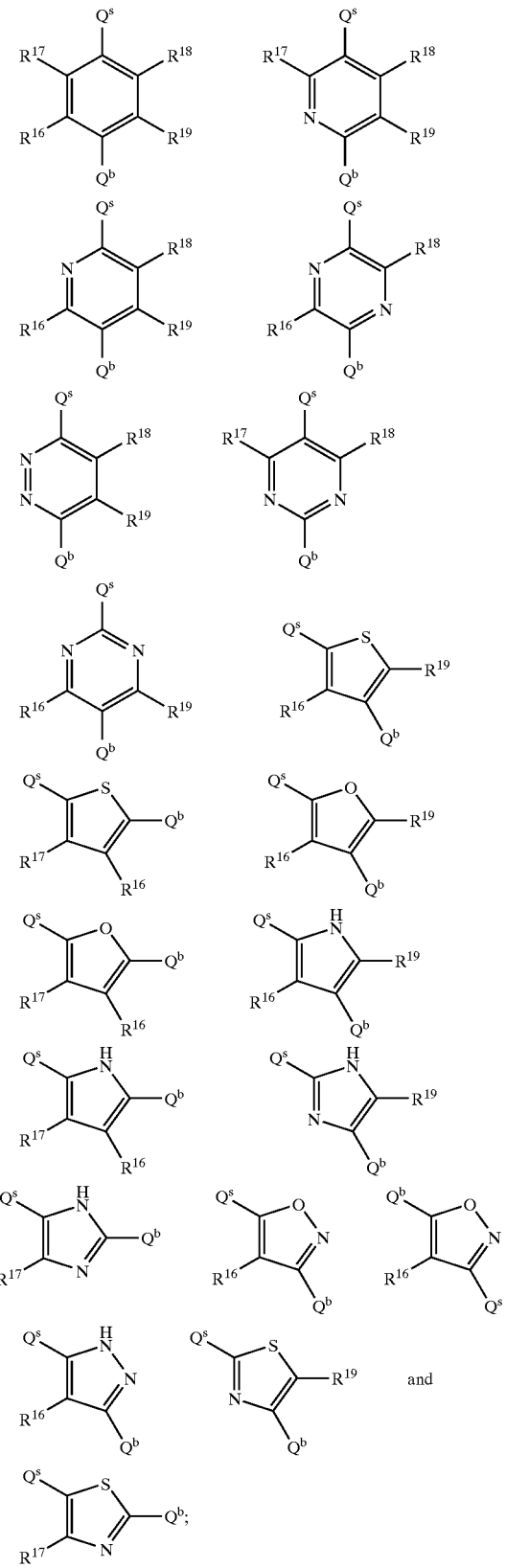

and $R^{16}$, $R^{17}$, $R^{18}$, and $R^{19}$ are independently selected from the group consisting of hydrido, methoxy, ethoxy, trifluoromethyl, pentafluoroethyl, 2,2,2-trifluoroethyl, trifluoromethoxy, fluoro, chloro, bromo, acetyl, trifluoroacetyl, methoxycarbonyl, ethoxycarbonyl, and cyano;

$Q^b$ is selected from the group consisting of $NR^{20}R^{21}$, $^+NR^{20}R^{21}R^{22}$, dimethylsulfonium, methylethylsulfonium, diethylsulfonium, trimethylphosphonium, $C(NR^{25})NR^{23}R^{24}$, $N(R^{26})C(NR^{25})N(R^{23})(R^{24})$, $C(O)N(R^{26})C(NR^{25})N(R^{23})(R^{24})$, $N(R^{26})N(R^{25})N(R^{23})(R^{24})$, $N(R^{26})N(R^{26})C(NR^{25})N(R^{23})(R^{24})$, $N(R^{26})N(R^{26})SO_2N(R^{23})(R^{24})$, $C(O)NR^{23}R^{24}$, and $C(O)NR^{23}R^{24}$ with the provisos that no more than one of $R^{20}$, $R^{21}$, and $R^{22}$ can be hydroxy, methoxy, ethoxy, N-methylamino, N,N-dimethylamino, N,N,N-trimethylamino, or amino and that no more than one of $R^{23}$, $R^{24}$, and $R^{26}$ can be hydroxy, methoxy, ethoxy, N-methylamino, N,N-dimethylamino, N,N,N-trimethylamino, or amino when two of the group consisting of $R^{23}$, $R^{24}$, and $R^{26}$ are bonded to the same atom and that said $Q^b$ group is bonded directly to a carbon atom;

$R^{20}$, $R^{21}$, $R^{22}$, $R^{23}$, $R^{24}$, $R^{25}$, and $R^{26}$ are independently selected from the group consisting of hydrido, methyl, ethyl, hydroxy, methoxy, ethoxy, 2-aminoethyl, 2-(N-methylamino)ethyl, 2-(N,N-dimethylamino)ethyl, 2-(N,N,N-trimethylamino)ethyl, N-(2-hydroxyethyl)amino, N,N-bis-(2-hydroxyethyl)amino, N-(2-hydroxyethyl)-N-(2-aminoethyl)amino, N-methylamino, N,N-dimethylamino, and N,N,N-trimethylamino;

$Q^s$ is selected from the group consisting of a single covalent bond, $CH_2$, $CH_3CH$, $CF_2$, $CF_3CH$, $CH_2O$, $CH_3C(H)O$, $CF_3C(H)O$, $CH_2C(O)$, $CH_3C(H)C(O)$, $CF_3C(H)C(O)$, and $CF_2C(O)$ with the proviso that $Q^s$ is bonded to $E^0$ through a carbon atom.

In another preferred embodiment of a compound of Formula I, said compound is the Formula:

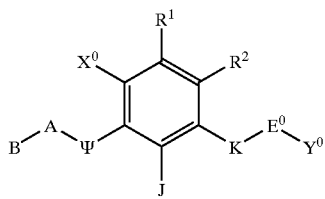

or a pharmaceutically acceptable salt thereof, wherein;

J is selected from the group consisting of halo, haloalkyl, hydroxy, hydroxyalkyl, amino, aminoalkyl, amidino, carboxy, carboxamido, alkylsulfinyl, acyl, cyano, O—$R^6$, NH—$R^6$, and S—$R^6$, wherein $R^6$ is alkyl or haloalkyl;

B is phenyl or a heteroaryl of 5 or 6 ring members, wherein a nitrogen with a removable hydrogen or a carbon adjacent to the carbon at the point of attachment of said phenyl or heteroaryl ring to A is optionally substituted by $R^{32}$, a nitrogen with a removable hydrogen or a carbon at the other position adjacent to the point of attachment is optionally substituted by $R^{36}$, a nitrogen with a removable hydrogen or a carbon adjacent to $R^{32}$ and two atoms from the point of attachment is optionally substituted by $R^{33}$, a nitrogen with a removable hydrogen or a carbon adjacent to $R^{36}$ and two atoms from the point of attachment is optionally substituted by $R^{35}$, and a nitrogen with a removable hydrogen or a carbon adjacent to both $R^{33}$ and $R^{35}$ is optionally substituted by $R^{34}$;

$R^9$, $R^{10}$, $R^{11}$, $R^{12}$, $R^{13}$, $R^{32}$, $R^{33}$, $R^{34}$, $R^{35}$, and $R^{36}$ are independently selected from the group consisting of hydrido, acetamido, haloacetamido, amidino, guanidino, alkylenedioxy, haloalkylthio, alkanoyloxy, alkoxy, cycloalkoxy, cycloalkylalkoxy, aralkoxy, aryloxy, heteroaryloxy, heteroaralkoxy, heterocyclyloxy, heterocyclylalkoxy, alkoxyalkyl, haloalkoxyalkyl, hydroxy, amino, alkoxyamino, nitro, alkylamino, N-alkyl-N-arylamino, arylamino, aralkylamino, heteroarylamino, heteroaralkylamino, heterocyclylamino, heterocyclylalkylamino, alkylthio, alkylthioalkyl, alkylsulfinyl, arylsulfinyl, aralkylsulfinyl, cycloalkylsulfinyl, heteroarylsulfinyl, alkylsulfonyl, arylsulfonyl, aralkylsulfonyl, cycloalkylsulfonyl, heteroarylsulfonyl, alkylsulfonylalkyl, aryl, aralkyl, cycloalkyl, cycloalkylalkyl, heteroaryl, heterocyclyl, alkylsulfonamido, amidosulfonyl, alkanoyl, haloalkanoyl, alkyl, alkenyl, halo, haloalkyl, haloalkenyl, haloalkoxy, hydroxyhaloalkyl, hydroxyalkyl, aminoalkyl, haloalkoxyalkyl, carboxyalkyl, carboalkoxy, carboxy, carboxamido, carboxamidoalkyl, and cyano;

$R^{32}$, $R^{33}$, $R^{34}$, $R^{35}$, and $R^{36}$ are independently optionally $Q^b$;

B is optionally selected from the group consisting of hydrido, trialkylsilyl, C2–C8 alkyl, C3–C8 alkylenyl, C3–C8 alkenyl, C3–C8 alkynyl, and C2–C8 haloalkyl, wherein each member of group B is optionally substituted at any carbon up to and including 6 atoms from the point of attachment of B to A with one or more of the group consisting of $R^{32}$, $R^{33}$, $R^{34}$, $R^{35}$, and $R^{36}$;

B is optionally a C3–C12 cycloalkyl or C4–C9 saturated heterocyclyl, wherein each ring carbon is optionally substituted with $R^{33}$, a ring carbon other than the ring carbon at the point of attachment of B to A is optionally substituted with oxo provided that no more than one ring carbon is substituted by oxo at the same time, ring carbons and a nitrogen adjacent to the carbon atom at the point of attachment are optionally substituted with $R^9$ or $R^{13}$, a ring carbon or nitrogen atom adjacent to the $R^9$ position and two atoms from the point of attachment is optionally substituted with $R^{10}$, a ring carbon or nitrogen adjacent to the $R^{13}$ position and two atoms from the point of attachment is optionally substituted with $R^{12}$, a ring carbon or nitrogen three atoms from the point of attachment and adjacent to the $R^{10}$ position is optionally substituted with $R^{11}$, a ring carbon or nitrogen three atoms from the point of attachment and adjacent to the $R^{12}$ position is optionally substituted with $R^{33}$, and a ring carbon or nitrogen four atoms from the point of attachment and adjacent to the $R^{11}$ and $R^{33}$ positions is optionally substituted with $R^{34}$;

A is selected from the group consisting of a bond, $(W^7)_{rr}$—$(CH(R^{15}))_{pa}$, and $(CH(R^{15}))_{pa}$—$(W^7)_{rr}$ wherein rr is 0 or 1, pa is an integer selected from 0 through 6, and $W^7$ is selected from the group consisting of O, S, C(O), $(R^7)NC(O)$, $(R^7)NC(S)$, and $N(R^7)$ with the proviso that no more than one of the group consisting of rr and pa is 0 at the same time and with the further proviso that $W^7$ is selected from other than C(O) when $W^7$ is bonded to Ψ;

$R^7$ is selected from the group consisting of hydrido, hydroxy, and alkyl;

$R^{15}$ is selected from the group consisting of hydrido, hydroxy, halo, alkyl, and haloalkyl;

Ψ is NH or NOH;

$X^0$ and $R^1$ are independently selected from the group consisting of hydrido, alkyl, alkenyl, cyano, halo, haloalkyl, haloalkoxy, haloalkylthio, amino, aminoalkyl, alkylamino, amidino, hydroxy, hydroxyamino, alkoxy, hydroxyalkyl, alkoxyamino, thiol, and alkylthio;

$R^2$ is $Z^0$—Q;

$Z^0$ is selected from the group consisting of a bond, $(CR^{41}R^{42})_q$ wherein q is an integer selected from 1 through 3, and $(CH(R^{41}))_g$—$W^0$—$(CH(R^{42}))_p$ wherein g and p are integers independently selected from 0 through 3 and $W^0$ is selected from the group consisting of O, S, C(O), S(O), $N(R^{41})$, and $ON(R^{41})$;

$Z^0$ is optionally $(CH(R^{41}))_e$—$W^{22}$—$(CH(R^{42}))_h$ wherein e and h are independently 0 or 1 and $W^{22}$ is selected from the group consisting of $CR^{41}$=$CR^{42}$, 1,2-cyclopropyl, 1,2-cyclobutyl, 1,2-cyclohexyl, 1,3-cyclohexyl, 1,2-cyclopentyl, 1,3-cyclopentyl, 2,3-morpholinyl, 2,4-morpholinyl, 2,6-morpholinyl, 3,4-morpholinyl, 3,5-morpholinyl, 1,2-piperazinyl, 1,3-piperazinyl, 2,3-piperazinyl, 2,6-piperazinyl, 1,2-piperidinyl, 1,3-piperidinyl, 2,3-piperidinyl, 2,4-piperidinyl, 2,6-piperidinyl, 3,4-piperidinyl, 1,2-pyrrolidinyl, 1,3-pyrrolidinyl, 2,3-pyrrolidinyl, 2,4-pyrrolidinyl, 2,5-pyrrolidinyl, 3,4-pyrrolidinyl, 2,3-tetrahydrofuranyl, 2,4-tetrahydrofuranyl, 2,5-tetrahydrofuranyl, and 3,4-tetrahydrofuranyl, wherein $Z^0$ is directly bonded to the benzene ring and $W^{22}$ is optionally substituted with one or more substituents selected from the group consisting of $R^9$, $R^{10}$, $R^{11}$, $R^{12}$, and $R^{13}$;

$R^{41}$ and $R^{42}$ are independently selected from the group consisting of amidino, hydroxyamino, hydrido, hydroxy, amino, and alkyl;

Q is phenyl or a heteroaryl of 5 or 6 ring members, wherein a nitrogen with a removable hydrogen or a carbon adjacent to the carbon at the point of attachment of said phenyl or heteroaryl ring to $Z^0$ is optionally substituted by $R^9$, a nitrogen with a removable hydrogen or a carbon at the other position adjacent to the point of attachment is optionally substituted by $R^{13}$, a nitrogen with a removable hydrogen or a carbon adjacent to $R^9$ and two atoms from the point of attachment is optionally substituted by $R^{10}$, a nitrogen with a removable hydrogen or a carbon adjacent to $R^{13}$ and two atoms from the point of attachment is optionally substituted by $R^{12}$, and a nitrogen with a removable hydrogen or a carbon adjacent to both $R^{10}$ and $R^{12}$ is optionally substituted by $R^{11}$;

Q is optionally hydrido with the proviso that $Z^0$ is selected from other than a bond;

K is $CR^{4a}R^{4b}$;

$R^{4a}$ and $R^{4b}$ are independently selected from the group consisting of halo, hydrido, hydroxy, alkyl, and haloalkyl;

$E^0$, with the proviso that K is $CR^{4a}R^{4b}$, is $E^1$ wherein $E^1$ is selected from the group consisting of a covalent single bond, C(O)N(H), (H)NC(O), C(S)N(H), (H)NC(S), $S(O)_2N(H)$, $N(H)S(O)_2$, $S(O)_2N(H)C(O)$, and $C(O)N(H)S(O)_2$;

K is optionally $(CH(R^{14}))_j$—T wherein j is 0 or 1 and T is a bond or $N(R^7)$ with the proviso that $(CH(R^{14}))_j$ is bonded to the phenyl ring;

$R^{14}$ is selected from the group consisting of hydrido, halo, alkyl, and haloalkyl;

$E^0$, with the proviso that K is $(CH(R^{14}))_j$—T, is $E^2$ wherein $E^2$ is selected from the group consisting of C(O)N(H), (H)NC(O), C(S)N(H), (H)NC(S), $S(O)_2N$ (H), $N(H)S(O)_2$, $S(O)_2N(H)C(O)$, and $C(O)N(H)S(O)_2$;

$Y^0$ is phenyl or a heteroaryl of 5 or 6 ring members, wherein one carbon of said phenyl or said heteroaryl is substituted by $Q^s$, a carbon two or three contiguous atoms from the point of attachment of $Q^s$ to said phenyl or said heteroaryl to said phenyl or said heteroaryl is substituted by $Q^b$, a carbon adjacent to the point of attachment of $Q^s$ is optionally substituted by $R^{17}$, another carbon adjacent to the point of attachment of $Q^s$ is optionally substituted by $R^{18}$, a carbon adjacent to $Q^b$ is optionally substituted by $R^{16}$, and another carbon adjacent to $Q^b$ is optionally substituted by $R^{19}$;

$R^{16}$, $R^{17}$, $R^{18}$, and $R^{19}$ are independently selected from the group consisting of hydrido, amidino, guanidino, carboxy, haloalkylthio, alkoxy, hydroxy, amino, nitro, alkoxyamino, alkylamino, alkylthio, alkylsulfinyl, alkylsulfonyl, alkanoyl, haloalkanoyl, alkyl, alkenyl, halo, haloalkyl, haloalkoxy, hydroxyalkyl, aminoalkyl, haloalkoxyalkyl, carboalkoxy, and cyano;

$R^{16}$ or $R^{19}$ is optionally selected from the group consisting of $NR^{20}R^{21}$, $N(R^{26})C(NR^{25})N(R^{23})(R^{24})$, and $C(NR^{25})NR^{23}R^{24}$, with the proviso that $R^{16}$, $R^{19}$, and $Q^b$ are not simultaneously hydrido;

$Q^b$ is selected from the group consisting of $NR^{20}R^{21}$, aminoalkyl, hydrido, $N(R^{26})C(NR^{25})N(R^{23})(R^{24})$, and $C(NR^{25})NR^{23}R^{24}$, with the proviso that no more than one of $R^{20}$ and $R^{21}$ is selected from the group consisting of hydroxy, amino, alkylamino, and dialkylamino at the same time, with the further proviso that no more than one of $R^{23}$ and $R^{24}$ is selected from the group consisting of hydroxy, amino, alkylamino, and dialkylamino at the same time;

$R^{20}$, $R^{21}$, $R^{23}$, $R^{24}$, $R^{25}$, and $R^{26}$ are independently selected from the group consisting of hydrido, alkyl, hydroxy, aminoalkyl, amino, dialkylamino, alkylamino, and hydroxyalkyl;

$Q^s$ is selected from the group consisting of a bond, $(CR^{37}R^{38})_b$ wherein b is an integer selected from 1 through 4, and $(CH(R^{14}))_c$—$W^1$—$(CH(R^{15}))_d$ wherein c and d are integers independently selected from 1 through 3 and $W^1$ is selected from the group consisting of $C(O)N(R^{14})$, $(R^{14})NC(O)$, S(O), $S(O)_2$, $S(O)_2N$ $(R^{14})$, $N(R^{14})S(O)_2$, and $N(R^{14})$, with the proviso that $R^{14}$ is selected from other than halo when directly bonded to N, and with the additional proviso that $(CR^{37}R^{38})_b$ and $(CH(R^{14}))_c$ are bonded to $E^0$;

$R^{37}$ and $R^{38}$ are independently selected from the group consisting of hydrido, alkyl, and haloalkyl;

$R^{38}$ is optionally aroyl or heteroaroyl, wherein $R^{38}$ is optionally substituted with one or more substituents selected from the group consisting of $R^{16}$, $R^{17}$, $R^{18}$, and $R^{19}$;

$Y^0$ is optionally $Y^{AT}$ wherein $Y^{AT}$ is $Q^b$—$Q^s$;

$Y^0$ is optionally $Q^b$—$Q^{ss}$ wherein $Q^{ss}$ is $(CH(R^{14}))_e$—$W^2$—$(CH(R^{15}))_h$, wherein e and h are independently 1 or 2 and $W^2$ is $CR^{4a}$=$CR^{4b}$, with the proviso that $(CH(R^{14}))_e$ is bonded to $E^0$.

In another more preferred embodiment of a compound of Formula I, said compound is the Formula:

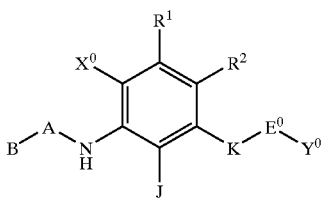

or a pharmaceutically acceptable salt thereof, wherein;

J is selected from the group consisting of halo, haloalkyl, hydroxy, hydroxyalkyl, amino, aminoalkyl, amidino, carboxy, carboxamido, alkylsulfinyl, formyl, cyano, O—$R^6$, NH—$R^6$, and S—$R^6$, wherein $R^6$ is alkyl or haloalkyl;

B is phenyl or a heteroaryl of 5 or 6 ring members, wherein a carbon adjacent to the carbon at the point of attachment of said phenyl or heteroaryl ring to A is optionally substituted by $R^{32}$, the other carbon adjacent to the carbon at the point of attachment is optionally substituted by $R^{36}$, a carbon adjacent to $R^{32}$ and two atoms from the carbon at the point of attachment is optionally substituted by $R^{33}$, a carbon adjacent to $R^{36}$ and two atoms from the carbon at the point of attachment is optionally substituted by $R^{35}$, and any carbon adjacent to both $R^{33}$ and $R^{35}$ is optionally substituted by $R^{34}$;

$R^{32}$, $R^{33}$, $R^{34}$, $R^{35}$, and $R^{36}$ are independently selected from the group consisting of hydrido, acetamido, haloacetamido, amidino, guanidino, alkylenedioxy, haloalkylthio, alkanoyloxy, alkoxy, hydroxy, amino, alkoxyamino, haloalkanoyl, nitro, alkylamino, alkylthio, aryl, aralkyl, cycloalkyl, cycloalkylalkyl, heteroaryl, heterocyclyl, alkylsulfonamido, amidosulfonyl, alkyl, alkenyl, halo, haloalkyl, haloalkenyl, haloalkoxy, hydroxyalkyl, hydroxyhaloalkyl, aminoalkyl, carboalkoxy, carboxy, carboxamido, cyano, and $Q^b$;

B is optionally selected from the group consisting of hydrido, trialkylsilyl, C2–C8 alkyl, C3–C8 alkylenyl, C3–C8 alkenyl, C3–C8 alkynyl, and C2–C8 haloalkyl, wherein each member of group B is optionally substituted at any carbon up to and including 6 atoms from the point of attachment of B to A with one or more of the group consisting of $R^{32}$, $R^{33}$, $R^{34}$, $R^{35}$, and $R^{36}$;

B is optionally a C3–C12 cycloalkyl or a C4–C9 saturated heterocyclyl, wherein each ring carbon is optionally substituted with $R^{33}$, a ring carbon other than the ring carbon at the point of attachment of B to A is optionally substituted with oxo provided that no more than one ring carbon is substituted by oxo at the same time, ring carbons and a nitrogen adjacent to the carbon atom at the point of attachment are optionally substituted with $R^9$ or $R^{13}$, a ring carbon or nitrogen atom adjacent to the $R^9$ position and two atoms from the point of attachment is optionally substituted with $R^{10}$, a ring carbon or nitrogen atom adjacent to the $R^{13}$ position and two atoms from the point of attachment is optionally substituted with $R^{12}$, a ring carbon or nitrogen atom three atoms from the point of attachment and adjacent to the $R^{10}$ position is optionally substituted with $R^{11}$, a ring carbon or nitrogen atom three atoms from the point of attachment and adjacent to the $R^{12}$ position is optionally substituted with $R^{33}$, and a ring carbon or nitrogen atom four atoms from the point of attachment and adjacent to the $R^{11}$ and $R^{33}$ positions is optionally substituted with $R^{34}$;

$R^9$, $R^{10}$, $R^{11}$, $R^{12}$, and $R^{13}$ are independently selected from the group consisting of hydrido, acetamido, haloacetamido, alkoxyamino, alkanoyl, haloalkanoyl, amidino, guanidino, alkylenedioxy, haloalkylthio, alkoxy, cycloalkoxy, cycloalkylalkoxy, aralkoxy, aryloxy, heteroaryloxy, heteroaralkoxy, heterocyclyloxy, heterocyclylalkoxy, hydroxy, amino, alkylamino, N-alkyl-N-arylamino, arylamino, aralkylamino, heteroarylamino, heteroaralkylamino, heterocyclylamino, heterocyclylalkylamino, alkylthio, alkylsulfinyl, arylsulfinyl, aralkylsulfinyl, cycloalkylsulfinyl, heteroarylsulfinyl, alkylsulfamido, akylsulfonyl, arylsulfonyl, aralkylsulfonyl, cycloalkylsulfonyl, heteroarylsulfonyl, amidosulfonyl, alkyl, aryl, aralkyl, cycloalkyl, cycloalkylalkyl, heteroaryl, heterocyclyl, halo, haloalkyl, haloalkoxy, hydroxyalkyl, hydroxyhaloalkyl, aminoalkyl, carboalkoxy, carboxy, carboxyalkyl, carboxamido, and cyano;

A is bond or $(CH(R^{15}))_{pa}$—$(W^7)_{rr}$ wherein rr is 0 or 1, pa is an integer selected from 0 through 3, and $W^7$ is selected from the group consisting of O, S, C(O), $(R^7)NC(O)$, $(R^7)NC(S)$, and $N(R^7)$, with the further proviso that $W^7$ is selected from other than C(O) when $W^7$ is bonded to the N(H) on the benzene ring;

$R^7$ is selected from the group consisting of hydrido, hydroxy and alkyl;

$R^{15}$ is selected from the group consisting of hydrido, hydroxy, halo, alkyl, and haloalkyl;

$R^1$ and $X^0$ is selected from the group consisting of hydrido, alkyl, cyano, halo, haloalkyl, haloalkoxy, amino, aminoalkyl, alkylamino, amidino, hydroxy, hydroxyamino, alkoxy, hydroxyalkyl, alkoxyamino, thiol, and alkylthio;

$R^2$ is $Z^0$—Q;

$Z^0$ is selected from the group consisting of a bond, $(CR^{41}R^{42})_q$ wherein q is 1 or 2, and $(CH(R^{41}))_g$—$W^0$—$(CH(R^{42}))_p$ wherein g and p are integers independently selected from 0 through 3 and $W^0$ is selected from the group consisting of O, S, C(O), S(O), $N(R^{41})$, and $ON(R^{41})$;

$Z^0$ is optionally $(CH(R^{41}))_e$—$W^{22}$—$(CH(R^{42})_h$ wherein e and h are independently 0 or 1 and $W^{22}$ is selected from the group consisting of $CR^{41}$=$CR^{42}$, 1,2-cyclopropyl, 1,2-cyclobutyl, 1,2-cyclohexyl, 1,3-cyclohexyl, 1,2-cyclopentyl, 1,3-cyclopentyl, 2,3-morpholinyl, 2,4-morpholinyl, 2,6-morpholinyl, 3,4-morpholinyl, 3,5-morpholinyl, 1,2-piperazinyl, 1,3-piperazinyl, 2,3-piperazinyl, 2,6-piperazinyl, 1,2-piperidinyl, 1,3-piperidinyl, 2,3-piperidinyl, 2,4-piperidinyl, 2,6-piperidinyl, 3,4-piperidinyl, 1,2-pyrrolidinyl, 1,3-pyrrolidinyl, 2,3-pyrrolidinyl, 2,4-pyrrolidinyl, 2,5-pyrrolidinyl, 3,4-pyrrolidinyl, 2,3-tetrahydrofuranyl, 2,4-tetrahydrofuranyl, 2,5-tetrahydrofuranyl, and 3,4-tetrahydrofuranyl, wherein $Z^0$ is directly bonded to the benzene ring and $W^{22}$ is optionally substituted with one or more substituents selected from the group consisting of $R^9$, $R^{10}$, $R^{11}$, $R^{12}$, and $R^{13}$;

$R^{41}$ and $R^{42}$ are independently selected from the group consisting of hydrido, hydroxy, and amino;

Q is phenyl or a heteroaryl of 5 or 6 ring members, wherein a carbon adjacent to the carbon at the point of attachment of said phenyl or heteroaryl ring to $Z^0$ is optionally substituted by $R^9$, the other carbon adjacent to the carbon at the point of attachment is optionally substituted by $R^{13}$, a carbon adjacent to $R^9$ and two atoms from the carbon at the point of attachment is optionally substituted by $R^{10}$, a carbon adjacent to $R^{13}$ and two atoms from the carbon at the point of attachment is optionally substituted by $R^{12}$, and any carbon adjacent to both $R^{10}$ and $R^{12}$ is optionally substituted by $R^{11}$;

Q is optionally hydrido with the proviso that $Z^0$ is other than a bond;

K is $CR^{4a}R^{4b}$;

$R^{4a}$ and $R^{4b}$ are independently selected from the group consisting of halo, hydrido, and hydroxy;

$E^0$, with the proviso that K is $CR^{4a}R^{4b}$, is $E^1$ wherein $E^1$ is selected from the group consisting of a covalent single bond, C(O)N(H), (H)NC(O), S(O)$_2$N(H), and N(H)S(O)$_2$;

K is optionally $(CH(R^{14}))_j$—T wherein j is 0 or 1 and T is a bond or $N(R^7)$ with the proviso that $(CH(R^{14}))_j$ is bonded to the phenyl ring;

$R^{14}$ is hydrido or halo;

$E^0$, with the proviso that K is $(CH(R^{14}))_j$—T, is $E^2$ wherein $E^2$ is selected from the group consisting of C(O)N(H), (H)NC(O), C(S)N(H), (H)NC(S), S(O)$_2$N(H), N(H)S(O)$_2$, S(O)$_2$N(H)C(O), and C(O)N(H)S(O)$_2$;

$Y^0$ is phenyl or a heteroaryl of 5 or 6 ring members, wherein one carbon of said phenyl or said heteroaryl is substituted by $Q^s$, a carbon two or three atoms from the point of attachment of $Q^s$ to said phenyl or said heteroaryl is substituted by $Q^b$, a carbon adjacent to the point of attachment of $Q^s$ is optionally substituted by $R^{17}$, another carbon adjacent to the point of attachment of $Q^s$ is optionally substituted by $R^{18}$, a carbon adjacent to $Q^b$ is optionally substituted by $R^{16}$, and another carbon adjacent to $Q^b$ is optionally substituted by $R^{19}$;

$R^{16}$, $R^{17}$, $R^{18}$, and $R^{19}$ are independently selected from the group consisting of hydrido, amidino, guanidino, carboxy, haloalkylthio, alkoxy, hydroxy, amino, alkoxyamino, alkylamino, alkylthio, alkylsulfinyl, alkylsulfonyl, alkanoyl, haloalkanoyl, alkyl, halo, haloalkyl, haloalkoxy, hydroxyalkyl, aminoalkyl, and cyano;

$R^{16}$ or $R^{19}$ is optionally selected from the group consisting of $NR^{20}R^{21}$, $N(R^{26})C(NR^{25})N(R^{23})(R^{24})$, and $C(NR^{25})NR^{23}R^{24}$, with the proviso that $R^{16}$, $R^{19}$, and $Q^b$ are not simultaneously hydrido;

$Q^b$ is selected from the group consisting of $NR^{20}R^{21}$, hydrido, $N(R^{26})C(NR^{25})N(R^{23})(R^{24})$, and $C(NR^{25})NR^{23}R^{24}$, with the proviso that no more than one of $R^{20}$ and $R^{21}$ is selected from the group consisting of hydroxy, amino, alkylamino, and dialkylamino at the same time, with the further proviso that no more than one of $R^{23}$ and $R^{24}$ is selected from the group consisting of hydroxy, amino, alkylamino, and dialkylamino at the same time;

$R^{20}$, $R^{21}$, $R^{23}$, $R^{24}$, $R^{25}$, and $R^{26}$ are independently selected from the group consisting of hydrido, alkyl, hydroxy, amino, alkylamino and dialkylamino;

$Q^s$ is selected from the group consisting of a bond, $(CR^{37}R^{38})_b$ wherein b is an integer selected from 1 through 4, and $(CH(R^{14}))_c$—$W^1$—$(CH(R^{15}))_d$ wherein c and d are integers independently selected from 1 through 3 and $W^1$ is selected from the group consisting of $C(O)N(R^{14})$, $(R^{14})NC(O)$, S(O), S(O)$_2$, S(O)$_2$N $(R^{14})$, $N(R^{14})S(O)_2$, and $N(R^{14})$, with the proviso that $R^{14}$ is selected from other than halo when directly bonded to N, and with the additional proviso that $(CR^{37}R^{38})_b$ and $(CR^{37}R^{38})_b$, and $(CH(R^{14}))_c$ are bonded to $E^0$;

$R^{37}$ and $R^{38}$ are independently selected from the group consisting of hydrido, alkyl, and haloalkyl;

$R^{38}$ is optionally aroyl or heteroaroyl, wherein $R^{38}$ is optionally substituted with one or more substituents selected from the group consisting of $R^{16}$, $R^{17}$, $R^{18}$, and $R^{19}$;

$Y^0$ is optionally $Y^{AT}$ wherein $Y^{AT}$ is $Q^b$—$Q^s$;

$Y^0$ is optionally $Q^b$—$Q^{ss}$ wherein $Q^{ss}$ is $(CH(R^{14}))_e$—$W^2$—$(CH(R^{15}))_h$, wherein e and h are independently 1 or 2 and $W^2$ is $CR^{4a}$=$CR^{4b}$ with the proviso that $(CH(R^{14}))_e$ is bonded to $E^0$.

In another even more preferred embodiment of a compound of Formula I, said compound is the Formula:

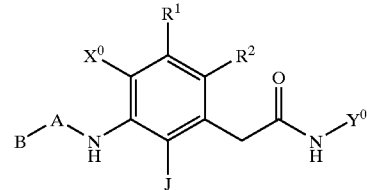

or a pharmaceutically acceptable salt thereof, wherein;

B is phenyl or heteroaryl of 5 or 6 members, wherein a carbon adjacent to the carbon at the point of attachment is optionally substituted by $R^{32}$, the other carbon adjacent to the carbon at the point of attachment is optionally substituted by $R^{36}$, a carbon adjacent to $R^{32}$ and two atoms from the carbon at the point of attachment is optionally substituted by $R^{33}$, a carbon adjacent to $R^{36}$ and two atoms from the carbon at the point of attachment is optionally substituted by $R^{35}$, and any carbon adjacent to both $R^{33}$ and $R^{35}$ is optionally substituted by $R^{34}$;

$R^{32}$, $R^{33}$, $R^{34}$, $R^{35}$, and $R^{36}$ are independently selected from the group consisting of hydrido, acetamido, haloacetamido, amidino, guanidino, alkoxy, hydroxy, amino, alkoxyamino, alkylamino, alkylthio, amidosulfonyl, alkyl, halo, haloalkyl, haloalkoxy, hydroxyalkyl, hydroxyhaloalkyl, carboalkoxy, carboxy, carboxamido, cyano, and $Q^b$;

$R^{16}$, $R^{17}$, $R^{18}$, and $R^{19}$ are independently selected from the group consisting of hydrido, amidino, guanidino, carboxy, haloalkylthio, alkoxy, hydroxy, amino, alkylamino, alkylthio, alkylsulfinyl, alkylsulfonyl, alkanoyl, haloalkanoyl, alkyl, halo, haloalkyl, haloalkoxy, hydroxyalkyl, aminoalkyl, and cyano;

$R^{16}$ or $R^{19}$ is optionally $NR^{20}R^{21}$ or $C(NR^{25})NR^{23}R^{24}$, with the proviso that $R^{16}$, $R^{19}$, and $Q^b$ are not simultaneously hydrido;

$Q^b$ is selected from the group consisting of $NR^{20}R^{21}$, hydrido, and $C(NR^{25})NR^{23}R^{24}$, with the provisos that no more than one of $R^{20}$ and $R^{21}$ is hydroxy at the same time and that no more than one of $R^{23}$ and $R^{24}$ is hydroxy at the same time;

$R^{20}$, $R^{21}$, $R^{23}$, $R^{24}$, and $R^{25}$ are independently selected from the group consisting of hydrido, alkyl, and hydroxy.

In still another even more preferred embodiment of a compound of Formula I, said compound is the Formula:

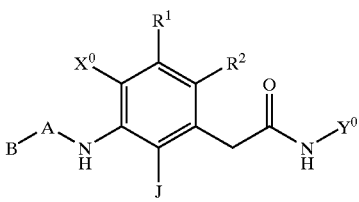

or a pharmaceutically acceptable salt thereof, wherein;

B is selected from the group consisting of hydrido, C2–C8 alkyl, C3–C8 alkenyl, C3–C8 alkynyl, and C2–C8 haloalkyl, wherein each member of group B is optionally substituted at any carbon up to and including 6 atoms from the point of attachment of B to A with one or more of the group consisting of $R^{32}$, $R^{33}$, $R^{34}$, $R^{35}$, and $R^{36}$;

$R^{32}$, $R^{33}$, $R^{34}$, $R^{35}$, and $R^{36}$ are independently selected from the group consisting of hydrido, acetamido, haloacetamido, amidino, guanidino, alkoxy, hydroxy, amino, alkoxyamino, alkylamino, alkylthio, amidosulfonyl, alkyl, halo, haloalkyl, haloalkoxy, hydroxyalkyl, hydroxyhaloalkyl, carboalkoxy, carboxy, carboxamido, cyano, and $Q^b$;

$R^{16}$, $R^{17}$, $R^{18}$, and $R^{19}$ are independently selected from the group consisting of hydrido, amidino, guanidino, carboxy, haloalkylthio, alkoxy, hydroxy, amino, alkylamino, alkylthio, alkylsulfinyl, alkylsulfonyl, alkanoyl, haloalkanoyl, alkyl, halo, haloalkyl, haloalkoxy, hydroxyalkyl, aminoalkyl, and cyano;

$R^{16}$ or $R^{19}$ is optionally selected from the group consisting of $NR^{20}R^{21}$, $N(R^{26})C(NR^{25})N(R^{23})(R^{24})$, and $C(NR^{25})NR^{23}R^{24}$, with the proviso that $R^{16}$, $R^{19}$, and $Q^b$ are not simultaneously hydrido;

$Q^b$ is selected from the group consisting of $NR^{20}R^{21}$, hydrido, $C(NR^{25})NR^{23}R^{24}$, and $N(R^{26})C(NR^{25})N(R^{23})(R^{24})$, with the provisos that no more than one of $R^{20}$ and $R^{21}$ is hydroxy at the same time and that no more than one of $R^{23}$ and $R^{24}$ is hydroxy at the same time;

$R^{20}$, $R^{21}$, $R^{23}$, $R^{24}$, $R^{25}$, and $R^{26}$ are independently selected from the group consisting of hydrido, alkyl, and hydroxy.

In an additional even more preferred embodiment of a compound of Formula I, said compound is the Formula:

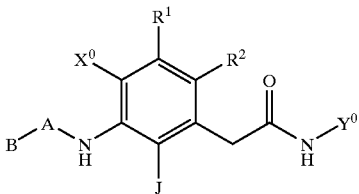

or a pharmaceutically acceptable salt thereof, wherein;

B is a C3–C7 cycloalkyl or a C4–C6 saturated heterocyclyl, wherein each ring carbon is optionally substituted with $R^{33}$, a ring carbon other than the ring carbon at the point of attachment of B to A is optionally substituted with oxo provided that no more than one ring carbon is substituted by oxo at the same time, ring carbons and a nitrogen adjacent to the carbon atom at the point of attachment are optionally substituted with $R^9$ or $R^{13}$, a ring carbon or nitrogen adjacent to the $R^9$ position and two atoms from the point of attachment is optionally substituted with $R^{10}$, a ring carbon or nitrogen adjacent to the $R^{13}$ position and two atoms from the point of attachment is optionally substituted with $R^{12}$, a ring carbon or nitrogen three atoms from the point of attachment and adjacent to the $R^{10}$ position is optionally substituted with $R^{11}$, a ring carbon or nitrogen three atoms from the point of attachment and adjacent to the $R^{12}$ position is optionally substituted with $R^{33}$, and a ring carbon or nitrogen four atoms from the point of attachment and adjacent to the $R^{11}$ and $R^{33}$ positions is optionally substituted with $R^{34}$;

$R^{33}$ and $R^{34}$ are independently selected from the group consisting of hydrido, acetamido, haloacetamido, amidino, guanidino, alkoxy, hydroxy, amino, alkoxyamino, alkylamino, alkylthio, amidosulfonyl, alkyl, halo, haloalkyl, haloalkoxy, hydroxyalkyl, hydroxyhaloalkyl, carboalkoxy, carboxy, carboxamido, and cyano;

$R^{33}$ is optionally $Q^b$;

$R^{16}$, $R^{17}$, $R^{18}$, and $R^{19}$ are independently selected from the group consisting of hydrido, amidino, guanidino, carboxy, haloalkylthio, alkoxy, hydroxy, amino, alkylamino, alkylthio, alkylsulfinyl, alkylsulfonyl, alkanoyl, haloalkanoyl, alkyl, halo, haloalkyl, haloalkoxy, hydroxyalkyl, aminoalkyl, and cyano;

$R^{16}$ or $R^{19}$ is optionally $NR^{20}R^{21}$ or and $C(NR^{25})NR^{23}R^{24}$, with the proviso that $R^{16}$, $R^{19}$, and $Q^b$ are not simultaneously hydrido;

$Q^b$ is selected from the group consisting of $NR^{20}R^{21}$, hydrido, and $C(NR^{25})NR^{23}R^{24}$, with the provisos that no more than one of $R^{20}$ and $R^{21}$ is hydroxy at the same time and that no more than one of $R^{23}$ and $R^{24}$ is hydroxy at the same time;

$R^{20}$, $R^{21}$, $R^{23}$, $R^{24}$, and $R^{25}$ are independently selected from the group consisting of hydrido, alkyl, and hydroxy.

The three groups of even more preferred embodiment compounds of the present invention described above and having the Formula:

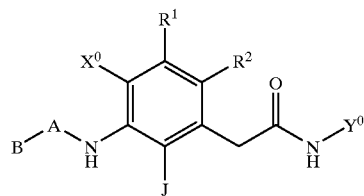

or a pharmaceutically acceptable salt thereof, have common structural units, wherein;

J is selected from the group consisting of halo, haloalkyl, hydroxy, hydroxyalkyl, amino, aminoalkyl, cyano, O—$R^6$, NH—$R^6$, and S—$R^6$, wherein $R^6$ is alkyl or haloalkyl;

$R^9$, $R^{11}$, and $R^{13}$ are independently selected from the group consisting of hydrido, hydroxy, amino, amidino, guanidino, alkylamino, alkylthio, alkylsulfonamido, alkylsulfinyl, alkylsulfonyl, amidosulfonyl, alkyl, alkoxy, halo, haloalkyl, haloalkoxy, hydroxyalkyl, hydroxyhaloalkyl, carboxy, carboxamido, and cyano;

$R^{10}$ and $R^{12}$ are independently selected from the group consisting of hydrido, acetamido, haloacetamido, amidino, guanidino, alkyl, aryl, aralkyl, cycloalkyl, cycloalkylalkyl, heteroaryl, heterocyclyl, alkoxy, cycloalkoxy, cycloalkylalkoxy, aralkoxy, aryloxy, heteroaryloxy, heteroaralkoxy, heterocyclyloxy, heterocyclylalkoxy, hydroxy, amino, alkoxyamino, alkylamino, arylamino, aralkylamino, heteroarylamino, heteroalkylamino, heterocyclylamino, heterocyclylalkylamino, alkylsulfonamido, amidosulfonyl, arylsulfinyl, aralkylsulfinyl, cycloalkylsulfinyl, heteroarylsulfinyl, arylsulfonyl, aralkylsulfonyl, cycloalkylsulfonyl, heteroarylsulfonyl, hydroxyalkyl, hydroxyhaloalkyl, aminoalkyl, carboalkoxy, carboxy, carboxyalkyl, carboxamido, halo, haloalkyl, and cyano;

A is a single covalent bond or $(CH(R^{15}))_{pa}$—$(W^7)_{rr}$ wherein rr is 0 or 1, pa is an integer selected from 0 through 3, and $W^7$ is $(R^7)NC(O)$ or $N(R^7)$;

$R^7$ is selected from the group consisting of hydrido, hydroxy and alkyl;

$R^{15}$ is selected from the group consisting of hydrido, halo, alkyl, and haloalkyl;

$R^1$ and $X^o$ are independently selected from the group consisting of hydrido, hydroxy, hydroxyamino, amino, amino, cyano, hydroxyalkyl, alkoxy, alkyl, alkylamino, aminoalkyl, alkylthio, alkoxyamino, haloalkyl, haloalkoxy, and halo;

$R^2$ is $Z^o$—Q;

$Z^o$ is selected from the group consisting of a covalent single bond, $CH_2$, $CH_2CH_2$, $W^o$—$(CH(R^{42}))_p$ wherein p is 0 or 1 and $W^o$ is selected from the group consisting of O, S, and $N(R^{41})$;

$R^{41}$ and $R^{42}$ are independently hydrido or alkyl;

Q is phenyl or a heteroaryl of 5 or 6 ring members, wherein a carbon adjacent to the carbon at the point of attachment is optionally substituted by $R^9$, the other carbon adjacent to the carbon at the point of attachment is optionally substituted by $R^{13}$, a carbon adjacent to $R^9$ and two atoms from the carbon at the point of attachment is optionally substituted by $R^{10}$, a carbon adjacent to $R^{13}$ and two atoms from the carbon at tile point of attachment is optionally substituted by $R^{12}$, and any carbon adjacent to both $R^{10}$ and $R^{12}$ is optionally substituted by $R^{11}$;

$Y^o$ is phenyl or a heteroaryl of 5 or 6 ring members, wherein one carbon of said phenyl or said heteroaryl is substituted by $Q^s$, a carbon two or three contiguous atoms from the point of attachment of $Q^s$ is substituted by $Q^b$, a carbon adjacent to the point of attachment of $Q^s$ is optionally substituted by $R^{17}$, another carbon adjacent to the point of attachment of $Q^s$ is optionally substituted by $R^{18}$, a carbon adjacent to $Q^b$ is optionally substituted by $R^{16}$, and another carbon adjacent to $Q^b$ is optionally substituted by $R^{19}$;

$Q^s$ is selected from the group consisting of a single covalent bond, $CH_2$, and $CH_2CH_2$.

In a fourth group of an even more preferred embodiment of a compound of Formula I, said compound is the Formula:

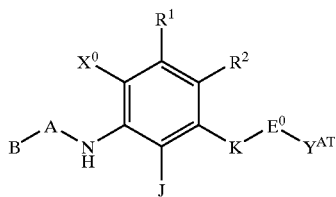

or a pharmaceutically acceptable salt thereof, have common structural units, wherein;

J is selected from the group consisting of halo, haloalkyl, hydroxy, hydroxyalkyl, amino, aminoalkyl, cyano, O—$R^6$, NH—$R^6$, and S—$R^6$, wherein $R^6$ is alkyl or haloalkyl;

B is phenyl or a heteroaryl of 5 or 6 ring members, wherein a carbon adjacent to the carbon at the point of attachment is optionally substituted by $R^{32}$, the other carbon adjacent to the carbon at the point of attachment is optionally substituted by $R^{36}$, a carbon adjacent to $R^{32}$ and two atoms from the carbon at the point of attachment is optionally substituted by $R^{33}$, a carbon adjacent to $R^{36}$ and two atoms from the carbon at the point of attachment is optionally substituted by $R^{35}$, and any carbon adjacent to both $R^{33}$ and $R^{35}$ is optionally substituted by $R^{34}$;

$R^{32}$, $R^{33}$, $R^{34}$, $R^{35}$, and $R^{36}$ are independently selected from the group consisting of hydrido, acetamido, haloacetamido, amidino, guanidino, alkylenedioxy, haloalkylthio, alkanoyloxy, alkoxy, hydroxy, amino, alkoxyamino, haloalkanoyl, nitro, alkylamino, alkylthio, aryl, aralkyl, cycloalkyl, cycloalkylalkyl, heteroaryl, heterocyclyl, alkylsulfonamido, amidosulfonyl, alkyl, alkenyl, halo, haloalkyl, haloalkenyl, haloalkoxy, hydroxyalkyl, alkylamino, carboalkoxy, carboxy, carboxamido, cyano, and $Q^b$;

B is optionally selected from the group consisting of hydrido, trialkylsilyl, C2–C8 alkyl, C3–C8 alkylenyl, C3–C8 alkenyl, C3–C8 alkynyl, and C2–C8 haloalkyl, wherein each member of group B is optionally substituted at any carbon up to and including 6 atoms from the point of attachment of B to A with one or more of the group consisting of $R^{32}$, $R^{33}$, $R^{34}$, $R^{35}$, and $R^{36}$;

B is optionally a C3–C12 cycloalkyl or a C4–C9 saturated heterocyclyl, wherein each ring carbon is optionally substituted with $R^{33}$, a ring carbon other than the ring carbon at the point of attachment of B to A is optionally substituted with oxo provided that no more than one ring carbon is substituted by oxo at the same time, ring carbons and a nitrogen adjacent to the carbon atom at the point of attachment are optionally substituted with $R^9$ or $R^{13}$, a ring carbon or nitrogen adjacent to the $R^9$ position and two atoms from the point of attachment is optionally substituted with $R^{10}$, a ring carbon or nitrogen adjacent to the $R^{13}$ position and two atoms from the point of attachment is optionally substituted with $R^{12}$, a ring carbon or nitrogen three atoms from the point of attachment and adjacent to the $R^{10}$ position is optionally substituted with $R^{11}$, a ring carbon or nitrogen three atoms from the point of attachment and adjacent to the $R^{12}$ position is optionally substituted with $R^{33}$, and a ring carbon or nitrogen four atoms from the point of attachment and adjacent to the $R^{11}$ and $R^{33}$ positions is optionally substituted with $R^{34}$;

$R^9$, $R^{10}$, $R^{11}$, $R^{12}$, and $R^{13}$ are independently selected from the group consisting of hydrido, acetamido, haloacetamido, alkoxyamino, alkanoyl, haloalkanoyl, amidino, guanidino, alkylenedioxy, haloalkylthio, alkoxy, cycloalkoxy, cycloalkylalkoxy, aralkoxy, aryloxy, heteroaryloxy, heteroaralkoxy, heterocyclyloxy, heterocyclylalkoxy, hydroxy, amino, alkylamino, N-alkyl-N-arylamino, arylamino, aralkylamino, heteroarylamino, heteroaralkylamino, heterocyclylamino, heterocyclylalkylamino, alkylthio, alkylsulfinyl, arylsulfinyl, aralkylsulfinyl, cycloalkylsulfinyl, heteroarylsulfinyl, alkylsulfamido, alkylsulfonyl, arylsulfonyl, aralkylsulfonyl, cycloalkylsulfonyl, heteroarylsulfonyl, amidosulfonyl, alkyl, aryl, aralkyl, cycloalkyl, cycloalkylalkyl, heteroaryl, heterocyclyl, halo, haloalkyl, haloalkoxy, hydroxyalkyl, hydroxyhaloalkyl, aminoalkyl, carboalkoxy, carboxy, carboxyalkyl, carboxamido, and cyano;

A is a single covalent bond or $(CH(R^{15}))_{pa}$—$(W^7)_{rr}$ wherein rr is 0 or 1, pa is an integer selected from 0 through 3, and $W^7$ is selected from the group consisting of O, S, C(O), $(R^7)NC(O)$, $(R^7)NC(S)$, and $N(R^7)$;

$R^7$ is selected from the group consisting of hydrido, hydroxy and alkyl;

$R^{15}$ is selected from the group consisting of hydrido, hydroxy, halo, alkyl, and haloalkyl;

$R^1$ and $X^o$ are independently selected from the group consisting of hydrido, alkyl, cyano, halo, haloalkyl, haloalkoxy, amino, aminoalkyl, alkylamino, amidino, hydroxy, hydroxyamino, alkoxy, hydroxyalkyl, alkoxyamino, thiol, and alkylthio;

$R^2$ is $Z^0$—Q;

$Z^0$ is selected from the group consisting of covalent single bond, $(CR^{41}R^{42})_q$ wherein q is 1 or 2, $(CH(R^{41}))_g$—$W^0$—$(CH(R^{42}))_p$ wherein g and p are integers independently selected from 0 through 3 and $W^0$ is selected from the group consisting of O, S, C(O), S(O), $N(R^{41})$, and $ON(R^{41})$;

$Z^0$ is optionally $(CH(R^{41}))_e$—$W^{22}$—$(CH(R^{42}))_h$ wherein e and h are independently 0 or 1 and $W^{22}$ is selected from the group consisting of $CR^{41}$=$CR^{42}$, 1,2-cyclopropyl, 1,2-cyclobutyl, 1,2-cyclohexyl, 1,3-cyclohexyl, 1,2-cyclopentyl, 1,3-cyclopentyl, 2,3-morpholinyl, 2,4-morpholinyl, 2,6-morpholinyl, 3,4-morpholinyl, 3,5-morpholinyl, 1,2-piperazinyl, 1,3-piperazinyl, 2,3-piperazinyl, 2,6-piperazinyl, 1,2-piperidinyl, 1,3-piperidinyl, 2,3-piperidinyl, 2,4-piperidinyl, 2,6-piperidinyl, 3,4-piperidinyl, 1,2-pyrrolidinyl, 1,3-pyrrolidinyl, 2,3-pyrrolidinyl, 2,4-pyrrolidinyl, 2,5-pyrrolidinyl, 3,4-pyrrolidinyl, 2,3-tetrahydrofuranyl, 2,4-tetrahydrofuranyl, 2,5-tetrahydrofuranyl, and 3,4tetrahydrofuranyl, wherein $Z^0$ is directly bonded to the benzene ring and $W^{22}$ is optionally substituted with one or more substituents selected from the group consisting of $R^9$, $R^{10}$, $R^{11}$, $R^{12}$, and $R^{13}$;

$R^{41}$ and $R^{42}$ are independently selected from the group consisting of hydrido, hydroxy, and amino;

Q is phenyl or a heteroaryl of 5 or 6 ring members, wherein a carbon adjacent to the carbon at the point of attachment is optionally substituted by $R^9$, the other carbon adjacent to the carbon at the point of attachment is optionally substituted by $R^{13}$, a carbon adjacent to $R^9$ and two atoms from the carbon at the point of attachment is optionally substituted by $R^{10}$, a carbon adjacent to $R^{13}$ and two atoms from the carbon at the point of attachment is optionally substituted by $R^{12}$, and any carbon adjacent to both $R^{10}$ and $R^{12}$ is optionally substituted by $R^{11}$;

Q is optionally hydrido with the proviso that $Z^0$ is other than a covalent single bond;

K is $CHR^{4a}$ wherein $R^{4a}$ is selected from the group consisting of hydrido, hydroxyalkyl, alkyl, alkoxyalkyl, alkylthioalkyl, and haloalkyl;

$E^0$ is selected from the group consisting of a covalent single bond, C(O)N(H), (H)NC(O), $(R^7)NS(O)_2$, and $S(O)_2N(R^7)$;

$Y^{AT}$ is $Q^b$—$Q^s$;

$Q^s$ is $(CR^{37}R^{38})_b$ wherein b is an integer selected from 1 through 4, $R^{37}$ is selected from the group consisting of hydrido, alkyl and haloalkyl, and $R^{38}$ is selected from the group consisting of hydrido, alkyl, haloalkyl, aroyl, and heteroaroyl with the provisos that there is at least one aroyl or heteroaroyl substituent, that no more than one aroyl or heteroaroyl is bonded to $(CR^{37}R^{38})_b$ at the same time, that said aroyl and said heteroaroyl are optionally substituted at from one through three of the ring carbons with a substituent selected from the group consisting of $R^{16}$, $R^{17}$, $R^{18}$, and $R^{19}$, that said aroyl and said heteroaroyl are bonded to the $CR^{37}R^{38}$ that is directly bonded to $E^0$, that no more than one alkyl or one haloalkyl is bonded to a $CR^{37}R^{38}$ at the same time, and that said alkyl and haloalkyl are bonded to a carbon other than the one bonding said aroyl or said heteroaroyl;

$R^{16}$, $R^{17}$, $R^{18}$, and $R^{19}$ are independently selected from the group consisting of hydrido, amidino, guanidino, carboxy, haloalkylthio, alkoxy, hydroxy, amino, alkoxyamino, alkylamino, alkylthio, alkylsulfinyl, alkylsulfonyl, alkanoyl, haloalkanoyl, alkyl, halo, haloalkyl, haloalkoxy, hydroxyalkyl, aminoalkyl, and cyano;

$R^{16}$ or $R^{19}$ is optionally selected from the group consisting of $NR^{20}R^{21}$, $N(R^{26})C(NR^{25})N(R^{23})(R^{24})$, and $C(NR^{25})NR^{23}R^{24}$, with the proviso that $R^{16}$, $R^{19}$, and $Q^b$ are not simultaneously hydrido;

$Q^b$ is selected from the group consisting of $NR^{20}R^{21}$, hydrido, $N(R^{26})C(NR^{25})N(R^{23})(R^{24})$, and $C(NR^{25})NR^{23}R^{24}$, with the provisos that no more than one of $R^{20}$ and $R^{21}$ is hydroxy, amino, alkylamino, or dialkylamino at the same time and that no more than one of $R^{23}$ and $R^{24}$ is hydroxy, amino, alkylamino, or dialkylamino at the same time;

$R^{20}$, $R^{21}$, $R^{23}$, $R^{24}$, $R^{25}$, and $R^{26}$ are independently selected from the group consisting of hydrido, alkyl, hydroxy, amino, alkylamino and dialkylamino.

In a most preferred embodiment of a compound of Formula I, said compound is the Formula:

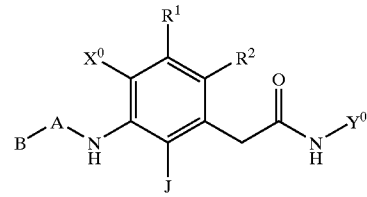

or a pharmaceutically acceptable salt thereof, wherein;

B is phenyl or a heteroaryl of 5 or 6 ring members, wherein a carbon adjacent to the carbon at the point of attachment of said phenyl or heteroaryl ring to A is optionally substituted by $R^{32}$, the other carbon adjacent to the carbon at the point of attachment is optionally substituted by $R^{36}$, a carbon adjacent to $R^{32}$ and two atoms from the carbon at the point of attachment is optionally substituted by $R^{33}$, a carbon adjacent to $R^{36}$ and two atoms from the carbon at the point of attachment is optionally substituted by $R^{35}$, and any carbon adjacent to both $R^{33}$ and $R^{35}$ is optionally substituted by $R^{34}$;

$R^{32}$, $R^{33}$, $R^{34}$, $R^{35}$, and $R^{36}$ are independently selected from the group consisting of hydrido, acetamido, haloacetamido, amidino, guanidino, alkoxy, hydroxy, amino, alkoxyamino, alkylamino, alkylthio, amidosulfonyl, alkyl, halo, haloalkyl, haloalkoxy, hydroxyalkyl, carboalkoxy, carboxy, carboxamido, cyano, and $Q^b$;

$R^{16}$, $R^{17}$, $R^{18}$, and $R^{19}$ are independently selected from the group consisting of hydrido, amidino, guanidino, carboxy, haloalkylthio, alkoxy, hydroxy, amino, alkylamino, alkylthio, alkylsulfinyl, alkylsulfonyl, alkanoyl, haloalkanoyl, alkyl, halo, haloalkyl, haloalkoxy, hydroxyalkyl, aminoalkyl, and cyano;

$R^{16}$ or $R^{19}$ is optionally $NR^{20}R^{21}$ or $C(NR^{25})NR^{23}R^{24}$, with the proviso that $R^{16}$, $R^{19}$, and $Q^b$ are not simultaneously hydrido;

$Q^b$ is selected from the group consisting of $NR^{20}R^{21}$, hydrido, and $C(NR^{25})NR^{23}R^{24}$;

$R^{20}$, $R^{21}$, $R^{23}$, $R^{24}$, and $R^{25}$ are independently hydrido or alkyl.

In another most preferred embodiment of a compound of Formula I, said compound is the Formula:

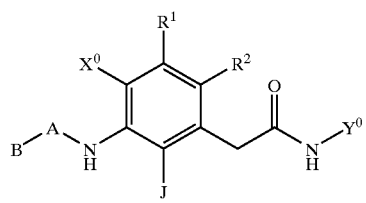

or a pharmaceutically acceptable salt thereof, wherein;

B is selected from the group consisting of hydrido, C2–C8 alkyl, C3–C8 alkenyl, C3–C8 alkynyl, and C2–C8 haloalkyl, wherein each member of group B is optionally substituted at any carbon up to and including 6 atoms from the point of attachment of B to A with one or more of the group consisting of $R^{32}$, $R^{33}$, $R^{34}$, $R^{35}$, and $R^{36}$;

$R^{32}$, $R^{33}$, $R^{34}$, $R^{35}$, and $R^{36}$ are independently selected from the group consisting of hydrido, acetamido, haloacetamido, amidino, guanidino, alkoxy, hydroxy, amino, alkoxyamino, alkylamino, alkylthio, amidosulfonyl, alkyl, halo, haloalkyl, haloalkoxy, hydroxyalkyl, carboalkoxy, carboxy, carboxamido, cyano, and $Q^b$;

$R^{16}$, $R^{17}$, $R^{18}$, and $R^{19}$ are independently selected from the group consisting of hydrido, amidino, guanidino, carboxy, haloalkylthio, alkoxy, hydroxy, amino, alkylamino, alkylthio, alkylsulfinyl, alkylsulfonyl, alkanoyl, haloalkanoyl, alkyl, halo, haloalkyl, haloalkoxy, hydroxyalkyl, aminoalkyl, and cyano;

$R^{16}$ or $R^{19}$ is optionally selected from the group consisting of $NR^{20}R^{21}$, $N(R^{26})C(NR^{25})N(R^{23})(R^{24})$, and $C(NR^{25})NR^{23}R^{24}$, with the proviso that $R^{16}$, $R^{19}$, and $Q^b$ are not simultaneously hydrido;

$Q^b$ is selected from the group consisting of $NR^{20}R^{21}$, hydrido, $N(R^{26})C(NR^{25})N(R^{23})(R^{24})$, and $C(NR^{25})NR^{23}R^{24}$;

$R^{20}$, $R^{21}$, $R^{23}$, $R^{24}$, $R^{25}$, and $R^{26}$ are independently hydrido or alkyl.

In still another most preferred embodiment of a compound of Formula I, said compound is the Formula:

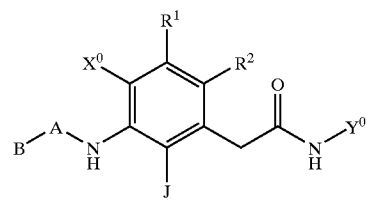

or a pharmaceutically acceptable salt thereof, wherein;

B is a C3–C7 cycloalkyl or a C4–C6 saturated heterocyclyl, wherein each ring carbon is optionally substituted with $R^{33}$, a ring carbon other than the ring carbon at the point of attachment of B to A is optionally substituted with oxo provided that no more than one ring carbon is substituted by oxo at the same time, ring carbons and a nitrogen adjacent to the carbon atom at the point of attachment are optionally substituted with $R^9$ or $R^{13}$, a ring carbon or nitrogen adjacent to the $R^9$ position and two atoms from the point of attachment is optionally substituted with $R^{10}$, a ring carbon or nitrogen adjacent to the $R^{13}$ position and two atoms from the point of attachment is optionally substituted with $R^{12}$, a ring carbon or nitrogen three atoms from the point of attachment and adjacent to the $R^{10}$ position is optionally substituted with $R^{11}$, a ring carbon or nitrogen three atoms from the point of attachment and adjacent to the $R^{12}$ position is optionally substituted with $R^{33}$, and a ring carbon or nitrogen four atoms from the point of attachment and adjacent to the $R^{11}$ and $R^{33}$ positions is optionally substituted with $R^{34}$;

$R^{33}$ and $R^{34}$ are independently selected from the group consisting of hydrido, acetamido, haloacetamido, amidino, guanidino, alkoxy, hydroxy, amino, alkoxyamino, alkylamino, alkylthio, amidosulfonyl, alkyl, halo, haloalkyl, haloalkoxy, hydroxyalkyl, carboalkoxy, carboxy, carboxamido, and cyano;

$R^{33}$ is optionally $Q^b$;

$R^{16}$, $R^{17}$, $R^{18}$, and $R^{19}$ are independently selected from the group consisting of hydrido, amidino, guanidino, carboxy, haloalkylthio, alkoxy, hydroxy, amino, alkylamino, alkylthio, alkylsulfinyl, alkylsulfonyl, alkanoyl, haloalkanoyl, alkyl, halo, haloalkyl, haloalkoxy, hydroxyalkyl, aminoalkyl, and cyano;

$R^{16}$ or $R^{19}$ is optionally $NR^{20}R^{21}$ or $C(NR^{25})NR^{23}R^{24}$, with the proviso that $R^{16}$, $R^{19}$, and $Q^b$ are not simultaneously hydrido;

$Q^b$ is selected from the group consisting of $NR^{20}R^{21}$, hydrido, and $C(NR^{25})NR^{23}R^{24}$;

$R^{20}$, $R^{21}$, $R^{23}$, $R^{24}$, and $R^{25}$ are independently hydrido or alkyl.

The three groups of most preferred embodiment compounds of the present invention described above and having the Formula:

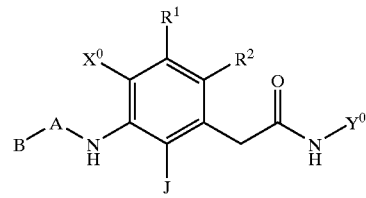

or a pharmaceutically acceptable salt thereof, have common structural units, wherein;

J is selected from the group consisting of halo, haloalkyl, hydroxy, hydroxyalkyl, amino, and aminoalkyl;

A is a single covalent bond or $(CH(R^{15}))_{pa}$—$(W^7)_{rr}$ wherein rr is 0 or 1, pa is an integer selected from 0 through 3, and $W^7$ is $N(R^7)$;

$R^7$ is hydrido or alkyl;

$R^{15}$ is selected from the group consisting of hydrido, halo, alkyl, and haloalkyl;

$R^1$ and $X^o$ are independently selected from the group consisting of hydrido, hydroxy, hydroxyamino, amidino, amino, cyano, hydroxyalkyl, alkoxy, alkyl, alkylamino, aminoalkyl, alkylthio, alkoxyamino, haloalkyl, haloalkoxy, and halo;

$R^2$ is $Z^o$—Q;

$Z^o$ is a covalent single bond;

Q is phenyl or a heteroaryl of 5 or 6 ring members, wherein a carbon adjacent to the carbon at the point of attachment is optionally substituted by $R^9$, the other carbon adjacent to the carbon at the point of attachment is optionally substituted by $R^{13}$, a carbon adjacent to $R^9$ and two atoms from the carbon at the point of attachment is optionally substituted by $R^{10}$, a carbon adjacent to $R^{13}$ and two atoms from the carbon at the point of attachment is optionally substituted by $R^{12}$, and any carbon adjacent to both $R^{10}$ and $R^{12}$ is optionally substituted by $R^{11}$;

$R^9$, $R^{11}$, and $R^{13}$ are independently selected from the group consisting of hydrido, hydroxy, amino, amidino, guanidino, alkylamino, alkylthio, alkoxy, alkylsulfinyl, alkylsulfonyl, amidosulfonyl, alkyl, halo, haloalkyl, haloalkoxy, hydroxyalkyl, carboxy, carboxamido, and cyano;

$R^{10}$ and $R^{12}$ are independently selected from the group consisting of hydrido, acetamido, haloacetamido, amidino, guanidino, alkyl, alkoxy, alkoxyamino, hydroxy, amino, alkylamino, alkylsulfonamido, amidosulfonyl, hydroxyalkyl, aminoalkyl, halo, haloalkyl, carboalkoxy, carboxy, carboxamido, carboxyalkyl, and cyano;

$Y^o$ is phenyl or a heteroaryl of 5 or 6 ring members, wherein one carbon of said phenyl or said heteroaryl is substituted by $Q^s$, a carbon two or three contiguous atoms from the point of attachment of $Q^s$ is substituted by $Q^b$, a carbon adjacent to the point of attachment of $Q^s$ is optionally substituted by $R^{17}$, another carbon adjacent to the point of attachment of $Q^s$ is optionally substituted by $R^{18}$, a carbon adjacent to $Q^b$ is optionally substituted by $R^{16}$, and another carbon adjacent to $Q^b$ is optionally substituted by $R^{19}$;

$Q^s$ is $CH_2$.

In another even more preferred specific embodiment of Formula I, compounds have the formula:

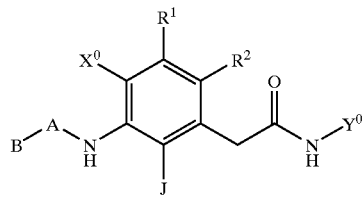

or a pharmaceutically acceptable salt thereof, wherein;

B is selected from the group consisting of phenyl, 2-thienyl, 3-thienyl, 2-furyl, 3-furyl, 2-pyrrolyl, 3-pyrrolyl, 2-imidazolyl, 4-imidazolyl, 3-pyrazolyl, 4-pyrazolyl, 2-thiazolyl, 3-isoxazolyl, 5-isoxazolyl, 2-pyridyl, 3-pyridyl, 4-pyridyl, 2-pyrazinyl, 2-pyrimidinyl, 4-pyrimidinyl, 5-pyrimidinyl, 3-pyridazinyl, 4-pyridazinyl, and 1,3,5-triazin-2-yl, wherein a carbon adjacent to the carbon at the point of attachment is optionally substituted by $R^{32}$, the other carbon adjacent to the carbon at the point of attachment is optionally substituted by $R^{36}$, a carbon adjacent to $R^{32}$ and two atoms from the carbon at the point of attachment is optionally substituted by $R^{33}$, a carbon adjacent to $R^{36}$ and two atoms from the carbon at the point of attachment is optionally substituted by $R^{35}$, and any carbon adjacent to both $R^{33}$ and $R^{35}$ is optionally substituted by $R^{34}$;

$R^{32}$, $R^{33}$, $R^{34}$, $R^{35}$, and $R^{36}$ are independently selected from the group consisting of hydrido, amidino, guanidino, carboxy, methoxy, ethoxy, isopropoxy, propoxy, hydroxy, amino, methoxyamino, ethoxyamino, acetamido, trifluoroacetamido, N-methylamino, dimethylamino, N-ethylamino, methylthio, ethylthio, isopropylthio, trifluoromethyl, pentafluoroethyl, 2,2,2-trifluoroethyl, 2,2,3,3,3-pentafluoropropyl, trifluoromethoxy, 1,1,2,2-tetrafluoroethoxy, fluoro, chloro, bromo, amidosulfonyl, N-methylamidosulfonyl, N,N-dimethylamidosulfonyl, hydroxymethyl, 1-hydroxyethyl, 2-hydroxyethyl, 2,2,2-trifluoro-1-hydroxyethyl, methoxycarbonyl, ethoxycarbonyl, amidocarbonyl, N-methylamidocarbonyl, N,N-dimethylamidocarbonyl, cyano, and $Q^b$;

A is selected from the group consisting of single covalent bond, NH, $N(CH_3)$, N(OH), $CH_2$, $CH_3CH$, $CF_3CH$, NHC(O), $N(CH_3)C(O)$, C(O)NH, $C(O)N(CH_3)$, $CH_2CH_2$, $CH_2CH_2CH_2$, $CH_3CHCH_2$, and $CF_3CHCH_2$;

$R^{16}$, $R^{17}$, $R^{18}$, and $R^{19}$ are independently selected from the group consisting of hydrido, methyl, ethyl, isopropyl, propyl, carboxy, amidino, guanidino, methoxy, ethoxy, isopropoxy, propoxy, hydroxy, amino, aminomethyl, 1-aminoethyl, 2-aminoethyl, N-methylamino, dimethylamino, N-ethylamino, methylthio, ethylthio, isopropylthio, trifluoromethylthio, methylsulfinyl, ethylsulfinyl, methylsulfonyl, ethylsulfonyl, trifluoromethyl, pentafluoroethyl, 2,2,2-trifluoroethyl, 2,2,3,3,3-pentafluoropropyl, trifluoromethoxy, 1,1,2,2-tetrafluoroethoxy, fluoro, chloro, bromo, hydroxymethyl, 1-hydroxyethyl, 2-hydroxyethyl, and cyano;

$R^{16}$ or $R^{19}$ is optionally $C(NR^{25})NR^{23}R^{24}$ with the proviso that $R^{16}$, $R^{19}$, and $Q^b$ are not simultaneously hydrido;

$Q^b$ is $C(NR^{25})NR^{23}R^{24}$ or hydrido, with the proviso that no more than one of $R^{23}$ and $R^{24}$ is hydroxy at the same time;

$R^{23}$, $R^{24}$, and $R^{25}$ are independently selected from the group consisting of hydrido, methyl, ethyl, and hydroxy.

In still another even more preferred specific embodiment of Formula I, compounds have the formula:

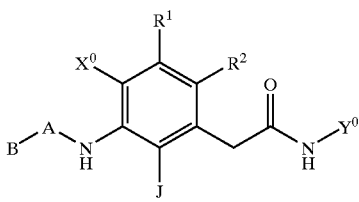

or a pharmaceutically acceptable salt thereof, wherein;
B is selected from the group consisting of hydrido, ethyl, 2-propenyl, 2-propynyl, propyl, isopropyl, butyl, 2-butenyl, 3-butenyl, 2-butynyl, sec-butyl, tert-butyl, isobutyl, 2-methylpropenyl, 1-pentyl, 2-pentenyl, 3-pentenyl, 4-pentenyl, 2-pentynyl, 3-pentynyl, 2-pentyl, 1-methyl-2-butenyl, 1-methyl-3-butenyl, 1-methyl-2-butynyl, 3-pentyl, 1-ethyl-2-propenyl, 2-methylbutyl, 2-methyl-2-butenyl, 2-methyl-3-butenyl, 2-methyl-3-butynyl, 3-methylbutyl, 3-methyl-2-butenyl, 3-methyl-3-butenyl, 1-hexyl, 2-hexenyl, 3-hexenyl, 4-hexenyl, 5-hexenyl, 2-hexynyl, 3-hexynyl, 4-hexynyl, 2-hexyl, 1-methyl-2-pentenyl, 1-methyl-3-pentenyl, 1-methyl-4-pentenyl, 1-methyl-2-pentynyl, 1-methyl-3-pentynyl, 3-hexyl, 1-ethyl-2-butenyl, 1-ethyl-3-butenyl, 1-propyl-2-propenyl, 1-ethyl-2-butynyl, 1-heptyl, 2-heptenyl, 3-heptenyl, 4-heptenyl, 5-heptenyl, 6-heptenyl, 2-heptynyl, 3-heptynyl, 4-heptynyl, 5-heptynyl, 2-heptyl, 1-methyl-2-hexenyl, 1-methyl-3-hexenyl, 1-methyl-4-hexenyl, 1-methyl-5-hexenyl, 1-methyl-2-hexynyl, 1-methyl-3-hexynyl, 1-methylhexynyl, 3-heptyl, 1-ethyl-2-pentenyl, 1-ethyl-3-pentenyl, 1-ethyl-4-pentenyl, 1-butyl-2-propenyl, 1-ethyl-2-pentynyl, 1-ethyl-3-pentynyl, 2,2,2-trifluoroethyl, 2,2-difluoropropyl, 4-trifluoromethyl-5,5,5-trifluoropentyl, 4-trifluoromethylpentyl, 5,5,6,6,6-pentafluorohexyl, and 3,3,3-trifluoropropyl, wherein each member of group B is optionally substituted at any carbon up to and including 5 atoms from the point of attachment of B to A with one or more of the group consisting of $R^{32}$, $R^{33}$, $R^{34}$, $R^{35}$, and $R^{36}$;

$R^{32}$, $R^{33}$, $R^{34}$, $R^{35}$, and $R^{36}$ are independently selected from the group consisting of hydrido, amidino, guanidino, carboxy, methoxy, ethoxy, isopropoxy, propoxy, hydroxy, amino, methoxyamino, ethoxyamino, acetamido, trifluoroacetamido, N-methylamino, dimethylamino, N-ethylamino, methylthio, ethylthio, isopropylthio, trifluoromethyl, pentafluoroethyl, 2,2,2-trifluoroethyl, 2,2,3,3,3-pentafluoropropyl, trifluoromethoxy, 1,1,2,2-tetrafluoroethoxy, fluoro, chloro, bromo, amidosulfonyl, N-methylamidosulfonyl, N,N-dimethylamidosulfonyl, hydroxymethyl, 1-hydroxyethyl, 2-hydroxyethyl, 2,2,2-trifluoro-1-hydroxyethyl, methoxycarbonyl, ethoxycarbonyl, amidocarbonyl, N-methylamidocarbonyl, N,N-dimethylamidocarbonyl, cyano, and $Q^b$;

A is selected from the group consisting of single covalent bond, NH, $N(CH_3)$, $N(OH)$, $CH_2$, $CH_3CH$, $CF_3CH$, NHC(O), $N(CH_3)C(O)$, C(O)NH, $C(O)N(CH_3)$, $CH_2CH_2$, $CH_2CH_2CH_2$, $CH_3CHCH_2$, and $CF_3CHCH_2$;

A is optionally selected from the group consisting of $CH_2N(CH_3)$, $CH_2N(CH_2CH_3)$, $CH_2CH_2N(CH_3)$, and $CH_2CH_2N(CH_2CH_3)$ with the proviso that B is hydrido;

$R^{16}$, $R^{17}$, $R^{18}$, and $R^{19}$ are independently selected from the group consisting of hydrido, methyl, ethyl, isopropyl, propyl, carboxy, amidino, guanidino, methoxy, ethoxy, isopropoxy, propoxy, hydroxy, amino, aminomethyl, 1-aminoethyl, 2-aminoethyl, N-methylamino, dimethylamino, N-ethylamino, methylthio, ethylthio, isopropylthio, trifluoromethylthio, methylsulfinyl, ethylsulfinyl, methylsulfonyl, ethylsulfonyl, trifluoromethyl, pentafluoroethyl, 2,2,2-trifluoroethyl, 2,2,3,3,3-pentafluoropropyl, trifluoromethoxy, 1,1,2,2-tetrafluoroethoxy, fluoro, chloro, bromo, hydroxymethyl, 1-hydroxyethyl, 2-hydroxyethyl, and cyano;

$R^{16}$ or $R^{19}$ is optionally selected from the group consisting of $NR^{20}R^{21}$, $C(NR^{25})NR^{23}R^{24}$, and $N(R^{26})C(NR^{25})N(R^{23})(R^{24})$, with the proviso that $R^{16}$, $R^{19}$, and $Q^b$ are not simultaneously hydrido;

$Q^b$ is selected from the group consisting of $NR^{20}R^{21}$, hydrido, $C(NR^{25})NR^{23}R^{25}$, and $N(R^{26})C(NR^{25})N(R^{23})(R^{24})$, with the provisos that no more than one of $R^{20}$ and $R^{21}$ is hydroxy at the same time and that no more than one of $R^{23}$ and $R^{24}$ is hydroxy at the same time;

$R^{20}$, $R^{21}$, $R^{23}$, $R^{24}$, $R^{25}$, and $R^{26}$ are independently selected from the group consisting of hydrido, methyl, ethyl, propyl, butyl, isopropyl, and hydroxy.

In an additional even more preferred specific embodiment of Formula I, compounds have the formula:

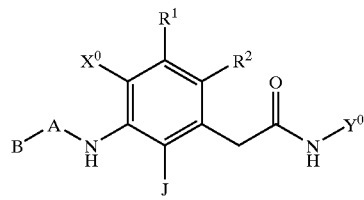

or a pharmaceutically acceptable salt thereof, wherein;
B is optionally selected from the group consisting of cyclopropyl, cyclobutyl, oxetan-3-yl, azetidin-1-yl, azetidin-2-yl, azetidin-3-yl, thiaetan-3-yl, cyclopentyl, cyclohexyl, norbornyl, 7-oxabicyclo[2.2.1]heptan-2-yl, bicyclo[3.1.0]hexan-6-yl, cycloheptyl, 2-morpholinyl, 3-morpholinyl, 4-morpholinyl, 1-piperazinyl, 2-piperazinyl, 1-piperidinyl, 2-piperidinyl, 3-piperidinyl, 4-piperidinyl, 1-pyrrolidinyl, 2-pyrrolidinyl, 3-pyrrolidinyl, 2-dioxanyl, 4H-2-pyranyl, 4H-3-pyranyl, 4H-4-pyranyl, 4H-pyran-4-one-2-yl, 4H-pyranone-3-yl, 2-tetrahydrofuranyl, 3-tetrahydrofuranyl, 2-tetrahydropyranyl, 3-tetrahydropyranyl, 4-tetrahydropyranyl, 2-tetrahydrothienyl, and 3-tetrahydrothienyl, wherein each ring carbon is optionally substituted with $R^{33}$, a ring carbon and nitrogen atoms adjacent to the carbon atom at the point of attachment is optionally substituted with $R^9$ or $R^{13}$, a ring carbon or nitrogen atom adjacent to the $R^9$ position and two atoms from the point of attachment is optionally substituted with $R^{10}$, and a ring carbon or nitrogen atom adjacent to the $R^{13}$ position and two atoms from the point of attachment is optionally substituted with $R^{12}$;

A is selected from the group consisting of single covalent bond, NH, $N(CH_3)$, $N(OH)$, $CH_2$, $CH_3CH$, $CF_3CH$, NHC(O), $N(CH_3)C(O)$, C(O)NH, $C(O)N(CH_3)$, $CH_2CH_2$, $CH_2CH_2CH_2$, $CH_3CHCH_2$, and $CF_3CHCH_2$;

$R^{33}$ is selected from the group consisting of hydrido, amidino, guanidino, carboxy, methoxy, ethoxy, isopropoxy, propoxy, hydroxy, amino, methoxyamino, ethoxyamino, acetamido, trifluoroacetamido, N-methylamino, dimethylamino, N-ethylamino, methylthio, ethylthio, isopropylthio, trifluoromethyl, pentafluoroethyl, 2,2,2-trifluoroethyl, 2,2,3,3,3-pentafluoropropyl, trifluoromethoxy, 1,1,2,2-tetrafluoroethoxy, fluoro, chloro, bromo, amidosulfonyl, N-methylamidosulfonyl, N,N-dimethylamidosulfonyl, hydroxymethyl, 1-hydroxyethyl, 2-hydroxyethyl, 2,2,2-trifluoro-1-hydroxyethyl, methoxycarbonyl, ethoxycarbonyl, amidocarbonyl, N-methylamidocarbonyl, N,N-dimethylamidocarbonyl, cyano, and $Q^b$;

$R^{16}$, $R^{17}$, $R^{18}$, and $R^{19}$ are independently selected from the group consisting of hydrido, methyl, ethyl, isopropyl, propyl, carboxy, amidino, guanidino, methoxy, ethoxy, isopropoxy, propoxy, hydroxy, amino, aminomethyl, 1-aminoethyl, 2-aminoethyl, N-methylamino, dimethylamino, N-ethylamino, methylthio, ethylthio, isopropylthio, trifluoromethylthio, methylsulfinyl, ethylsulfinyl, methylsulfonyl, ethylsulfonyl, trifluoromethyl, pentafluoroethyl, 2,2,2-trifluoroethyl, 2,2,3,3,3-pentafluoropropyl, trifluoromethoxy, 1,1,2,2-tetrafluoroethoxy, fluoro, chloro, bromo, hydroxymethyl, 1-hydroxyethyl, 2-hydroxyethyl, and cyano;

$R^{16}$ or $R^{19}$ is optionally $C(NR^{25})NR^{23}R^{24}$ with the proviso that $R^{16}$, $R^{19}$, and $Q^b$ are not simultaneously hydrido;

$Q^b$ is $C(NR^{25})NR^{23}R^{24}$ or hydrido, with the proviso that no more than one of $R^{23}$ and $R^{24}$ is hydroxy at the same time;

$R^{23}$, $R^{24}$, and $R^{25}$ are independently selected from the group consisting of hydrido, methyl, ethyl, and hydroxy.

The three groups of even more preferred specific embodiment compounds of the present invention described herein and having the formula:

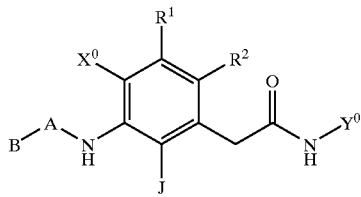

or a pharmaceutically acceptable salt thereof, have common struck units, wherein;

J is selected from the group consisting of fluoro, chloro, trifluoromethyl, hydroxy, hydroxymethyl, 1-hydroxyethyl, 2-hydroxyethyl, 1,2-dihydroxyethyl, amino, aminomethyl, 1-aminoethyl, 2-aminoethyl, methoxy, trifluoromethoxy, N-methylamino, methythio, and trifluoromethylthio;

$R^1$ and $X^o$ are independently selected from the group consisting of hydrido, hydroxy, amino, amidino, hydroxyamino, aminomethyl, 1-aminoethyl, methylamino, dimethylamino, cyano, methyl, ethyl, trifluoromethyl, pentafluoroethyl, 2,2,2-trifluoroethyl, methoxy, hydroxymethyl, 1-hydroxyethyl, 2-hydroxyethyl, methoxyamino, methylthio, ethylthio, trifluoromethoxy, 1,1,2,2-tetrafluoroethoxy, fluoro, chloro, and bromo;

$R^2$ is $Z^o$—Q;

$Z^o$ is selected from the group consisting of covalent single bond, $CH_2$, $CH_2CH_2$, O, S, NH, $N(CH_3)$, $OCH_2$, $SCH_2$, $N(H)CH_2$, and $N(CH_3)CH_2$;

Q is selected from the group consisting of phenyl, 2-thienyl, 3-thienyl, 2-furyl, 3-furyl, 2-pyrrolyl, 3-pyrrolyl, 2-imidazolyl, 4-imidazolyl, 3-pyrazolyl, 4-pyrazolyl, 2-thiazolyl, 3-isoxazolyl, 5-isoxazolyl, 2-pyridyl, 3-pyridyl, 4-pyridyl, 2-pyrazyl, 2-pyrimidinyl, 4-pyrimidinyl, 5-pyrimidinyl, 3-pyridazinyl, 4-pyridazinyl, and 1,3,5-triazin-2-yl, wherein a carbon adjacent to the carbon at the point of attachment is optionally substituted by $R^9$, the other carbon adjacent to the carbon at the point of attachment is optionally substituted by $R^{13}$, a carbon adjacent to $R^9$ and two atoms from the carbon at the point of attachment is optionally substituted by $R^{10}$, a carbon adjacent to $R^{13}$ and two atoms from the carbon at the point of attachment is optionally substituted by $R^{12}$, and any carbon adjacent to both $R^{10}$ and $R^{12}$ is optionally substituted by $R^{11}$;

$R^9$, $R^{11}$, and $R^{13}$ are independently selected from the group consisting of hydrido, amidino, guanidino, carboxy, methyl, ethyl, propyl, isopropyl, methoxy, ethoxy, isopropoxy, propoxy, hydroxy, amino, N-methylamino, N,N-dimethylamino, N-ethylamino, methylthio, ethylthio, isopropylthio, trifluoromethyl, pentafluoroethyl, 2,2,2-trifluoroethyl, 2,2,3,3,3-pentafluoropropyl, trifluoromethoxy, 1,1,2,2-tetrafluoroethoxy, fluoro, chloro, bromo, methanesulfonamido, amidosulfonyl, N-methylamidosulfonyl, N,N-dimethylamidosulfonyl, hydroxymethyl, 1-hydroxyethyl, 2-hydroxyethyl, 2,2,2-trifluoro-1-hydroxyethyl, amidocarbonyl, N-methylamidocarbonyl, N,N-dimethylamidocarbonyl, and cyano;

$R^{10}$ and $R^{12}$ are independently selected from the group consisting of hydrido, amidino, guanidino, carboxy, carboxymethyl, methyl, ethyl, propyl, isopropyl, methoxy, ethoxy, isopropoxy, propoxy, hydroxy, amino, methoxyamino, ethoxyamino, acetamido, trifluoroacetamido, aminomethyl, 1-aminoethyl, 2-aminoethyl, N-methylamino, dimethylamino, N-ethylamino, methanesulfonamido, amidosulfonyl, N-methylamidosulfonyl, N,N-dimethylamidosulfonyl, hydroxymethyl, 1-hydroxyethyl, 2-hydroxyethyl, 2,2,2-trifluoro-1-hydroxyethyl, methoxycarbonyl, ethoxycarbonyl, amidocarbonyl, N-methylamidocarbonyl, N,N-dimethylamidocarbonyl, N-benzylamidocarbonyl, N-(2-chlorobenzyl)amidocarbonyl, N-(3-fluorobenzyl)amidocarbonyl, N-(2-trifluoromethylbenzyl)amidocarbonyl, N-(1-phenylethyl)amidocarbonyl, N-(1-methyl-1-phenylethyl)amidocarbonyl, N-benzylamidosulfonyl, N-(2-chlorobenzyl)amidosulfonyl, N-ethylamidocarbonyl, N-isopropylamidocarbonyl, N-propylamidocarbonyl, N-isobutylamidocarbonyl, N-(2-butyl)amidocarbonyl, N-cyclobutylamidocarbonyl, N-cyclopentylamidocarbonyl, N-cyclohexylamidocarbonyl, fluoro, chloro, bromo, cyano, cyclobutoxy, cyclohexoxy, cyclohexylmethoxy, 4-trifluoromethycyclohexylmethoxy, cyclopentoxy, benzyl, benzyloxy, 4-bromo-3-fluorophenoxy, 3-bromobenzyloxy, 4-bromobenzyloxy, 4-bromobenzylamino, 5-bromopyrid-2-ylmethylamino, 4-butoxyphenamino, 3-chlorobenzyl, 4-chlorophenoxy, 4-chloro-3-ethylphenoxy, 4-chloro-3-ethylbenzylamino, 4-chloro-3-ethylphenylamino, 3-chlorobenzyloxy, 4-chlorobenzyloxy, 4-chlorobenzylsulfonyl, 4-chlorophenylamino, 4-chlorophenylsulfonyl, 5-chloropyrid-3-yloxy, 2-cyanopyrid-3-yloxy, 2,3-difluorobenzyloxy, 2,4-difluorobenzyloxy, 3,4-difluorobenzyloxy, 2,5-difluorobenzyloxy, 3,5-difluorophenoxy, 3,5-difluorobenzyloxy, 4-difluoromethoxybenzyloxy, 2,3-difluorophenoxy, 2,4-difluorophenoxy, 2,5-difluorophenoxy, 3,5-dimethylphenoxy, 3,4-dimethylphenoxy, 3,4-dimethylbenzyloxy, 3,5-dimethylbenzyloxy, 4-ethoxyphenoxy, 4-ethylbenzyloxy, 3-ethylphenoxy, 4-ethylaminophenoxy, 3-ethyl-5-methylphenoxy, 4-fluorobenzyloxy, 2-fluoro-3-trifuoromethylbenzyloxy, 3-fluoro-5-trifluoromethylbenzyloxy, 4-fluoro-2-trifluoromethylbenzyloxy, 4-fluoro-3-trifluoromethylbenzyloxy, 2-fluorophenoxy, 4-fluorophenoxy, 2-fluoro-3-trifluoromethylphenoxy, 2-fluorobenzyloxy, 4-fluorophenylamino, 2-fluoro-4-trifluoromethylphenoxy, 4-isopropylbenzyloxy, 3-isopropylphenoxy, 4-isopropylphenoxy, 4-isopropyl-3-methylphenoxy, 4-isopropylbenzyloxy, 3-isopropylphenoxy, 4-isopropylphenoxy, 4-isopropyl-3-methylphenoxy, phenylamino, 1-phenylethoxy, 2-phenylethoxy, 2-phenylethyl, 2-phenylethylamino, phenylsulfonyl, 3-trifluoromethoxybenzyloxy, 4-trifluoromethoxybenzyloxy, 3-trifluoromethoxyphenoxy, 4-trifluoromethoxyphenoxy, 3-trifluoromethylbenzyloxy, 4-trifluoromethylbenzyloxy, 2,4-bis-trifluoromethylbenzyloxy, 3-trifluoromethylbenzyl, 3,5-bis-trifluoromethylbenzyloxy, 4-trifluoromethylphenoxy, 3-trifluoromethylphenoxy, 3-trifluoromethylthiobenzyloxy, 4-trifluoromethylthiobenzyloxy, 2,3,4-trifluorophenoxy, 2,3,5-trifluorophenoxy, 3-pentafluoroethylphenoxy, 3-(1,1,2,2-tetrafluoroethoxy)phenoxy, and 3-trifluoromethylthiophenoxy;

$Y^o$ is selected from the group of formulas consisting of:

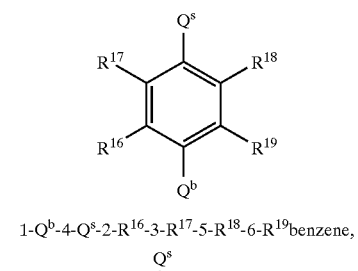

1-$Q^b$-4-$Q^s$-2-$R^{16}$-3-$R^{17}$-5-$R^{18}$-6-$R^{19}$benzene,

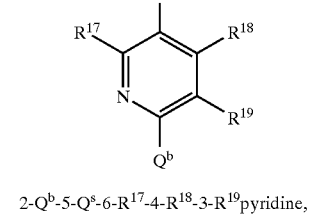

2-$Q^b$-5-$Q^s$-6-$R^{17}$-4-$R^{18}$-3-$R^{19}$pyridine,

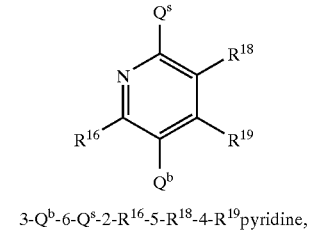

3-$Q^b$-6-$Q^s$-2-$R^{16}$-5-$R^{18}$-4-$R^{19}$pyridine,

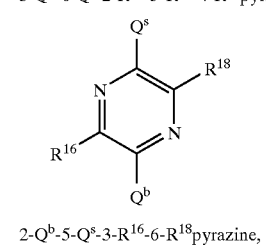

2-$Q^b$-5-$Q^s$-3-$R^{16}$-6-$R^{18}$pyrazine,

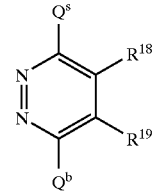

3-$Q^b$-6-$Q^s$-2-$R^{18}$-5-$R^{18}$-4-$R^{19}$pyridazine,

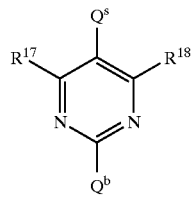

2-$Q^b$-5-$Q^s$-4-$R^{17}$-6-$R^{18}$pyrimidine,

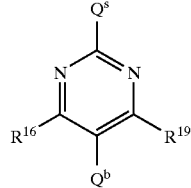

5-$Q^b$-2-$Q^s$-4-$R^{16}$-6-$R^{19}$pyrimidine,

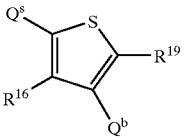 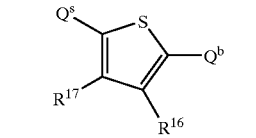

3-$Q^b$-5-$Q^s$-4-$R^{16}$-2-$R^{19}$thiopene,   2-$Q^b$-5-$Q^s$-3-$R^{16}$-4-$R^{17}$thiopene,

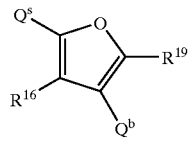 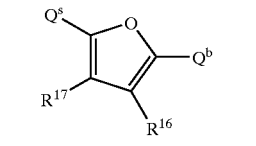

3-$Q^b$-5-$Q^s$-4-$R^{16}$-2-$R^{19}$furan,   2-$Q^b$-5-$Q^s$-3-$R^{16}$-4-$R^{17}$furan,

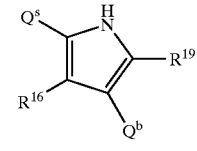 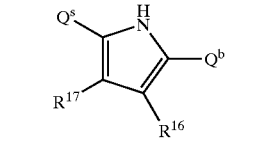

3-$Q^b$-5-$Q^s$-4-$R^{16}$-2-$R^{19}$pyrrole,   2-$Q^b$-5-$Q^s$-3-$R^{16}$-4-$R^{17}$pyrrole,

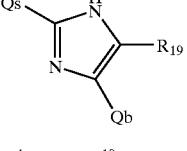 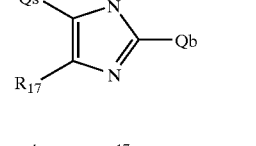

4-$Q^b$-2-$Q^s$-5-$R^{19}$imidazole,   2-$Q^b$-4-$Q^s$-5-$R^{17}$imidazole,

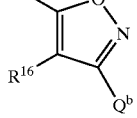 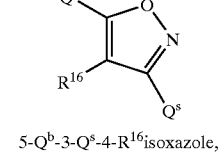

3-$Q^b$-5-$Q^s$-4-$R^{16}$isoxazole,   5-$Q^b$-3-$Q^s$-4-$R^{16}$isoxazole,

-continued

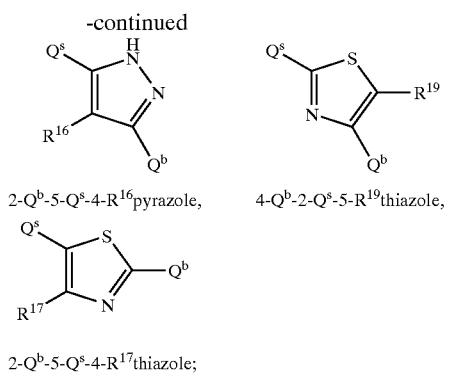

2-Q$^b$-5-Q$^s$-4-R$^{16}$pyrazole, 4-Q$^b$-2-Q$^s$-5-R$^{19}$thiazole,

2-Q$^b$-5-Q$^s$-4-R$^{17}$thiazole;

Q$^s$ is selected from the group consisting of a bond, CH$_2$, and CH$_2$CH$_2$.

In a most preferred specific embodiment of Formula I, compounds have the formula:

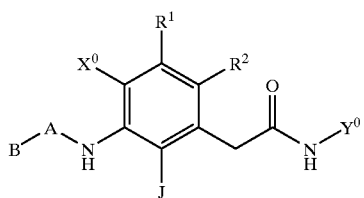

or a pharmaceutically acceptable salt thereof, wherein;

B is selected from the group consisting of phenyl, 2-thienyl, 3-thienyl, 2-furyl, 3-furyl, 2-pyrrolyl, 3-pyrrolyl, 2-imidazolyl, 4-imidazolyl, 3-pyrazolyl, 4-pyrazolyl, 2-thiazolyl, 3-isoxazolyl, and 5-isoxazolyl, wherein a carbon adjacent to the carbon at the point of attachment is optionally substituted by R$^{32}$, the other carbon adjacent to the carbon at the point of attachment is optionally substituted by R$^{36}$, a carbon adjacent to R$^{32}$ and two atoms from the carbon at the point of attachment is optionally substituted by R$^{33}$, a carbon adjacent to R$^{36}$ and two atoms from the carbon at the point of attachment is optionally substituted by R$^{35}$, and any carbon adjacent to both R$^{33}$ and R$^{35}$ is optionally substituted by R$^{34}$;

R$^{32}$, R$^{33}$, R$^{34}$, R$^{35}$, and R$^{36}$ are independently selected from the group consisting of hydrido, amidino, guanidino, methyl, ethyl, methoxy, ethoxy, hydroxy, amino, N-methylamino, dimethylamino, methoxyamino, methylthio, ethylthio, trifluoromethyl, pentafluoroethyl, 2,2,2-trifluoroethyl, fluoro, chloro, bromo, amidosulfonyl, N-methylamidosulfonyl, hydroxymethyl, amidocarbonyl, carboxy, cyano, and Q$^b$;

A is selected from the group consisting of single covalent bond, NH, N(CH$_3$), CH$_2$, CH$_3$CH, and CH$_2$CH$_2$;

Q$^b$ is NR$^{20}$R$^{21}$ or C(NR$^{25}$)NR$^{23}$R$^{24}$;

R$^{20}$, R$^{21}$, R$^{23}$, R$^{24}$, and R$^{25}$ are independently selected from the group consisting of hydrido, methyl, and ethyl.

In another most preferred specific embodiment of Formula I, compounds have the formula:

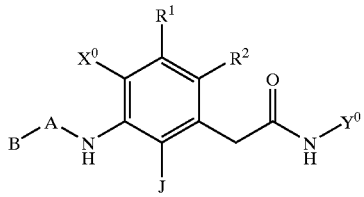

or a pharmaceutically acceptable salt thereof, wherein;

B is selected from the group consisting of hydrido, ethyl, 2-propenyl, 2-propynyl, propyl, isopropyl, butyl, 2-butenyl, 2-butynyl, sec-butyl, tert-butyl, isobutyl, 2-methylpropenyl, 1-pentyl, 2-pentenyl, 3-pentenyl, 2-pentynyl, 3-pentynyl, 2-pentyl, 3-pentyl, 2-methylbutyl, 2-methyl-2-butenyl, 3-methylbutyl, 3-methyl-2-butenyl, 1-hexyl, 2-hexenyl, 3-hexenyl, 4-hexenyl, 2-hexynyl, 3-hexynyl, 4-hexynyl, 2-hexyl, 1-methyl-2-pentenyl, 1-methyl-3-pentenyl, 1-methyl-2-pentynyl, 1-methyl-3-pentynyl, 3-hexyl, 1-ethyl-2-butenyl, 1-heptyl, 2-heptenyl, 3-heptenyl, 4-heptenyl, 5-heptenyl, 2-heptynyl, 3-heptynyl, 4-heptynyl, 5-heptynyl, 2-heptyl, 1-methyl-2-hexenyl, 1-methyl-3-hexenyl, 1-methylhexenyl, 1-methyl-2-hexynyl, 1-methyl-3-hexynyl, 1-methyl-4-hexynyl, 3-heptyl, 1-ethyl-2-pentenyl, 1-ethyl-3-pentenyl, 1-ethyl-2-pentynyl, 1-ethyl-3-pentynyl, 2,2,2-trifluoroethyl, 2,2-difluoropropyl, 4-trifluoromethyl-5,5,5-trifluoropentyl, 4-trifluoromethylpentyl, 5,5,6,6,6-pentafluorohexyl, and 3,3,3-trifluoropropyl, wherein each member of group B is optionally substituted at any carbon up to and including 5 atoms from the point of attachment of B to A with one or more of the group consisting of R$^{32}$, R$^{33}$, R$^{34}$, R$^{35}$, and R$^{36}$;

R$^{32}$, R$^{33}$, R$^{34}$, R$^{35}$, and R$^{36}$ are independently selected from the group consisting of hydrido, amidino, guanidino, methyl, ethyl, methoxy, ethoxy, hydroxy, amino, N-methylamino, dimethylamino, methoxyamino, methylthio, ethylthio, trifluoromethyl, pentafluoroethyl, 2,2,2-trifluoroethyl, fluoro, chloro, bromo, amidosulfonyl, N-methylamidosulfonyl, hydroxymethyl, amidocarbonyl carboxy, cyano, and Q$^b$;

A is selected from the group consisting of single covalent bond, NH, N(CH$_3$), CH$_2$, CH$_3$CH, and CH$_2$CH$_2$;

A is optionally selected from the group consisting of CH$_2$N(CH$_3$), CH$_2$N(CH$_2$CH$_3$), CH$_2$CH$_2$N(CH$_3$), and CH$_2$CH$_2$N(CH$_2$CH$_3$) with the proviso that B is hydrido;

Q$^b$ is selected from the group consisting of NR$^{20}$R$^{21}$, C(NR$^{25}$)NR$^{23}$R$^{24}$, and N(R$^{26}$)C(NR$^{25}$)N(R$^{23}$)(R$^{24}$);

R$^{20}$, R$^{21}$, R$^{23}$, R$^{24}$, R$^{25}$, and R$^{26}$ are independently selected from the group consisting of hydrido, methyl, and ethyl.

In still another most preferred specific embodiment of Formula I, compounds have the formula:

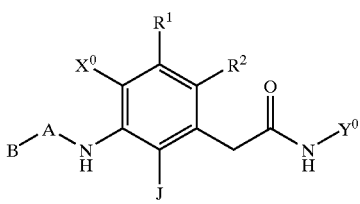

or a pharmaceutically acceptable salt thereof, wherein;
B is selected from the group consisting of cyclopropyl, cyclobutyl, cyclopentyl, cyclohexyl, cycloheptyl, oxalan-2-yl, 2-(2R)-bicyclo[2.2.1]-heptyl, oxetan-3-yl, azetidin-1-yl, azetidin-2-yl, azetidin-3-yl, bicyclo [3.1.0]hexan-6-yl, 2-morpholinyl, 3-morpholinyl, 4-morpholinyl, 1-piperazinyl, 2-piperazinyl, 1-piperidinyl, 2-piperidinyl, 3-piperidinyl, 4-piperidinyl, 1-pyridinyl, 2-pyrrolidinyl, 3-pyrrolidinyl, 2-dioxanyl, 2-tetrahydrofuranyl, 3-tetrahydrofuranyl, 2-tetrahydropyranyl, 3-tetrahydropyranyl, 4-tetrahydropyranyl, 2-tetrahydrothienyl, and 3-tetrahydrothienyl, wherein each ring carbon is optionally substituted with $R^{33}$, ring carbons and a nitrogen adjacent to the carbon atom at the point of attachment are optionally substituted with $R^9$ or $R^{13}$, a ring carbon or nitrogen adjacent to the $R^9$ position and two atoms from the point of attachment are optionally substituted with $R^{10}$, and a ring carbon or nitrogen atom adjacent to the $R^{13}$ position and two atoms from the point of attachment is optionally substituted with $R^{12}$;
$R^{33}$ is selected from the group consisting of hydrido, amidino, guanidino, methyl, ethyl, methoxy, ethoxy, hydroxy, carboxy, amino, N-methylamino, dimethylamino, methoxyamino, methylthio, ethylthio, trifluoromethyl, pentafluoroethyl, 2,2,2-trifluoroethyl, fluoro, chloro, bromo, amidosulfonyl, N-methylamidosulfonyl, hydroxymethyl, amidocarbonyl, cyano, and $Q^b$;
A is selected from the group consisting of single covalent bond, NH, N(CH$_3$), CH$_2$, CH$_3$CH, and CH$_2$CH$_2$;
$Q^b$ is NR$^{20}$R$^{21}$ or C(NR$^{25}$)NR$^{23}$R$^{24}$;
$R^{20}$, $R^{21}$, $R^{23}$, $R^{24}$, and $R^{25}$ are independently selected from the group consisting of hydrido, methyl, and ethyl.

The three groups of the most preferred specific embodiment compounds of the present invention having the formula:

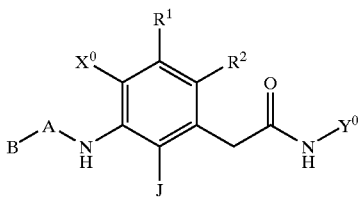

or a pharmaceutically acceptable salt thereof, have common structural units, wherein;
J is selected from the group consisting of fluoro, chloro, trifluoromethyl, hydroxy, hydroxymethyl, amino, and aminomethyl;
$X^o$ is selected from the group consisting of hydrido, hydroxy, amino, amidino, aminomethyl, cyano, methyl, trifluoromethyl, hydroxymethyl, chloro, and fluoro;

$R^1$ is selected from the group consisting of hydrido, hydroxy, hydroxymethyl, amino, aminomethyl, methylamino, cyano, methyl, trifluoromethyl, methoxy, methylthio, trifluoromethoxy, fluoro, and chloro;

$R^2$ is selected from the group consisting of phenyl, 2-thienyl, 2-furyl, 2-pyrrolyl, 2-imidazolyl, 2-thiazolyl, 3-isoxazolyl, 2-pyridyl, and 3-pyridyl, wherein a carbon adjacent to the carbon at the point of attachment is optionally substituted by $R^9$, the other carbon adjacent to the carbon at the point of attachment is optionally substituted by $R^{13}$, a carbon adjacent to $R^9$ and two atoms from the carbon at the point of attachment is optionally substituted by $R^{10}$, a carbon adjacent to $R^{13}$ and two atoms from the carbon at the point of attachment is optionally substituted by $R^{12}$, and any carbon adjacent to both $R^{10}$ and $R^{12}$ is optionally substituted by $R^{11}$;

$R^9$, $R^{11}$, and $R^{13}$ are independently selected from the group consisting of hydrido, methyl, ethyl, methoxy, ethoxy, hydroxy, amino, N-methylamino, N,N-dimethylamino, methylthio, trifluoromethyl, pentafluoroethyl, 2,2,2-trifluoroethyl, fluoro, chloro, bromo, amidosulfonyl, N-methylamidosulfonyl, N,N-dimethylamidosulfonyl, hydroxymethyl, 1-hydroxyethyl, amidocarbonyl, N-methylamidocarbonyl, carboxy, and cyano;

$R^{10}$ and $R^{12}$ are independently selected from the group consisting of hydrido, amidino, amidocarbonyl, N-methylamidocarbonyl, N-benzylamidocarbonyl, N-(2-chlorobenzyl)amidocarbonyl, N-3-fluorobenzyl)amidocarbonyl, N-(2-trifluoromethylbenzyl)amidocarbonyl, N-1-phenylethyl)amidocarbonyl, N-(1-methyl-1-phenylethyl)amidocarbonyl, N-benzylamidosulfonyl, N-(2-chlorobenzyl)amidosulfonyl, N-ethylamidocarbonyl, N-isopropylamidocarbonyl, N-propylamidocarbonyl, N-isobutylamidocarbonyl, N-(2-butyl)amidocarbonyl, N-cyclobutylamidocarbonyl, N-cyclopentylamidocarbonyl, N-cyclohexylamidocarbonyl, guanidino, methyl, ethyl, methoxy, ethoxy, hydroxy, hydroxymethyl, 1-hydroxyethyl, 2-hydroxyethyl, carboxy, carboxymethyl, amino, acetamido, trifluoromethyl, pentafluoroethyl, 2,2,2-trifluoroethyl, trifluoroacetamido, aminomethyl, N-methylamino, dimethylamino, methoxyamino, amidosulfonyl, N-methylamidosulfonyl, N,N-dimethylamidosulfonyl, methanesulfonamido, methoxycarbonyl, fluoro, chloro, bromo, and cyano;

$Y^o$ is selected from the group of formulas consisting of:

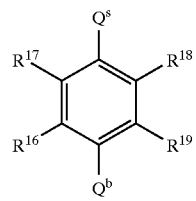

1-Q$^b$-4-Q$^s$-2-R$^{16}$-3-R$^{17}$-5-R$^{18}$-6-R$^{19}$benzene,

-continued

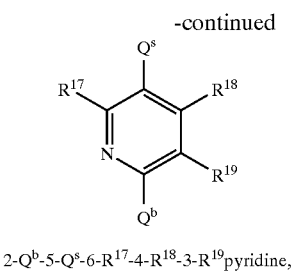

2-$Q^b$-5-$Q^s$-6-$R^{17}$-4-$R^{18}$-3-$R^{19}$pyridine,

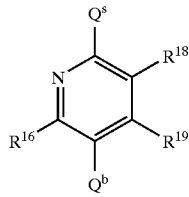

3-$Q^b$-6-$Q^s$-2-$R^{16}$-5-$R^{18}$-4-$R^{19}$pyridine,

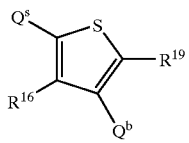 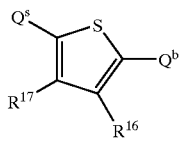

3-$Q^b$-5-$Q^s$-4-$R^{16}$-2-$R^{19}$thiopene,   2-$Q^b$-5-$Q^s$-3-$R^{16}$-4-$R^{17}$thiopene,

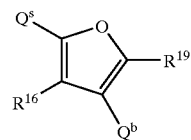

3-$Q^b$-5-$Q^s$-4-$R^{16}$-2-$R^{19}$furan,   2-$Q^b$-5-$Q^s$-3-$R^{16}$-4-$R^{17}$furan,

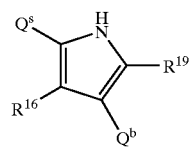

3-$Q^b$-5-$Q^s$-4-$R^{16}$-2-$R^{19}$pyrrole,   2-$Q^b$-5-$Q^s$-3-$R^{16}$-4-$R^{17}$pyrrole,

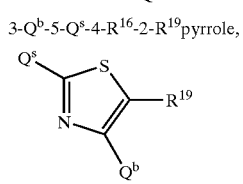 and 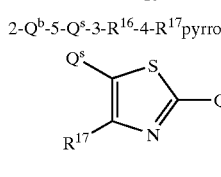

4-$Q^b$-2-$Q^s$-5-$R^{19}$thiazole,   2-$Q^b$-5-$Q^s$-4-$R^{17}$thiazole;

$R^{16}$, $R^{17}$, $R^{18}$, and $R^{19}$ are independently selected from the group consisting of hydrido, methyl, ethyl, amidino, guanidino, methoxy, hydroxy, amino, aminomethyl, 1-aminoethyl, 2-aminoethyl, N-methylamino, dimethylamino, methylthio, ethylthio, trifluoromethylthio, methylsulfinyl, methylsulfonyl, trifluoromethyl, pentafluoroethyl, 2,2,2-trifluoroethyl, trifluoromethoxy, fluoro, chloro, hydroxymethyl, carboxy, and cyano;

$Q^s$ is $CH_2$.

The compounds of this invention can be used in anticoagulant therapy for the treatment and prevention of a variety of thrombotic conditions including coronary artery and cerebrovascular disease. The compounds of this invention can be used to inhibit serine protease associated with the coagulation cascade and factors II, VII, VIII, IX, X, XI, or XII. The compounds of the invention can inhibit the formation of blood platelet aggregates, inhibit the formation of fibrin, inhibit thrombus formation, and inhibiting embolus formation in a mammal; in blood, in blood products, and in mammalian organs. The compounds also can be used for treating or preventing unstable angina, refractory angina, myocardial infarction, transient ischemic attacks, atrial fibrillation, thrombotic stroke, embolic stroke, deep vein thrombosis, disseminated intravascular coagulation, ocular build up of fibrin, and reocclusion or restenosis of recanalized vessels in a mammal. The compounds can also be used in prophylactic treatment of subjects who are at risk of developing such disorders. The compounds can be used to lower the risk of atherosclerosis. The compounds of Formula (I) would also be useful in prevention of cerebral vascular accident (CVA) or stroke.

Besides being useful for human treatment, these compounds are also useful for veterinary treatment of companion animals, exotic animals and farm animals, including mammals, rodents, and the like. More preferred animals include horses, dogs, and cats.

In yet another embodiment of the present invention, the novel compounds are selected from the compounds set forth in the Examples, Table 1, and in the General Synthetic Procedures and Specific Examples section.

The use of generic terms in the description of the compounds are herein defined for clarity.

Standard single letter elemental symbols are used to represent specific types of atoms unless otherwise defined. The symbol "C" represents a carbon atom. The symbol "O" represents an oxygen atom. The symbol "N" represents a nitrogen atom. The symbol "P" represents a phosphorus atom. The symbol "S" represents a sulfur atom. The symbol "H" represents a hydrido atom. Double letter elemental symbols are used as defined for the elements of the periodical table (i.e., Cl represents chlorine, Se represents selenium, etc.).

As utilized herein, the term "alkyl", either alone or within other terms such as "haloalkyl" and "alkylthio", means an acyclic alkyl radical containing from 1 to about 10, preferably from 3 to about 8 carbon atoms and more preferably 3 to about 6 carbon atoms. Said alkyl radicals may be optionally substituted with groups as defined below. Examples of such radicals include methyl, ethyl, chloroethyl, hydroxyethyl, n-propyl, oxopropyl, isopropyl, n-butyl, cyanobutyl, isobutyl, sec-butyl, tert-butyl, pentyl, aminopentyl, iso-amyl, hexyl, octyl and the like.

The term "alkenyl" refers to an unsaturated, acyclic hydrocarbon radical in so much as it contains at least one double bond. Such alkenyl radicals, contain from about 2 to about 10 carbon atoms, preferably from about 3 to about 8 carbon atoms and more preferably 3 to about 6 carbon atoms. Said alkenyl radicals may be optionally substituted with groups as defined below. Examples of suitable alkenyl radicals include propenyl, 2-chloropropenyl, buten-1-yl, isobutenyl, penten-1-yl, 2-2-methylbuten-1-yl, 3-methylbuten-1-yl, hexen-1-yl, 3-hydroxyhexen-1-yl, hepten-1-yl, and octen-1-yl, and the like.

The term "alkynyl" refers to an unsaturated, acyclic hydrocarbon radical in so much as it contains one or more triple bonds, such radicals containing about 2 to about 10 carbon atoms, preferably having from about 3 to about 8 carbon atoms and more preferably having 3 to about 6 carbon atoms. Said alkynyl radicals may be optionally substituted with groups as defined below. Examples of suitable alkynyl radicals include ethynyl, propynyl, hydroxypropynyl, butyn-1-yl, butyn-2-yl, pentyn-1-yl, pentyn-2-yl, 4-methoxypentyn-2-yl, 3-methylbutyn-1-yl, hexyn-1-yl, hexyn-2-yl, hexyn-3-yl, 3,3-dimethylbutyn-1-yl radicals and the like.

The term "hydrido" denotes a single hydrogen atom (H). This hydrido radical may be attached, for example, to an oxygen atom to form a "hydroxyl" radical, one hydrido radical may be attached to a carbon atom to form a "methine" radical —CH=, or two hydrido radicals may be attached to a carbon atom to form a "methylene" (—CH$_2$—) radical.

The term "carbon" radical denotes a carbon atom without any covalent bonds and capable of forming four covalent bonds.

The term "cyano" radical denotes a carbon radical having three of four covalent bonds shared by a nitrogen atom.

The term "hydroxyalkyl" embraces radicals wherein any one or more of the alkyl carbon atoms is substituted with a hydroxyl as defined above. Specifically embraced are monohydroxyalkyl, dihydroxyalkyl and polyhydroxyalkyl radicals.

The term "alkanoyl" embraces radicals wherein one or more of the terminal alkyl carbon atoms are substituted with one or more carbonyl radicals as defined below. Specifically embraced are monocarbonylalkyl and dicarbonylalkyl radicals. Examples of monocarbonylalkyl radicals include formyl, acetyl, and pentanoyl. Examples of dicarbonylalkyl radicals include oxalyl, malonyl, and succinyl.

The term "alkylene" radical denotes linear or branched radicals having from 1 to about 10 carbon atoms and having attachment points for two or more covalent bonds. Examples of such radicals are methylene, ethylene, methylethylene, and isopropylidene.

The term "alkenylene" radical denotes linear or branched radicals having from 2 to about 10 carbon atoms, at least one double bond, and having attachment points for two or more covalent bonds. Examples of such radicals are 1,1-vinylidene (CH$_2$=C), 1,2-vinylidene (—CH=CH—), and 1,4-butadienyl (—CH=CH—CH=CH—).

The term "halo" means halogens such as fluorine, chlorine, bromine or iodine atoms.

The term "haloalkyl" embraces radicals wherein any one or more of the alkyl carbon atoms is substituted with halo as defined above. Specifically embraced are monohaloalkyl, dihaloalkyl and polyhaloalkyl radicals. A monohaloalkyl radical, for one example, may have either a bromo, chloro or a fluoro atom within the radical. Dihalo radicals may have two or more of the same halo atoms or a combination of different halo radicals and polyhaloalkyl radicals may have more than two of the same halo atoms or a combination of different halo radicals. More preferred haloalkyl radicals are "haloalkyl" radicals having one to about six carbon atoms. Examples of such haloalkyl radicals include fluoromethyl, difluoromethyl, trifluoromethyl, chloromethyl, dichloromethyl, trichloromethyl, trifluoroethyl, pentafluoroethyl, heptafluoropropyl, difluorochlormethyl, dichlorofluoromethyl, difluoroethyl, difluoropropyl, dichloroethyl and dichloropropyl.

The term "hydroxyhaloalkyl" embraces radicals wherein any one or more of the haloalkyl carbon atoms is substituted with hydroxy as defined above. Examples of "hydroxyhaloalkyl" radicals include hexafluorohydroxypropyl.

The term "haloalkylene radical" denotes alkylene radicals wherein any one or more of the alkylene carbon atoms is substituted with halo as defined above. Dihalo alkylene radicals may have two or more of the same halo atoms or a combination of different halo radicals and polyhaloalkylene radicals may have more than two of the same halo atoms or a combination of different halo radicals. More preferred hoalkylene radicals are "haloalkylene" radicals having one to about six carbon atoms. Examples of "haloalkylene" radicals include difluoromethylene, tetrafluoroethylene, tetrachloroethylene, alkyl substituted monofluoromethylene, and aryl substituted trifluoromethylene.

The term "haloalkenyl" denotes linear or branched radicals having from 1 to about 10 carbon atoms and having one or more double bonds wherein any one or more of the alkenyl carbon atoms is substituted with halo as defined above. Dihaloalkenyl radicals may have two or more of the same halo atoms or a combination of different halo radicals and polyhaloalkenyl radicals may have more than two of the same halo atoms or a combination of different halo radicals.

The terms "alkoxy" and "alkoxyalkyl" embrace linear or branched oxy-containing radicals each having alkyl portions of one to about ten carbon atoms, such as methoxy radical. The term "alkoxyalkyl" also embraces alkyl radicals having one or more alkoxy radicals attached to the alkyl radical, that is, to form monoalkoxyalkyl and dialkoxyalkyl radicals. More preferred alkoxy radicals are "alkoxy" radicals having one to six carbon atoms. Examples of such radicals include methoxy, ethoxy, propoxy, butoxy, isopropoxy and tert-butoxy alkyls. The "alkoxy" radicals may be further substituted with one or more halo atoms, such as fluoro, chloro or bromo, to provide "haloalkoxy" and "haloalkoxyalkyl" radicals. Examples of such haloalkoxy radicals include fluoromethoxy, chloromethoxy, trifluoromethoxy, difluoromethoxy, trifluoroethoxy, fluoroethoxy, tetrafluoroethoxy, pentafluoroethoxy, and fluoropropoxy. Examples of such haloakoxyalkyl radicals include fluoromethoxymethyl, chloromethoxyethyl, trifluoromethoxymethyl, difluoromethoxyethyl, and trifluoroethoxymethyl.

The terms "alkenyloxy" and "alkenyloxyalkyl" embrace linear or branched oxy-containing radicals each having alkenyl portions of two to about ten carbon atoms, such as ethenyloxy or propenyloxy radical. The term "alkenyloxyalkyl" also embraces alkenyl radicals having one or more alkenyloxy radicals attached to the alkyl radical, that is, to form monoalkenyloxyalkyl and dialkenyloxyalkyl radicals. More preferred alkenyloxy radicals are "alkenyloxy" radicals having two to six carbon atoms. Examples of such radicals include ethenyloxy, propenyloxy, butenyloxy, and isopropenyloxy alkyls. The "alkenyloxy" radicals may be further substituted with one or more halo atoms, such as fluoro, chloro or bromo, to provide "haloalkenyloxy" radicals. Examples of such radicals include trifluoroethenyloxy, fluoroethenyloxy, difluoroethenyhloxy, and fluoropropenyloxy.

The term "haloalkoxyalkyl" also embraces alkyl radicals having one or more haloalkoxy radicals attached to the alkyl radical, that is, to form monohaloalkoxyalkyl and dihaloalkoxyalkyl radicals. The term "haloalkenyloxy" also embraces oxygen radicals having one or more haloalkenyloxy radicals attached to the oxygen radical, that is, to form monohaloalkenyloxy and dihaloalkenyloxy radicals. The term "haloalkenyloxyalkyl" also embraces alkyl radicals having one or more haloalkenyloxy radicals attached to the alkyl radical, that is, to form monohaloalkenyloxyalkyl and dihaloalkenyloxyalkyl radicals.

The term "alkylenedioxy" radicals denotes alkylene radicals having at least two oxygens bonded to a single alkylene group. Examples of "alkylenedioxy" radicals include methlylenedioxy, ethylenedioxy, alkylsubstituted methylenedioxy, and arylsubstituted methylenedioxy. The term "haloalkylenedioxy" radicals denotes haloalkylene radicals having at least two oxy groups bonded to a single haloalkyl group. Examples of "haloalkylenedioxy" radicals include difluoromethylenedioxy, tetrafluoroethylenedioxy, tetrachloroethylenedioxy, alkylsubstituted monofluoromethylenedioxy, and arylsubstituted monofluoromethylenedioxy.

The term "aryl", alone or in combination, means a carbocyclic aromatic system containing one, two or three rings wherein such rings may be attached together in a pendant manner may be fused. The term "fused" means that a second ring is present (ie, attached or formed) by having two adjacent atoms in common (ie, shared) with the first ring. The term "fused" is equivalent to the term "condensed". The term "aryl" embraces aromatic radicals such as phenyl, naphthyl, tetrahydronaphthyl, indane and biphenyl.

The term "perhaloaryl" embraces aromatic radicals such as phenyl, naphthyl, tetrahydronaphthyl, indane and biphenyl wherein the aryl radical is substituted with 3 or more halo radicals as defined below.

The term "heterocyclyl" embraces saturated and partially saturated heteroatom-containing ring-shaped radicals having from 4 through 15 ring members, herein referred to as "C4–C15 heterocyclyl", selected from carbon, nitrogen, sulfur and oxygen, wherein at least one ring atom is a heteroatom. Heterocyclyl radicals may contain one, two or three rings wherein such rings may be attached in a pendant manner or may be fused. Examples of saturated heterocyclic radicals include saturated 3 to 6-membered heteromonocylic group containing 1 to 4 nitrogen atoms[e.g. pyrrolidinyl, imidazolidinyl, piperidino, piperazinyl, etc.]; saturated 3 to 6-membered heteromonocyclic group containing 1 to 2 oxygen atoms and 1 to 3 nitrogen atoms [e.g morpholinyl, etc]; saturated 3 to 6-membered heteromonocyclic group containing 1 to 2 sulfur atoms and 1 to 3 nitrogen atoms [e.g. thiazolidinyl, etc.]. Examples of partially saturated heterocyclyl radicals include dihydrothiophene, dihydropyran, dihydrofuran and dihydrothiazole. Non-limiting examples of heterocyclic radicals include 2-pyrrolinyl, 3-pyrrolinyl, pyrrolindinyl, 1,3-dioxolanyl, 2H-pyranyl, 4H-pyranyl, piperidinyl, 1,4-dioxanyl, morpholinyl, 1,4-dithianyl, thiomorpholinyl, and the like. Said "heterocyclyl" group may be substituted as defined herein. Preferred heterocyclic radicals include five to twelve membered fused or unfused radicals.

The term "heteroaryl" embraces-fully unsaturated heteroatom-containing ring-shaped aromatic radicals having from 4 through 15 ring members selected from carbon, nitrogen, sulfur and oxygen, wherein at least one ring atom is a heteroatom. Heteroaryl radicals may contain one, two or three rings wherein such rings may be attached in a pendant manner or may be fused. Examples of "heteroaryl" radicals, include the unsaturated heteromonocyclyl group of 5 to 6 contiguous members containing 1 to 4 nitrogen atoms, for example, pyrrolyl, pyrrolinyl, imidazolyl, pyrazolyl, 2-pyridyl, 3-pyridyl, 4-pyridyl, pyrimidyl, pyrazinyl, pyridazinyl, triazolyl [e.g., 4H-1,2,4-triazolyl, 1H-1,2,3-triazolyl, 2H-1,2,3-triazolyl, etc.] tetrazolyl [e.g. 1H-tetrazolyl, 2H-tetrazolyl, etc.], etc.; unsaturated condensed heterocyclic group containing 1 to 5 nitrogen atoms, for example, indolyl, isoindolyl, indolizinyl, benzimidazol, quinolyl, isoquinolyl, indazolyl, benzotriazolyl, tetrazolopyridazinyl [e.g., tetrazolo[1,5-b]pyridazinyl, etc.], etc.; unsaturated 3 to 6-membered heteromonocyclic group containing an oxygen atom, for example, pyranyl, 2-furyl, 3-furyl, etc.; unsaturated 5 to 6-membered heteromonocyclic group containing a sulfur atom, for example, 2-thienyl, 3-thienyl, etc.; unsaturated 5 to 6-membered heteromonocyclic group containing 1 to 2 oxygen atoms and 1 to 3 nitrogen atoms, for example, oxazolyl, isoxazolyl, oxadiazolyl [e.g., 1,2,4-oxadiazolyl, 1,3,4-oxadiazolyl, 1,2,5-oxadiazolyl, etc.] etc.; unsaturated condensed heterocyclic group containing 1 to 2 oxygen atoms and 1 to 3 nitrogen atoms [e.g. benzoxazolyl, benzoxadiazolyl, etc.]; unsaturated 5 to 6-membered heteromonocyclic group containing 1 to 2 sulfur atoms and 1 to 3 nitrogen atoms, for example, thiazolyl, thiadiazolyl [e.g., 1,2,4-thiadiazolyl, 1,3,4-thiadiazolyl, 1,2,5-thiadiazolyl, etc.] etc.; unsaturated condensed heterocyclic group containing 1 to 2 sulfur atoms and 1 to 3 nitrogen atoms [e.g., benzothiazolyl, benzothiadiazolyl, etc.] and the like. The term also embraces radicals where heterocyclic radicals are fused with aryl radicals. Examples of such fused bicyclic radicals include benzofuran, benzothiophene, and the like. Said "heteroaryl" group may be substituted as defined herein. Preferred heteroaryl radicals include five and six membered unfused radicals. Non-limiting examples of heteroaryl radicals include 2-thienyl, 3-thienyl, 2-furyl, 3-furyl, 2-pyrrolyl, 3-pyrrolyl, 2-imidazolyl, 4-imidazolyl, 3-pyrazolyl, 4-pyrazolyl, 1,2,4-triazol-3-yl, 1,2,4-triazol-5-yl, 1,2,4-oxadiazol-3-yl, 1,2,4-oxadiazol-5-yl, 1,3,4-oxadiazol-3-yl, 1,3,4-oxadiazol-5-yl, 3-isothiazolyl, 5-isothiazolyl, 2-oxazolyl, 2-thiazolyl, 3-isoxazolyl, 5-isoxazolyl, 2-pyridyl, 3-pyridyl, 4-pyridyl, 2-pyrazinyl, 2-pyrimidinyl, 4-pyrimidinyl, 5-pyrimidinyl, 3-pyridazinyl, 4-pyridazinyl, 1,3,5-triazin-2-yl, 1,2,4-triazin-3-yl, 1,2,4-triazin-5-yl, 1,2,4-triazin-6-yl, 1,2,3-triazin-4-yl, and 1,2,3-triazin-5-yl, and the like.

The term "sulfonyl", whether used alone or linked to other terms such as alkylsulfonyl, denotes respectively divalent radicals —SO$_2$—. "Alkylsulfonyl", embraces alkyl radicals attached to a sulfonyl radical, where alkyl is defined as above. "Alkylsulfonylalkyl", embraces alkylsulfonyl radicals attached to an alkyl radical, where alkyl is defined as above. "Haloalkylsulfonyl", embraces haloalkyl radicals attached to a sulfonyl radical, where haloalkyl is defined as above. "Haloalkylsulfonylalkyl", embraces haloalksulfonyl radicals attached to an alkyl radical, where alkyl is defined as above.

The term "amidosulfonyl" embraces amino, monalkylamino, dialkylamino, monocycloalkylamino, alkyl cycloalkylamino, dicycloalkylamino, N-alkyl-N-arylamino, arylamino, aralkylamino, nitrogen containing heterocyclyl, heterocyclylamino, N-alkyl-N-heterocyclylamino, heteroarylamino, and heteroaralkylamino radicals, attached to one of two unshared bonds in a sulfonyl radical.

The term "sulfinyl", whether used alone or linked to other terms such as alkylsulfinyl, denotes respectively divalent radicals —S(O)—. "Alkylsulfinyl", embraces alkyl radicals attached to a sulfinyl radical, where alkyl is defined as above. "Alkylsulfinylalkyl", embraces alkylsulfinyl radicals attached to an alkyl radical, where alkyl is defined as above. "Haloalkylsulfinyl", embraces haloalkyl radicals attached to a sulfinyl radical, where haloalkyl is defined as above. "Haloalkylsulfinylalkyl", embraces haloalkylsulfinyl radicals attached to an alkyl radical, where alkyl is defined as above.

The term "aralkyl" embraces aryl-substituted alkyl radicals. Preferable aralkyl radicals are "aralkyl" radicals having aryl radicals attached to alkyl radicals having one to six carbon atoms. Examples of such radicals include benzyl, diphenylmethyl, triphenylmethyl, phenylethyl and diphenylethyl. The terms benzyl and phenylmethyl are interchangeable.

The term "heteroaralkyl" embraces heteroaryl-substituted alkyl radicals wherein the heteroaralkyl radical may be additionally substituted with three or more substituents as defined above for aralkyl radicals. The term "perhaloaralkyl" embraces aryl-substituted alkyl radicals wherein the aralkyl radical is substituted with three or more halo radicals as defined above.

The term "aralkylsulfinyl", embraces aralkyl radicals attached to a sulfinyl radical, where aralkyl is defined as above. "Aralkylsulfinylalkyl", embraces aralkylsulfinyl radicals attached to an alkyl radical, where alkyl is defined as above.

The term "aralkylsulfonyl", embraces aralkyl radicals attached to a sulfonyl radical, where aralkyl is defined as above. "Aralkylsulfonylalkyl", embraces aralkylsulfonyl radicals attached to an alkyl radical, where alkyl is defined as above.

The term "cycloalkyl" embraces radicals having three to 15 carbon atoms. More preferred cycloalkyl radicals are "cycloalkyl" radicals having three to seven carbon atoms. Examples include radicals such as cyclopropyl, cyclobutyl, cyclopentyl, cyclohexyl and cycloheptyl. The term cycloalkyl embraces radicals having seven to 15 carbon atoms and having two to four rings. Examples include radicals such as norbornyl (i.e., bicyclo[2.2.1]heptyl) and adamantyl. The term "cycloalkylalkyl" embraces cycloalkyl-substituted alkyl radicals. Preferable cycloalkylalkyl radicals are "cycloalkylalkyl" radicals having cycloalkyl radicals attached to alkyl radicals having one to six carbon atoms. Examples of such radicals include cyclohexylhexyl. The term "cycloalkenyl" embraces radicals having three to ten carbon atoms and one or more carbon-carbon double bonds. Preferred cycloalkenyl radicals are "cycloalkenyl" radicals having three to seven carbon atoms. Examples include radicals such as cyclobutenyl, cyclopentenyl, cyclohexenyl and cycloheptenyl. The term "halocycloalkyl" embraces radicals wherein any one or more of the cycloalkyl carbon atoms is substituted with halo as defined above. Specifically embraced are monohalocycloalkyl, dihalocycloalkyl and polyhalocycloalkyl radicals. A monohalocycloalkyl radical, for one example, may have either a bromo, chloro or a fluoro atom within the radical. Dihalo radicals may have two or more of the same halo atoms or a combination of different halo radicals and polyhalocycloalkyl radicals may have more than two of the same halo atoms or a combination of different halo radicals. More preferred halocycloalkyl radicals are "halocycloalkyl" radicals having three to about eight carbon atoms. Examples of such halocycloalkyl radicals include fluorocyclopropyl, difluorocyclobutyl, trifluorocyclopentyl, tetrafluorocyclohexyl, and dichlorocyclopropyl. The term "halocycloalkenyl" embraces radicals wherein any one or more of the cycloalkenyl carbon atoms is substituted with halo as defined above. Specifically embraced are monohalocycloalkenyl, dihalocycloalkenyl and polyhalocycloalkenyl radicals.

The term "cycloalkoxy" embraces cycloalkyl radicals attached to an oxy radical. Examples of such radicals includes cyclohexoxy and cyclopentoxy. The term "cycloalkoxyalkyl" also embraces alkyl radicals having one or more cycloalkoxy radicals attached to the alkyl radical, that is, to form monocycloalkoxyalkyl and dicycloalkoxyalkyl radicals. Examples of such radicals include cyclohexoxyethyl. The "cycloalkoxy" radicals may be further substituted with one or more halo atoms, such as fluoro, chloro or bromo, to provide "halocycloalkoxyl" and "halocycloalkoxyalkyl" radicals.

The term "cycloalkylalkoxy" embraces cycloalkyl radicals attached to an alkoxy radical. Examples of such radicals includes cyclohexylmethoxy and cyclopentylmethoxy.

The term "cycloalkenyloxy" embraces cycloalkenyl radicals attached to an oxy radical. Examples of such radicals includes cyclohexenyloxy and cyclopentenyloxy. The term "cycloalkenyloxyalkoxyl" also embraces alkyl radicals having one or more cycloalkenyloxy radicals attached to the alkyl radical, that is, to form monocycloalkenyloxyalkyl and dicycloalkenyloxyalkyl radicals. Examples of such radicals include cyclohexenyloxyethyl. The "cycloalkenyloxy" radicals may be further substituted with one or more halo atoms, such as fluoro, chloro or bromo, to provide "halocycloalkenyloxy" and "halocycloalkenyloxyalkyl" radicals.

The term "cycloalkylenedioxy" radicals denotes cycloalkylene radicals having at least two oxygens bonded to a single cycloalkylene group. Examples of "alkylenedioxy" radicals include 1,2-dioxycyclohexylene.

The term "cycloalkylsulfinyl", embraces cycloalkyl radicals attached to a sulfinyl radical, where cycloalkyl is defined as above. "Cycloalkylsulfinylalkyl", embraces cycloalkylsulfinyl radicals attached to an alkyl radical, where alkyl is defined as above. The term "Cycloalkylsulfonyl", embraces cycloalkyl radicals attached to a sulfonyl radical, where cycloalkyl is defined as above. "Cycloalkylsulfonylalkyl", embraces cycloalkylsulfonyl radicals attached to an alkyl radical, where alkyl is defined as above.

The term "cycloalkylalkanoyl" embraces radicals wherein one or more of the cycloalkyl carbon atoms are substituted with one or more carbonyl radicals as defined below. Specifically embraced are monocarbonylcycloalkyl and dicarbonylcycloalkyl radicals. Examples of monocarbonylcycloalkyl radicals include cyclohexylcarbonyl, cyclohexylacetyl, and cyclopentylcarbonyl. Examples of dicarbonylcycloalkyl radicals include 1,2-dicarbonylcyclohexane.

The term "alkylthio" embraces radicals containing a linear or branched alkyl radical, of one to ten carbon atoms, attached to a divalent sulfur atom. More preferred alkylthio radicals are "alkylthio" radicals having one to six carbon atoms. An example of "alkylthio" is methylthio ($CH_3$—S—). The "alkylthio" radicals may be further substituted with one or more halo atoms, such as fluoro, chloro or bromo, to provide "haloalkylthio" radicals. Examples of such radicals include fluoromethylthio, chloromethylthio, trifluoromethylthio, difluoromethylthio, trifluoroethylthio, fluoroethylthio, tetrafluoroethylthio, pentafluoroethylthio, and fluoropropylthio.

The term "alkyl aryl amino" embraces radicals containing a linear or branched alkyl radical, of one to ten carbon atoms, and one aryl radical both attached to an amino radical. Examples include N-methyl-4-methoxyaniline, N-ethyl-4-methoxyaniline, and N-methyl-4-trifluoromethoxyaniline.

The term alkylamino denotes "monoalkylamino" and "dialkylamino" containing one or two alkyl radicals, respectively, attached to an amino radical. One or two alkyl radicals of the alkylamino may be optionally substituted with hydrogen bonding substitutents selected from the group consisting of hydroxy, amino, monoalkylamino, dialkylamino, amidino, guanidino, thiol, and alkoxy provided the alkyl radicals comprises two or more carbons.

The terms arylamino denotes "monoarylamino" and "diarylamino" containing one or two aryl radicals, respectively, attached to an amino radical. Examples of such radicals include N-phenylamino and N-naphthylamino.

The term "aralkylamino", embraces aralkyl radicals attached to an amino radical, where aralkyl is defined as above. The term aralkylamino denotes "monoaralkylamino" and "diaralkylamino" containing one or two aralkyl radicals, respectively, attached to an amino radical. The term aralkylamino further denotes "monoaralkyl monoalkylamino" containing one aralkyl radical and one alkyl radical attached to an amino radical.

The term "arylsulfinyl" embraces radicals containing an aryl radical, as defined above, attached to a divalent S(O) atom. The term "arylsulfinylalkyl" denotes arylsulfinyl radicals attached to a linear or branched alkyl radical, of one to ten carbon atoms.

The term "arylsulfonyl", embraces aryl radicals attached to a sulfonyl radical, where aryl is defined as above. "arylsulfonylalkyl", embraces arylsulfonyl radicals attached to an alkyl radical, where alkyl is defined as above. The term "heteroarylsulfinyl" embraces radicals containing an heteroaryl radical, as defined above, attached to a divalent S(O) atom. The term "heteroarylsulfinylalkyl" denotes heteroarylsulfinyl radicals attached to a linear or branched alkyl radical, of one to ten carbon atoms. The term "Heteroarylsulfonyl", embraces heteroaryl radicals attached to a sulfonyl radical, where heteroaryl is defined as above. "Heteroarylsulfonylalkyl", embraces heteroarylsulfonyl radicals attached to an alkyl radical, where alkyl is defined as above.

The term "aryloxy" embraces aryl radicals, as defined above, attached to an oxygen atom. Examples of such radicals include phenoxy, 4-chloro-3-ethylphenoxy, 4-chloro-3-methylphenoxy, 3-chloro-4-ethylphenoxy, 3,4-dichlorophenoxy, 4-methylphenoxy, 3-trifluoromethoxyphenoxy, 3-trifluoromethylphenoxy, 4-fluorophenoxy, 3,4-dimethylphenoxy, 5-bromo-2-fluorophenoxy, 4-bromo-3-fluorophenoxy, 4-fluoro-3-methylphenoxy, 5,6,7,8-tetrahydronaphthyloxy, 3-isopropylphenoxy, 3-cyclopropylphenoxy, 3-ethylphenoxy, 3-pentafluoroethylphenoxy, 3-(1,1,2,2-tertrafluoroethoxy)-phenoxy, and 4-tert-butylphenoxy.

The term "aroyl" embraces aryl radicals, as defined above, attached to an carbonyl radical as defined above. Examples of such radicals include benzoyl and toluoyl.

The term "aralkanoyl" embraces aralkyl radicals, as defined herein, attached to an carbonyl radical as defined above. Examples of such radicals include, for example, phenylacetyl.

The term "aralkoxy" embraces oxy-containing aralkyl radicals attached through an oxygen atom to other radicals. More preferred aralkoxy radicals are "aralkoxy" radicals having phenyl radicals attached to alkoxy radical as described above. Examples of such radicals include benzyloxy, 1-phenylethoxy, 3-trifluoromethoxybenzyloxy, 3-trifluoromethylbenzyloxy, 3,5-difluorobenzyloxy, 3-bromobenzyloxy, 4-propylbenzyloxy, 2-fluoro-3-trifluoromethylbenzyloxy, and 2-phenylethoxy.

The term "aryloxyalkyl" embraces aryloxy radicals, as defined above, attached to an alkyl group. Examples of such radicals include phenoxymethyl.

The term "haloaryloxyalkyl" embraces aryloxyalkyl radicals, as defined above, wherein one to five halo radicals are attached to an aryloxy group.

The term "heteroaroyl" embraces heteroaryl radicals, as defined above, attached to an carbonyl radical as defined above. Examples of such radicals include furoyl and nicotinyl.

The term "heteroaralkanoyl" embraces heteroaralkyl radicals, as defined herein, attached to an carbonyl radical as defined above. Examples of such radicals include, for example, pyridylacetyl and furylbutyryl.

The term "heteroaralkoxy" embraces oxy-containing heteroaralkyl radicals attached through an oxygen atom to other radicals. More preferred heteroaralkoxy radicals are "heteroaralkoxy" radicals having heteroaryl radicals attached to alkoxy radical as described above. The term "heterocyclylalkoxy" embraces oxy-containing heterocyclylalkyl radicals attached through an oxygen atom to other radicals.

The term "haloheteroaryloxyalkyl" embraces heteroaryloxyalkyl radicals, as defined above, wherein one to four halo radicals are attached to an heteroaryloxy group.

The term "heteroarylamino" embraces heteroaryl radicals, as defined above, attached to an amino group. Examples of such radicals include pyridylamino. The term "heterocyclylamino" embraces heterocyclyl radicals, as defined above, attached to an amino group.

The term "heteroaralkylamino" embraces heteroaralkyl radicals, as defined above, attached to an amino group. Examples of such radicals include pyridylmethylamino. The term "heterocyclylalkylamino" embraces heterocyclylalkyl radicals, as defined above, attached to an amino group.

The term "heteroaryloxy" embraces heteroaryl radicals, as defined above, attached to an oxy group. Examples of such radicals include 2-thiophenyloxy, 2-pyrimidyloxy, 2-pyridyloxy, 3-pyridyloxy, and 4-pyridyloxy. The term "heterocyclyloxy" embraces heterocyclyl radicals, as defined above, attached to an oxy group.

The term "heteroaryloxyalkyl" embraces heteroaryloxy radicals, as defined above, attached to an alkyl group. Examples of such radicals include 2-pyridyloxymethyl, 3-pyridyloxyethyl, and 4-pyridyloxymethyl. The term "heterocyclyloxyalkyl" embraces heterocyclyloxy radicals, as defined above, attached to an alkyl group.

The term "arylthio" embraces aryl radicals, as defined above, attached to an sulfur atom. Examples of such radicals include phenylthio.

The term "arylthioalkyl" embraces arylthio radicals, as defined above, attached to an alkyl group. Examples of such radicals include phenylthiomethyl.

The term "alkylthioalkyl" embraces alkylthio radicals, as defined above, attached to an alkyl group. Examples of such radicals include methylthiomethyl. The term "alkoxyalkyl" embraces alkoxy radicals, as defined above, attached to an alkyl group. Examples of such radicals include methoxymethyl.

The term "carbonyl" denotes a carbon radical having two of the four covalent bonds shared with an oxygen atom. The term "carboxy" embraces a hydroxyl radical, as defined above, attached to one of two unshared bonds in a carbonyl group. The term "carboxamido" embraces amino, monoalkylamino, dialkylamino, monocycloalkylamino, alkylcycloalkylamino, dicycloalkylamino, N-alkyl-N-arylamino, arylamino, aralkylamino, nitrogen containing heterocyclyl, heterocyclylamino, N-alkyl-N-heterocyclylamino, heteroarylamino, and heteroaralkylamino radicals, attached to one of two unshared bonds in a carbonyl group. The term "carboxamidoalkyl" embraces carboxamido radicals, as defined above, attached to an alkyl group. The term "carboxyalkyl" embraces a carboxy radical, as defined above, attached to an alkyl group. The term "carboalkoxy" embraces alkoxy radicals, as defined above, attached to one of two unshared bonds in a carbonyl group. The term "carboaralkoxy" embraces aralkoxy radicals, as defined above, attached to one of two unshared bonds in a carbonyl group. The term "monocarboalkoxyalkyl" embraces one carboalkoxy radical, as defined above, attached to an alkyl group. The term "dicarboalkoxyalkyl" embraces two carboalkoxy radicals, as defined above, attached to an alkylene group. The term "monocyanoalkyl" embraces one cyano radical, as defined above, attached to an alkyl group. The term "dicyanoalkylene" embraces two cyano radicals, as defined above, attached to an alkyl group. The term "carboalkoxycyanoalkyl" embraces one cyano radical, as defined above, attached to an carboalkoxyalkyl group.

The term "acyl", alone or in combination, means a carbonyl or thionocarbonyl group bonded to a radical selected from, for example, hydrido, alkyl, alkenyl, alkynyl, haloalkyl, alkoxy, alkoxyalkyl, haloalkoxy, aryl, heterocyclyl, heteroaryl, alkylsulfinylalkyl, alkylsulfonylalkyl, aralkyl, cycloalkyl, cycloalkylalkyl, cycloalkenyl, alkylthio, arylthio, amino, alkylamino, dialkylamino, aralkoxy, arylthio, and alkylthioalkyl. Examples of "acyl" are formyl, acetyl, benzoyl, trifluoroacetyl, phthaloyl, malonyl, nicotinyl, and the like. The term "haloalkanoyl" embraces one or more halo radicals, as defined herein, attached to an alkanoyl radical as defined above. Examples of such radicals include, for example, chloroacetyl, trifluoroacetyl, bromopropanoyl, and heptafluorobutanoyl.

The term "phosphono" embraces a pentavalent phosphorus attached with two covalent bonds to an oxygen radical. The term "dialkoxyphosphono" denotes two alkoxy radicals, as defined above, attached to a phosphono radical with two covalent bonds. The term "diaralkoxyphosphono" denotes two aralkoxy radicals, as defined above, attached to a phosphono radical with two covalent bonds. The term "dialkoxyphosphonoalkyl" denotes dialkoxyphosphono radicals, as defined above, attached to an alkyl radical. The term "diaralkoxyphosphonoalkyl" denotes diaralkoxyphosphono radicals, as defined above, attached to an alkyl radical.

The term "amino" denotes a nitrogen atom containing two substituents such as hydrido, hydroxy or alkyl and having one covalent bond available for bonding to a single atom such as carbon. Examples of such amino radicals include, for example, $-NH_2$, $-NHCH_3$, $-NHOH$, and $-NHOCH_3$. The term "imino" denotes a nitrogen atom containing one substituent such as hydrido, hydroxy or alkyl and having two covalent bonds available for bonding to a single atom such as carbon. Examples of such imino radicals include, for example, $=NH$, $=NCH_3$, $=NOH$, and $=NOCH_3$. The term "imino carbonyl" denotes a carbon radical having two of the four covalent bond sites shared with an imino group. Examples of such imino carbonyl radicals include, for example, $C=NH$, $C=NCH_3$, $C=NOH$, and $C=NOCH_3$. The term "amidino" embraces a substituted or unsubstituted amino group bonded to one of two available bonds of an aminocarbonyl radical. Examples of such amidino radicals include, for example, $NH_2-C=NH$, $NH_2-C=NCH_3$, $NH_2-C=NOCH_3$ and $CH_3NH-C=NOH$. The term "guanidino" denotes an amidino group bonded to an amino group as defined above where said amino group can be bonded to a third group. Examples of such guanidino radicals include, for example, $NH_2-C(NH)-NH-$, $NH_2-C(NCH_3)-NH-$, $NH_2-C(NOCH_3)-NH-$, and $CH_3NH-C(NOH)-NH-$.

The term "sulfonium" denotes a positively charged trivalent sulfur atom where said sulfur is substituted with three carbon based groups such as alkyl, alkenyl, aralkyl, or aryl. The term "dialkyl sulfonium" denotes a sulfonium group where said sulfur is substituted with two alkyl groups. Examples of such dialkylsulfonium radicals include, for example, $(CH_3)_2S^+-$. The term "dialkyl sulfonium alkyl" denotes a dialkyl sulfonium group where said group is bonded to one bond of an alkylene group as defined above. Examples of such dialkylsulfoniumalkyl radicals include $(CH_3)_2S^+-CH_2CH_2-$.

The term "phosphonium" denotes a positively charged tetravalent phosphorus atom where said phosphorus is substituted with four carbon based groups such as alkyl, alkenyl, aralkyl, or aryl. The term "trialkyl phosphonium" denotes a phosphonium group where said phosphorus is substituted with three alkyl groups. Examples such trialkylphosphonium radicals include, for example, $(CH_3)_3P^+-$.

Said "alkyl", "alkenyl", "alkynyl", "alkanoyl", "alkylene", "alkenylene", "hydroxyalkyl", "haloalkyl", "haloalkylene", "haloalkenyl", "alkoxy", "alkenyloxy", "alkenyloxyalkyl", "alkoxyalkyl", "aryl", "perhaloaryl", "haloalkoxy", "haloalkoxyalkyl", "haloalkenyloxy", "haloalkenyloxyalkyl", "alkylenedioxy", "haloalkylenedioxy", "heterocyclyl", "heteroaryl", "hydroxyhaloalkyl", "alkylsulfonyl", "haloalkylsulfonyl", "alkylsulfonylalkyl", "haloalkylsulfonylalkyl", "alkylsulfinyl", "alkylsufinylalkyl", "haloalkylsulfinylalkyl", "aralkyl", "heteroaralkyl", "perhaloaralkyl", "aralkylsulfonyl", "aralkylsulfonylalkyl", "aralkylsulfinyl", "aralkylsulfinylalkyl", "cycloalkyl", "cycloalkylalkanoyl", "cycloalkylalkyl", "cycloalkenyl", "halocycloalkyl", "halocycloalkenyl", "cycloalkylsulfinyl", "cycloalkylsulfinylalkyl", "cycloalkylsulfonyl", "cycloalkylsulfonylalkyl", "cycloalkoxy", "cycloalkoxyalkyl", "cycloalkylalkoxy", "cycloalkenyloxy", "cycloalkenyloxyalkyl", "cycloalkylenedioxy", "halocycloalkoxy", "halocycloalkoxyalkyl", "halocycloalkenyloxy", "halocycloalkenyloxyalkyl", "alkylthio", "haloalkylthio", "alkylsulfinyl", "amino", "oxy", "thio", "alkylamino", "arylamino", "aralkylamino", "arylsulfinyl", "arylsulfinylalkyl", "arylsulfonyl", "arylsulfonylalkyl", "heteroarylsulfinyl", "heteroarylsulfinylalkyl", "heteroarylsulfonyl", "heteroarylsulfonylalkyl", "heteroarylamino", "heteroaralkylamino", "heteroaryloxy", "heteroaryloxyalkyl", "aryloxy", "aroyl", "aralkanoyl", "aralkoxy", "aryloxyalkyl", "haloaryloxyalkyl", "heteroaroyl", "heteroaralkanoyl", "heteroaralkoxy", "heteroaralkoxyalkyl", "arylthio", "arylthioalkyl", "alkoxyalkyl", "acyl", "amidino", "guanidino", "dialkylsulfonium", "trialkylphosphonium", and "dialkylsulfoniumalkyl" groups defined above may optionally have 1 or more non-hydrido substituents such as amidino, guanidino, dialkylsulfonium, trialkylphosphonium, dialkylsulfoniumalkyl, perhaloaralkyl, aralkysulfonyl, aralkylsulonylalkyl, aralkylsulfinyl, aralkylsulfinylalkyl, halocycloalkyl, halocycloalkenyl, cycloalkylsulfinyl, cycloalkylsulfinylalkyl, cycloalkylsulfonyl, cycloalkylsulfonylalkyl, heteroarylamino, N-heteroarylamino-N-alkylamino, heteroaralkylamino, heteroaryloxy, heteroaryloxylalkyl, haloalkylthio, alkanoyloxy, alkoxy, alkoxyalkyl, haloalkoxylalkyl, heteroaralkoxy, cycloalkoxy, cycloalkenyloxy, cycloalkoxyalkyl, cycloalkylalkoxy, cycloalkenyloxyalkyl, cycloalkylenedioxy, halocycloalkoxy, halocycloalkoxyalkyl, halocycloalkenyloxy, halocycloalkenyloxyalkyl, hydroxy, amino, thio, nitro, alkylamino, alkylthio, alkylthioalkyl, arylamino, aralkylamino, arylthio, arylthioalkyl, heteroaralkoxyalkyl, alkylsulfinyl, alkylsulfinylalkyl, arylsufinylalkyl, arylsulfonylalkyl, heteroarylsulfinylalkyl, heteroarylsulfonylalkyl, alkylsulfonyl, alkylsulfonylalkyl, haloalkylsulfinylalkyl, haloalkylsulfonylalkyl, alkylsulfonamido, alkylaminosulfonyl, amidosulfonyl, monoalkyl amidosulfonyl, dialkyl, amidosulfonyl, monoarylamidosulfonyl, arylsulfonamido, diarylamidosulfonyl, monoalkyl monoaryl amidosulfonyl, arylsulfonyl, arylsulfonyl, heteroarylthio, heteroarylsulfinyl, heteroarylsulfonyl, alkanoyl, alkenoyl, aroyl, heteroaroyl, aralkanoyl, heteroaralkanoyl, haloalkanoyl, alkyl, alkenyl, alkynyl, alkenyloxy, alkenyloxyalkyl, alkylenedioxy, haloalkylenedioxy, cycloalkyl, cycloalkylalkanoyl, cycloalkenyl, cycloalkylalkyl, cycloalkenylalkyl, halo, haloalkyl, haloalkenyl, haloalkoxy, hydroxyhaloalkyl, hydroxyaralkyl, hydroxyalkyl, aminoalkyl, hydoxyheteroaralklyl, haloalkoxyalkyl, aryl, aralkyl, aryloxy, aralkoxy, aryloxyalkyl, saturated heterocyclyl, partially saturated heterocyclyl, heteroaryl, heteroaryloxy, heteroaryloxyalkyl, arylalkyl, heteroaralkyl, arylalkenyl, heteroarylalkenyl, carboxyalkyl, carboalkoxy, alkoxycarbonyl, carboaralkoxy, carboxamido, carboxamidoalkyl, cyano, carbohaloalkoxy, phosphono, phosphonoalkyl, diaralkoxyphosphono, and diaralkoxyphosphonoalkyl.

The term "spacer" can include a covalent bond and a linear moiety having a backbone of 1 to 7 contiguous atoms. The spacer may have 1 to 7 atoms of a univalent or multi-valent chain. Univalent chains may be constituted by a radical selected from =C(H)—, =C($R^{2a}$)—, —O—, —S—, —S(O)—, —S(O)$_2$—, —NH—, —N($R^{2a}$)—, —N=, —CH(OH)—, =C(OH)—, —CH(O$R^{2a}$)—, =C(O$R^{2a}$)—, and —C(O)— wherein $R^{2a}$ is selected from alkyl, alkenyl, aryl, heteoaryl, aralkyl, aryloxyalkyl, alkoxyalkyl, alkylthioalkyl, arylthioalkyl, cycloalkyl, cycloalkylalkyl, haloalkyl, haloalkenyl, haloalkoxyalkyl, perhaloaralkyl, heteroarylalkyl, heteroaryloxyalkyl, heteroarylthioalkyl, and heteroarylalkenyl. Multi-valent chains may consist of a straight chain of 1 or 2 or 3 or 4 or 5 or 6 or 7 atoms or a straight chain of 1 or 2 or 3 or 4 or 5 or 6 atoms with a side chain. The chain may be constituted of one or more radicals selected from: alkylene, alkenyl, —O—, —O—CH$_2$—, —S—CH$_2$—, —CH$_2$CH$_2$—, ethenyl, —CH=C(OH)—, —OCH$_2$O—, —O(CH$_2$)$_2$O—, —NHCH$_2$—, —OCH($R^{2a}$)O—, —O(CH$_2$CH$R^{2a}$)O—, —OCF$_2$O—, —O(CF$_2$)$_2$O—, —S—, —S(O)—, —S(O)$_2$—, —N(H)—, —N(H)O—, —N($R^{2a}$)O—, —N($R^{2a}$)—, —C(O)—, —C(O)NH—, —C(O)N$R^{2a}$—, —N=, —OCH$_2$—, —SCH$_2$—, S(O)CH$_2$—, —CH$_2$C(O)—, —CH(OH)—, =C(OH)—, —CH(O$R^{2a}$)—, =C(O$R^{2a}$)—, S(O)$_2$CH$_2$—, and —N$R^{2a}$CH$_2$— and many other radicals defined above or generally known or ascertained by one of skill-in-the art. Side chains may include substituents such as 1 or more non-hydrido substituents such as amidino, guanidino, dialkylsulfonium, trialkylphosphonium, dialkylsulfoniumalkyl, perhaloaralkyl, aralkylsulfonyl, aralkylsulfonylalkyl, aralkylsulfinyl, aralkylsulfinylalkyl, halocycloalkyl, halocycloalkenyl, cycloalkylsulfinyl, cycloalkylsulfinylalkyl, cycloalkylsulfonyl, cycloalkylsulfonylalkyl, heteroarylamino, N-heteroarylamino-N-alkylamino, heteroaralkylamino, heteroaryloxy, heteroaryloxylalkyl, haloalkylthio, alkanoyloxy, alkoxy, alkoxyalkyl, haloalkoxylalkyl, heteroaralkoxy, cycloalkoxy, cycloalkenyloxy, cycloalkoxyalkyl, cycloalkylalkoxy, cycloalkenyloxyalkyl, cycloalkylenedioxy, halocycloalkoxy, halocycloalkoxyalkyl, halocycloalkenyloxy, halocycloalkenyloxyalkyl, hydroxy, amino, thio, nitro, alkylamino, alkylthio, alkylthioalkyl, arylamino, aralkylamino, arylthio, arylthioalkyl, heteroaralkoxyalkyl, alkylsulfinyl, alkylsulfinylalkyl, arylsulfinylalkyl, arylsulfonylalkyl, heteroarylsulfinylalkyl, heteroarylsulfonylalkyl, alkylsulfonyl, alkylsulfonylalkyl, haloalkylsulfinylalkyl, haloalkylsulfonylalkyl, alkylsulfonamido, alkylaminosulfonyl, amidosulfonyl, monoalkyl amidosulfonyl, dialkyl amidosulfonyl, monoarylamidosulfonyl, arylsulfonamido, diarylamidosulfonyl, monoalkyl monoaryl amidosulfonyl, arylsulfinyl, arylsulfonyl, heteroarylthio, heteroarylsulfinyl, heteroarylsulfonyl, alkanoyl, alkenoyl, aroyl, heteroaroyl, aralkanoyl, heteroalkanoyl, haloalkanoyl, alkyl, alkenyl, alkynyl, alkenyloxy, alkenyloxyalky, alkylenedioxy, haloalkylenedioxy, cycloalkyl, cycloalkenyl, cycloalkylalkyl, cycloalkenylalkyl, halo, haloalkyl, haloalkenyl, haloalkoxy, hydroxyhaloalkyl, hydroxyaralkyl, hydroxyalkyl, aminoalkyl, hydroxyheteroalkyl, haloalkoxyalkyl, aryl, aralkyl, aryloxy, aralkoxy, aryloxyalkyl, saturated heterocyclyl, partially saturated heterocyclyl, heteroaryl, heteroaryloxy, heteroaryloxyalkyl, arylalkyl, heteroarylalkyl, arylalkenyl, heteroarylalkenyl, carboxyalkyl, carboalkoxy, carboaralkoxy, carboxamido, carboxamidoalkyl, cyano, carbohaloalkoxy, phosphono, phosphonoalkyl, diaralkoxyphosphono, and diaralkoxyphosphonoalkyl.

Compounds of the present invention can exist in tautomeric, geometric or stereoisomeric forms. The present invention contemplates all such compounds, including cis- and trans-geometric isomers, E- and Z-geometric isomers, R- and S-enantiomers, diastereomers, d-isomers, l-isomers, the racemic mixtures thereof and other mixtures thereof, as falling within the scope of the invention. Pharmaceutically acceptable sales of such tautomeric, geometric or stereoisomeric forms are also included within the invention.

The terms "cis" and "trans" denote a form of geometric isomerism in which two carbon atoms connected by a double bond will each have a hydrogen atom on the same side of the double bond ("cis") or on opposite sides of the double bond ("trans").

Some of the compounds described contain alkenyl groups, and are meant to include both cis and trans or "E" and "Z" geometric forms.

Some of the compounds described contain one or more stereocenters and are meant to include R, S, and mixtures of R and S forms for each stereocenter present.

Some of the compounds described herein may contain one or more ketonic or aldehydic carbonyl groups or combinations thereof alone or as part of a heterocyclic ring system. Such carbonyl groups may exist in part or principally in the "keto" form and in part or principally as one or more "enol" forms of each aldehyde and ketone group present. Compounds of the present invention having aldehydic or ketonic carbon groups are meant to include both "keto" and "enol" tautometric forms.

Some of the compounds described herein may contain one or more amide carbonyl groups or combinations thereof alone or as part of a heteocyclic ring system. Such carbonyl groups may exist in part or principally in the "keto" form and in part or principally as one or more "enol" forms of each amide group present. Compounds of the present invention having amidic carbonyl groups are meant to include both "keto" and "enol" tautomeric forms. Said amide carbonyl groups may be both oxo (C=O) and thiono (C=S) in type.

Some of the compounds described herein may contain one or more imine or enamine groups or combinations thereof. Such groups may exist in part or principally in the "imine" form and in part or principally as one or more "enamine" forms of each group present. Compounds of the present invention having said imine or enamine groups are meant to include both "imine" and "enamine" tautomeric forms.

The present invention also comprises a treatment and prophylaxis in anticoagulant therapy for the treatment and prevention of a variety of thrombotic conditions including coronary artery and cerebrovascular disease in a subject, comprising administering to the subject having such disorder a therapeutically-effective amount of a compound of Formula (I):

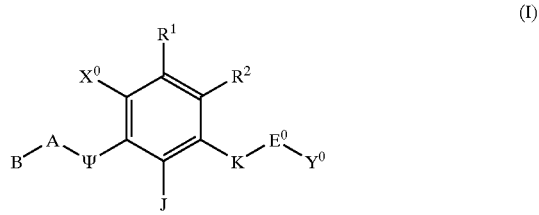

or a pharmaceutically-acceptable salt thereof.

As a further embodiment, compounds of the present invention of Formula (I) or a pharmaceutically-acceptable salt thereof as defined above, comprise a treatment and prophylaxis of coronary artery disease, cerebrovascular disease and other coagulation cascade related disorders in a subject, comprising administering to the subject having such disorder a therapeutically-effective amount of compounds of formula (I) of the present invention or a pharmaceutically-acceptable salt thereof.

Compounds of the present invention of Formula (I) or a pharmaceutically-acceptable salt thereof can also be used whenever inhibition of blood coagulation is required such as to prevent coagulation of stored whole blood and to prevent coagulation in other biological samples for testing or storage. Thus coagulation inhibitors of the present inhibition can be added to or contacted with stored whole blood and any medium containing or suspected of containing plasma coagulation factors and in which it is desired that blood coagulation be inhibited, e.g. when contacting the mammal's blood with material selected from the group consisting of vascular grafts, stents, orthopedic prothesis, cardiac prosthesis, and extracorporeal circulation systems.

Compounds of Formula (I) are capable of inhibiting activity of serine proteases related to the coagulation cascade, and thus could be used in the manufacture of a medicament, a method for the prophylactic or therapeutic treatment of diseases mediated by coagulation cascade serine protease, such as inhibiting the formation of blood platelet aggregates, inhibiting the formation of fibrin, inhibiting thrombus formation, and inhibiting embolus formation in a mammal, in blood, in blood products, and in mammalian organs. The compounds also can be used for treating or preventing unstable angina, refractory angina, myocardial infarction, transient ischemic attacks, atrial fibrillation, thrombotic stroke, embolic stroke, deep vein thrombosis, disseminated intravascular coagulation, ocular build up or fibrin, and reocclusion or restenosis of recanalized vessels in a mammal. The compounds also can be used to study the mechanism of action of coagulation cascade serine proteases to enable the design of better inhibitors and development of better assay methods. The compounds of Formula (I) would be also useful in prevention of cerebral vascular accident (CVA) or stroke.

Also included in the family of compounds of Formula (I) are the pharmaceutically-acceptable salts thereof. The term "pharmaceutically-acceptable salt" embraces salts commonly used to form alkali metal salts and to form addition salts of free acids or free base. The nature of the salt is not critical, provided that it is pharmaceutically acceptable. Suitable pharmaceutically-acceptable acid addition salts of compounds of Formula (I) may be prepared from inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, araliphatic, heterocyclic, carboxylic and sulfonic classes of organic acids, examples of which are formic, acetic, propionic, succinic, glycolic, gluconic, lactic, malic, tartaric, citric, ascorbic, glucoronic, maleic, fumaric, pyruvic, aspartic, glutamic, benzoic, anthranilic, mesylic, salicylic, p-hydroxybenzoic, phenylacetic, mandelic, embonic (pamoic), methanesulfonic, ethylsulfonic, benzenesulfonic, sulfanilic, stearic, cyclohexylaminosulfonic, algenic, galacturonic acid. Suitable pharmaceutically-acceptable base addition salts of compounds of Formula (I) include metallic salts made from aluminum, calcium, lithium, magnesium, potassium, sodium and zinc or organic salts made from N,N'-dibenzylethyleneldiamine, choline, chloroprocaine, diethanolamine, ethylenediamine, meglumine (N-methylglucamine) and procain. All of these salts may be prepared by conventional means from the corresponding compound of Formula (I) by reacting, for example, the appropriate acid or base with the compound of Formula (I).

The present invention also comprises a pharmaceutical composition comprising a therapeutically-effective amount of a compound of Formulas (I) in association with at least one pharmaceutically-acceptable carrier, adjuvant or diluent. Pharmaceutical compositions of the present invention can comprise the active compounds of Formula (I) in association with one or more non-toxic, pharmaceutically-acceptable carriers and/or diluents and/or adjuvants (collectively referred to herein as "carrier" materials) and, if desired, other active ingredients. The active compounds of the present invention may be administered by any suitable route, preferably in the form of a pharmaceutical composition adapted to such a route, and in a dose effective for the treatment intended.

The active compounds and composition may, for example, be administered orally, intravascularly, intraperitoneally, subcutaneously, intramuscularly, oculary, or topically. For treating ocular build up of fibrin, the compounds may be administered intraocularly or topically as well as orally or parentally.

The compounds can be administered in the form of a depot injection or implant preparation which may be formulated in such a manner as to permit a sustained release of the active ingredient. The active ingredient can be compressed into pellets or small cylinders and implanted subcutaneously or intramusculary as depot injections or implants. Implants may employ inert materials such as biodegradable polymers or synthetic silicones, for example, Silastic, silicone rubber or other silicon containing polymers.

The compounds can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The compounds may also be delivered by the use of monoclonal antibodies as individual carriers to which the compound molecules are coupled. The compounds may also be coupled with soluble polymers as targetable drug carriers. Such polymers can include polyvinylpyrrolidone, pyran copolymer, polyhydroxy-propyl-methacrylamide-phenol, polyhydroxyethyl-aspartamide-phenol, or ployethyleneoxide-polylysine substituted with palmitoyl residues. Furthermore, the compounds may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross linked or amphitpathic block copolymers of hydrogels.

For oral administration, the pharmaceutical composition may be in the form of, for example, tablets, capsules (each of which includes sustained release or timed release formulations), pills, powders, granules, elixers, tinctures, suspensions, liquids including syrups, and emulsions. The pharmaceutical composition is preferably made in the form of a dosage unit containing a particular amount of the active ingredient. Examples of such dosage units are tablets or capsules. The active ingredient may also be administered by injection as a composition wherein, for example, saline, dextrose or water may be used as a suitable carrier.

The amount of therapeutically active compounds which are administered and the dosage regimen for treating a disease condition with the compounds and/or compositions of this invention depends on a variety of factors, including the age, weight, sex and medical condition of the subject, the severity of the disease, the route and frequency of administration, and the particular compound employed, and thus may vary widely.

The pharmaceutical compositions may contain active ingredients in the range of about 0.1 to 2000 mg, and preferably in the range of about 0.5 to 500 mg. A daily dose of about 0.01 to 100 mg/kg body weight, and preferably between about 0.5 and about 20 mg/kg body weight, may be appropriate. The daily dose can be administered in one to four doses per day.

The compounds may be formulated in topical ointment or cream, or as a suppository, containing the active ingredients in a total amount of, for example, 0.075 to 30% w/w, preferably 0.2 to 20% w/w and most preferably 0.4 to 15% w/w. When formulated in an ointment, the active ingredients may be employed with either paraffinic or a water-miscible ointment base.

Alternatively, the active ingredients may be formulated in a cream with an oil-in-water cream base. If desired, the aqueous phase of the cream base may include, for example at least 30% w/w of a polyhydric alcohol such as propylene glycol, butane-1,3-diol, mannitol, sorbitol, glycerol, polyethylene glycol and mixtures thereof. The topical formulation may desirably include a compound which enhances absorption or penetration of the active ingredient through the skin or other affected areas. Examples of such dermal penetration enhancers include dimethylsufoxide and related analogs. The compounds of this invention can also be administered by a transdermal device. Preferably topical administration will be accomplished using a patch either of the reservoir and porous membrane type or of a solid matrix variety. In either case, the active agent is delivered continuously from the reservoir or microcapsules through a membrane into the active agent permeable adhesive, which is in contact with the skin or mucosa of the recipient. If the active agent is absorbed through the skin, a controlled and predetermined flow of the active agent is administered to the recipient. In the case of microcapsules, the encapsulating agent may also function as the membrane.

The oily phase of the emulsions of this invention may be constituted from known ingredients in a known manner. While the phase may comprise merely an emulsifier, it may comprise a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base which forms the oily dispersed phase of the cream formulations. Emulsifiers and emulsion stabilizers suitable for use in the formulation of the present invention include Tween 60, Span 80, cetostearyl alcohol, myristyl alcohol, glyceryl monostearate, and sodium lauryl sulfate, among others.

The choice of suitable oils or fats for the formulation is based on achieving the desired cosmetic properties, since the solubility of the active compound in most oils likely to be used in pharmaceutical emulsion formulations is very low. Thus, the cream should preferably be a non-greasy, non-staining and washable product with suitable consistency to avoid leakage from tubes or other containers. Straight or branched chain, mono- or dibasic alkyl esters such as diisoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters may be used. These may be used alone or in combination depending on the properties required. Alternatively, high melting point lipids such as white soft paraffin and/or liquid paraffin or other mineral oils can be used.

For therapeutic purposes, the active compounds of the present invention are ordinarily combined with one or more adjuvants appropriate to the indicated route of administration. If administered per os, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose. Formulations for parenteral administration may be in the form of aqueous or non-aqueous isotonic sterile injection solutions or suspensions. These solutions and suspensions may be prepared from sterile powders or granules having one or more of the carriers or diluents mentioned for use in the formulations for oral administration. The compounds may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

In practicing the methods of the present invention for the treatment and prevention of a variety of thrombotic conditions including coronary artery and cerebrovascular disease, the compounds and pharmaceutical compositions of the present invention are administered alone or in combination with one another, or in combination with other therapeutics or in vivo diagnostic agents. The coagulation cascade inhibitors of the present invention can also be co-administered with suitable anti-platelet agreggation agents, including, but not limited to ticlopidine or clopidrogel, fibrinogen receptor antagonists (e.g. to treat or prevent unstable angina or to prevent reocculsion after angioplasty and restenosis), anticoagulants such as aspirin, warfarin or heparins, thrombolytic agents such as plasminogen activators or streptokinase to achieve synergistic effects in the treatment of various pathologies, lipid lowering agents including antihypercholesterolemics (e.g. HMG CoA reductase inhibitors such as mevastatin, lovastatin, simvastatin, pravastatin, and fluvastalin, HMG CoA synthatase inhibitors, etc.), anti-diabetic drugs, or other cardiovascular agents (loop diuretics, thiazide type diuretics, nitrates, aldosterone antagonistics (i.e., spironolactone and epoxymexlerenone), angiotensin converting enzyme (e.g. ACE) inhibitors, angiotensin II receptor antagonists, beta-blockers, antiarrythmics, anti-hypertension agents, and calcium channel blockers) to treat or prevent atheriosclerosis. For example, patients suffering from coronary artery disease, and patients subjected to angioplasty procedures, would benefit from coadministration of fibrinogen receptor antagonists and coagulation cascade inhibitors of the present invention. Also, coagulation cascade inhibitors could enhance the efficiency of tissue plasminogen activator-mediated thrombolytic reperfusion.

Typical doses of coagulation cascade inhibitors of the present invention with other suitable anti-platelet agents, anticoagulation agents, cardiovascular therapeutic agents, or thrombolytic agents may be the same as those doses of coagulation cascade inhibitors administered without coadministration of additional anti-platelet agents, anticoagulation agents, cardiovascular therapeutic agents, or thrombolytic agents, or may be substantially less than those doses of coagulation cascade inhibitors administered without coadministration of additional anti-platelet agents, anticoagulation agents, cardiovascular therapeutic agents, or thrombolytic agents, depending on a patient's therapeutic needs.

The present novel methods preferably employ compounds which selectively inhibit human TF-VIIA over the inhibition of both human Thrombin II and human factor Xa. Preferably, the compounds have a human TF-VIIA $IC_{50}$ of less than 0.5 µM and also have a selectivity ratio of TF-VIIA inhibition over both human Thrombin II and human factor Xa inhibition of at least 10, and more preferably at least 100. Even more preferably, the compounds have a human TF-VIIA $IC_{50}$ of less than 0.1 µM and also have a selectivity ratio of TF-VIIA inhibition over both human Thrombin II and human factor Xa inhibition of at least 1000, and most preferably at least 10,000.

All mentioned references are incorporated by reference as if here written.

Although this invention has been described with respect to specific embodiments, the details of these embodiments are not to be construed as limitations. The following examples are provided to illustrate the present invention and are not intended to limit the scope thereof. Without further elaboration, it is believed that one skilled in the art can, using the preceding descriptions, utilize the present invention to its fullest extent. Therefore the following preferred specific embodiments are to be construed as merely illustrative and not limitative of the remainder of the disclosure in any way whatsoever. Compounds containing multiple variations of the structural modifications illustrated in the schemes or the following Examples are also contemplated. Those skilled in the art will readily understand that known variations of the conditions and processes of the following preparative procedures can be used to prepare these compounds.

One skilled in the art may use these generic methods to prepare the following specific examples, which have been or may be properly characterized by $^1$H NMR, mass spectrometry, elemental composition, and similar procedures. These compounds also may be formed in vivo. The following examples contain detailed descriptions of the methods of preparation of compounds of Formula (I). These detailed descriptions fall within the scope and are presented for illustrative purposes only and are not intended as a restriction on the scope of the invention. All parts are by weight and temperatures are Degrees centigrade unless otherwise indicated.

The following general synthetic sequences are useful in making the present invention. Abbreviations used in the schemes are as follows: "AA" represents amino acids, "AcCN" represents acetonitrile, "AcOH" represents acetic acid, "BINAP" represents 2,2'-bis(diphenylphosphino)-1,1'-binaphthyl, "BnOH" represents benzyl alcohol, "BnCHO" represents 2-phenylethanal, "BnSO$_2$Cl" represents benzylsulfonyl chloride, "Boc" represents tert-butyloxycarbonyl, "BOP" represents benzotriazol-1-yl-oxy-tris-(dimethylamino), "bu" represents butyl, "dba" represents dibenzylideneacetone, "DCC" represents 1,3-dicyclohexylcarbodiimide, "DCM" represents dichloromethane or methylene chloride, "DIBAH" or "DIBAL" represents diisobutylaluminum hydride, "DMF" represents dimethylformamide, "DMSO" represents dimethylsulfoxide, "DPPA" represents diphenylphosphoryl azide", "EDC" represents 1-[3-(dimethylamino)propyl]-3-ethylcarbodiimide hydrochloride, "Fmoc" represents 9-fluorenylmethoxycarbonyl, "HOBt" represents hydroxybenzoltriazole", "LDA" represents lithium diisopropylamide, "NMM" represents N-methylmorpholine, "Ph" represents phenyl or aryl, "PHTH" represents a phthaloyl group, "pnZ" represents 4-nitrobenzyloxycarbonyl, "PTC" represents a phase transfer catalyst, "py" represents pyridine, "RNH$_2$" represents a primary organic amine, "p-TsOH" represents paratoluenesulfonic acid, "TBAF" represents tetrabutylammonium fluoride, "TBTU" represents 2-(1H-benzotriozole-1-yl)-1,1,3,3-tetramethyl uronium tetrafluoroborate, "TEA" represents triethylamine, "TFA" represents trifluoroacetic acid, "THF" represents tetrahydrofuran, "TMS" represents trimethylsilyl, "TMSCN" represents trimethylsilyl cyanide, and "Cbz" or "Z" represents benzyloxycarbonyl.

GENERAL SYNTHETIC PROCEDURES AND SPECIFIC EXAMPLES

The benzene compounds of the present invention can be synthesized, for example, according to the following procedures and Schemes given below. Schemes 1 and 2 below summarize generic procedures that permit the preparation of a wide variety of the compounds of the present invention through the ability to introduce numerous $R^2$ substituents represented by $Z°$—Q, a wide variety of amino substituting groups represented by B-A, and a large number of amide forming Y groups at the carboxylic acid group in which K is a covalent single bond.

SCHEME 1
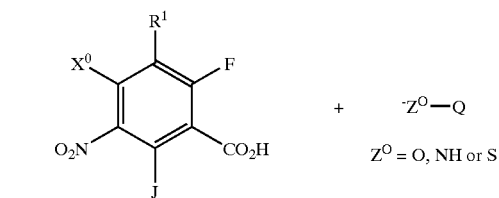
J = hydrido, cyano, alkyl, alkenyl, haloalkyl, haloalkenyl, carboxy, carboxyalkyl, carboalkoxy, amidocarbonyl, acyl, phosphono, sulfo, O—$R^6$, NH—$R^6$, S—$R^6$, S(O)—$R^6$, and S(O)$_2$—$R^8$.
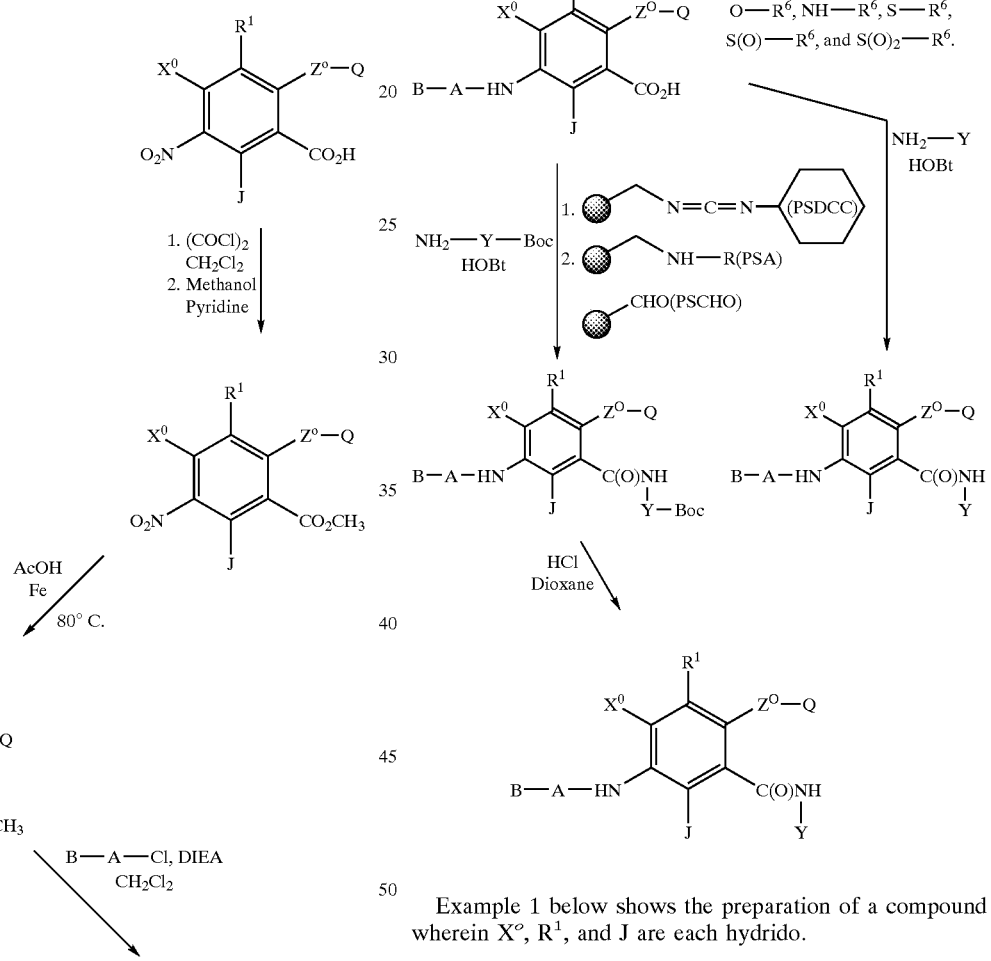
Example 1 below shows the preparation of a compound wherein $X^o$, $R^1$, and J are each hydrido.
Example 1
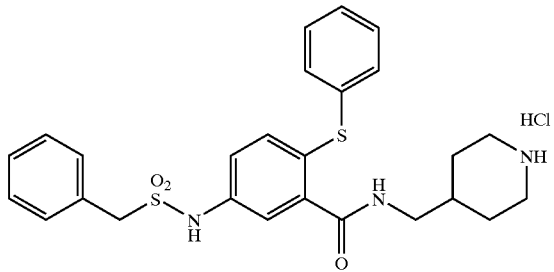

Triethylamine (8.3 mL, 0.060 mol) was added to a solution of 2-fluoro-5-nitrobenzoic acid (5.0 g, 0.027 mol) and thiophenol (2.8 mL, 0.027 mol) in tetrahydrofuran. After stirring at reflux for 20 hours, a saturated solution of ammonium chloride was added until solution became neutral. The solution was extracted with dichloromethane and the organic layer was washed with water, brine, dried over magnesium sulfate, and filtered. The solvent was removed by evaporation to afford 8.85 g (87%) of a yellow solid of product EX-1A; $^1$H NMR ppm: 1.40 (t, 9H), 3.21 (q, 6H), 6.75 (d, 1H, J=8.7 Hz), 7.47 (m, 3H), 7.57 (m, 2H), 7.85 (d, 1H, J=8.7 Hz), 8.85 (d, 1H, J=2.4 Hz).

Oxalyl chloride (7.7 mL, 0.088 mol) was added to a solution of the acid EX-1A (6.68 g, 0.017 mol) in dichloromethane followed by a drop of dimethylformamide. After stirring at room temperature for 1 hour, the solvent was removed by evaporation to afford the acid chloride. The acid chloride was redissolved into dichloromethane and an excess of methanol (50 mL) was added followed by addition of pyzidine (2.0 ml, 0.024 mol). The solution stirred at room temperature for 2.5 hours. The solution was washed with water, brine, dried over magnesium sulfate, and filtered. The solvent was removed by evaporation to afford the crude product. The product was purified by column chromatography (30% ethyl acetate-hexane) to afford 4.21 g (82%) of a yellow solid of product EX-1B; $^1$H NMR ppm: 4.05 (s, 3H), 6.89 (d, 1H, J=9.0 Hz), 7.61 (m, 5H), 8.05 (dd, 1H, J=8.7, 2.4 Hz), 8.88 (d, 1H, J=2.4 Hz); HRMS calcd for $C_{14}H_{11}O_4N_1S_1$ (M$^+$+H) 290.0487, found 290.0491.

The nitro compound EX-1B (3.71 g, 0.012 mmol) was stirred in glacial acetic acid. Powdered iron (3.58 g, 0.064 mmol) was added and the solution was heated to 80° C. with vigorous stirring. The solution was stirred at 80° C. for 15 minutes at which point the iron had turned gray. The reaction mixture was filtered through celite and the solid was washed with ether. The resultant organic layer was washed with water, stirred with saturated sodium bicarbonate until basic, and washed with water again. The solution was dried over magnesium sulfate, filtered and the solvent was removed to afford 2.48 g (75%) of a yellow oil of product EX-1C; $^1$H NMR ppm: 3.90 (s, 3H), 6.89 (dd, 1H, J=8.4, 2.7 Hz), 6.96 (d, 1H, J=8.4 Hz), 7.22 (d, 1H, J=2.7 Hz), 7.32 (m, 5H); HPLC purity (retention time): >99% (2.81 min); HRMS calcd for $C_{14}H_{13}O_2N_1S_1$ (M$^+$+H) 260.0745, found 260.0718.

Diisopropylethylamine (2.5 mL, 1.42 mmol) was added to a solution of the aniline EX-1C (2.46 g, 9.48 mmol) and a-toluenesulfonyl chloride (3.17 g, 16.6 mmol) in dichloromethane, and the resulting solution stirred at room temperature for 3 hours. The solution was washed with 2 N hydrochloric acid, brine, dried over magnesium sulfate, and filtered. The solvent was removed by evaporation to afford a mixture of two products. Fraction one of column chromatography (30% ethyl acetate-hexane) afforded 2.64 g (49%) of a white solid of product EX-1D; $^1$H NMR ppm: 3.94 (s, 3H), 4.85 (s, 4H), 6.22 (dd, 1H, J=9.0, 2.4 Hz), 6.44 (d, 1H, J=9.0 Hz), 7.07 (d, 1H, J=2.4 Hz), 7.40 (m, 7H), 7.50 (m, 9H); HRMS calcd for $C_{28}H_{25}O_6N_1S_3$ (M$^+$+NH$_4$) 585.1188, found 585.1141.

Following the same procedure described for EX-1D, fraction two of column chromatography (30% ethyl acetate-hexane) afforded 1.16 g (30%) of a white solid of product EX-1E; $^1$H NMR ppm: 3.98(s, 3H), 4.32 (s, 2H), 6.66 (s, 1H), 6.80 (d, 1H), 7.28 (dd, 1H), 7.29–7.73 (m, 11H); HPLC purity (retention time): 97.2% (4.20 min); HRMS calcd for $C_{21}H_{19}O_4N_1S_2$ (M$^+$+NH$_4$) 431.1099, found 431.1069.

Aqueous sodium hydroxide (10%) (3.0 mL, 7.5 mmol) was added to a solution of the methyl ester EX-1E (0.70 g, 1.7 mmol) in methanol and the resulting solution stirred at 65° C. for 4 hours. The solution was acidified with 2 N hydrochloric acid and extracted with ether. The solution was washed with brine, dried over magnesium sulfate, and filtered. The solvent was removed by evaporation to afford 0.66 g (98%) of a white solid of product EX-1F; $^1$H NMR ppm: 3.86 (s, 2H), 6.31 (dd, 1H), 6.83 (m, 6H), 6.97 (m, 3H), 7.06 (m, 2H), 7.52 (d, 1H), 9.35 (s, 1H); HPLC purity (retention time): 93.9% (3.69 min); HRMS calcd for $C_{20}H_{17}O_4N_1S_2$ (M$^+$+NH$_4$) 417.0943, found 417.0933.

Under conditions of parallel reaction synthesis, 1-hydroxybenzotriazole (16.2 mg, 0.12 mmol) was added to a slurry of the acid EX-1F (47.9 mg, 0.12 mmole) and PolyStyrenyl-carbodiimide (PSDCC) (1.00 mmol/g) (200 mg, 0.20 mmol) in 3 mL of dichloromethane and 0.5 mL of dimethylformamide. The suspension was agitated for 15 minutes. The amine, N-Boc-piperidinyl-4-ylmethylamine (0.10 mmol) was added, N-methylmorpholine (13.1 uL, 0.12 mmol) was added when the amine is a hydrochloride salt, and the suspension was agitated for 2 hours. Upon completion of the reaction, the polyamine resin (PSA) (2.69 mmol/g) (0.40 g, 1.0 mmol) and polymer-bound aldehyde (PSCHO) (23 mmol/g) (0.43 g, 1.0 mmol) was added and the suspension was agitated for 3 hours. The solution was filtered and the polymer was rinsed with dimethylformamide and dichloromethane until no more UV activity was seen in the dichloromethane washing. The combined filtrate and washings were evaporated to afford the pure product EX-IG.

Under conditions of parallel reaction synthesis, hydrochloric acid in dioxane (4N) (3 mL) was added to the Boc protected compound EX-IG, and the solution was agitated at room temperature for 19 hours. Evaporation of the solvents afforded 58.4 mg (98%) of a clear oil of product; $^1$H NMR ppm: 1.21 (m, 2H), 1.45 (s, 9H), 1.62 (m, 3H), 2.63 (m, 2H), 3.25 (m, 2H), 4.03 (m, 2H), 4.35 (s, 2H), 7.27 (m, 13H), 7.66 (s, 1H); HPLC purity (retention time): >99% (4.41 min).

Example 2

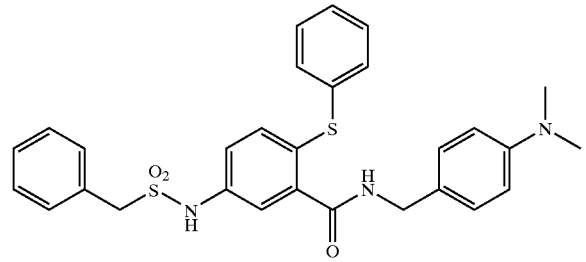

Using the procedure of Example 1, use of 4-dimethylaminobenzylamine afforded 30.0 mg (70%) of a white solid of product; $^1$H NMR ppm: 2.95 (s, 6H), 4.35 (s, 2H), 4.44 (d, 2H), 6.70 (d, 2H), 7.23 (m, 16H), 7.62 (s, 1H); HPLC purity (retention time): >99% (3.15 min); HRMS calcd for $C_{29}H_{29}O_3N_3S_2$ (M$^+$+H) 532.1729, found 532.1681.

Example 3

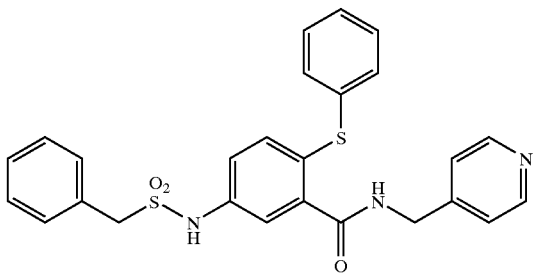

Using the procedure of Example 1, use of 4-pyridymethylamine afforded 30.5 mg (62%) of a white solid of product; $^1$H NMR ppm: 4.35 (s, 2H), 4.55 (d, 2H), 7.13 (d, 2H), 7.26 (m, 13H), 7.66 (s, 2H), 8.39 (d, 2H); HPLC purity (retention time): >99% (3.00 min); HRMS calcd for $C_{26}H_{23}O_3N_3S_2$ (M$^+$+H) 490.1259, found 490.1222.

Example 4

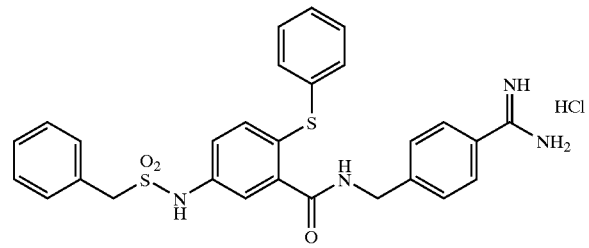

Using the procedures of Example 1 and 4-(N-Boc-amidino)benzylamine, 89.9 mg (71%) of a clear oil of product EX-4A was produced; $^1$H NMR ppm: 1.56 (s, 9H), 4.31 (s, 2H), 4.52 (d, 2H), 7.12–7.68 (m, 19H); HPLC purity (retention time): 66.4% (3.41 min).

Using the procedures of Example 1, EX-4A afforded 89.9 mg (71%) of a clear oil of product; $^1$H NMR ppm: 4.85 (s, 2H), 4.90 (d, 2H), 7.52–8.22 (m, 18H), 9.31 (m, 1H), 9.82 (bs, 1H), 10.22 (s, 1H), 10.49 (s, 1H); HPLC purity (retention time): >83.7% (3.15 min); HRMS calcd for $C_{28}H_{26}O_3N_4S_2$ (M$^+$+H) 531.1525, found 531.1583.

Based on the procedures of Examples 1 through 4 and using the appropriate amide forming amine, additional examples prepared are summarized in Table 1.

TABLE 1

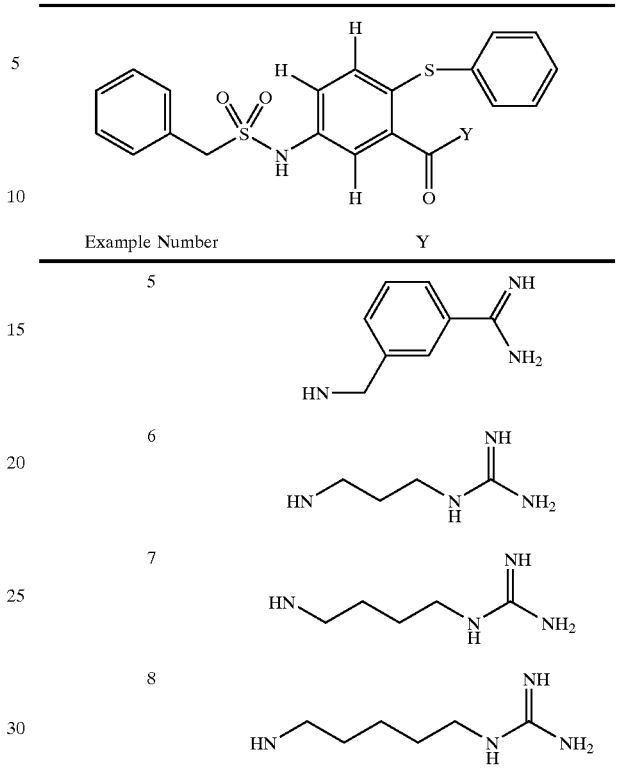

| Example Number | Y |
| --- | --- |
| 5 | |
| 6 | |
| 7 | |
| 8 | |

Schemes 3 and 4 below summarize generic procedures that permit the preparation of a wide variety of the compounds of the present invention through the ability to introduce numerous $R^2$ substituents, a wide variety of amino substituting

SCHEME 3

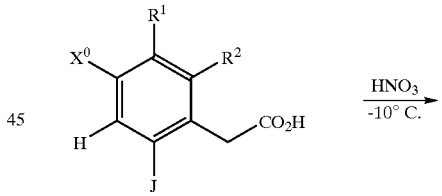

J = hydrido, cyano, alkyl, alkenyl, haloalkyl, haloalkenyl, carboxy, carboxyalkyl, carboalkoxy, amidocarbonyl, acyl, phosphono, sulfo, O—R$^6$, NH—R$^6$, S—R$^6$, S(O)—R$^6$, and S(O)$_2$—R$^6$.

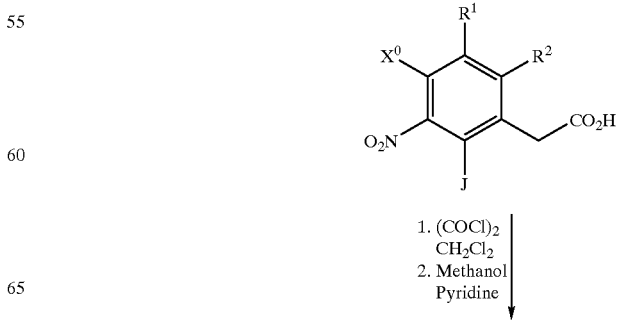

1. (COCl)$_2$ CH$_2$Cl$_2$
2. Methanol Pyridine

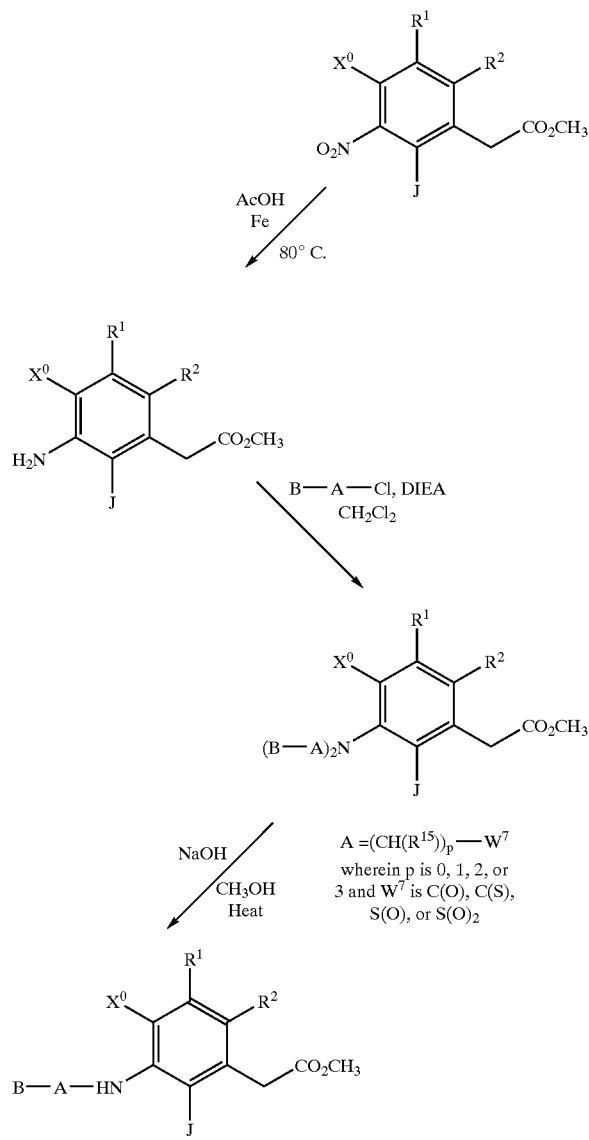

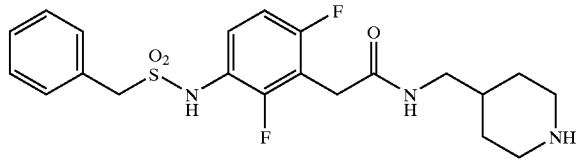

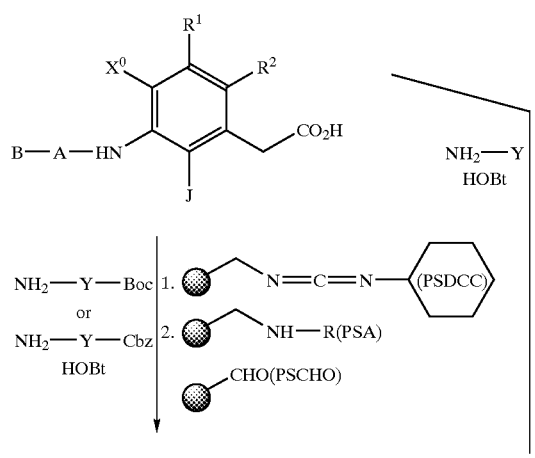

groups represented by B-A, and a large number of amide forming Y groups at the carboxylic acid group in which K is an alkylene, methylene. Example 9 below shows the preparation of a compound wherein $X^o$ and $R^1$ are each hydrido and J and $R^2$ are each fluoro.

Example 9

2,6-Difluorophenylacetic acid was added in small portions over a period of 20 minutes to fuming nitric acid chilled to $-10°$ C. (methanol/ice). The addition was closely monitored to keep the temperature below $5°$ C. Upon complete addition, the solution stirred at $-10°$ C. for 15 minutes. The solution was poured over ice/water and extracted with ether. The organic layer was washed with brine, dried over magnesium sulfate, and filtered. The solvent was removed by evaporation to afford 5.75 g (91%) of a white solid of product EX-9A; $^1$H NMR ppm: 3.89 (s, 2H), 7.11(m, 1H), 8.16 (m, 1H);. $^{19}$F NMR ppm: $-101.66$ (m, 1F), $-115.43$ (m, 1F).

Oxalyl chloride (12.6 mL, 0.144 mol) was added to a solution of the acid EX-9A (5.75 g, 0.026 mol) in dichloromethane followed by a drop of dimethyl formamide. After stirring at room temperature for 1 hour, the solvent was removed by evaporation to afford the acid chloride. The acid chloride was redissolved into dichloromethane and an excess of methanol (50 mL) was added followed by addition of pyridine (3.5 ml, 0.043 mol). The solution stirred at room temperature. for 5 hours. The solution was washed with water, brine, and dried over magnesium sulfate and the solvent was removed by evaporation to afford the crude product. The product was purified by column chromatography (30% ethyl acetate-hexane) to afford 5.47 g (91%) of an orange oil of product EX-9B; $^1$H NMR ppm: 3.78 (s, 3H), 3.84 (s, 2H), 7.09 (m, 1H), 8.12 (m, 1H); $^{19}$F NMR ppm: $-101.76$ (m, 1F), $-115.58$ (m, 1F); HPLC purity (retention time): >99% (2.88 min).

The nitro compound EX-9B (6.87 g, 0.029 mmol) was stirred in glacial acetic acid. Powdered iron (8.29 g, 0.148 mmol) was added and the solution was heated to 80° C. with vigorous stirring. The solution was stirred at 80° C. for 15 minutes at which point the iron had turned gray. The reaction mixture was filtered through celite and the solid was washed with ether. The resultant organic layer was washed with water, stirred with saturated sodium bicarbonate until basic, and washed with water again. The solution was dried over magnesium sulfate, filtered and the solvent was removed to afford the crude product. The product was purified by column chromatography (30% ethyl acetate-hexane) to afford 4.07 g (68%) of a clear oil of product EX-9C; $^1$H NMR ppm: 3.62 (bs, 2H), 3.71 (s, 2H), 3.74 (s, 3H), 6.70 (m, 2H); $^{19}$F NMR ppm: −115.58 (m, 1F), −129.12 (m, 1F); HPLC purity (retention time): >99% (1.57 min).

Diisopropylethylamine (5.1 mL, 0.029 mol) was added to a solution of the aniline EX-9C (4.0 g, 0.019 mmol) and a-toluenesulfonyl chloride (8.34 g, 0.042 mol) in dichloromethane, and the resulting solution stirred at room temperature for 20 hours. The solution was washed with 2 N hydrochloric acid, brine, dried over magnesium sulfate, and filtered. The solvent was removed by evaporation to afford the crude product. The product was purified by column chromatography (30% ethyl acetate-hexane) to afford 6.2 g (61%) of a tan solid of product EX-9D; $^1$H NMR ppm: 3.73 (s, 2H), 3.75 (s, 3H), 4.63 (d, 2H), 5.10 (d, 2H), 5.91 (m, 1H), 6.47 (m, 1H), 7.45 (m, 10H); $^{19}$F NMR ppm: −109.09 (m, 1F), −115.57 (m, 1F); HPLC purity (retention time): 85.3% (4.45 min).

Aqueous sodium hydroxide (10%) (10.3 mL, 0.025 mol) was added to a solution of the methyl ester EX-9D (3.29 g, 0.0064 mol) in methanol and the resulting solution stirred at 65° C. for 4 hours. The solution was acidified with 2 N hydrochloric acid and extracted with ether. The solution was washed with brine, dried over magnesium sulfate, and filtered. The solvent was removed by evaporation to afford 2.1 g (95%) of a white solid of product EX-9E; $^1$H NMR ppm: 3.87 (s, 2H), 4.60 (s, 2H), 7.11 (m, 1H), 7.51 (m, 6H), 9.77 (s, 1H); $^{19}$F NMR ppm: −119.10 (m, 1F), −123.54 (m, 1F); HPLC purity (retention time): >99% (2.86 min); HRMS calcd for $C_{15}H_{13}O_4N_1S_1F_2$ (M$^+$+NH$_4$) 359.0877, found 359.0867.

Reaction of EX-9E with N-Boc-piperidine-4-ylmethylamine afforded 67.2 mg (125%) of a clear oil of product EX-9F; $^1$H NMR ppm: 1.14 (m, 2H), 1.47 (s, 9H), 1.65 (m, 3H), 2.69 (m, 2H), 3.18 (m, 2H), 3.62 (s, 2H), 4.10 (m, 2H), 4.38 (s, 2H), 6.01 (m, 1H), 6.90 (m, 2H), 7.35 (m, 6H); $^{19}$F NMR ppm: −117.94 (m, 1F), −126.43 (m, 1F); HPLC purity (retention time): 56.6% (3.57 min).

Deprotection of EX-9F using the procedures of Example 1 afforded 40.6 mg (93%) of a white solid of product; $^1$H NMR ppm: 1.04 (m, 2H), 1.32 (m, 3H), 2.35 (m, 3H), 2.86 (m, 2H), 3.06 (s, 2H), 3.78 (s, 2H), 6.26 (m, 1H), 6.74 (m, 6H), 7.57 (bs, 1H), 8.73 (m, 1H), 8.99 (m, 1H); $^{19}$F NMR ppm: −118.93 (m, 1F), −123.81 (m, 1F); HPLC purity (retention time): 88.1% (2.36 min); HRMS calcd for $C_{21}H_{25}O_3N_3S_1F_2$ (M$^+$+H) 438.1663, found 438.1642.

Example 10

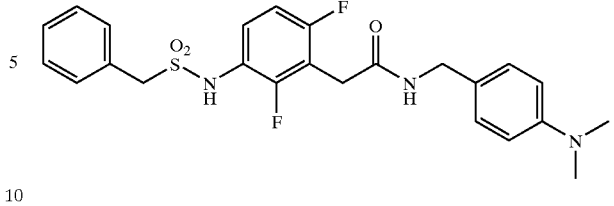

Using the procedure of Example 9 with 4-dimethylaminobenzylamine afforded 55.5 mg (117%) of a white solid of product; $^1$H NMR ppm: 2.50 (s, 6H), 3.26 (s, 2H), 3.89 (s, 2H), 3.93 (d, 2H), 6.27 (bd, 1H), 6.43 (m, 1H), 6.72 (m, 2H), 6.93 (m, 6H), 7.44 (m, 1H), 7.58 (s, 1H), 8.84 (s, 1H); $^{19}$F NMR ppm: −118.49 (m, 1F), −124.01 (m, 1F); HPLC purity (retention time): >99% (2.57 min); HRMS calcd for $C_{24}H_{25}O_3N_3S_1F_2$ (M$^+$+H) 474.1663, found 474.1647.

Example 11

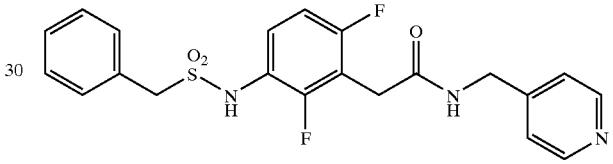

Using the procedure of Example 9 with pyrid-4-ylmethylamine afforded 51.2 mg (118%) of a white solid of product; $^1$H NMR ppm: 3.21 (s, 2H), 3.82 (s, 2H), 3.93 (d, 2H), 6.37 (m, 1H), 6.78 (m, 8H), 7.29 (s, 1H), 7.46 (s, 1H), 8.91 (s, 1H); $^{19}$F NMR ppm: −118.95 (m, 1F), −123.95 (m, 1F); HPLC purity (retention time): 91% (2.34 min); HRMS calcd for $C_{21}H_{19}O_3N_3S_1F_2$ (M$^+$+H) 432.1193, found 432.1164.

Example 12

Using the procedure of Example 9 with 3-(imidazol-1-yl)propylamine afforded 55.5 mg (123%) of a clear oil of product; $^1$H NMR ppm: 1.97 (m, 2H), 3.24 (m, 2H), 3.58 (s, 2H), 3.94 (m, 2H), 4.34 (s, 2H), 6.61 (m, 1H), 7.71 (m, 2H), 6.89 (m, 3H), 7.32 (m, 7H), 8.02 (s, 1H); $^{19}$F NMR ppm: −118.56 (m, 1F), −125.29 (m, 1F); HPLC purity (retention time): 51.0% (2.28 min); HRMS calcd for $C_{21}H_{22}O_3N_4S_1F_2$ (M$^+$+H) 449.1459, found 449.1455.

Example 13

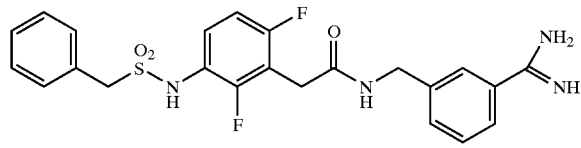

Using the procedures of Example 9 and the amine 3-(N-Cbz-amidino)benzylamine afforded 37.7 mg (62%) of a clear oil of product EX-13A; $^1$H NMR ppm: 3.62 (m, 2H), 4.29 (s, 2H), 4.42 (d, 2H), 5.12 (s, 2H), 6.80 (m, 2H), 7.38 (m, 14H), 7.71 (m, 2H); $^{19}$F NMR ppm: −117.61 (m, 1F), −125.19 (m, 1F); HPLC purity (retention time): 69.6% (3.25 min).

The benzyloxycarbonyl (Cbz) compound EX-13A (0.010 mmol), sodium iodide (60.0 mg, 0.040 mmol), and trimethylsilyl chloride (50.7 uL, 0.040 mmol) were stirred in acetonitrile at 55° C. for 18 hours. Methanol (100 uL) was added and the solution stirred at room temperature for 2 hours. The dimethylbenzylamine resin (3.58 meq/g) (0.60 g, 2.1 mmol) was added and the solution stirred at room temperature for 4 hours. The reaction mixture was filtered through celite and the solid was rinsed with acetonitrile. The combined filtrate and washings were evaporated to afford 89.9 mg (71%) of a white solid of product; $^1$H NMR ppm: 3.00 (s, 2H), 3.62 (s, 2H), 3.76 (d, 2H), 6.12 (m, 1H), 6.58–7.32 (m, 13H), 7.88 (m, 1H); $^{19}$F NMR ppm: −120.82 (m, 1F), −124.52 (m, 1F); HPLC purity (retention time): 66.4% (2.60 min); HRMS calcd for $C_{23}H_{22}O_3N_4S_1F_2$ (M$^+$+H) 473.1459, found 473.1449.

Example 14

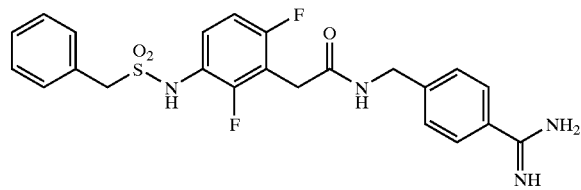

Using the procedures of Example 9 and the amine, 4-(N-Cbz-amidino)benzylamine, afforded 49.9 mg (82%) of a clear oil of product EX-14A; $^1$H NMR ppm: 3.58 (m, 2H), 4.27 (s, 2H), 4.32 (d, 2H), 5.18 (s, 2H), 6.74 (m, 2H), 7.14 (d, 2H), 7.37 (m, 12H), 7.68 (d,2H); $^{19}$F NMR ppm: −117.58 (m, 1F), −124.63 (m, 1F); HPLC purity (retention time): 81.7% (3.14 min).

Using the procedure of Example 13, EX-14A afforded 89.9 mg (71%) of a white solid of product x; $^1$H NMR ppm: 3.21 (s, 2H), 3.94 (s, 2H), 4.06 (m, 2H), 5.94 (bs, 1H), 6.42 (m, 1H), 6.91 (m, 8H), 7.12 (d, 2H), 7.49 (d, 2H), 8.18(m, 1H); $^{19}$F NMR ppm: −119.65 (m, 1F), −124.41 (m, 1F); HPLC purity (retention time): 44.1% (2.57 min); HRMS calcd for $C_{23}H_{22}O_3N_4S_1F_2$ (M$^+$+H) 473.1459, found 473.1447.

Example 15

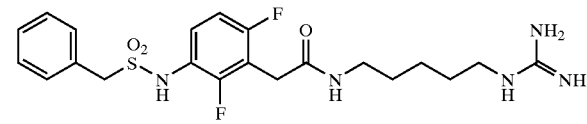

Using the procedures of Example 9 and the amine, 5-(N,N-bis-Boc-guanidino)pentylamine, afforded 67.1 mg (100%) of a clear oil of product EX-15A; $^1$H NMR ppm: 1.57 (m, 18H), 1.58 (m, 6H), 3.26 (m, 2H), 3.40 (m, 2H), 3.60 (s, 2H), 4.35 (s, 2H), 6.10 (m, 1H), 6.86 (m, 1H), 7.37 (m, 8H), 8.31 (m, 1H); $^{19}$F NMR ppm: −117.86 (m, 1F), −125.96 (m, 1F); HPLC purity (retention time): 39.2% (3.48 min).

Reaction of EX-15A using the procedure of Example 1 for deprotection afforded 41.2 mg (88%) of a white solid of product; $^1$H NMR ppm: 0.83 (m, 6H), 2.71 (m, 2H), 3.05 (s, 2H), 3.16 (m, 2H), 3.68 (s, 2H), 6.25 (m, 1H), 6.74 (m, 8H); HPLC purity (retention time): >99% (2.66 min); HRMS calcd for $C_{21}H_{27}O_3N_5S_1F_2$ (M$^+$+H) 468.1881, found 468.1842.

Scheme 5 below summarizes a generic procedure that permits the preparation of a wide variety of the compounds of the present invention through the ability to introduce numerous R$^2$ substituents, a wide variety of amino substituting groups represented by B-A, and a large number of amide forming Y groups at the carboxylic acid group in which K is an alkylene, methylene. Example 16 below shows the preparation of a compound wherein X$^o$ and R$^1$ are each hydrido and J and R$^2$ are each fluoro.

SCHEME 5

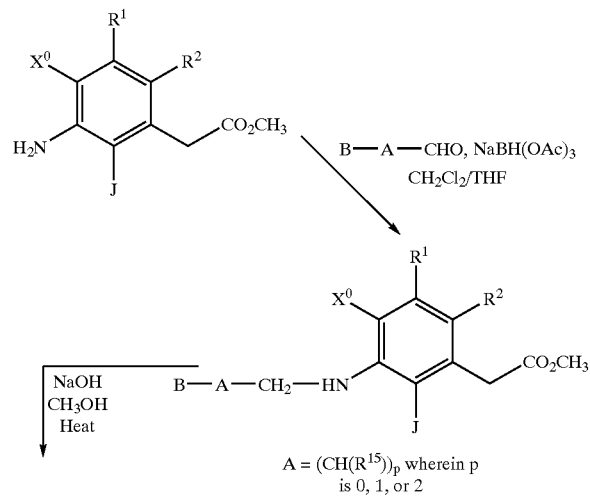

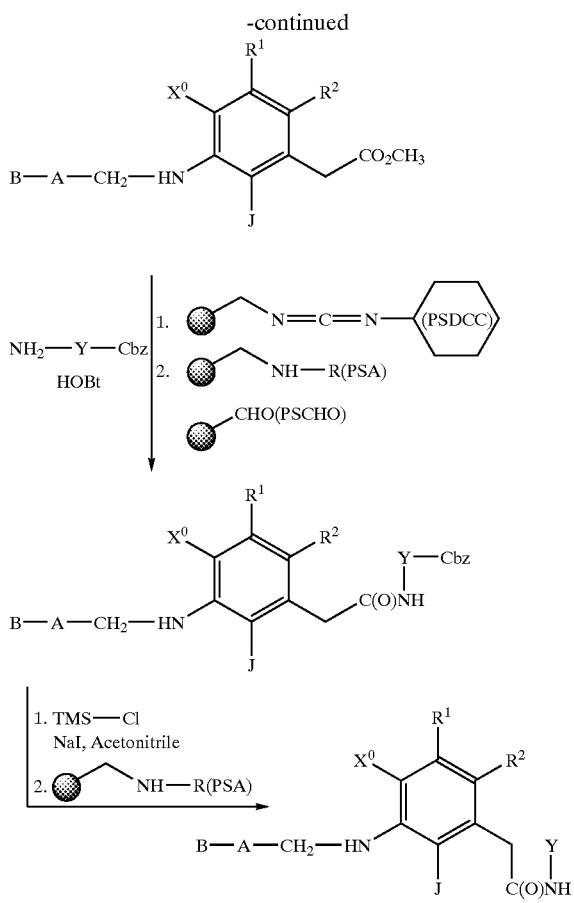

Example 16

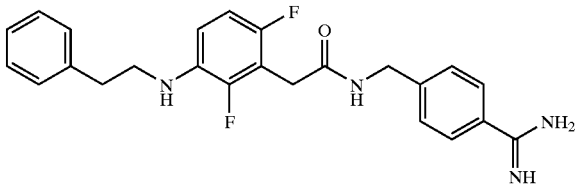

Sodium triacetoxyborohydride (7.2 g, 0.033 mol) was added to a solution of the methyl 3-amino-2,6-difluorophenylacetate (1.72 g, 0.0085 mol), phenylacetaldehyde (2.0 mL, 0.015 mol), and a drop of acetic acid in a tetrahydrofuran-dichloromethane (1:1) solution. After stirring at room temperature for 18 hours, sodium hydroxide (1N) was added until basic. The solution was extracted with dichloromethane and the organic layer was washed with brine, dried over magnesium sulfate, and filtered. The solvent was removed by evaporation to afford a mixture of two products. Fraction one of column chromatography (10% ethyl acetate-hexane) afforded 1.25 g (36%) of a clear oil of the N,N-bis-phenylethyl; $^1$H NMR ppm: 2.79 (t, 4H), 3.40 (t, 4H), 3.79 (s, 5H), 6.87 (m, 2H), 7.25 (m, 10H); $^{19}$F NMR ppm: −122.50 (m, 1F), −123.67 (m, 1F); HPLC purity (retention time): 95.7% (4.71 min); HRMS calcd for $C_{25}H_{25}O_2N_1F_2$ (M$^+$+H) 410.1932, found 410.1926. Fraction two of the column chromatography (10% ethyl acetate-hexane) afforded 1.06 g (41%) of a clear oil of product EX-16A; $^1$H NMR ppm: 2.97 (t, 2H), 3.42 (t, 2H), 3.73 (s, 2H), 3.75 (s, 3H), 6.62 (m, 1H), 6.82 (m, 1H), 7.29 (m, 5H); $^{19}$F NMR ppm: −131.28 (m, 1F), −137.00 (m, 1F); HPLC purity (retention time): 96.1% (3.93 min); HRMS calcd for $C_{17}H_{17}O_2N_1F_2$ (M$^+$+H) 306.1306, found 306.1309.

Aqueous sodium hydroxide (10%) (5.5 mL, 13.7 mmol) was added to a solution of the methyl ester Ex-16A (1.06 g, 3.47 mmol) in methanol and the resulting solution stirred at 60° C. for 1 hour. The solution was acidified with 2 N hydrochloric acid and extracted with ether. The solution was washed with brine, dried over magnesium sulfate, and filtered. The solvent was removed by evaporation to afford 0.93 g (92%) of a white solid of product EX-16B; $^1$H NMR ppm: 2.64 (t, 2H), 3.02 (t, 2H), 3.19 (s, 2H), 6.46 (m, 1H), 6.75 (m, 6H), 7.10 (bd, 1H), 9.30 (bs, 1H); $^{19}$F NMR ppm: −119.37 (m, 1F), −128.26 (m, 1F); HPLC purity (retention time): >99% (3.26 min); HRMS calcd for $C_{16}H_{15}O_2N_1F_2$ (M$^+$+H) 292.1149, found 292.1150.

1-Hydroxybenzotriazole (43.1 mg, 0.31 mmol) was added to a slurry of the acid EX-16B (0.93 g, 3.19 mmole) and PS-carbodiimide (PSDCC) (1.00 mmol/g) (9.57 g, 9.57 mmol) in a dichloromethane-dimethylformamide (3:1) solution. The suspension was agitated for 15 minutes. The amine, 4-(N-Cbz-amidino)benzylamine (0.96 g, 3.16 mmol) and N-methylmorpholine (2.0 mL, 18.1 mmol) was added and the suspension was agitated for 2 hours. Upon completion of the reaction, the polyamine resin (PSA) (2.69 mmol/g) (1.0 g, 2.69 mmol) and polymer-bound aldehyde (PSCHO) (2.3 mmol/g) (0.50 g, 1.15 mmol) was added and the suspension was agitated for 1 hour. The solution was filtered and the polymers were rinsed with dimethylformamide and dichloromethane until no more UV activity was seen in the dichloromethane washing. The combined filtrate and washings were evaporated to afford the product. The product was purified by column chromatography (70% ethyl acetatehexane) to afford 1.14 g (64%) of a white solid of product EX-16C; $^1$H NMR ppm: 2.92 (t, 2H), 3.37 (m, 2H), 3.64 (s, 2H), 3.86 (bs, 1H), 4.39 (d, 2H), 5.23 (s, 2H), 6.41 (m, 1H), 6.57 (m, 1H), 6.79 (m, 1H), 7.34 (m, 14H), 7.72 (d, 2H), 9.43 (bs, 1H); $^{19}$F NMR ppm: −131.01 (m, 1F), −136.68 (m, 1F); HPLC purity (retention time): 83.6% (3.38 min); HRMS calcd for $C_{32}H_{30}O_3N_4F_2$ (M$^+$+H) 557.2364, found 557.2326.

Reaction of EX-16C according to Example 13 afforded 0.58 g (82%) of a yellow oil of product; $^1$H NMR ppm: 3.16 (t, 2H), 3.72 (m, 2H), 3.86 (s, 2H), 4.66 (s, 2H), 7.32 (m, 7H), 7.68 (m, 3H), 7.82 (d, 2H), 8.78 (bs, 1H), 9.27 (bs, 1H); $^{19}$F NMR ppm: −112.97 (m, 1F), −125.49 (m, 1F); HPLC purity (retention time): 63.3% (2.77 min); HRMS calcd for $C_{24}H_{24}O_1N_4F_2$ (M$^+$+H) 423.1996, found 423.1953.

Schemes 6 and 7 below summarize a generic procedure that permits the preparation of a wide variety of the compounds of the present invention through the ability to introduce numerous Q (R$^2$, wherein Z$^o$ is a covalent bond) aryl and heteroaryl substituents, a wide variety of amino substituting groups represented by B-A, and a large number of amide forming Y groups at the carboxylic acid group in which K is an alkylene, methylene. Example 17 below shows the preparation of a compound wherein X$^o$ and R$^1$ are each hydrido, J is fluoro, Z$^o$ is a covalent bond, and Q is the substituent, phenyl.

SCHEME 6
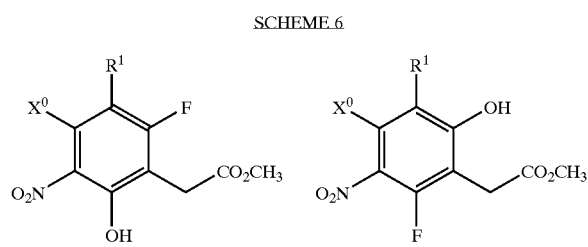
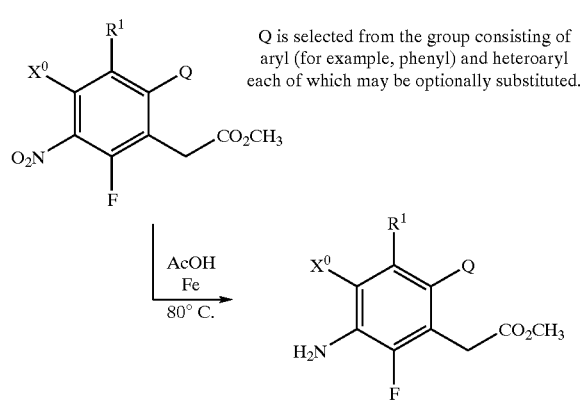
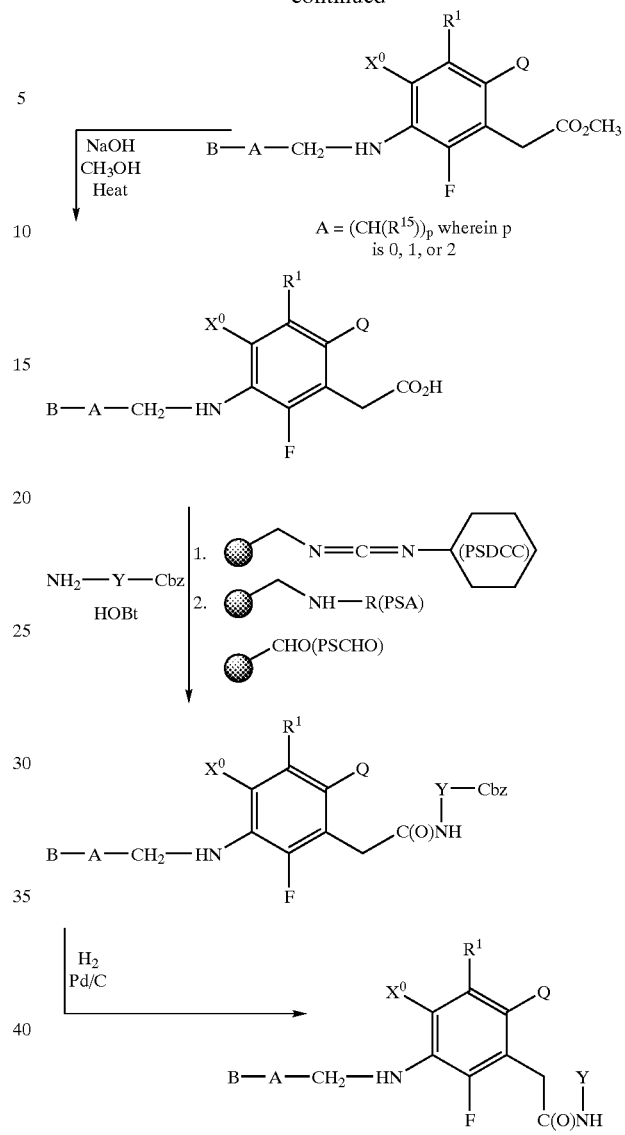
SCHEME 7
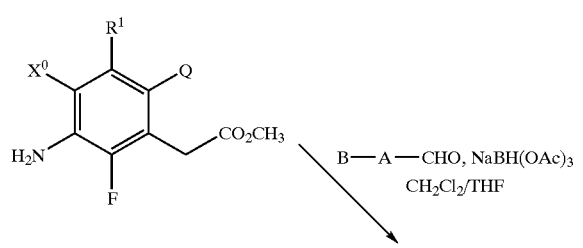
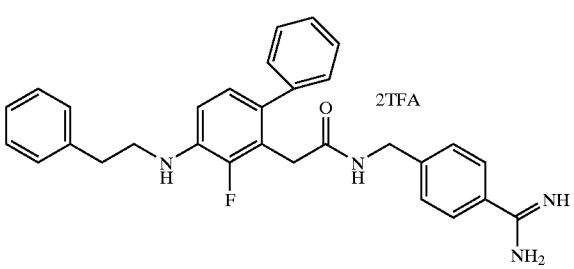
Example 17
The nitro compound methyl 3-nitro-2,6-difluorophenylacetate (18.3 g, 0.079 mol) was added to a solution of trimethylacetic acid (24.3 g, 0.23 mol) and potassium carbonate (54.5 g, 0.39 mol) in dimethylsulfoxide and the resulting solution stirred at 80° C. for 15 minutes. The reaction was diluted with water and diethyl ether and the resulting solution was acidified with 2 N hydrochloric acid and extracted with ether. The solution was washed with brine, dried over magnesium sulfate, and filtered. The solvent was removed by evaporation to afford a mixture of two products. Fraction one of column chromatography (40% ethyl acetate-hexane) afforded 12.1 g (67%) of a yellow solid of product methyl 3-nitro-2-hydroxy-6-fluorophenylacetate; $^1$H NMR ppm: 3.71 (s, 3H), 3.81 (s, 2H), 6.80 (m, 1H), 8.18 (m, 1H); $^{19}$F NMR ppm: −99.71 (m, 1F); HPLC purity (retention time): >99% (2.63 min). Fraction two of column chromatography (40% ethyl acetate-hexane) afforded 4.97 g (27%) of a yellow solid of product EX-17A; $^1$H NMR ppm: 3.71 (s, 3H), 3.80 (d, 2H, $J_{HF}$=1.7 Hz), 6.95 (dd, 1H, , $J_{HH}$=9.2 Hz, $J_{HF}$=1.1 Hz), 8.05 (m, 1H); $^{19}$F NMR ppm: −120.02 (d, 1F, $J_{HF}$=8.7 Hz); HPLC purity (retention time): >99% (2.25 min).

Triethylamine (729 uL, 5.2 mmol) was added to a solution of the phenol EX-17A (1.0 g, 4.36 mmol) and triflic anhydride (807 uL, 4.7 mmol) in dichloromethane at −10° C. After stirring at room temperature for 18 hours, the solution was acidified with hydrochloric acid 2N and extracted with dichloromethane. The organic layer was washed with brine, dried over magnesium sulfate, and filtered. The solvent was removed by evaporation to afford the crude product. The product was purified by column chromatography (20% ethyl acetate-hexane) to afford 1.0 g (68%) of a clear oil of product EX-17B; $^1$H NMR ppm: 3.79 (s, 3H), 3.90 (d, 2H, $J_{HF}$=2.0 Hz), 7.38 (dd, 1H, $J_{HH}$=7.6 Hz, $J_{HF}$=1.8 Hz), 8.18 (m, 1H); $^{19}$F NMR ppm: −73.61 (s, 3F), −113.78 (m, 1F); HPLC purity (retention time): 94.6% (3.69 min).

The triflate compound EX-17B (1.0 g, 2.76 mmol) was added to a solution of tri-n-butylphenylstannane (1.0 mL, 3.0 mmol), lithium chloride (351 mg, 8.28 mmol), and tetrakis(triphenylphosphine)palladium(0) (63.9 mg, 0.055 mmol) in 14 mL of anhydrous dioxane. The solution was heated to 85° C. for 4 hours and then at room temperature for 12 hours. The organic layer was washed with brine, dried over magnesium sulfate, and filtered. The solvent was removed by evaporation to afford the crude product. The product was purified by column chromatography (20% ethyl acetate-hexane) to afford 0.62 g (78%) of a yellow oil of product EX-17C; $^1$H NMR ppm: 3.73 (s, 5H), 7.28 (m, 3H), 7.49 (m, 3H), 8.07 (m, 1H); $^{19}$F NMR ppm: −118.75 (m, 1F); HPLC purity (retention time): >99% (3.81 min).

The nitro compound EX-17C (0.60 g, 2.0 mmol) was stirred in glacial acetic acid. Powdered iron (0.60 g, 10.7 mmol) was added and the solution was heated to 70° C. with vigorous stirring. The solution was stirred at 70° C. for 30 minutes at which point the iron had turned gray. The reaction mixture was filtered through celite and the solid was washed with ether. The resultant organic layer was washed with water, brine, dried over magnesium sulfate, and filtered. The solvent was removed by evaporation to afford 0.47 g (91%) of a clear oil of product EX-17D; $^1$H NMR ppm: 3.64 (d, 2H, $J_{HF}$=2.3 Hz), 3.71 (s, 3H), 6.83 (m, 1H), 7.27 (dd, 1H), 7.37 (m, 5H); $^{19}$F NMR ppm: −137.27 (d, 1F, $J_{HF}$=8.7 Hz); HPLC purity (retention time): 93.2% (2.76 min); HRMS calcd for $C_{15}H_{14}O_2N_1F_1$ (M$^+$+NH$_4$) 277.1352, found 277.1337.

Sodium triacetoxyborohydride (1.7 g, 8.0 mmol) was added to a solution of the aniline EX-17D (0.051 g, 2.0 mmol), phenylacetaldehyde (281 uL, 0.015 mol), and a drop of acetic acid in a tetrahydrofuran-dichloromethane (1:1) solution. After stirring at room temperature for 5 hours, the solution was diluted with ether and water. The organic layer was washed with brine, dried over magnesium sulfate, and filtered. The solvent was removed by evaporation to afford 0.58 g (80%) of a yellow oil of product EX-17E; $^1$H NMR ppm: 3.02 (t, 2H), 3.51 (m, 2H), 3.64 (d, 2H, $J_{HF}$=2.9 Hz), 3.70 (s, 3H), 6.80 (m, 1H), 7.02 (dd, 1H), 7.31 (m, 10H); $^{19}$F NMR ppm: −138.50 (d, 1F); HPLC purity (retention time): 83.2% (4.69 min); HRMS calcd for $C_{23}H_{22}O_2N_1F_1$ (M$^+$+H) 364.1713, found 364.1703.

Aqueous sodium hydroxide (10%) (2.5 mL, 6.2 mmol) was added to a solution of the methyl ester EX-17E (0.58 g, 1.6 mmol) in methanol and the resulting solution stirred at 65° C. for 5 hours. The solution was acidified with 2 N hydrochloric acid and extracted with diethyl ether. The solution was washed with brine, dried over magnesium sulfate, and filtered. The solvent was removed by evaporation to afford 0.47 g (84%) of an orange glass of product EX-17F; $^1$H NMR ppm: 3.02 (t, 2H), 3.51 (m, 2H), 3.68 (d, 2H, $J_{HF}$=2.6 Hz), 6.84 (m, 1H), 7.04 (dd, 1H), 7.31 (m, 10H); $^{19}$F NMR ppm: −137.47 (d, 1F); HPLC purity (retention time): >99% (4.08 min); HRMS calcd for $C_{22}H_{20}O_2N_1F_1$ (M$^+$+H) 350.1556, found 350.1532.

1-Hydroxybenzotriazole (180 mg, 1.3 mmol) was added to a slurry of the acid EX-17F (0.47 g, 1.34 mmole) and PS-carbodiimide (1.00 mmol/g) (2.6 g, 2.6 mmol) in a dichloromethane-dimethylformamide (3:1) solution. The suspension was agitated for 15 minutes. The amine 4(N-Cbz-amidino)benzylamine (0.51 g, 1.6 mmol) and N-methylmorpholine (295 uL, 2.6 mmol) was added and the suspension was agitated for 2 hours. Upon completion of the reaction, the polyamine resin (PSA) (2.81 mmol/g) (1.0 g, 2.81 mmol) and polymer-bound aldehyde (PSCHO) (2.3 mmol/g) (1.0 g, 2.30 mmol) were added and the suspension was agitated for 1 hour. The solution was filtered and the polymer was rinsed with dimethylformamide and dichloromethane until no more UV activity was seen in the dichloromethane washing. The combined filtrate and washings were evaporated to afford the product. The product was purified by column chromatography (60% ethyl acetate-hexane) to afford 0.79 g (96%) of a white solid of product EX-17G; $^1$H NMR ppm: 2.92 (m, 2H), 3.19 (m, 2H), 3.77 (d, 2H), 4.67 (d, 2H), 5.40 (s, 2H), 5.60 (bm, 1H), 7.08 (m, 1H), 7.15 (dd, 1H), 7.54 (m, 16H), 8.28 (m, 3H), 8.59 (bt, 1H), 9.40 (bs, 1H), 9.65 (bs, 1H); $^{19}$F NMR ppm: 138.15 (d, 1F); HPLC purity (retention time): >99% (4.00 min); HRMS calcd for $C_{22}H_{20}O_2N_1F_1$ (M$^+$+H) 615.2771, found 615.2760.

A catalytic amount of palladium on carbon (10%) in dioxane was added to a methanol-4N hydrochloric acid/dioxane (3:1) solution of the Cbz compound EX-17G (200 mg, 0.32 mmol) and the mixture was stirred under a balloon of hydrogen at room temperature for 12 hours. The mixture was filtered through celite and the solvent was evaporated to afford the product. The product was purified by reverse-phase chromatography to afford 142 mg (92%) of a white solid of product; $^1$H NMR ppm: 2.97 (t, 2H), 3.48 (t, 2H), 3.61 (d, 2H), 4.64 (d, 2H), 6.80 (m, 1H), 6.97 (dd, 1H), 7.33 (m, 11H), 7.47 (d, 2H), 7.79 (d, 2H); $^{19}$F NMR ppm: −77.60 (s, 6F), −139.78 (d, 1F); HPLC purity (retention time): >99% (3.22 min).

Schemes 8 and 9 below summarize a generic procedure that permits the preparation of a wide variety of the compounds of the present invention through the ability to introduce numerous Q (R$^2$, wherein Z$^o$ is a covalent bond) aryl and heteroaryl substituents, a wide variety of amino substituting groups represented by B-A, and a large number of amide forming Y groups at the carboxylic acid group in which K is an alkylene, methylene. Example 18 below shows the preparation of a compound wherein $X^o$ and $R^1$ are each hydrido, J is methoxy, $Z^o$ is a covalent bond, and Q is the substituent, phenyl.

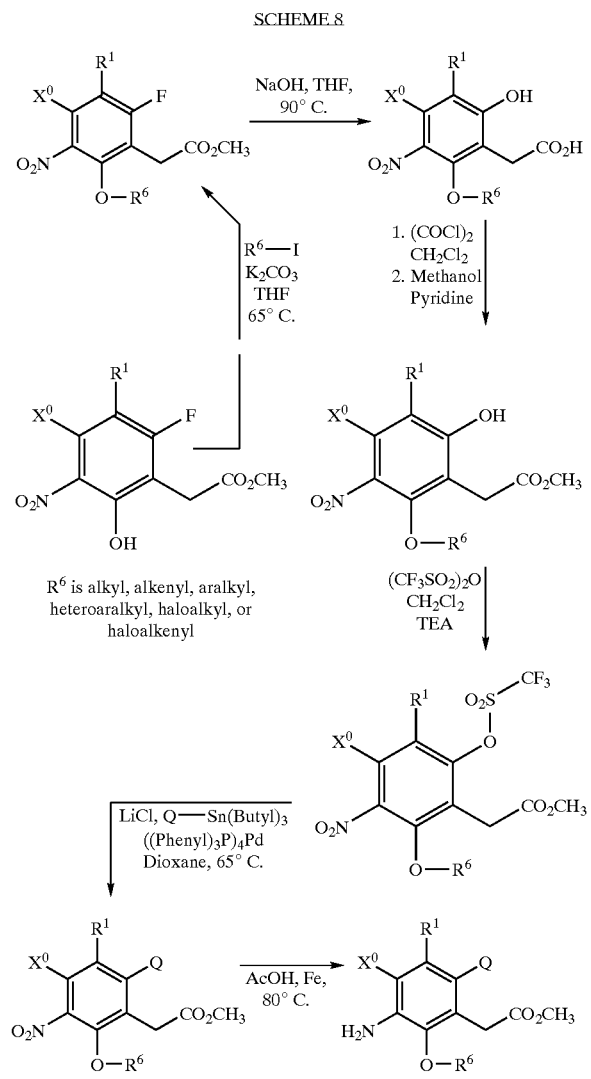

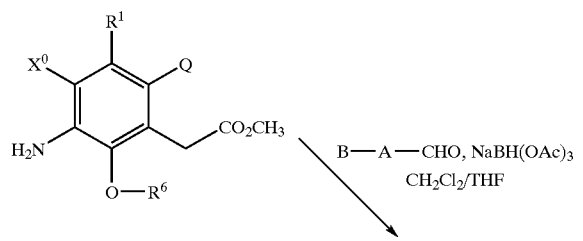

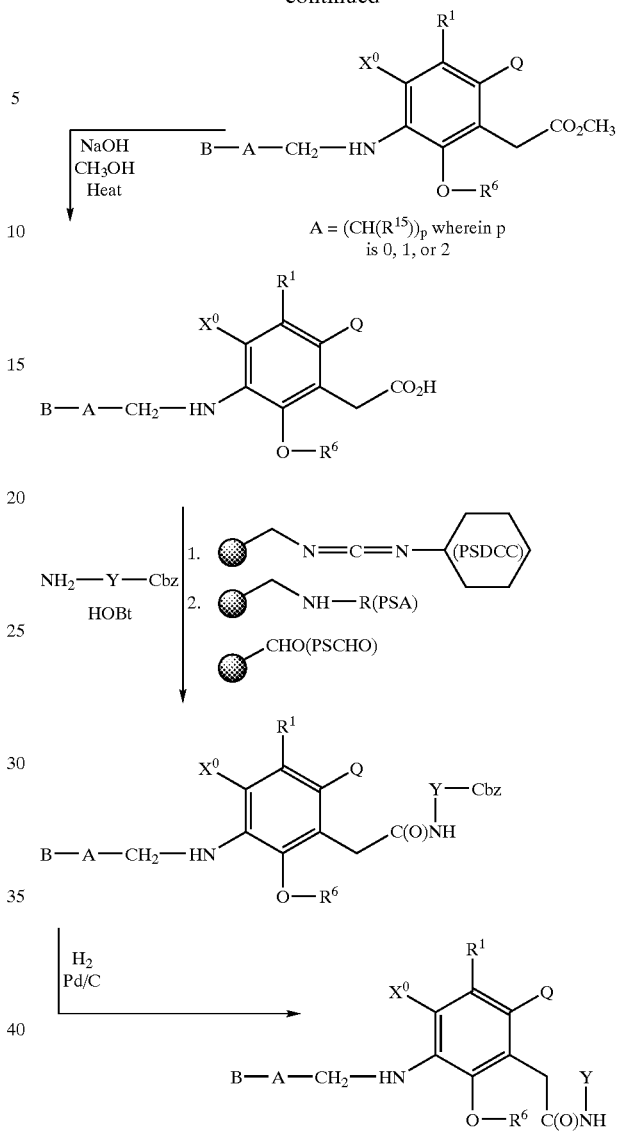

Example 18

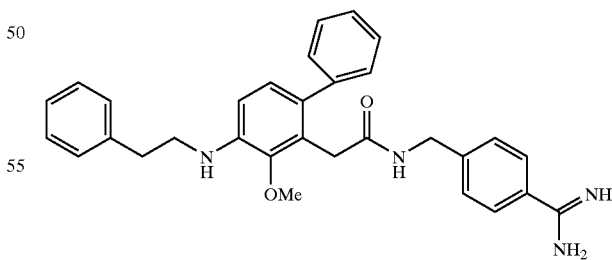

Iodomethane (20.0 mL, 0.32 mol) was added to a solution of the phenol, methyl, 2-hydroxy-3-nitro-6-fluorophenylacetate, (5.0 g, 0.022 mol) and potassium carbonate (9.0 g, 0.065 mol) in tetrahydrofuran. After stirring at 65° C. for 18 hours, the was diluted with water extracted with diethyl ether. The organic layer was washed with brine, dried over magnesium sulfate, and filtered. The solvent was removed by evaporation to afford the crude product. The product was purified by column chromatography (15% ethyl acetate-hexane) to afford 4.18 g (79%) of a yellow oil of product EX-18A; $^1$H NMR ppm: 3.76 (s, 3H), 3.70 (d, 2H, $J_{HF}$=1.5 Hz), 3.93 (s, 3H), 7.00 (m, 1H), 7.94 (m, 1H); $^{19}$F NMR ppm: −103.51 (m, 1F); HPLC purity (retention time): >99% (2.60 min).

Aqueous sodium hydroxide (10%) (25 mL, 0.062 mol) was added to a solution of the fluoro compound EX-18A (4.0 g, 0.016 mol) in tetrahydrofuran and the resulting solution stirred at 90° C. for 14 hours. The solution was acidified with 4 N hydrochloric acid and extracted with ether. The solution was washed with brine, dried over magnesium sulfate, and filtered. The solvent was removed by evaporation to afford the crude product in which fluorine NMR revealed no signal. The product was dissolved into dichloromethane and oxalyl chloride (7.0 mL, 0.080 mol) was added to the solution followed by a drop of dimethylformamide. After stirring at room temperature for 1.5 hours, the solvent was removed by evaporation to afford the acid chloride. The acid chloride was redissolved into dichloromethane and an excess of methanol (50 mL) was added followed by addition of pyridine (2.6 mL, 0.032 mol). The solution stirred at room temperature for 5 hours. The solution was washed with water, brine, dried over magnesium sulfate, and filtered. The solvent was removed by evaporation to afford a mixture of two products. Fraction one of column chromatography (25% ethyl acetate-hexane) afforded 2.0 g (49%) of a yellow solid of product methyl 2,6-dimethoxy-3-nitrophenylacetate; $^1$H NMR ppm: 3.73 (s, 3H), 3.76 (s, 2H), 3.90 (s, 3H), 3.93 (s, 3H), 6.75 (d, 1H, J=9.3 Hz), 8.03 (d, 1H, J=9.3 Hz); HPLC purity (retention time): >99% (2.64 min). Fraction two of column chromatography (25% ethyl acetate-hexane) afforded 1.33 g (34%) of a white solid of phenol product EX-18B; $^1$H NMR ppm: 3.84 (s, 3H), 3.85 (s, 2H), 3.94 (s, 3H), 6.78 (d, 1H, J=8.9 Hz), 7.90 (d, 1H, J=8.9 Hz), 8.19 (s, 1H); HPLC purity (retention time): >99% (2.14 min).

Triethylamine (910 uL, 6.5 mmol) was added to a solution of the phenol EX-18B (1.3 g, 5.5 mmol) and triflic anhydride (1.0 mL, 5.9 mmol) in dichloromethane at −10° C. After stirring at room temperature for 18 hours, the solution was acidified with hydrochloric acid 2N and extracted with dichloromethane. The organic layer was washed with brine, dried over magnesium sulfate, and filtered. The solvent was removed by evaporation to afford the crude product. The product was purified by column chromatography (15% ethyl acetate-hexane) to afford 1.7 g (83%) of a clear oil of product EX-18C; $^1$H NMR ppm: 3.78 (s, 3H), 3.87 (d, 2H), 3.96 (s, 3H), 7.27 (d, 1H, J=9.2 Hz), 7.95 (d, 1H, J=9.2 Hz); $^{19}$F NMR ppm: −73.89 (s, 3F); HPLC purity (retention time): >99% (3.62 min).

The triflate compound EX-18C (1.7 g, 4.5 mmol) was added to a solution of tri-n-butylphenylstannane (1.8 mL, 5.5 mmol), lithium chloride (580 mg, 13.6 mmol), and tetrakis(triphenylphosphine)palladium(0) (11.0 mg, 0.095 mmol) in 23 mL of anhydrous dioxane. The solution was heated to 85° C. for 18 hours. The organic layer was washed with brine, dried over magnesium sulfate, and filtered. The solvent was removed by evaporation to afford the crude product. The product was purified by column chromatography (15% ethyl acetate-hexane) to afford 1.0 g (73%) of a white solid of product EX-18D; $^1$H NMR ppm: 3.69 (s, 5H), 3.94 (s, 3H), 7.17 (d, 1H, J=8.3 Hz), 7.29 (m, 2H), 7.45 (m, 3H), 7.89 (d, 1H, J=83 Hz); HPLC purity (retention time): >99% (3.60 min).

The nitro compound EX-18D (1.0 g, 3.3 mmol) was stirred in glacial acetic acid. Powdered iron (0.92 g, 16.4 mmol) was added and the solution was heated to 80° C. with vigorous stirring. The solution was stirred at 80° C. for 15 minutes at which point the iron had turned gray. The reaction mixture was filtered through celite and the solid was washed with ether. The resultant organic layer was washed with water, brine, dried over magnesium sulfate, and filtered. The solvent was removed to afford the product EX-18E. The product was not purified and carried on to the next step. HPLC purity (retention time): >99% (2.48 min).

Sodium triacetoxyborohydride (2.8 g, 13.2 mmol) was added to a solution of the aniline EX-18E (0.89 g, 3.3 mmol), phenylacetaldehyde (540 uL, 39.2 mmol), and a drop of acetic acid in a tetrahydrofuran-dichloromethane (1:1) solution. After stirring at room temperature for 2 hours, the solution was diluted with dichloromethane and water. The organic layer was washed with brine, dried over magnesium sulfate, and filtered. The solvent was removed by evaporation to afford the crude product. The product was purified by column chromatography (25% ethyl acetate-hexane) to afford 0.69 g (56%) of a yellow oil of product EX-18F; $^1$H NMR ppm: 3.04 (t, 2H), 3.50 (t, 2H), 3.69 (s, 3H), 3.67 (s, 2H), 3.69 (s, 3H), 6.75 (d, 1H, J=8.3 Hz), 7.02 (d, 1H, J=8.3 Hz), 7.35 (m, 10H); HPLC purity (retention time): >99% (4.37 min).

Aqueous sodium hydroxide (10%) (2.9 mL, 7.2 mmol) was added to a solution of the methyl ester EX-18F (0.69 g, 1.8 mmol) in methanol and the resulting solution stirred at 60° C. for 5 hours. The solution was acidified with 2 N hydrochloric acid and extracted with diethyl ether. The solution was washed with brine, dried over magnesium sulfate, and filtered. The solvent was removed by evaporation to afford 0.66 g (100%) of an orange foam of product EX-18G; HPLC purity (retention time): 80% (3.83 min).

1-Hydroxybenzotriazole (247 mg, 1.8 mmol) was added to a slurry of the acid EX-18G (0.66 g, 1.83 mmole) and PS-carbodiimide (PSDCC) (1.00 mmol/g) (3.6 g, 3.6 mmol) in a dichloromethane-dimethylformamide (3:1) solution. The suspension was agitated for 15 minutes. The amine, 4-(N-Cbz-amidino)benzylamine, (0.70 g, 2.2 mmol) and N-methylmorpholine (1.0 mL, 9.0 mmol) was added and the suspension was agitated for 18 hours. Upon completion of the reaction, the polyamine resin (PSA) (2.81 mmol/g) (1.0 g, 2.81 mmol) and polymer-bound aldehyde (PSCHO) (2.3 mmol/g) (1.0 g, 2.30 mmol) were added and the suspension was agitated for 1 hour. The solution was filtered and the polymer was rinsed with dimethylformamide and dichloromethane until no more UV activity was seen in the dichloromethane washing. The combined filtrate and washings were evaporated to afford the product. The product was purified by column chromatography (60% ethyl acetate-hexane) to afford 0.52 g (45%) of a white solid of product EX-18H; $^1$H NMR ppm: 3.17 (m, 2H), 3.65 (m, 2H), 3.77 (s, 2H), 3.86 (s, 3H), 4.64 (d, 2H), 5.27 (bt, 1H), 4.40 (s, 2H), 6.96 (d, 1H), 7.11 (d, 1H), 7.56 (m, 16H), 8.23 (m, 3H), 8.41 (bt, 1H), 9.40 (bs, 1H), 9.75 (bs, 1H); HPLC purity (retention time): >99% (3.80 min).

A catalytic amount of palladium on carbon (5%) in dioxane was added to 3 mL of a methanol-4N hydrochloric acid/dioxane (3:1) solution of the Cbz compound EX-18H (22.8 mg, 0.036 mmol) and the mixture was stirred under a balloon of hydrogen at room temperature for 12 hours. The mixture was filtered through celite and the solvent was evaporated to afford the product. The product was purified by reverse-phase chromatography to afford 14.6 mg (81%) of a white solid of product x; $^1$H NMR ppm: 3.00 (t, 2H), 3.50 (t, 2H), 3.63 (s, 2H), 3.67 (s, 3H), 4.41 (s, 2H), 6.86 (m, 1H), 6.96 (m, 1H), 7.35 (m, 10H), 7.46 (d, 2H), 7.77 (d, 2H), 8.21 (bs, 1H); HPLC purity (retention time): >99% (3.29 min).

Scheme 10 below summarizes a generic procedure that permits the preparation of a wide variety of the phenolic compounds of the present invention through the ability to introduce numerous Q (R$^2$, wherein Z$^o$ is a covalent bond) aryl and heteroaryl substituents, a wide variety of amino substituting groups represented by B-A, and a large number of amide forming Y groups at the carboxylic acid group in which K is an alkylene, methylene. Example 19 below shows the preparation of a compound wherein X$^o$ and R$^1$ are each hydrido, J is hydroxy, Z$^o$ is a covalent bond, and Q is the substituent, phenyl.

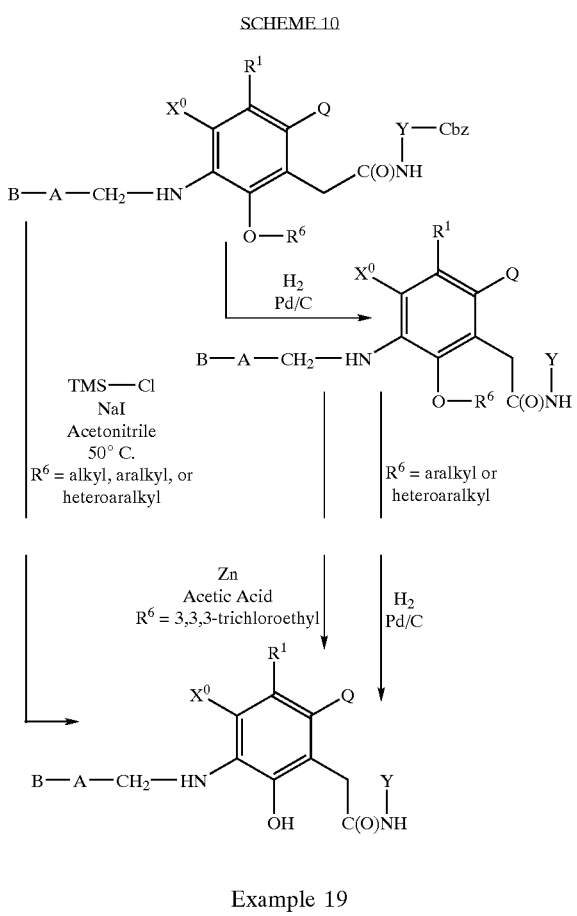

Example 19

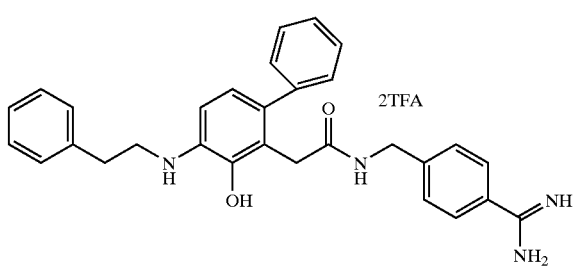

The benzyloxycarbonyl (Cbz) compound from Example 18 (0.10 g, 0.16 mmol), sodium iodide (0.19 g, 1.2 mmol), and trimethylsilyl chloride (162 uL, 1.2 mmol) were stirred in acetonitrile at 55° C. for 18 hours. Methanol (100 uL) was added and the solution stirred at room temperature for 1 hour. The dimethylbenzylamine resin (3.58 meq/g) (0.60 g, 2.1 mmol) was added and the solution stirred at room temperature for 1 hour. The reaction mixture was filtered through celite and the solid was rinsed with acetonitrile. The combined filtrate and washings were evaporated to afford a mixture of two products. Fraction one of reverse-phase chromatography afforded 4.5 mg (4%) of a white solid of product; $^1$H NMR ppm: 3.12 (t, 2H), 3.66 (m, 4H), 4.51 (s, 2H), 6.96 (d, 1H), 7.36 (m, 12H), 7.55 (d, 2H), 7.80 (d, 2H); HPLC purity (retention time): 92% (2.53 min). Fraction two of reverse-phase chromatography afforded 17.7 mg (32%) of a white solid of by-product, 2,3-dihydro-2-oxo-3-phenyl-6-(N-(2-phenylethyl)amino-benzofuran, having the properties of $^1$H NMR ppm: 3.06 (t, 2H), 3.63 (t, 2H), 3.88 (s, 2H), 7.09 (d, 1H), 7.39 (m, 11H); HPLC purity (retention time): >99% (4.33 min).

Schemes 11, 12, and 13 below summarize a generic procedure that permits the preparation of a wide variety of the substituted phenyl compounds of the present invention through the ability to introduce numerous Q (R$^2$, wherein Z$^o$ is a covalent bond) aryl and heteroaryl substituents, a wide variety of amino substituting groups represented by B-A, and a large number of amide forming Y$^o$ groups at the carboxylic acid group in which K is an alkylene, such as methylene. Example 20 below shows the preparation of a compound wherein X$^o$ and R$^1$ are each hydrido, J is fluoro, Z$^o$ is a covalent bond, and Q is the substituent, 3-aminophenyl.

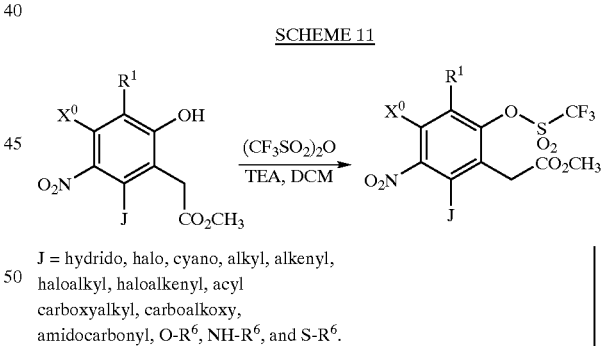

J = hydrido, halo, cyano, alkyl, alkenyl, haloalkyl, haloalkenyl, acyl carboxyalkyl, carboalkoxy, amidocarbonyl, O-R$^6$, NH-R$^6$, and S-R$^6$.

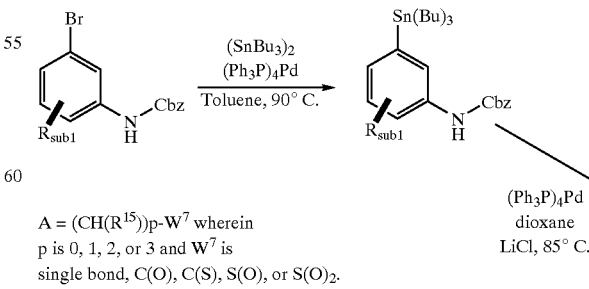

A = (CH(R$^{15}$))p-W$^7$ wherein p is 0, 1, 2, or 3 and W$^7$ is single bond, C(O), C(S), S(O), or S(O)$_2$.

-continued
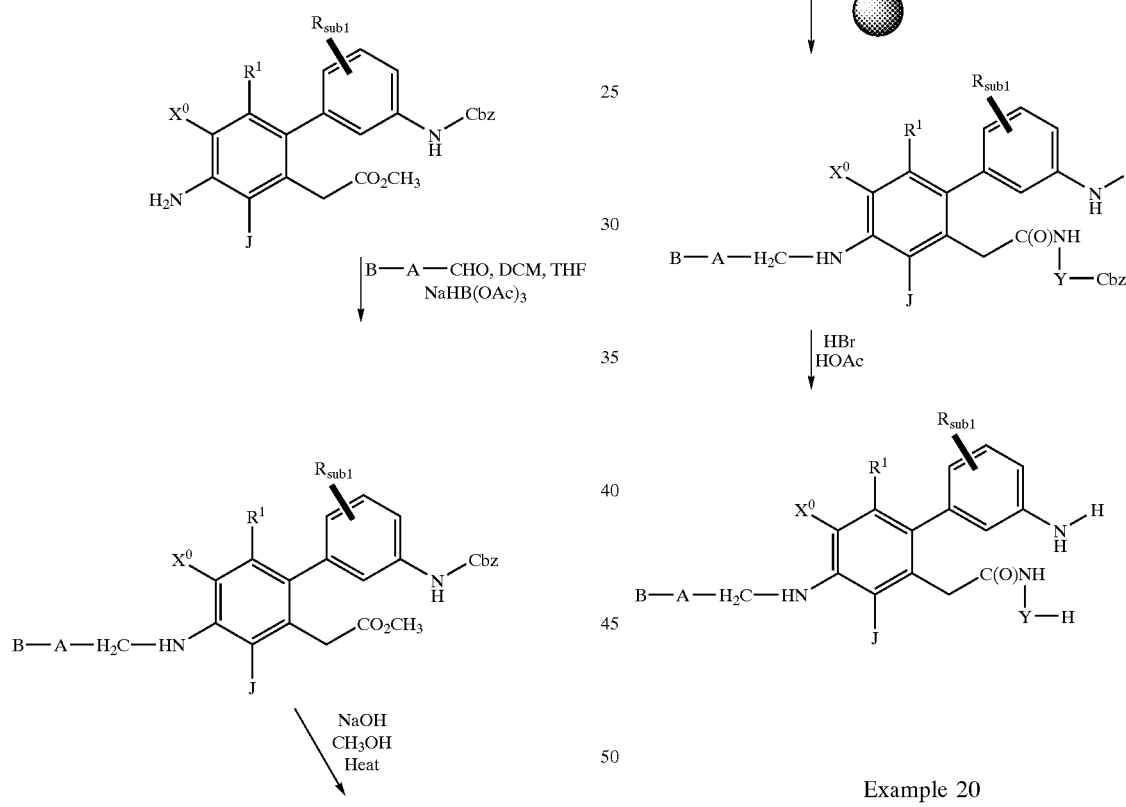
SCHEME 12
SCHEME 13
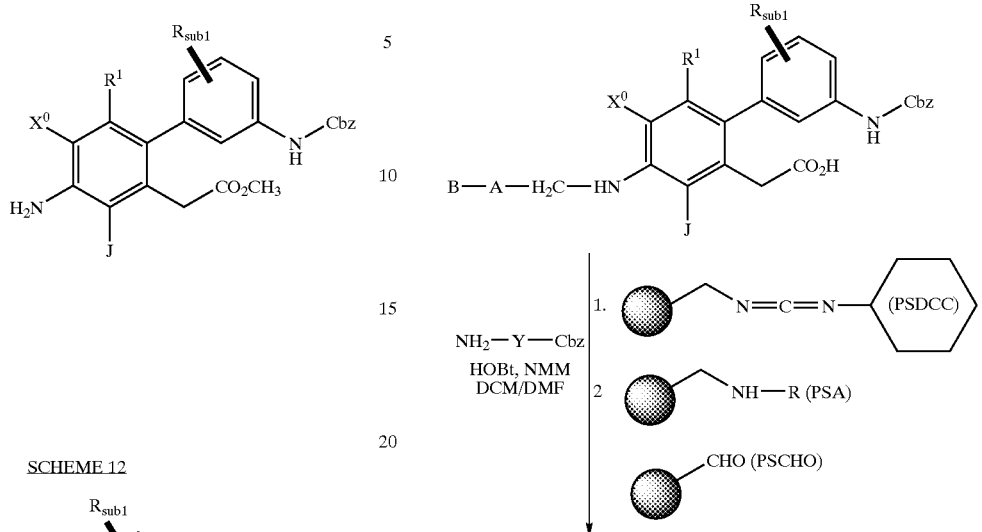
Example 20
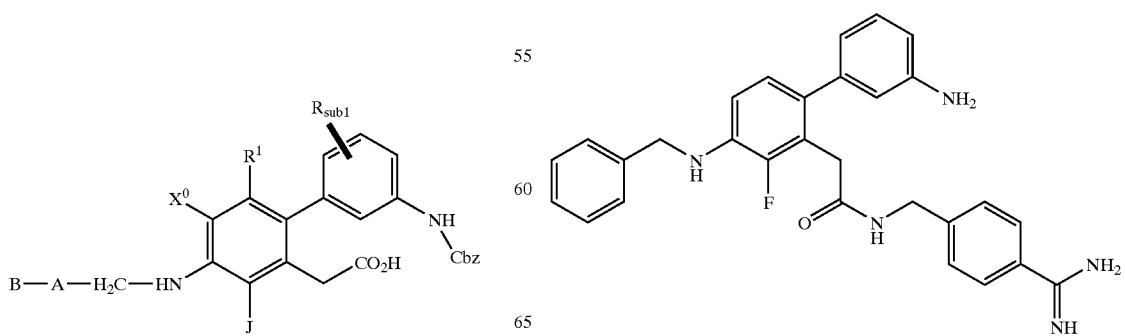

Triethylamine (15.3 mL, 0.109 mol) was added to a solution of the m-bromoaniline (10.0 mL, 0.092 mol) and benzylchloroformate (13.7 mL, 0.092 mol) in dichloromethane at 0° C. After stirring at room temperature for 2 hours, the solution was acidified with hydrochloric acid 2N and extracted with dichloromethane. The organic layer was washed with brine, dried over magnesium sulfate, and filtered. The solvent was removed by evaporation to afford the crude product. The product was purified by column chromatography (10% ethyl acetate-hexane) to afford 14.8 g (53%) of a clear oil of product EX-20A; $^1$H NMR ppm: 5.23 (s, 2H), 6.80 (bs, 1H), 7.29 (m, 9H); HPLC purity (retention time): >99% (4.05 min).

The bromo compound EX-20A (1.72 g, 5.6 mmol) was added to a solution of bis(tributyltin) (8.5 mL 16.0 mmol), and tetrakis(triphenylphosphine)palladium(0) (64.7 mg, 0.056 mmol) in 15 mL of toluene. The solution was heated to 90° C. for 18 hours. The solution was diluted with diethyl ether and the organic layer was washed with a saturated solution of potassium fluoride, brine, dried over magnesium sulfate, and filtered. The solvent was removed by evaporation to afford the crude product. The product was purified by column chromatography (10% ethyl acetate-hexane) to afford 1.36 g (47%) of a brown oil of product EX-20B; $^1$H NMR ppm: 0.90 (t, 9H), 1.04 (t, 6H), 1.33 (m, 6H), 1.53 (m, 6H), 5.20 (s, 2H), 6.63 (bs, 1H), 7.37 (m, 9H).

The triflate compound EX-20B (1.31 g, 3.6 mmol) was added to a solution of the tin compound (2.17 mL, 4.2 mmol), lithium chloride (440 mg, 10.0 mmol), and tetrakis (triphenylphosphine)palladium(0) (80.8 mg, 0.070 mmol) in 18 mL of anhydrous dioxane. The solution was heated to 85° C. for 21 hours. The organic layer was washed with brine, dried over magnesium sulfate, and filtered. The solvent was removed by evaporation to afford the crude product. The product was purified by column chromatography (40% ethyl acetate-hexane) to afford 0.56 g (38%) of a yellow oil of product EX-20C; $^1$H NMR ppm: 3.64 (d, 2H), 3.70 (s, 3H), 5.23 (s, 2H), 6.90 (m, 4H), 7.40 (m, 8H); $^{19}$F NMR ppm: −136.68 (d, 1F); HPLC purity (retention time): >99% (3.50 min).

Sodium triacetoxyborohydride (1.12 g, 5.28 mmol) was added to a solution of the aniline EX-20C (0.54 g, 1.32 mmol), benzaldehyde (147.8 uL, 1.45 mmol), and a drop of acetic acid in a tetrahydrofuran-dichloromethane (1:1) solution. After stirring at room temperature for 6 days, the solution was diluted with ether and water. The organic layer was washed with brine, dried over magnesium sulfate, and filtered. The solvent was removed by evaporation to afford the crude product. The product was purified by column chromatography (20% ethyl acetate-hexane) to afford 0.44 g (67%) of a yellow oil of product EX-20D; $^1$H NMR ppm: 3.65 (d, 2H), 3.71 (s, 3H), 4.44 (s, 2H), 5.23 (s, 2H), 6.72 (m, 2H), 6.97 (m, 2H), 7.36 (m, 8H); $^{19}$F NMR ppm: −138.06 (d, 1F); HPLC purity (retention time): >99% (4.58 min).

Aqueous sodium hydroxide (10%) (1.4 mL, 3.5 mmol) was added to a solution of the methyl ester EX-20D (0.44 g, 0.88 mmol) in methanol and the resulting solution stirred at 60° C. for 5 hours. The solution was acidified with 2 N hydrochloric acid and extracted with diethyl ether. The solution was washed with brine, dried over magnesium sulfate, and filtered. The solvent was removed by evaporation to afford 0.29 g (100%) of a white solid of two products EX-20E-1 and EX-20E-2. The products were carried on to the next step.

PS-carbodiimide (PSDCC) (1.00 mmol/g) (1.4 g, 1.4 mmol) was added to a slurry of the acids EX-20E-1 and EX-20E-2 (0.29 g, 0.71 mmole), 1-hydroxybenzotriazole (95.9 mg, 0.71 mmol), amine (0.27 g, 0.84 mmol), and N-methylmorpholine (624 uL, 5.6 mmol) in a dichloromethane diethylformamide (3:1) solution and the suspension was agitated for 3 hours. Upon completion of the reaction, the polyamine resin (PSA) (2.81 mmol/g) (2.0 g, 5.6 mmol) and polymer-bound aldehyde (PSCHO) (2.3 mmol/g) (1.0 g, 2.30 mmol) were added and the suspension was agitated for 1 hour. The solution was filtered and the polymer was rinsed with dimethylformamide and dichloromethane until no more UV activity was seen in the dichloromethane washing. The combined filtrate and washings were evaporated to afford a mixture of two products. Fraction one of reverse-phase chromatography afforded 240 mg (50%) of a yellow solid of product EX-20F; $^1$H NMR ppm: 3.60 (s, 3H), 3.69 (d, 2H), 4.09 (s, 2H), 4.33 (s, 2H), 5.26 (s, 2H), 6.60–7.68 (m, 23H); $^{19}$F NMR ppm: −138.00 (d, 1F); HPLC purity (retention time): 76% (3.71 min).

Fraction two of reverse-phase chromatography for EX-20F afforded 180 mg (34%) of an orange oil of product EX-20G; $^1$H NMR ppm: 3.68 (m, 4H), 4.34 (s, 2H), 5.08 (s, 2H), 5.26 (s, 2H), 6.68–7.60 (m, 28H); $^{19}$F NMR ppm: −136.67 (bs, 1F); HPLC purity (retention time): 61% (4.15 min).

Hydrogen bromide in acetic acid (30% wt) was added to the carbamate EX-20F or EX-20G and the solution stirred at room temperature for 16 hours. The solution was evaporated to afford a mixture of two products. Fraction one of reverse-phase chromatography afforded 32 mg (52%) of an orange solid of the trihydrogen bromide product; $^1$H NMR ppm: 3.64 (s, 3H), 4.36 (d, 2H), 4.45 (s, 2H), 6.64 (m, 1H), 6.84 (dd, 1H), 7.37 (m, 13H), 7.67 (d, 2H), 7.90 (bs, 2H), 8.97 (bs, 2H); $^{19}$F NMR ppm: −76.96 (s, 9F), −138.72 (d, 1F); HPLC purity (retention time): >99% (2.62 min).

Examples 21 and 22 summarize additional compounds prepared using Schemes 11, 12, and 13.

Example 21

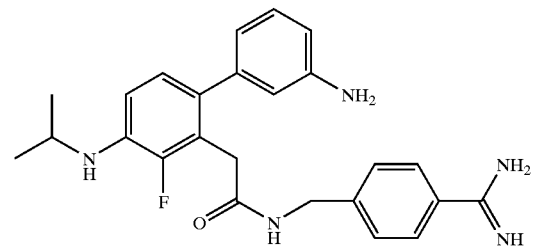

The triflate compound, methyl 2-fluoro-3-nitro-trifluoromethyl-sulfonyloxyphenylacetate, (6.5 g, 0.018 mol) was added to a solution of the tin compound (11.2 mL, 0.022 mol), lithium chloride (2.2 g, 0.051 mol), and tetrakis (triphenylphosphine)palladium(0) (410 mg, 0.35 mmol) in 90 mL of anhydrous dioxane. The solution was heated to 85° C. for 191 hours. The organic layer was washed with brine, dried over magnesium sulfate, and filtered. The solvent was removed by evaporation to afford a mixture of products. Fraction two from a column chromatography (30% ethyl acetate-hexane) afforded 3.8 g (48%) of an orange oil of the nitro product EX-21A; $^1$H NMR ppm: 3.71 (m, 5H), 5.21 (s, 2H), 6.86 (bs, 1H), 6.99 (m, 1H), 7.23 (d, 1H), 7.37 (m, 8H), 8.03 (t, 1H); $^{19}$F NMR ppm: −118.69 (m, 1F); HPLC purity (retention time): >99% (4.09 min); HRMS calcd for $C_{23}H_{19}O_6N_2F_1$ (M$^+$+NH$_4$) 456.1571, found 456.1564. Fraction three of the column chromatography (30% ethyl acetate-hexane) afforded 2.99 g (41%) of a brown solid of the aniline product EX-21B; $^1$H NMR ppm: 3.64 (d, 2H), 3.70 (s, 3H), 5.23 (s, 2H), 6.90 (m, 4H), 7.40 (m, 8H); $^{19}$F NMR ppm: −136.68 (d, 1F); HPLC purity (retention time): >99% (3.50 min); HRMS calcd for $C_{23}H_{21}O_4N_2F_1$ (M$^+$+NH$_4$) 426.1829, found 426.1846.

Sodium triacetoxyborohydride (5.6 g, 26.4 mmol) was added to a solution of the aniline EX-21B (2.69 g, 6.6 mmol), acetone (8.0 mL, excess), and a drop of acetic acid in a tetrahydrofuran-dichloromethane (1:1) solution. After stirring at room temperature for 26 hours, the solution was diluted with ether and water. The organic layer was washed with brine, dried over magnesium sulfate, and filtered. The solvent was removed by evaporation to afford the crude product. The product was purified by column chromatography (30% ethyl acetate-hexane) to afford 1.34 g (45%) of a white solid of the methyl ester N-isopropylaniline product EX-21C; $^1$H NMR ppm: 1.30 (d, 6H), 3.62 (d, 2H), 3.68 (s, 3H), 4.13 (m, 1H), 5.21 (s, 2H), 6.70 (m, 2H), 6.99 (m, 2H), 7.36 (m, 9H); HPLC purity (retention time); >99% (3.84 min); HRMS calcd for $C_{26}H_{27}O_4N_2F_1$ (M$^+$+H) 451.2033, found 451.2023.

Aqueous sodium hydroxide (10%) (4.3 mL, 10.0 mmol) was added to a solution of the methyl ester EX-21C (1.21 g, 2.6 mmol) in tetrahydrofuran and the resulting solution stirred at 60° C. for 48 hours. Partial Cbz deprotection occurred so, benzyl chloroformate (382 uL, 2.6 mmol) was added to the solution and the resulting solution stirred at room temperature for 1 hour. The solution was acidified with 2 N hydrochloric acid and extracted with diethyl ether. The solution was washed with brine, dried over magnesium sulfate, and filtered. The solvent was removed by evaporation to afford the crude product. The product was purified by column chromatography (50% ethyl acetate-hexane) to afford 0.24 g (21%) of a brown oil of the acetic acid product EX-21D; $^1$H NMR ppm: 1.28 (d, 6H), 3.65 (d, 2H), 4.12 (m, 1H), 5.19 (s, 2H), 6.69 (m, 1H), 6.97 (m, 2H), 7.36 (m, 9H); HPLC purity (retention time): >99% (2.84 min).

PS-carbodiimide (1.00 mmol/g) (0.59 g, 0.59 mmol) was added to a slurry of the acid EX-21D (0.13 g, 0.29 mmole), 1-hydroxybenzotriazole (40.2 mg, 0.29 mmol), 4-(N-benzyloxycarbonylamidino) benzylamine hydrochloride (0.11 g, 0.34 mmol), and N-methylmorpholine (163 uL, 1.4 mmol) in a dichloromethane-dimethylformamide (3:1) solution and the suspension was agitated for 4 hours. Upon completion of the reaction, polyamine resin (2.81 mmol/g) (0.50 g, 1.4 mmol) and polymer-bound aldehyde (2.3 mmol/g) (0.050 g, 1.15 mmol) were added and the suspension was agitated for 1 hour. The solution was filtered, and the polymer was rinsed with dimethylformamide and dichloromethane until no more UV activity was seen in the dichloromethane washing. The combined filtrate and washings were evaporated to afford the crude product. The product EX-21E was carried on to the next step. HPLC purity (retention time): 79% (2.77 min); HRMS calcd for $C_{41}H_{40}O_5N_5F_1$ (M$^+$+H) 702.3092, found 702.3114.

A catalytic amount of palladium on carbon (5%) in methanol was added to a methanol solution of the Cbz compound EX-21E (0.298 mmol), and the mixture was stirred under a balloon of hydrogen at room temperature until the reaction was complete. The mixture was filtered through celite, and the solvent was evaporated to afford the product. The product was purified by reverse-phase chromatography to afford 14.6 mg (81%) of a white solid of the product; $^1$H NMR ppm: 1.68 (d, 6H), 4.04 (d, 2H), 4.15 (sept, 1H), 4.85 (d, 2H), 7.27 (m, 6H), 7.65 (t, 1H), 7.83 (d, 2H), 8.07 (bt, 1H), 8.24 (d, 2H), 9.20 (bs, 1H), 10.38 (bs, 1H); $^{19}$F NMR ppm: −76.41 (s, 9F), −138.02 (d, 1F); HPLC purity (retention time): >99% (1.37 min); HRMS calcd for $C_{25}H_{29}O_1N_5F_1$ (M$^+$+H) 434.2356, found 434.2360.

Example 22

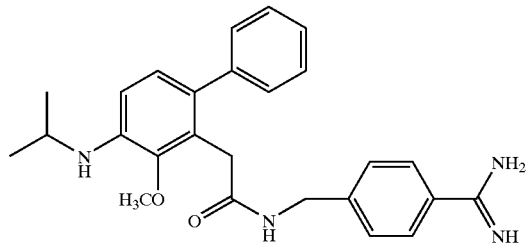

Sodium triacetoxyborohydride (9.3 g, 43.0 mmol) was added to a solution of the aniline, methyl 2-[2-methoxy-3-aminophenylphenyl]acetate, (2.99 g, 11.0 mmol), acetone (1.0 mL, 13.6 mmol), and a drop of acetic acid in a tetrahydrofuran-dichloromethane (1:1) solution. After stirring at room temperature for 14 hours, additional acetone (1.0 mL, 13.6 mmol) and acetic acid (excess) was added, and the solution was stirred at room temperature for 18 hours. The solution was diluted with ether and water. The organic layer was washed with brine, dried over magnesium sulfate, and filtered. The solvent was removed by evaporation to afford the crude product. The product was purified by column chromatography (15% ethyl acetate-hexane) to afford 3.55 g (100%) of a yellow oil of the the methyl ester product EX-22A; $^1$H NMR ppm: 1.24 (d, 6H), 3.59 (s, 3H), 3.62 (m, 2H), 3.72 (s, 3H), 4.09 (m, 1H), 6.62 (d, 1H, J=8.3 Hz), 6.92 (d, 1H, J=8.3 Hz), 7.28 (m, 5H); HPLC purity (retention time): 97.5% (2.57 min); HRMS calcd for $C_{19}H_{23}O_3N_1$ (M$^+$+H) 314.1756, found 314.1758.

Aqueous sodium hydroxide (10%) (7.6 mL, 19.0 mmol) was added to a solution of the methyl ester EX-22A (1.51 g, 4.81 mmol) in methanol and the resulting solution stirred at 60° C. for 3 hours. The solution was acidified with 2 N hydrochloric acid and extracted with diethyl ether. The solution was washed with brine, dried over magnesium sulfate, and filtered. The solvent was removed by evaporation to afford the crude product. The product was purified by column chromatography (40% ethyl acetate-hexane) to afford 0.44 g (31%) of a white solid of the carboxylic acid product EX-22B; $^1$H NMR ppm: 1.25 (d, 6H), 3.62 (m, 3H), 3.75 (s, 3H), 6.50 (d, 1H, J=8.3 Hz), 6.94 (d, 1H, J=8.3 Hz), 7.27 (m, 5H); HPLC purity (retention time): >99% (2.11 min); HRMS calcd for $C_{18}H_{21}O_3N_1$ (M$^+$+H) 300.1600, found 300.1587.

PS-carbodiimide (1.00 mmol/g) (2.8 g, 2.8 mmol) was added to a slurry of the acid EX-22B (0.42 g, 1.4 mmole), 1-hydroxybenzotriazole (0.19 mg, 1.4 mmol), 4-(N-benzyloxycarbonylamidino) benzylamine hydrochloride (0.54 g, 1.6 mmol), and N-methylmorpholine (620 uL, 5.6 mmol) in a dichloromethane-dimethylformamide (3:1) solution, and the suspension was agitated for 18 hours. Upon completion of the reaction, the polyamine resin (2.81 mmol/g) (1.0 g, 2.8 mmol) and polymer-bound aldehyde (2.3 mmol/g) (1.0 g, 2.30 mmol) were added, and the suspension was agitated for 1 hour. The solution was filtered, and the polymer was rinsed with dimethylformamide and dichloromethane until no more UV activity was seen in the dichloromethane washing. The combined filtrate and washings were evaporated to afford the crude product. The protected product EX-22C was purified by column chromatography (60% ethyl acetate-hexane) and then was washed off with 100% ethyl acetate to afford 0.73 g (92%) of a white solid EX-22C; $^1$H NMR ppm: 1.25 (d, 6H), 3.62 (m, 3H), 3.71 (s, 3H), 4.33 (d, 2H), 5.19 (s, 2H), 6.05 (bt, 1H), 6.63 (d, 2H, J=8.3 Hz), 6.93 (d, 2H, J=8.3 Hz), 7.29 (m, 13H), 7.7 (d, 2H); HPLC purity (retention time): >99% (2.55 min); HRMS calcd for $C_{34}H_{36}O_4N_4$ (M$^+$+H) 565.2815, found 565.2839.

A catalytic amount of palladium on carbon (5%) in dioxane was added to 3 mL of a methanol-4N hydrochloric acid/dioxane (3:1) solution of the Cbz compound EX-22C (50.0 mg, 0.88 mmol), and the mixture was stirred under a balloon of hydrogen at room temperature for 12 hours. The mixture was filtered through celite, and the solvent was evaporated to afford the product. The product was purified by reverse-phase chromatography to afford 22.0 mg (60%) of a purple-white solid; $^1$H NMR ppm: 1.41 (m, 6H), 3.65 (s, 2H), 3.82 (m, 1H), 3.95 (s, 3H), 4.39 (s, 2H), 6.98 (d, 1H), 7.19 (d, 1H), 7.42 (m, 7H), 7.78 (d, 2H); HPLC purity (retention time): >99% (1.50 min); HRMS calcd for $C_{26}H_{30}O_2N_4$ (M$^+$+H) 431.2447, found 431.2447.

Using the disclosed examples and methods described herein, the following further compounds having an amidinoaralkyl type Y$^o$ group and various J-substituents can be prepared of the Formula:

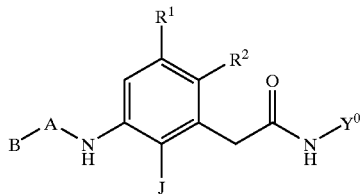

wherein;

$R^2$ is 3-aminophenyl, B is 3-chlorophenyl, A is CH$_2$CH$_2$, Y$^o$ is 4-amidinobenzyl, J is fluoro, and R$^1$ is chloro;

$R^2$ is 3-aminophenyl, B is phenyl, A is CH$_2$, Y$^o$ is 4-amidinobenzyl, J is fluoro, and R$^1$ is hydrido;

$R^2$ is 3-aminophenyl, B is 2-imidazoyl, A is CH$_2$CH$_2$CH$_2$, Y$^o$ is 4-amidinobenzyl, J is fluoro, and R$^1$ is chloro;

$R^2$ is 3-amidocarbonyl-5-aminophenyl, B is 3-chlorophenyl, A is CH$_2$CH$_2$, Y$^o$ is 4-amidinobenzyl, J is fluoro, and R$^1$ is chloro;

$R^2$ is 3-amino-5-(N-benzylamidocarbonyl)phenyl, B is 3-chlorophenyl, A is CH$_2$CH$_2$, Y$^o$ is 4-amidinobenzyl, J is fluoro, and R$^1$ is chloro;

$R^2$ is 3-amino-5-(N-(2-chlorobenzyl)amidocarbonyl)phenyl, B is 3-chlorophenyl, A is CH$_2$CH$_2$, Y$^o$ is 4-amidinobenzyl, J is fluoro, and R$^1$ is chloro;

$R^2$ is 3-amino-5-(N-(2-chlorobenzyl)amidosulfonyl)phenyl, B is 3-chlorophenyl, A is CH$_2$CH$_2$, Y$^o$ is 4-amidinobenzyl, J is fluoro, and R$^1$ is chloro;

$R^2$ is 3-amino-5-(N-(2-trifluoromethylbenzyl)amidocarbonyl)-phenyl, B is 3-chlorophenyl, A is CH$_2$CH$_2$, Y$^o$ is 4-amidinobenzyl, J is fluoro, and R$^1$ is chloro;

$R^2$ is 3,5-diaminophenyl, B is 3-chlorophenyl, A is CH$_2$CH$_2$, Y$^o$ is 4-amidinobenyl, J is fluoro, and R$^1$ is chloro;

$R^2$ is 3-amino-5-carboxyphenyl, B is 3-chlorophenyl, A is CH$_2$CH$_2$, Y$^o$ is 4-amidinobenzyl, J is fluoro, and R$^1$ is chloro;

$R^2$ is 3-amidocarbonyl-5-aminophenyl, B is 3-chlorophenyl, A is CH$_2$CH$_2$, Y$^o$ is 4-amidinobenzyl, J is fluoro, and R$^1$ is hydrido;

$R^2$ is 3-amino-5-(N-benzylamidocarbonyl)phenyl, B is 3-chlorophenyl, A is CH$_2$CH$_2$, Y$^o$ is 4-amidinobenzyl, J is fluoro, and R$^1$ is hydrido;

$R^2$ is 3-amino-5-(N-(2chlorobenzyl)amidocarbonyl)phenyl, B is 3-chlorophenyl, A is CH$_2$CH$_2$, Y$^o$ is 4-amidinobenzyl, J is fluoro, and R$^1$ is hydrido;

$R^2$ is 3-amino-5-(N-2-chlorobenzyl)amidosulfonyl)phenyl, B is 3-chlorophenyl, A is CH$_2$CH$_2$, Y$^o$ is 4-amidinobenzyl, J is fluoro, and R$^1$ is hydrido;

$R^2$ is 3-amino-5(N-(2-trifluoromethylbenzyl)amidocarbonyl)-phenyl, B is 3-chlorophenyl, A is CH$_2$CH$_2$, Y$^o$ is 4-amidinobenzyl, J is fluoro, and R$^1$ is hydrido;

$R^2$ is 3,5-diaminophenyl, B is 3-chlorophenyl, A is CH$_2$CH$_2$, Y$^o$ is 4-amidinobenzyl, J is fluoro, and R$^1$ is hydrido;

$R^2$ is 3-amino-5-carboxyphenyl, B is 3-chlorophenyl, A is CH$_2$CH$_2$, Y$^o$ is 4-amidinobenzyl, J is fluoro, and R$^1$ is hydrido;

$R^2$ is 3-aminophenyl, B is 3-chlorophenyl, A is CH$_2$CH$_2$, Y$^o$ is 4-amidinobenzyl, J is hydroxy, and R$^1$ is chloro;

$R^2$ is 3-aminophenyl, B is phenyl, A is CH$_2$, Y$^o$ is 4-amidinobenzyl, J is hydroxy, and R$^1$ is chloro;

$R^2$ is 3-aminophenyl, B is 2-imidazoyl, A is CH$_2$CH$_2$CH$_2$, Y$^o$ is 4-amidinobenzyl, J is hydroxy, and R$^1$ is chloro;

$R^2$ is 3-amidocarbonyl-5-aminophenyl, B is 3-chlorophenyl, A is CH$_2$CH$_2$, Y$^o$ is 4-amidinobenzyl, J is hydroxy, and R$^1$ is chloro;

$R^2$ is 3-amino-5-(N-benzylamidocarbonyl)phenyl, B is 3-chlorophenyl, A is CH$_2$CH$_2$, Y$^o$ is 4-amidinobenzyl, J is hydroxy, and R$^1$ is chloro;

$R^2$ is 3-amino-5-(N-(2-chlorobenzyl)amidocarbonyl)phenyl, B is 3-chlorophenyl, A is CH$_2$CH$_2$, Y$^o$ is 4-amidinobenzyl, J is hydroxy, and R$^1$ is chloro;

$R^2$ is 3-amino-5-(N-(2-chlorobenzyl)amidosulfonyl)phenyl, B is 3-chlorophenyl, A is CH$_2$CH$_2$, Y$^o$ is 4-amidinobenzyl, J is hydroxy, and R$^1$ is chloro;

$R^2$ is 3-amino-5-(N-(2-trifluoromethylbenzyl)amidocarbonyl)-phenyl, B is 3-chlorophenyl, A is CH$_2$CH$_2$, Y$^o$ is 4-amidinobenzyl, J is hydroxy, and R$^1$ is chloro;

$R^2$ is 3,5-diaminophenyl, B is 3-chlorophenyl, A is CH$_2$CH$_2$, Y$^o$ is 4-amidinobenzyl, J is hydroxy, and R$^1$ is chloro;

$R^2$ is 3-amino-5-carboxyphenyl, B is 3-chlorophenyl, A is CH$_2$CH$_2$, Y$^o$ is 4-amidinobenzyl, J is hydroxy, and R$^1$ is chloro;

$R^2$ is 3-amidocarbonyl-5-aminophenyl, B is 3-chlorophenyl, A is CH$_2$CH$_2$, Y$^o$ is 4-amidinobenzyl, J is hydroxy, and R$^1$ is hydrido;

$R^2$ is 3-amino-5-(N-benzylamidocarbonyl)phenyl, B is 3-chlorophenyl, A is CH$_2$CH$_2$, Y$^o$ is 4-amidinobenzyl, J is hydroxy, and R$^1$ is hydrido;

$R^2$ is 3-amino-5-(N-(2-chlorobenzyl)amidocarbonyl)phenyl, B is 3-chlorophenyl, A is CH$_2$CH$_2$, Y$^o$ is 4-amidinobenzyl, J is hydroxy, and R$^1$ is hydrido;

$R^2$ is 3-amino-5-(N-(2-chlorobenzyl)amidosulfonyl)phenyl, B is 3-chlorophenyl, A is CH$_2$CH$_2$, Y$^o$ is 4-amidinobenzyl, J is hydroxy, and R$^1$ is hydrido;

$R^2$ is 3-amino-5-N-(2-trifluoromethylbenzyl)amidocarbonyl)-phenyl, B is 3-chlorophenyl, A is CH$_2$CH$_2$, Y$^o$ is 4-amidinobenzyl, J is hydroxy, and R$^1$ is hydrido;

$R^2$ is 3,5-diaminophenyl, B is 3-chlorophenyl, A is $CH_2CH_2$, $Y^0$ is 4-amidinobenzyl, J is hydroxy, and $R^1$ is hydrido;

$R^2$ is 3-amino-5-carboxyphenyl, B is 3-chlorophenyl, A is $CH_2CH_2$, $Y^0$ is 4-amidinobenzyl, J is hydroxy, and $R^1$ is hydrido;

$R^2$ is 3-aminophenyl, B is 2,2,2-trifluoroethyl, A is a bond, $Y^0$ is 4-amidinobenzyl, J is hydroxy, and $R^1$ is chloro;

$R^2$ is 3-aminophenyl, B is (S)-2-butyl, A is a bond, $Y^0$ is 4-amidinobenzyl, J is hydroxy, and $R^1$ is chloro;

$R^2$ is 5-amino-2-fluorophenyl, B is isopropyl, A is a bond, $Y^0$ is 4-amidinobenzyl, J is hydroxy, and $R^1$ is chloro;

$R^2$ is 2-methyl-3-aminophenyl, B is isopropyl, A is a bond, $Y^0$ is 4-amidinobenzyl, J is hydroxy, and $R^1$ is chloro;

$R^2$ is 3-aminophenyl, B is ethyl, A is a bond, $Y^0$ is 4-amidinobenzyl, J is hydroxy, and $R^1$ is chloro;

$R^2$ is 3-aminophenyl, B is ethyl, A is a bond, $Y^0$ is 4-amidino-2-fluorobenzyl, J is hydroxy, and $R^1$ is chloro;

$R^2$ is 3-aminophenyl, B is 2-propenyl, A is a bond, $Y^0$ is 4-amidinobenzyl, J is hydroxy, and $R^1$ is chloro;

$R^2$ is 3-aminophenyl, B is isopropyl, A is a bond, $Y^0$ is 4-amidino-2-fluorobenzyl, J is hydroxy, and $R^1$ is chloro;

$R^2$ is 3-aminophenyl, B is isopropyl, A is a bond, $Y^0$ is 4-amidinobenzyl, J is hydroxy, and $R^1$ is chloro;

$R^2$ is 3-aminophenyl, B is 2-butyl, A is a bond, $Y^0$ is 4-amidinobenzyl, J is hydroxy, and $R^1$ is chloro;

$R^2$ is 3-aminophenyl, B is (R)-2-butyl, A is a bond, $Y^0$ is 4-amidinobenzyl, J is hydroxy, and $R^1$ is chloro;

$R^2$ is 3-aminophenyl, B is 2-propynyl, A is a bond, $Y^0$ is 4-amidinobenzyl, J is hydroxy, and $R^1$ is chloro;

$R^2$ is 3-aminophenyl, B is 3-pentyl, A is a bond, $Y^0$ is 4-amidinobenzyl, J is hydroxy, and $R^1$ is hydrido;

$R^2$ is 3-aminophenyl, B is hydrido, A is $CH_2$, $Y^0$ is 4-amidinobenzyl, J is hydroxy, and $R^1$ is chloro;

$R^2$ is 3-aminophenyl, B is ethyl, A is $CH_2$, $Y^0$ is 4-amidinobenzyl, J is hydroxy, and $R^1$ is chloro;

$R^2$ is 3-aminophenyl, B is 2-methypropyl, A is a bond, $Y^0$ is 4-amidinobenzyl, J is hydroxy, and $R^1$ is chloro;

$R^2$ is 3-aminophenyl, B is 2-propyl, A is $CH_3CH$, $Y^0$ is 4-amidinobenzyl, J is hydroxy, and $R^1$ is chloro;

$R^2$ is 3-aminophenyl, B is propyl, A is a bond, $Y^0$ is 4-amidino-2-fluorobenzyl, J is hydroxy, and $R^1$ is chloro;

$R^2$ is 3-aminophenyl, B is 6-amidocarbonylhexyl, A is a bond, $Y^0$ is 4-amidinobenzyl, J is hydroxy, and $R^1$ is chloro;

$R^2$ is 3-aminophenyl, B is tert-butyl, A is a bond, $Y^0$ is 4-amidinobenzyl, J is hydroxy, and $R^1$ is hydrido;

$R^2$ is 3-aminophenyl, B is tert-butyl, A is a bond, $Y^0$ is 4-amidinobenzyl, J is hydroxy, and $R^1$ is chloro;

$R^2$ is 3-aminophenyl, B is 3-hydroxypropyl, A is a bond, $Y^0$ is 4-amidinobenzyl, J is hydroxy, and $R^1$ is chloro;

$R^2$ is 3-aminophenyl, B is 2-methylpropyl, A is a bond, $Y^0$ is 4-amidino-2-fluorobenzyl, J is hydroxy, and $R^1$ is chloro;

$R^2$ is 3-aminophenyl, B is butyl, A is a bond, $Y^0$ is 4-amidinobenzyl, J is hydroxy, and $R^1$ is chloro;

$R^2$ is 3-aminophenyl, B is 1-methoxy-2-propyl, A is a bond, $Y^0$ is 4-amidinobenzyl, J is hydroxy, and $R^1$ is chloro;

$R^2$ is 3-aminophenyl, B is 2-methoxyethyl, A is a bond, $Y^0$ is 4-amidinobenzyl, J is hydroxy, and $R^1$ is chloro;

$R^2$ is 3-aminophenyl, B is 2-propyl, A is a bond, $Y^0$ is 5-amidino-2-thienylmethyl, J is hydroxy, and $R^1$ is chloro;

$R^2$ is 5-amino-2-methylthiophenyl, B is 2-propyl, A is a bond, $Y^0$ is 4-amidinobenzyl, J is hydroxy, and $R^1$ is chloro;

$R^2$ is 3-amino-5-carboxyphenyl, B is isopropyl, A is a bond, $Y^0$ is 4-amidinobenzyl, J is hydroxy, and $R^1$ is chloro;

$R^2$ is 3-amino-5-carbomethoxyphenyl, B is isopropyl, A is a bond, $Y^0$ is 4-amidinobenzyl, J is hydroxy, and $R^1$ is chloro;

$R^2$ is 3-aminophenyl, B is isopropyl, A is a bond, $Y^0$ is 4-amidinobenzyl, J is hydroxy, and $R^1$ is bromo;

$R^2$ is 3-amino-5-carboxamidophenyl, B is isopropyl, A is a bond, $Y^0$ is 4-amidinobenzyl, J is hydroxy, and $R^1$ is chloro;

$R^2$ is 3-amino-5-(N-benzyl-N-methylamidocarbonyl)phenyl, B is isopropyl, A is a bond, $Y^0$ is 4-amidinobenzyl, J is hydroxy, and $R^1$ is chloro;

$R^2$ is 3-amino-5-(N-(1-phenylethyl)amidocarbonyl)phenyl, B is isopropyl, A is a bond, $Y^0$ is 4-amidinobenzyl, J is hydroxy, and $R^1$ is chloro;

$R^2$ is 3-amino-5-(N-(2-phenyl-2-propyl)amidocarbonyl)phenyl, B is isopropyl, A is a bond, $Y^0$ is 4-amidinobenzyl, J is hydroxy, and $R^1$ is chloro;

$R^2$ is 3-amino-5-(N-(2,4-dichlorobenzyl)amidocarbonyl)phenyl, B is isopropyl, A is a bond, $Y^0$ is 4-amidinobenzyl, J is hydroxy, and $R^1$ is chloro;

$R^2$ is 3-amino-5-(N-(4-bromobenzyl)amidocarbonyl)phenyl, B is isopropyl, A is a bond, $Y^0$ is 4-amidinobenzyl, J is hydroxy, and $R^1$ is chloro;

$R^2$ is 3-amino-5-(N-benzylamidocarbonyl)phenyl, B is isopropyl, A is a bond, $Y^0$ is 4-amidinobenzyl, J is hydroxy, and $R^1$ is chloro;

$R^2$ is 3-amino-5-(N-(2-chlorobenzyl)amidocarbonyl)phenyl, B is isopropyl, A is a bond, $Y^0$ is 4-amidinobenzyl, J is hydroxy, and $R^1$ is chloro;

$R^2$ is 3-amino-5-(N-(2-trifluoromethylbenzyl)amidocarbonyl)phenyl, B is isopropyl, A is abond, $Y^0$ is 4-amidinobenzyl, J is hydroxy, and $R^1$ is chloro;

$R^2$ is 3-amino-5-(N-(3-fluorobenzyl)amidocarbonyl)phenyl, B is isopropyl, A is a bond, $Y^0$ is 4-amidinobenzyl, J is hydroxy, and $R^1$ is chloro;

$R^2$ is 3-amino-5-(N-(3-trifluoromethylbenzyl)amidocarbonyl)phenyl, B is isopropyl, A is a bond, $Y^0$ is 4-amidinobenzyl, J is hydroxy, and $R^1$ is chloro;

$R^2$ is 3-amino-5-(N-isobutylamidocarbonyl)phenyl, B is isopropyl, A is a bond, $Y^0$ is 4-amidinobenzyl, J is hydroxy, and $R^1$ is chloro;

$R^2$ is 3-amino-5-(N-cyclobutylamidocarbonyl)phenyl, B is isopropyl, A is a bond, $Y^0$ is 4-amidinobenzyl, J is hydroxy, and $R^1$ is chloro;

$R^2$ is 3-amino-5-(N-cyclopentylamidocarbonyl)phenyl, B is isopropyl, A is a bond, $Y^0$ is 4-amidinobenzyl, J is hydroxy, and $R^1$ is chloro;

$R^2$ is 3-amino-5-(N-cycloheptylamidocarbonyl)phenyl, B is isopropyl, A is a bond, $Y^0$ is 4-amidinobenzyl, J is hydroxy, and $R^1$ is chloro;

$R^2$ is 3-amino-5-N-(2-pyridylmethyl)amidocarbonyl)phenyl, B is isopropyl, A is a bond, $Y^0$ is 4-amidinobenzyl, J is hydroxy, and $R^1$ is chloro;

$R^2$ is 3-amino-5-(N-(3-pyridylmethyl)amidocarbonyl)phenyl, B is isopropyl, A is a bond, $Y^0$ is 4-amidinobenzyl, J is hydroxy, and $R^1$ is chloro;

$R^2$ is 3-amino-5-(N-(2-(4-methoxyphenyl)ethyl)amidocarbonyl)phenyl, B is isopropyl, A is a bond, $Y^0$ is 4-amidinobenzyl, J is hydroxy, and $R^1$ is chloro;

$R^2$ is 3-amino-5-(N-(3-phenylpropyl)amidocarbonyl)phenyl, B is isopropyl, A is a bond, $Y^0$ is 4-amidinobenzyl, J is hydroxy, and $R^1$ is chloro;

$R^2$ is 3-amino-5-(N-(2,2-diphenylethyl)amidocarbonyl)phenyl, B is isopropyl, A is a bond, $Y^0$ is 4-amidinobenzyl, J is hydroxy, and $R^1$ is chloro;

$R^2$ is 3-amino-5-(N-(2-naphthylmethyl)amidocarbonyl)phenyl, B is isopropyl, A is a bond, $Y^0$ is 4-amidinobenzyl, J is hydroxy, and $R^1$ is chloro;

$R^2$ is 3-amino-5-(N-(1,2,3,4-tetrahydronaphth-2-ylmethyl)amidocarbonyl)phenyl, B is isopropyl, A is a bond, $Y^0$ is 4-amidinobenzyl, J is hydroxy, and $R^1$ is chloro;

$R^2$ is 3-aminophenyl, B is 2-propyl, A is a bond, $Y^0$ is 4-amidino-3-fluorobenzyl, J is hydroxy, and $R^1$ is hydrido;

$R^2$ is 3-carboxyphenyl, B is 2-propyl, A is a bond, $Y^0$ is 4-amidinobenzyl, J is hydroxy, and $R^1$ is hydrido;

$R^2$ is 3-aminophenyl, B is 2-propyl, A is a bond, $Y^0$ is 4-amidino-3-fluorobenzyl, J is hydroxy, and $R^1$ is chloro;

$R^2$ is 3,5-diaminophenyl, B is 2,2,2-trifluoroethyl, A is a bond, $Y^0$ is 4-amidinobenzyl, J is hydroxy, and $R^1$ is chloro;

$R^2$ is 3,5-diaminophenyl, B is (S)-2-butyl, A is a bond, $Y^0$ is 4-amidinobenzyl, J is hydroxy, and $R^1$ is chloro;

$R^2$ is 3,5-diaminophenyl, B is isopropyl, A is a bond, $Y^0$ is 4-amidinobenzyl, J is hydroxy, and $R^1$ is chloro;

$R^2$ is 3,5-diaminophenyl, B is isopropyl, A is a bond, $Y^0$ is 4-amidino-2-fluorobenzylbenzyl, J is hydroxy, and $R^1$ is chloro;

$R^2$ is 3,5-diaminophenyl, B is ethyl, A is a bond, $Y^0$ is 4-amidinobenzyl, J is hydroxy, and $R^1$ is chloro;

$R^2$ is 3,5-diaminophenyl, B is ethyl, A is a bond, $Y^0$ is 4-amidino-2-fluorobenzyl, J is hydroxy, and $R^1$ is chloro;

$R^2$ is 3-amino-5-carboxyphenyl, B is 2,2,2-trifluoroethyl, A is a bond, $Y^0$ is 4-amidinobenzyl, J is hydroxy, and $R^1$ is chloro;

$R^2$ is 3-amino-5-carboxyphenyl, B is (S)-2-butyl, A is a bond, $Y^0$ is 4-amidinobenzyl, J is hydroxy, and $R^1$ is chloro;

$R^2$ is 3-amino-5-carboxyphenyl, B is isopropyl, A is a bond, $Y^0$ is 4-amidino-2-fluorobenzylbenzyl, J is hydroxy, and $R^1$ is chloro;

$R^2$ is 3-amino-5-carboxyphenyl, B is ethyl, A is a bond, $Y^0$ is 4-amidinobenzyl, J is hydroxy, and $R^1$ is chloro;

$R^2$ is 3-amino-5-carboxyphenyl, B is ethyl, A is a bond, $Y^0$ is 4-amidino-2-fluorobenzyl, J is hydroxy, and $R^1$ is chloro;

$R^2$ is 3-amino-5-(N-benzylamidocarbonyl)phenyl, B is 2,2,2-trifluoroethyl, A is a bond, $Y^0$ is 4-amidinobenzyl, J is hydroxy, and $R^1$ is chloro;

$R^2$ is 3-amino-5-(N-benzylamidocarbonyl)phenyl, B is (S)-2-butyl, A is a bond, $Y^0$ is 4-amidinobenzyl, J is hydroxy, and $R^1$ is chloro;

$R^2$ is 3-amino-(N-benzylamidocarbonyl)phenyl, B is isopropyl, A is a bond, $Y^0$ is 4-amidino-2-fluorobenzylbenzyl, J is hydroxy, and $R^1$ is chloro;

$R^2$ is 3-amino-5-(N-benzylamidocarbonyl)phenyl, B is ethyl, A is a bond, $Y^0$ is 4-amidinobenzyl, J is hydroxy, and $R^1$ is chloro;

$R^2$ is 3-amino-5-(N-benzylamidocarbonyl)phenyl, B is ethyl, A is a bond, $Y^0$ is 4-amidino-2-fluorobenzyl, J is hydroxy, and $R^1$ is chloro;

$R^2$ is 3,5-diaminophenyl, B is isopropyl, A is a bond, $Y^0$ is 4-amidinobenzylbenzyl, J is hydroxy, and $R^1$ is hydrido;

$R^2$ is 3-aminophenyl, B is 2,2,2-trifluoroethyl, A is a bond, $Y^0$ is 4-amidinobenzyl, J is fluoro, and $R^1$ is chloro;

$R^2$ is 3-aminophenyl, B is (S)-2-butyl, A is a bond, $Y^0$ is 4-amidinobenzyl, J is fluoro, and $R^1$ is chloro;

$R^2$ is 5-amino-2-fluorophenyl, B is isopropyl, A is a bond, $Y^0$ is 4-amidinobenzyl, J is fluoro, and $R^1$ is chloro;

$R^2$ is 2-methyl-3-aminophenyl, B is isopropyl, A is a bond, $Y^0$ is 4-amidinobenzyl, J is fluoro, and $R^1$ is chloro;

$R^2$ is 3-aminophenyl, B is ethyl, A is a bond, $Y^0$ is 4-amidinobenzyl, J is fluoro, and $R^1$ is chloro;

$R^2$ is 3-aminophenyl, B is ethyl, A is a bond, $Y^0$ is 4-amidino-2-fluorobenzyl, J is fluoro, and $R^1$ is chloro;

$R^2$ is 3-aminophenyl, B is 2-propenyl, A is a bond, $Y^0$ is 4-amidinobenzyl, J is fluoro, and $R^1$ is chloro;

$R^2$ is 3-aminophenyl, B is isopropyl, A is a bond, $Y^0$ is 4-amidino-2-fluorobenzyl, J is fluoro, and $R^1$ is chloro;

$R^2$ is 3-aminophenyl, B is isopropyl, A is a bond, $Y^0$ is 4-amidinobenzyl, J is fluoro, and $R^1$ is chloro;

$R^2$ is 3-aminophenyl, B is 2-butyl, A is a bond, $Y^0$ is 4-amidinobenzyl, J is fluoro, and $R^1$ is chloro;

$R^2$ is 3-aminophenyl, B is (R)-2-butyl, A is a bond, $Y^0$ is 4-amidinobenzyl, J is fluoro, and $R^1$ is chloro;

$R^2$ is 3-aminophenyl, B is 2-propynyl, A is a bond, $Y^0$ is 4-amidinobenzyl, J is fluoro, and $R^1$ is chloro;

$R^2$ is 3-aminophenyl, B is 3-pentyl, A is a bond, $Y^0$ is 4-amidinobenzyl, J is fluoro, and $R^1$ is hydrido;

$R^2$ is 3-aminophenyl, B is hydrido, A is $CH_2$, $Y^0$ is 4-amidinobenzyl, J is fluoro, and $R^1$ is chloro;

$R^2$ is 3-aminophenyl, B is ethyl, A is $CH_2$, $Y^0$ is 4-amidinobenzyl, J is fluoro, and $R^1$ is chloro;

$R^2$ is 3-aminophenyl, B is 2-methypropyl, A is a bond, $Y^0$ is 4-amidinobenzyl, J is fluoro, and $R^1$ is chloro;

$R^2$ is 3-aminophenyl, B is 2-propyl, A is $CH_3CH$, $Y^0$ is 4-amidinobenzyl, J is fluoro, and $R^1$ is chloro;

$R^2$ is 3-aminophenyl, B is propyl, A is a bond, $Y^0$ is 4-amidino-2-fluorobenzyl, J is fluoro, and $R^1$ is chloro;

$R^2$ is 3-aminophenyl, B is 6-amidocarbonylhexyl, A is a bond, $Y^0$ is 4-amidinobenzyl, J is fluoro, and $R^1$ is chloro;

$R^2$ is 3-aminophenyl, B is tert-butyl, A is a bond, $Y^0$ is 4-amidinobenzyl, J is fluoro, and $R^1$ is hydrido;

$R^2$ is 3-aminophenyl, B is tert-butyl, A is a bond, $Y^0$ is 4-amidinobenzyl, J is fluoro, and $R^1$ is chloro;

$R^2$ is 3-aminophenyl, B is 3-hydroxypropyl, A is a bond, $Y^0$ is 4-amidinobenzyl, J is fluoro, and $R^1$ is chloro;

$R^2$ is 3-aminophenyl, B is 2-methylpropyl, A is a bond, $Y^0$ is 4-amidino-2-fluorobenzyl, J is fluoro, and $R^1$ is chloro;

$R^2$ is 3-aminophenyl, B is butyl, A is a bond, $Y^0$ is 4-amidinobenzyl, J is fluoro, and $R^1$ is chloro;

$R^2$ is 3-aminophenyl, B is 1-methoxy-2-propyl, A is a bond, $Y^0$ is 4-amidinobenzyl, J is fluoro, and $R^1$ is chloro;

R² is 3-aminophenyl, B is 2-methoxyethyl, A is a bond, Y⁰ is 4-amidinobenzyl, J is fluoro, and R¹ is chloro;

R² is 3-aminophenyl, B is 2-propyl, A is a bond, Y⁰ is 5-amidino-2-thienylmethyl, J is fluoro, and R¹ is chloro;

R² is 5-amino-2-methylthiophenyl, B is 2-propyl, A is a bond, Y⁰ is 4-amidinobenzyl, J is fluoro, and R¹ is chloro;

R² is 3-amino-5-carboxyphenyl, B is isopropyl, A is a bond, Y⁰ is 4-amidinobenzyl, J is fluoro, and R¹ is chloro;

R² is 3-amino-5-carbomethoxyphenyl, B is isopropyl, A is a bond, Y⁰ is 4-amidinobenzyl, J is fluoro, and R¹ is chloro;

R² is 3-aminophenyl, B is isopropyl, A is a bond, Y⁰ is 4-amidinobenzyl, J is fluoro, and R¹ is bromo;

R² is 3-amino-5-carboxamidophenyl, B is isopropyl, A is a bond, Y⁰ is 4-amidinobenzyl, J is fluoro, and R¹ is chloro;

R² is 3-amino-5-(N-benzyl-N-methylamidocarbonyl)phenyl, B is isopropyl, A is a bond, Y⁰ is 4-amidinobenzyl, J is fluoro, and R¹ is chloro;

R² is 3-amino-5-(N-(1-phenylethyl)amidocarbonyl)phenyl, B is isopropyl, A is a bond, Y⁰ is 4-amidinobenzyl, J is fluoro, and R¹ is chloro;

R² is 3-amino-5-(N-(2-phenyl-2-propyl)amidocarbonyl)phenyl, B is isopropyl, A is a bond, Y⁰ is 4-amidinobenzyl, J is fluoro, and R¹ is chloro;

R² is 3-amino-5-(N-(2,4-dichlorobenzyl)amidocarbonyl)phenyl, B is isopropyl, A is a bond, Y⁰ is 4-amidinobenzyl, J is fluoro, and R¹ is chloro;

R² is 3-amino-5-(N-(4-bromobenzyl)amidocarbonyl)phenyl, B is isopropyl, A is a bond, Y⁰ is 4-amidinobenzyl, J is fluoro, and R¹ is chloro;

R² is 3-amino-5-(N-benzylamidocarbonyl)phenyl, B is isopropyl, A is a bond, Y⁰ is 4-amidinobenzyl, J is fluoro, and R¹ is chloro;

R² is 3-amino-5-(N-(2-chlorobenzyl)amidocarbonyl)phenyl, B is isopropyl, A is a bond, Y⁰ is 4-amidinobenzyl, J is fluoro, and R¹ is chloro;

R² is 3-amino-5-(N-(2-trifluoromethylbenzyl)amidocarbonyl)phenyl, B is isopropyl, A is a bond, Y⁰ is 4-amidinobenzyl, J is fluoro, and R¹ is chloro;

R² is 3-amino-5-(N-(3fluorobenzyl)amidocarbonyl)phenyl, B is isopropyl, A is a bond, Y⁰ is 4-amidinobenzyl, J is fluoro, and R¹ is chloro;

R² is 3-amino-5-(N-(3-trifluoromethylbenzyl)amidocarbonyl)phenyl, B is isopropyl, A is a bond, Y⁰ is 4-amidinobenzyl, J is fluoro, and R¹ is chloro;

R² is 3-amino-5-(N-isobutylamidocarbonyl)phenyl, B is isopropyl, A is a bond, Y⁰ is 4-amidinobenzyl, J is fluoro, and R¹ is chloro;

R² is 3-amino-5-(N-cyclobutylamidocarbonyl)phenyl, B is isopropyl, A is a bond, Y⁰ is 4-amidinobenzyl, J is fluoro, and R¹ is chloro;

R² is 3-amino-5-(N-cyclopentylamidocarbonyl)phenyl, B is isopropyl, A is a bond, Y⁰ is 4-amidinobenzyl, J is fluoro, and R¹ is chloro;

R² is 3-amino-5-(N-cycloheptylamidocarbonyl)phenyl, B is isopropyl, A is a bond, Y⁰ is 4-amidinobenzyl, J is fluoro, and R¹ is chloro;

R² is 3-amino-5-(N-(2-pyridylmethyl)amidocarbonyl)phenyl, B is isopropyl, A is a bond, Y⁰ is 4-amidinobenzyl, J is fluoro, and R¹ is chloro;

R² is 3-amino-5-(N-(3-pyridylmethyl)amidocarbonyl)phenyl, B is isopropyl, A is a bond, Y⁰ is 4-amidinobenzyl, J is fluoro, and R¹ is chloro;

R² is 3-amino-5-(N-(2-(4-methoxyphenyl)ethyl)amidocarbonylphenyl, B is isopropyl, A is a bond, Y⁰ is 4-amidinobenzyl, J is fluoro, and R¹ is chloro;

R² is 3-amino-5-(N-(3-phenylpropyl)amidocarbonyl)phenyl, B is isopropyl, A is a bond, Y⁰ is 4-amidinobenzyl, J is fluoro, and R¹ is chloro;

R² is 3-amino-5-(N-(2,2-diphenylethyl)amidocarbonyl)phenyl, B is isopropyl, A is a bond, Y⁰ is 4-amidinobenzyl, J is fluoro, and R¹ is chloro;

R² is 3-amino-5-(N-(2-naphthylmethyl)amidocarbonyl)phenyl, B is isopropyl, A is a bond, Y⁰ is 4-amidinobenzyl, J is fluoro, and R¹ is chloro;

R² is 3-amino-5-(N-1,2,3,4-tetrahydronaphth-2-ylmethyl)amidocarbonyl)phenyl, B is isopropyl, A is a bond, Y⁰ is 4-amidinobenzyl, J is fluoro, and R¹ is chloro;

R² is 3-aminophenyl, B is 2-propyl, A is a bond, Y⁰ is 4-amidino-3-fluorobenzyl, J is fluoro, and R¹ is hydrido;

R² is 3-carboxyphenyl, B is 2-propyl, A is a bond, Y⁰ is 4-amidinobenzyl, J is fluoro, and R¹ is hydrido;

R² is 3-aminophenyl, B is 2-propyl, A is a bond, Y⁰ is 4-amidino-3-fluorobenzyl, J is fluoro, and R¹ is chloro;

R² is 3,5-diaminophenyl, B is 2,2,2-trifluoroethyl, A is a bond, Y⁰ is 4-amidinobenzyl, J is fluoro, and R¹ is chloro;

R² is 3,5-diaminophenyl, B is (S)-2-butyl, A is a bond, Y⁰ is 4-amidinobenzyl, J is fluoro, and R¹ is chloro;

R² is 3,5-diaminophenyl, B is isopropyl, A is a bond, Y⁰ is 4-amidinobenzyl, J is fluoro, and R¹ is chloro;

R² is 3,5-diaminophenyl, B is isopropyl, A is a bond, Y⁰ is 4-amidino-2-fluorobenzylbenzyl, J is fluoro, and R¹ is chloro;

R² is 3,5-diaminophenyl, B is ethyl, A is a bond, Y⁰ is 4-amidinobenzyl, J is fluoro, and R¹ is chloro;

R² is 3,5-diaminophenyl, B is ethyl, A is a bond, Y⁰ is 4-amidino-2-fluorobenzyl, J is fluoro, and R¹ is chloro;

R² is 3-amino-5-carboxyphenyl, B is 2,2,2-trifluoroethyl, A is a bond, Y⁰ is 4-amidinobenzyl, J is fluoro, and R¹ is chloro;

R² is 3-amino-5-carboxyphenyl, B is (S)-2-butyl, A is a bond, Y⁰ is 4-amidinobenzyl, J is fluoro, and R¹ is chloro;

R² is 3-amino-5-carboxyphenyl, B is isopropyl, A is a bond, Y⁰ is 4-amidino-2-fluorobenzylbenzyl, J is fluoro, and R¹ is chloro;

R² is 3-amino-5-carboxyphenyl, B is ethyl, A is a bond, Y⁰ is 4-amidinobenzyl, J is fluoro, and R¹ is chloro;

R² is 3-amino-5-carboxyphenyl, B is ethyl, A is a bond, Y⁰ is 4-amidino-2-fluorobenzyl, J is fluoro, and R¹ is chloro;

R² is 3-amino-5-(N-benzylamidocarbonyl)phenyl, B is 2,2,2-trifluoroethyl, A is a bond, Y⁰ is 4-amidinobenzyl, J is fluoro, and R¹ is chloro;

R² is 3-amino-5-(N-benzylamidocarbonyl)phenyl, B is (S)-2-butyl, A is a bond, Y⁰ is 4-amidinobenzyl, J is fluoro, and R¹ is chloro;

R² is 3-amino-5-(N-benzylamidocarbonyl)phenyl, B is isopropyl, A is a bond, Y⁰ is 4-amidino-2-fluorobenzylbenzyl, J is fluoro, and R¹ is chloro;

R² is 3-amino-5-(N-benzylamidocarbonyl)phenyl, B is ethyl, A is a bond, Y⁰ is 4-amidinobenzyl, J is fluoro, and R¹ is chloro;

$R^2$ is 3-amino-5-(N-benzylamidocarbonyl)phenyl, B is ethyl, A is a bond, $Y^0$ is 4-amidino-2-fluorobenzyl, J is fluoro, and $R^1$ is chloro;

$R^2$ is 3,5-diaminophenyl, B is isopropyl, A is a bond, $Y^0$ is 4-amidinobenzylbenzyl, J is fluoro, and $R^1$ is hydrido;

$R^2$ is 3-aminophenyl, B is cyclopropyl, A is a bond, $Y^0$ is 4-amidinobenzyl, J is hydroxy, and $R^1$ is chloro;

$R^2$ is 3-aminophenyl, B is cyclobutyl, A is a bond, $Y^0$ is 4-amidino-2-fluorobenzyl, J is hydroxy, and $R^1$ is chloro;

$R^2$ is 3-aminophenyl, B is cyclobutyl, A is a bond, $Y^0$ is 4-amidinobenzyl, J is hydroxy, and $R^1$ is chloro;

$R^2$ is 3-aminophenyl, B is cyclopropyl, A is a bond, $Y^0$ is 4-amidino-2-fluorobenzyl, J is hydroxy, and $R^1$ is chloro;

$R^2$ is 3-aminophenyl, B is cyclobutyl, A is a bond, $Y^0$ is 4-amidinobenzyl, J is hydroxy, and $R^1$ is hydrido;

$R^2$ is 3-aminophenyl, B is cyclobutyl, A is a bond, $Y^0$ is 4-amidino-3-fluorobenzyl, J is hydroxy, and $R^1$ is chloro;

$R^2$ is 3-aminophenyl, B is cyclopentyl, A is a bond, $Y^0$ is 4-amidinobenzyl, J is hydroxy, and $R^1$ is chloro;

$R^2$ is 5-amino-2-thienyl, B is cyclobutyl, A is a bond, $Y^0$ is 4-amidinobenzyl, J is hydroxy, and $R^1$ is chloro;

$R^2$ is 3-aminophenyl, B is cyclopropyl, A is $CH_2$, $Y^0$ is 4-amidinobenzyl, J is hydroxy, and $R^1$ is chloro;

$R^2$ is 3-aminophenyl, B is 2-(2R)-bicyclo[2.2.1]-heptyl, A is a bond, $Y^0$ is 4-amidinobenzyl, J is hydroxy, and $R^1$ is chloro;

$R^2$ is 3-aminophenyl, B is cyclopentyl, A is a bond, $Y^0$ is 4-amidino-2-fluorobenzyl, J is hydroxy, and $R^1$ is chloro;

$R^2$ is 3-aminophenyl, B is cyclohexyl, A is $CH_2CH_2$, $Y^0$ is 4-amidinobenzyl, J is hydroxy, and $R^1$ is hydrido;

$R^2$ is 3-aminophenyl, B is oxalan-2-yl, A is $CH_2$, $Y^0$ is 4-amidinobenzyl, J is hydroxy, and $R^1$ is chloro;

$R^2$ is 3-aminophenyl, B is 1-piperidinyl, A is $CH_2CH_2$, $Y^0$ is 4-amidinobenzyl, J is hydroxy, and $R^1$ is chloro;

$R^2$ is 3-aminophenyl, B is 1-pyrrolidinyl, A is $CH_2CH_2CH_2$, $Y^0$ is 4-amidinobenzyl, J is hydroxy, and $R^1$ is chloro;

$R^2$ is 3-amino-5-carbomethoxyphenyl, B is cyclobutyl, A is a bond, $Y^0$ is 4-amidinobenzyl, J is hydroxy, and $R^1$ is hydrido;

$R^2$ is 3-amino-5-carboxyphenyl, B is cyclobutyl, A is a bond, $Y^0$ is 4-amidinobenzyl, J is hydroxy, and $R^1$ is hydrido;

$R^2$ is 3,5-diaminophenyl, B is cyclobutyl, A is a bond, $Y^0$ is 4-amidinobenzyl, J is hydroxy, and $R^1$ is hydrido;

$R^2$ is 2-amino-6-carboxy-4-pyridyl, B is cyclobutyl, A is a bond, $Y^0$ is 4-amidinobenzyl, J is hydroxy, and $R^1$ is hydrido;

$R^2$ is 3-amino-5-carbomethoxyphenyl, B is cyclobutyl, A is a bond, $Y^0$ is 4-amidinobenzyl, J is hydroxy, and $R^1$ is chloro;

$R^2$ is 3-amino-5-carboxyphenyl, B is cyclobutyl, A is a bond, $Y^0$ is 4-amidinobenzyl, J is hydroxy, and $R^1$ is chloro;

$R^2$ is 3,5-diaminophenyl, B is cyclopropyl, A is a bond, $Y^0$ is 4-amidinobenzyl, J is hydroxy, and $R^1$ is chloro;

$R^2$ is 3,5-diaminophenyl, B is cyclobutyl, A is a bond, $Y^0$ is 4-amidino-2-fluorobenzyl, J is hydroxy, and $R^1$ is chloro;

$R^2$ is 3,5-diaminophenyl, B is cyclopropyl, A is a bond, $Y^0$ is 4-amidino-2-fluorobenzyl, J is hydroxy, and $R^1$ is chloro;

$R^2$ is 3,5-diaminophenyl, B is cyclobutyl, A is a bond, $Y^0$ is 4-amidinobenzyl, J is hydroxy, and $R^1$ is hydrido;

$R^2$ is 3,5-diaminophenyl, B is cyclobutyl, A is a bond, $Y^0$ is 4-amidino-3-fluorobenzyl, J is hydroxy, and $R^1$ is chloro;

$R^2$ is 3,5-diaminophenyl, B is cyclopentyl, A is a bond, $Y^0$ is 4-amidinobenzyl, J is hydroxy, and $R^1$ is chloro;

$R^2$ is 3-carboxy-5-aminophenyl, B is cyclopropyl, A is a bond, $Y^0$ is 4-amidinobenzyl, J is hydroxy, and $R^1$ is chloro;

$R^2$ is 3-carboxy-5-aminophenyl, B is cyclobutyl, A is a bond, $Y^0$ is 4-amidino-2-fluorobenzyl, J is hydroxy, and $R^1$ is chloro;

$R^2$ is 3-carboxy-5-aminophenyl, B is cyclopropyl, A is a bond, $Y^0$ is 4-amidino-2-fluorobenzyl, J is hydroxy, and $R^1$ is chloro;

$R^2$ is 3-carboxy-5-aminophenyl, B is cyclobutyl, A is a bond, $Y^0$ is 4-amidinobenzyl, J is hydroxy, and $R^1$ is hydrido;

$R^2$ is 3-carboxy-5-aminophenyl, B is cyclobutyl, A is a bond, $Y^0$ is 4-amidino-3-fluorobenzyl, J is hydroxy, and $R^1$ is chloro;

$R^2$ is 3-carboxy-5-aminophenyl, B is cyclopentyl, A is a bond, $Y^0$ is 4-amidinobenzyl, J is hydroxy, and $R^1$ is chloro;

$R^2$ is 3-amino-5-(N-benzylamidocarbonyl)phenyl, B is cyclopropyl, A is a bond, $Y^0$ is 4-amidinobenzyl, J is hydroxy, and $R^1$ is chloro;

$R^2$ is 3-amino-5-(N-benzylamidocarbonyl)phenyl, B is cyclobutyl, A is a bond, $Y^0$ is 4-amidino-2-fluorobenzyl, J is hydroxy, and $R^1$ is chloro;

$R^2$ is 3-amino-5-(N-benzylamidocarbonyl)phenyl, B is cyclobutyl, A is a bond, $Y^0$ is 4-amidinobenzyl, J is hydroxy, and $R^1$ is chloro;

$R^2$ is 3-amino-5-(N-benzylamidocarbonyl)phenyl, B is cyclopropyl, A is a bond, $Y^0$ is 4-amidino-2-fluorobenzyl, J is hydroxy, and $R^1$ is chloro;

$R^2$ is 3-amino-5-(N-benzylamidocarbonyl)phenyl, B is cyclobutyl, A is a bond, $Y^0$ is 4-amidinobenzyl, J is hydroxy, and $R^1$ is hydrido;

$R^2$ is 3-amino-5-(N-benzylamidocarbonyl)phenyl, B is cyclobutyl, A is a bond, $Y^0$ is 4-amidino-3-fluorobenzyl, J is hydroxy, and $R^1$ is chloro;

$R^2$ is 3-amino-5-(N-benzylamidocarbonyl)phenyl, B is cyclopentyl, A is a bond, $Y^0$ is 4-amidinobenzyl, J is hydroxy, and $R^1$ is chloro;

$R^2$ is 3-amino-5-(N-(2-chlorobenzyl)amidosulfonyl)phenyl, B is cyclopropyl, A is a bond, $Y^0$ is 4-amidinobenzyl, J is hydroxy, and $R^1$ is chloro;

$R^2$ is 3-amino-5-(N-(2-chlorobenzyl)amidosulfonyl)phenyl, B is cyclobutyl, A is a bond, $Y^0$ is 4-amidino-2-fluorobenzyl, J is hydroxy, and $R^1$ is chloro;

$R^2$ is 3-amino-5-(N-(2-chlorobenzyl)amidosulfonyl)phenyl, B is cyclobutyl, A is a bond, $Y^0$ is 4-amidinobenzyl, J is hydroxy, and $R^1$ is chloro;

$R^2$ is 3-amino-5-(N-(2-chlorobenzyl)amidosulfonyl)phenyl, B is cyclopropyl, A is a bond, $Y^0$ is 4-amidino-2-fluorobenzyl, J is hydroxy, and $R^1$ is chloro;

$R^2$ is 3-amino-5-(N-(2-chlorobenzyl)amidosulfonyl)phenyl, B is cyclobutyl, A is a bond, $Y^0$ is 4-amidinobenzyl, J is hydroxy, and $R^1$ is hydrido;

R² is 3-amino-5-(N-(2chlorobenzyl)amidosulfonyl) phenyl, B is cyclobutyl, A is a bond, Y⁰ is 4-amidino-3-fluorobenzyl, J is hydroxy, and R¹ is chloro;

R² is 3-amino-5-(N-(2-chlorobenzyl)amidosulfonyl) phenyl, B is cyclopentyl, A is a bond, Y⁰ is 4-amidinobenzyl, J is hydroxy, and R¹ is chloro;

R² is 3-amino-5-(N-(2-trifluoromethylbenzyl) amidocarbonyl)-phenyl, B is cyclopropyl, A is a bond, Y⁰ is 4-amidinobenzyl, J is hydroxy, and R¹ is chloro;

R² is 3-amino-5-(N-(2-trifluoromethylbenzyl) amidocarbonyl)-phenyl, B is cyclobutyl, A is a bond, Y⁰ is 4-amidino-2-fluorobenzyl, J is hydroxy, and R¹ is chloro;

R² is 3-amino-5-(N-(2-trifluoromethylbenzyl) amidocarbonyl)-phenyl, B is cyclobutyl, A is a bond, Y⁰ is 4-amidinobenzyl, J is hydroxy, and R¹ is chloro;

R² is 3-amino-5-(N-(2-trifluoromethylbenzyl) amidocarbonyl)-phenyl, B is cyclopropyl, A is a bond, Y⁰ is 4-amidino-2-fluorobenzyl, J is hydroxy, and R¹ is chloro;

R² is 3-amino-5-(N-(2-trifluoromethylbenzyl) amidocarbonyl)-phenyl, B is cyclobutyl, A is a bond, Y⁰ is 4-amidinobenzyl, J is hydroxy, and R¹ is hydrido;

R² is 3-amino-5-(N-(2-trifluoromethylbenzyl) amidocarbonyl)-phenyl, B is cyclobutyl, A is a bond, Y⁰ is 4-amidino-3-fluorobenzyl, J is hydroxy, and R¹ is chloro;

R² is 3-amino-5-N-(2-trifluoromethylbenzyl) amidocarbonyl)-phenyl, B is cyclopentyl, A is a bond, Y⁰ is 4-amidinobenzyl, J is hydroxy, and R¹ is chloro;

R² is 3-aminophenyl, B is cyclopropyl, A is a bond, Y⁰ is 4-amidinobenzyl, J is fluoro, and R¹ is chloro;

R² is 3-aminophenyl, B is cyclobutyl, A is a bond, Y⁰ is 4-amidino-2-fluorobenzyl, J is fluoro, and R¹ is chloro;

R² is 3-aminophenyl, B is cyclobutyl, A is a bond, Y⁰ is 4-amidinobenzyl, J is fluoro, and R¹ is chloro;

R² is 3-aminophenyl, B is cyclopropyl, A is a bond, Y⁰ is 4-amidino-2-fluorobenzyl, J is fluoro, and R¹ is chloro;

R² is 3-aminophenyl, B is cyclobutyl, A is a bond, Y⁰ is 4-amidinobenzyl, J is fluoro, and R¹ is hydrido;

R² is 3-aminophenyl, B is cyclobutyl, A is a bond, Y⁰ is 4-amidino-3-fluorobenzyl, J is fluoro, and R¹ is chloro;

R² is 3-aminophenyl, B is cyclopentyl, A is a bond, Y⁰ is 4-amidinobenzyl, J is fluoro, and R¹ is chloro;

R² is 5-amino-2-thienyl, B is cyclobutyl, A is a bond, Y⁰ is 4-amidinobenzyl, J is fluoro, and R¹ is chloro;

R² is 3-aminophenyl, B is cyclopropyl, A is CH₂, Y⁰ is 4-amidinobenzyl, J is fluoro, and R¹ is chloro;

R² is 3-aminophenyl, B is 2-(2R)bicyclo[2.2.1]-heptyl, A is a bond, Y⁰ is 4-amidinobenzyl, J is fluoro, and R¹ is chloro;

R² is 3-aminophenyl, B is cyclopentyl, A is a bond, Y⁰ is 4-amidino-2-fluorobenzyl, J is fluoro, and R¹ is chloro;

R² is 3-aminophenyl, B is cyclohexyl, A is CH₂CH₂, Y⁰ is 4-amidinobenzyl, J is fluoro, and R¹ is hydrido;

R² is 3-aminophenyl, B is oxalan-2-yl, A is CH₂, Y⁰ is 4-amidinobenzyl, J is fluoro, and R¹ is chloro;

R² is 3-aminophenyl, B is 1-piperidinyl, A is CH₂CH₂, Y⁰ is 4-amidinobenzyl, J is fluoro, and R¹ is chloro;

R² is 3-aminophenyl, B is 1-pyrrolidinyl, A is CH₂CH₂CH₂, Y⁰ is 4-amidinobenzyl, J is fluoro, and R¹ is chloro;

R² is 3-amino-5-carbomethoxyphenyl, B is cyclobutyl, A is a bond, Y⁰ is 4-amidinobenzyl, J is fluoro, and R¹ is hydrido;

R² is 3-amino-5-carboxyphenyl, B is cyclobutyl, A is a bond, Y⁰ is 4-amidinobenzyl, J is fluoro, and R¹ is hydrido;

R² is 3,5-diaminophenyl, B is cyclobutyl, A is a bond, Y⁰ is 4-amidinobenzyl, J is fluoro, and R¹ is hydrido;

R² is 2-amino-6-carboxypyridyl, B is cyclobutyl, A is a bond, Y⁰ is 4-amidinobenzyl, J is fluoro, and R¹ is hydrido;

R² is 3-amino-5-cabomethoxyphenyl, B is cyclobutyl, A is a bond, Y⁰ is 4-amidinobenzyl, J is fluoro, and R¹ is chloro;

R² is 3-amino-5-carboxyphenyl, B is cyclobutyl, A is a bond, Y⁰ is 4-amidinobenzyl, J is fluoro, and R¹ is chloro;

R² is 3,5-diaminophenyl, B is cyclopropyl, A is a bond, Y⁰ is 4-amidinobenzyl, J is fluoro, and R¹ is chloro;

R² is 3,5-diaminophenyl, B is cyclobutyl, A is a bond, Y⁰ is 4-amidino-2-fluorobenzyl, J is fluoro, and R¹ is chloro;

R² is 3,5-diaminophenyl, B is cyclopropyl, A is a bond, Y⁰ is 4-amidino-2-fluorobenzyl, J is fluoro, and R¹ is chloro;

R² is 3,5-diaminophenyl, B is cyclobutyl, A is a bond, Y⁰ is 4-amidinobenzyl, J is fluoro, and R¹ is hydrido;

R² is 3,5-diaminophenyl, B is cyclobutyl, A is a bond, Y⁰ is 4-amidino-3-fluorobenzyl, J is fluoro, and R¹ is chloro;

R² is 3,5-diaminophenyl, B is cyclopentyl, A is a bond, Y⁰ is 4-amidinobenzyl, J is fluoro, and R¹ is chloro;

R² is 3-carboxy-5-aminophenyl, B is cyclopropyl, A is a bond, Y⁰ is 4-amidinobenzyl, J is fluoro, and R¹ is chloro;

R² is 3-carboxy-5-aminophenyl, B is cyclobutyl, A is a bond, Y⁰ is 4-amidino-2-fluorobenzyl, J is fluoro, and R¹ is chloro;

R² is 3-carboxy-5-aminophenyl, B is cyclopropyl, A is a bond, Y⁰ is 4-amidino-2-fluorobenzyl, J is fluoro, and R¹ is chloro;

R² is 3-carboxy-5-aminophenyl, B is cyclobutyl, A is a bond, Y⁰ is 4-amidinobenzyl, J is fluoro, and R¹ is hydrido;

R² is 3-carboxy-5-aminophenyl, B is cyclobutyl, A is a bond, Y⁰ is 4-amidino-3-fluorobenzyl, J is fluoro, and R¹ is chloro;

R² is 3-carboxy-5-aminophenyl, B is cyclopentyl, A is a bond, Y⁰ is 4-amidinobenzyl, J is fluoro, and R¹ is chloro;

R² is 3-amino-5-(N-benzylamidocarbonyl)phenyl, B is cyclopropyl, A is a bond, Y⁰ is 4-amidinobenzyl, J is fluoro, and R¹ is chloro;

R² is 3-amino-5-(N-benzylamidocarbonyl)phenyl, B is cyclobutyl, A is a bond, Y⁰ is 4-amidino-2-fluorobenzyl, J is fluoro, and R¹ is chloro;

R² is 3-amino-5-(N-benzylamidocarbonyl)phenyl, B is cyclobutyl, A is a bond, Y⁰ is 4-amidinobenzyl, J is fluoro, and R¹ is chloro;

R² is 3-amino-5-(N-benzylamidocarbonyl)phenyl, B is cyclopropyl, A is a bond, Y⁰ is 4-amidino-2-fluorobenzyl, J is fluoro, and R¹ is chloro;

R² is 3-amino-5-(N-benzylamidocarbonyl)phenyl, B is cyclobutyl, A is a bond, Y⁰ is 4-amidinobenzyl, J is fluoro, and R¹ is hydrido;

R² is 3-amino-5-(N-benzylamidocarbonyl)phenyl, B is cyclobutyl, A is a bond, Y⁰ is 4-amidino-3-fluorobenzyl, J is fluoro, and R¹ is chloro;

$R^2$ is 3-amino-5-(N-benzylamidocarbonyl)phenyl, B is cyclopentyl, A is a bond, $Y^o$ is 4-amidinobenzyl, J is fluoro, and $R^1$ is chloro;

$R^2$ is 3-amino-5-(N-2-chlorobenzyl)amidosulfonyl) phenyl, B is cyclopropyl, A is a bond, $Y^o$ is 4-amidinobenzyl, J is fluoro, and $R^1$ is chloro;

$R^2$ is 3-amino-5-(N-(2-chlorobenzyl)amidosulfonyl) phenyl, B is cyclobutyl, A is a bond, $Y^o$ is 4-amidino-2-fluorobenzyl, J is fluoro, and $R^1$ is chloro;

$R^2$ is 3-amino-5-(N-(2-chlorobenzyl)amidosulfonyl) phenyl, B is cyclobutyl, A is a bond, $Y^o$ is 4-amidinobenzyl, J is fluoro, and $R^1$ is chloro;

$R^2$ is 3-amino-5-(N-(2-chlorobenzyl)amidosulfonyl) phenyl, B is cyclopropyl, A is a bond, $Y^o$ is 4-amidino-2-fluorobenzyl, J is fluoro, and $R^1$ is chloro;

$R^2$ is 3-amino-5-N-(2-chlorobenzyl)amidosulfonyl) phenyl, B is cyclobutyl, A is a bond, $Y^o$ is 4-amidinobenzyl, J is fluoro, and $R^1$ is hydrido;

$R^2$ is 3-amino-5-(N-(2-chlorobenzyl)amidosulfonyl) phenyl, B is cyclobutyl, A is a bond, $Y^o$ is 4-amidino-3-fluorobenzyl, J is fluoro, and $R^1$ is chloro;

$R^2$ is 3-amino-5-(N-(2-chlorobenzyl)amidosulfonyl) phenyl, B is cyclopentyl, A is a bond, $Y^o$ is 4-amidinobenzyl, J is fluoro, and $R^1$ is chloro;

$R^2$ is 3-amino-5-(N-(2-trifluoromethylbenzyl)amidocarbonyl)-phenyl, B is cyclopropyl, A is a bond, $Y^o$ is 4-amidinobenzyl, J is fluoro, and $R^1$ is chloro;

$R^2$ is 3-amino-5-(N-(2-trifluoromethylbenzyl)amidocarbonyl)phenyl, B is cyclobutyl, A is a bond, $Y^o$ is 4-amidino-2-fluorobenzyl, J is fluoro, and $R^1$ is chloro;

$R^2$ is 3-amino-5-(N-(2-trifluoromethylbenzyl)amidocarbonyl)-phenyl, B is cyclobutyl, A is a bond, $Y^o$ is 4-amidinobenzyl, J is fluoro, and $R^1$ is chloro;

$R^2$ is 3-amino-5-(N-(2-trifluoromethylbenzyl)amidocarbonyl)-phenyl, B is cyclopropyl, A is a bond, $Y^o$ is 4-amidino-2-fluorobenzyl, J is fluoro, and $R^1$ is chloro;

$R^2$ is 3-amino-5-(N-(2-trifluoromethylbenzyl)amidocarbonyl)-phenyl, B is cyclobutyl, A is a bond, $Y^o$ is 4-amidinobenzyl, J is fluoro, and $R^1$ is hydrido;

$R^2$ is 3-amino-5-(N-(2-trifluoromethylbenzyl)amidocarbonyl)phenyl, B is cyclobutyl, A is a bond, $Y^o$ is 4-amidino-3-fluorobenzyl, J is fluoro, and $R^1$ is chloro;

$R^2$ is 3-amino-5-N-(2-trifluoromethylbenzyl)amidocarbonyl)-phenyl, B is cyclopentyl, A is a bond, $Y^o$ is 4-amidinobenzyl, J is fluoro, and $R^1$ is chloro.

Formula (I) compounds of this invention possessing hydroxyl, thiol, and amine functional groups can be converted to a wide variety derivatives. A hydroxyl group in the form of an alcohol or phenol can be readily converted to esters of carboxylic, sulfonic, carbamic, phosphonic, and phosphoric acids. Acylation to form a carboxylic acid ester is readily effected using a suitable acylating reagent such as an aliphatic acid anhydride or acid chloride. The corresponding aryl and heteroaryl acid anhydrides and acid chlorides can also be used. Such reactions are generally carried out using an amine catalyst such as pyridine in an inert solvent Similarly, carbamic acid esters (urethanes) can be obtained by reacting a hydroxyl group with isocyanates and carbamoyl chlorides. Sulfonate, phosphonate, and phosphate esters can be prepared using the corresponding acid chloride and similar reagents. Compounds of Formula (I) that have at least one thiol group present can be converted to the corresponding thioesters derivatives analogous to those of alcohols and phenols using the same reagents and comparable reaction conditions. Compounds of Formula (I) that have at least one primary or secondary amine group present can be converted to the corresponding amide derivatives. Amides of carboxylic acids can be prepared using the appropriate acid chloride or anhydrides with reaction conditions analogous to those used with alcohols and phenols. Ureas of the corresponding primary or secondary amine can be prepared using isocyanates directly and carbamoyl chlorides in the presence of an acid scavenger such as triethylamine or pyridine. Sulfonamides can be prepared from the corresponding sulfonyl chloride in the presence of aqueous sodium hydroxide. Suitable procedures and methods for preparing these derivatives can be found in House's Modern Synthetic Reactions, W. A. Benjamin, Inc., Shriner, Fuson, and Curtin in The Systematic Identification of Organic Compounds, 5th Edition, John Wiley & Sons, and Fieser and Fieser in Reagents for Organic Synthesis, Volume 1, John Wiley & Sons. Reagents of a wide variety that can be used to derivatize hydroxyl, thiol, and amines of compounds of Formula (I) are available from commercial sources or the references cited above, which are incorporated herein by reference.

Formula (I) compounds of this invention possessing hydroxyl, thiol, and amine functional groups can be alkylated to a wide variety derivatives. A hydroxyl group of compounds of Formula (I) can be readily converted to ethers. Alkylation to form an ether is readily effected using a suitable alkylating reagent such as an alkyl bromide, alkyl iodide or alkyl sulfonate. The corresponding aralkyl, heteroaralkyl, alkoxyalkyl, aralkyloxyalkyl, and heteroaralkyloxyalkyl bromides, iodides, and sulfonates can also be used. Such reactions are generally carried out using an alkoxide forming reagent such as sodium hydride, potassium t-butoxide, sodium amide, lithium amide, and n-butyl lithium using an inert polar solvent such as DMF, DMSO, THF, and similar, comparable solvents. amine catalyst such as pyridine in an inert solvent. Compounds of Formula (I) that have at least one thiol group present can be converted to the corresponding thioether derivatives analogous to those of alcohols and phenols using the same reagents and comparable reaction conditions. Compounds of Formula (I) that have at least one primary, secondary or tertiary amine group present can be converted to the corresponding quaternary ammonium derivatives. Quaternary ammonium derivatives can be prepared using the appropriate bromides, iodides, and sulfonates analogous to those used with alcohols and phenols. Conditions involve reaction of the amine by warming it with the alkylating reagent with a stoichiometric amount of the amine (i.e., one equivalent with a tertiary amine, two with a secondary, and three with a primary). With primary and secondary amines, two and one equivalents, respectively, of an acid scavenger are used concurrently. Tertiary amines can be prepared from the corresponding primary or secondary amine by reductive alkylation with aldehydes and ketones using reduction methods. Suitable procedures and methods for preparing these derivatives can be found in House's Modern Synthetic Reactions, W. A. Benjamin, Inc., Shriner, Fuson, and Curtin in The Systematic Identification of Organic Compounds, 5th Edition, John Wiley & Sons, and Fieser and Fieser in Reagents for Organic Synthesis, Volume 1, John Wiley & Sons. Perfluoroalkyl derivatives can be prepared as described by DesMarteau in J. Chem. Soc. Chem. Commun. 2241 (1998). Reagents of a wide variety that can be used to derivatize hydroxyl, thiol, and amines of compounds of Formula (I) are available from commercial sources or the references cited above, which are incorporated herein by reference.

The biological activity of the compounds of Examples 1 through 22 are summarized in the Table 2.

Assays for Biological Activity

TF-VIIa Assay

In this assay 100 nM recombinant soluble tissue factor and 2 nM recombinant human factor VIIa are added to a 96-well assay plate containing 0.4 mM of the substrate, N-Methylsulfonyl-D-phe-gly-arg-p-nitroaniline and either inhibitor or buffer (5 mM CaCl$_2$,50 mM Tris-HCl, pH 8.0, 100 mM NaCl, 0.1% BSA). The reaction, in a final volume of 100 ul is measured immediately at 405 nm to determine background absorbance. The plate is incubated at room temperature for 60 min, at which time the rate of hydrolysis of the substrate is measured by monitoring the reaction at 405 nm for the release of p-nitroaniline. Percent inhibition of TF-VIIa activity is calculated from OD$_{405nm}$ value from the experimental and control sample.

Xa Assay 0.3 nM human factor Xa and 0.15 mM N-α-Benzyloxycarbonyl-D-arginyl-L-glycyl-L-arginine-p-nitroaniline-dihydrochloride (S-2765) are added to a 96-well assay plate containing either inhibitor or buffer (50 mM Tris-HCl, pH 8.0, 100 mM NaCl, 0.1% BSA). The reaction, in a final volume of 100 ul is measured immediately at 405 nm to determine background absorbance. The plate is incubated at room temperature for 60 min, at which time the rate of hydrolysis of the substrate is measured by monitoring the reaction at 405 nm for the release of p-nitroaniline. Percent inhibition of Xa activity is calculated from OD$_{405\,nm}$ value from the experimental and control sample.

Thrombin Assay 0.28 nM human thrombin and 0.06 mM H-D-Phenylalanyl-L-pipecolyl-L-arginine-p-nitroaniline dihydrochloride are added to a 96-well assay plate containing either inhibitor or buffer (50 mM Tris-HCl, pH 8.0, 100 mM NaCl, 0.1% BSA). The reaction, in a final volume of 100 ul is measured immediately at 405 nm to determine background absorbance. The plate is incubated at room temperature for 60 min, at which time the rate of hydrolysis of the substrate is measured by monitoring the reaction at 405 nm for the release of p-nitroaniline. Percent inhibition of thrombin activity is calculated from OD$_{450\,nm}$ value from the experimental and control sample.

Trypsin Assay 5 ug/ml trypsin, type IX from porcine pancreas and 0.375 mM N-α-Benzoyl-L-arginine-p-nitroanilide (LBAPNA) are added to a 96-well assay plate containing either inhibitor or buffer (50 mM Tris-HCl, pH 8.0, 100 mM NaCl, 0.1% BSA). The reactions, in a final volume of 100 ul are measured immediately at 405 nm to determine background absorbance. The plate is incubated at room temperature for 60 min, at which time the rate of hydrolysis of the substrate is measured by monitoring the reaction at 405 nm for the release of p-nitroaniline. Percent inhibition of trypsin activity is calculated from OD$_{405\,nm}$ value from the experimental and control sample.

Recombinant soluble TF, consisting of amino acids 1–219 of the mature protein sequence was expressed in *E. coli* and purified using a Mono Q Sepharose FPLC. Recombinant human VIIa was purchased from American Diagnostica, Greenwich Conn. and chromogenic substrate N-Methylsulfonyl-D-phe-gly-arg-p-nitroaniline was prepared by American Peptide Company, Inc., Sunnyvale, Calif. Factor Xa was obtained from Enzyme Research Laboratories, South Bend Ind., thrombin from Calbiochem, La Jolla, Calif., and trypsin and L-BAPNA from Sigma, St. Louis Mo. The chromogenic substrates S-2765 and S-2238 were purchased from Chromogenix, Sweden.

TABLE 2

Inhibitory Activity of Substituted Benzenes toward Factor Xa, TF-VIIA, Thrombin II, and Trypsin II.

| Example Number | TF-VIIA IC50 (uM) | Factor Xa IC50 (uM) | Thrombin II IC50 (uM) | Trpysin II IC50 (uM) |
| --- | --- | --- | --- | --- |
| 1 | >30 | >30 | >30 | 0.3 |
| 2 | >30 | >30 | >30 | >30 |
| 3 | >30 | >30 | >30 | >30 |
| 4 | >30 | >30 | 22% at 30 | 0.3 |
| 5 | >30 | 7% at 30 | 43% at 30 | 23 |
| 6 | >100 | >100 | >100 | >100 |
| 7 | >100 | >100 | >100 | >100 |
| 8 | >100 | >100 | >100 | >100 |
| 9 | >30 | >30 | >30 | 0.3 |
| 10 | >30 | >30 | >30 | >30 |
| 11 | >30 | >30 | >30 | >30 |
| 12 | >30 | >30 | >30 | >30 |
| 13 | >30 | >30 | >30 | >30 |
| 14 | >30 | >30 | ~30 | 7.3 |
| 15 | >30 | >30 | >30 | >30 |
| 16 | 16.4 | 1% at 30 | 1.6 | 0.8 |
| 17 | 4.0 | >30 | 7.0 | 0.2 |
| 18 | 25 | >30 | 9.5 | 0.5 |
| 19 | 2.7 | >30 | 7.0 | 0.2 |
| 20 | 0.67 | >30 | 9.0 | 0.2 |
| 21 | 0.34 | 18% | 0.95 | <0.04 |
| 22 | 14.7 | >30 | 7.9 | 0.10 |

What we claim is:
1. A compound of the Formula:

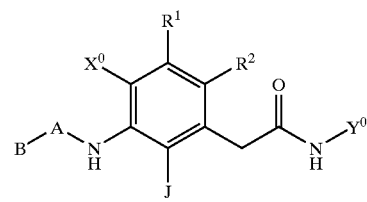

or a pharmaceutically acceptable salt thereof, wherein

J is hydroxy or fluoro;

B is a C3–C7 cycloalkyl, pyrrolidinyl, or piperidinyl wherein each ring carbon is optionally substituted with $R^{33}$, $R^{33}$ is selected from the group consisting of hydrido, acetamido, haloacetamido, amidino, guanidino, alkoxy, hydroxy, amine, alkexyamino, alkylamino, alkyithie, amidesulfenyl, alkyl, halo, haloalkyl, haloalkoxy, hydroxyalkyl, carboalkoxy, carboxy, carboxamido, and cyano;

A is a bond or $(CH_2)_{pa}$ where pa is 1–3;

$R^1$ and $X^0$ are independently hydrido, or halo;

$R^2$ is $Z^0$—Q;

$Z^0$ is a bond;

Q is phenyl, thinyl, or pyridyl, wherein (a) a ring carbon in a first alpha position relative to the ring carbon at the point of attachment is optionally substituted by $R^9$, (b) a ring carbon in a second alpha position relative to the ring carbon at the point of attachment is optionally substituted by $R^{13}$, (c) a ring carbon, in a first beta position relative to the ring carbon at the point of attachment and in an alpha position relative to the ring atom optionally substituted by $R^9$, is optionally substituted by $R^{10}$, (d) a ring carbon, in a second beta position relative to the ring carbon at the point of attachment and in an alpha position relative to the ring atom optionally substituted by $R^{13}$, is optionally substituted by $R^{12}$, and (e) a ring carbon, if present, in the gamma position relative to the ring carbon at the point of attachment and in an alpha position relative to each of the ring atoms optionally substituted by $R^{10}$ and $R^{12}$, respectively, is optionally substituted by $R^{11}$;

$R^9$, $R^{11}$, and $R^{13}$ are independently selected from the group consisting of hydrido, hydroxy, amino, amidino, guanidino, alkylamino, alkylthio, alkoxy, alkylsulfinyl, alkylsulfonyl, amidosulfonyl, alkyl, halo, haloalkyl, haloalkoxy, hydroxyalkyl, carboxy, carboxamido, and cyano;

$R^{10}$ and $R^{12}$ are independently selected from the group consisting of hydrido, acetamido, haloacetamido, amidino, guanidino, alkyl, alkoxy, alkoxyamino, hydroxy, amino, alkylamino, alkylsulfonamido, amidosulfonyl, hydroxyalkyl, aminoalkyl, halo, haloalkyl, carboalkoxy, carboxy, carboxamido, carboxyalkyl, and cyano; and $Y^0$ is 4-amidinobenzyl, 2-fluoro-4-amidinobenzyl, or 3-fluoro-4-amidinobenzyl.

2. Compound of claim 1 or a pharmaceutically acceptable salt thereof, wherein

B is selected from the group consisting of cyclopropyl, cyclobutyl, cyclopentyl, cyclohexyl, cycloheptyl, 1-piperidinyl, 2-piperidinyl, 3-piperidinyl, 4-piperidinyl, 1-pyrrolidinyl, 2-pyrrolidinyl, and 3-pyrrolidinyl, wherein each ring carbon is optionally substituted with $R^{33}$;

$R^{33}$ is selected from the group consisting of hydrido, amidino, guanidino, methyl, ethyl, methoxy, ethoxy, hydroxy, carboxy, amino, N-methylamino, dimethylamino, methoxyamino, methylthio, ethylthio, trifluoromethyl, pentafluoroethyl, 2,2,2-trifluoroethyl, fluoro, chloro, bromo, amidosulfonyl, N-methylamidosulfonyl, hydroxymethyl, amidocarbonyl, and cyano;

A is selected from the group consisting of a bond, $CH_2$, $CH_3CH$, $CH_2CH_2$, and $CH_2CH_2CH_2$;

$R^1$ and $X^0$ are independently chloro, fluoro or hydrido; hydrido;

$R^2$ is selected from the group consisting of phenyl, 2-thienyl, 2-pyridyl, and 3-pyridyl, wherein a ring carbon in a first alpha position relative to the ring carbon at the point of attachment is optionally substituted by $R^9$, (b) a ring carbon in a second alpha positive relative to the ring carbon at the point of attachment is optionally substituted by $R^{13}$, (c) a ring carbon, in a first beta positive relative to the ring carbon at the point of attachment and in an alpha position relative to the ring atom optionally substituted by $R^9$, is optionally substituted by $R^{10}$, (d) a ring carbon, in a second beta positive relative to the ring carbon at the point of attachment and in an alpha position relative to the ring atom optionally substituted by $R^{13}$, is optionally substituted by $R^{12}$, and (e) a ring carbon, if present, in the gamma position relative to the ring carbon at the point of attachment and in an alpha position relative to the ring atoms optionally substituted by $R^{10}$ and $R^{12}$, respectively, is optionally substituted by $R^{11}$;

$R^9$, $R^{11}$, and $R^{13}$ are independently selected from the group consisting of hydrido, hydroxy, amino, amidino, guanidino, alkylamino, alkylthio, alkoxy, alkylsulfinyl, alkylsulfonyl, amidosulfonyl, alkyl, halo, haloalkyl, haloalkoxy, hydroxyalkyl, carboxy, carboxamido, and cyano; and $R^{10}$ and $R^{12}$ are independently selected from the group consisting of hydrido, acetamido, haloacetamido, amidino, guanidino, alkyl, alkoxy, alkoxyamino, hydroxy, amino, alkylamino, alkylsulfonamido, amidosulfonyl, hydroxyalkyl, aminoalkyl, halo, haloalkyl, carboalkoxy, carboxy, carboxamido, carboxyalkyl, and cyano;

3. Compound of claim 2 or a pharmaceutically acceptable salt thereof, wherein;

B is selected from the group consisting of cyclopropyl, cyclobutyl, cyclopentyl, cyclohexyl, 1-pyrrolidinyl and 1-piperidinyl;

A is selected from the group consisting of a bond, $CH_2$, $CH_2CH_2$ and $CH_2CH_2CH_2$;

$R^1$ and $X^0$ are independently hydrido or fluoro; and $R^2$ is selected from the group consisting of 3-amidocarbonyl-5-aminophenyl, 3-amidocarbonyl-5-aminophenyl, 3-amino-5-(N-benzylamidocarbonyl)phenyl, 3-amino-5-(N-(2-chlorobenzyl)amidocarbonyl)phenyl, 3-amino-5-(N-(3-fluorobenzyl)amidocarbonyl)phenyl, 3-amino-5-(N-(2-trifluoromethylbenzyl)amidocarbonyl) phenyl, 3-amino-5-(N-(1-phenylethyl)amidocarbonyl)phenyl, 3-amino-5-(N-(1-methyl-1-phenylethyl)amidocarbonyl) phenyl, 3-amino-5-(N-benzylamidosulfonyl)phenyl, 3-amino-(N-(2-chlorobenzyl)amidosulfonyl)phenyl, 3-amino-5-(N-ethylamidocarbonyl)phenyl, 3-amino-5-(N-isopropylamidocarbonyl)phenyl, 3-amino-5-(N-propylamidocarbonyl)phenyl, 3-amino-5-(N-isobutylamidocarbonyl)phenyl, 3-amino-5-(N-(2-butyl)amidocarbonyl)phenyl, 3-amino-5-(N-cyclobutylamidocarbonyl)phenyl, 3-amino-5-(N-cyclopentylamidocarbonyl)phenyl, 3-amino-(N-cyclohexylamidocarbonyl)phenyl, 5-amino-2-fluorophenyl, 3-amino-5-hydroxymethylphenyl, 5-amino-3-methoxycarbonylphenyl, 3-amidinophenyl, 3-amino-2-methylphenyl, 5-amino-2-methylthiophenyl, 3-aminophenyl, 3-carboxyphenyl, 3-carboxy-5-aminophenyl, 3-carboxy-5-hydroxyphenyl, 3-carboxymethyl-5-aminophenyl, 3-carboxymethyl-5-hydroxyphenyl, 3-carboxymethyl-phenyl, 3-chlorophenyl, 2-chlorophenyl, 3-cyanophenyl, 3,5-diaminophenyl, 3-dimethylaminophenyl, 2-fluorophenyl, 3-fluorophenyl, 2,5-difluorophenyl, 2-hydroxyphenyl, 3-hydroxyphenyl, 3-methanesulfonylaminophenyl, 2-methoxyphenyl, 3-methoxyphenyl, 3-methoxyaminophenyl, 3-methoxycarbonylphenyl, 2-methylaminophenyl, 3-methylaminophenyl, 2-methylphenyl, 3-methylphenyl, 4-methylphenyl, phenyl, 3-trifluoroacetamidophenyl, 3-trifluoromethylphenyl,
2-trifluoromethylphenyl, 5-amino-2-thienyl, 5-amino-3-thienyl,
3-bromo-2-thienyl, 3-pyridyl, 4-pyridyl, 2-thienyl, and 3-thienyl.

4. Compound of claim 3 or a pharmaceutically acceptable salt thereof, wherein;
B is selected from the group consisting of cyclopropyl, cyclobutyl, cyclopentyl, cyclohexyl, and 1-piperidinyl; and
$R^2$ is selected from the group consisting of 3-amidocarbonyl-5-aminophenyl, 3-amino-5-(N-benzylamidocarbonyl)phenyl,
3-amino-5-(N-(2-chlorobenzyl)amidocarbonyl)phenyl,
3-amino-5-(N-(3-fluorobenzyl)amidocarbonyl)phenyl,
3-amino-5-(N-(2-fluoromethylbenzyl)amidocarbonyl)phenyl,
3-amino-5-(N-(1-phenylethyl)amidocarbonyl)phenyl,
3-amino-5-(N-(1-methyl-1-phenylethyl)amidocarbonyl)phenyl,
3-amino-5-(N-benzylamidosulfonyl)phenyl,
3-amino-5-(N-2-chlorobenzyl)amidosulfonyl)phenyl,
3-amino-5-(N-ethylamidocarbonyl)phenyl,
3-amino-5-(N-isopropylamidocarbonyl)phenyl,
3-amino-5-(N-propylamidocarbonyl)phenyl,
3-amino-5-(N-isobutylamidocarbonyl)phenyl,
3-amino-5-(N-(2-butyl)amidocarbonyl)phenyl,
3-amino-5-(N-cyclobutylamidocarbonyl)phenyl,
3-amino-5-(N-cyclopentylamidocarbonyl)phenyl,
3-amino-5-(N-cyclohexylamidocarbonyl)phenyl, 3-aminophenyl,
3-carboxy-5-aminophenyl, 3-chlorophenyl, 3,5-diaminophenyl,
3-dimethylaminophenyl, 3-hydroxyphenyl, 3-methanesulfonylaminophenyl,
3-methylaminophenyl, 2-methylphenyl, 3-methylphenyl, phenyl,
3-trifluoroacetamidophenyl, 3-bromo-2-thienyl, 2-thienyl, and 3-thienyl.

5. Compound of claim 1 where said compound is selected from the group of the Formula:

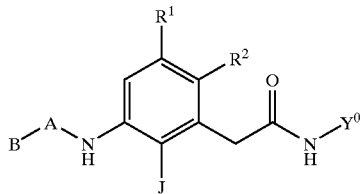

or a pharmaceutically acceptable salt thereof, wherein
$R^2$ is 3-aminophenyl, B is cyclopropyl, A is a bond, $Y^0$ is 4-amidinobenzyl, J is hydroxy, and $R^1$ is chloro;
$R^2$ is 3-aminophenyl, B is cyclobutyl, A is a bond, $Y^0$ is 4-amidino-2-fluorobenzyl, J is hydroxy, and $R^1$ is chloro;
$R^2$ is 3-aminophenyl, B is cyclobutyl, A is a bond, $Y^0$ is 4-amidinobenzyl, J is hydroxy, and $R^1$ is chloro;
$R^2$ is 3-aminophenyl, B is cyclopropyl, A is a bond, $Y^0$ is 4-amidino-2-fluorobenzyl, J is hydroxy, and $R^1$ is chloro;
$R^2$ is 3-aminophenyl, B is cyclobutyl, A is a bond, $Y^0$ is 4-amidinobenzyl, J is hydroxy, and $R^1$ is hydrido;
$R^2$ is 3-aminophenyl, B is cyclobutyl, A is a bond, $Y^0$ is 4-amidino-3-fluorobenzyl, J is hydroxy, and $R^1$ is chloro;
$R^2$ is 3-aminophenyl, B is cyclopentyl, A is a bond, $Y^0$ is 4-amidinobenzyl, J is hydroxy, and $R^1$ is chloro;
$R^2$ is 5-amino-2-thienyl, B is cyclobutyl, A is a bond, $Y^0$ is 4-amidinobenzyl, J is hydroxy, and $R^1$ is chloro;
$R^2$ is 3-aminophenyl, B is cyclopropyl, A is $CH_2$, $Y^0$ is 4-amidinobenzyl, J is hydroxy, and $R^1$ is chloro;
$R^2$ is 3-aminophenyl, B is 2-(2R)-bicyclo[2.2.1]-heptyl, A is a bond, $Y^0$ is 4-amidinobenzyl, J is hydroxy, and $R^1$ is chloro;
$R^2$ is 3-aminophenyl, B is cyclopentyl, A is a bond, $Y^0$ is 4-amidino-2-fluorobenzyl, J is hydroxy, and $R^1$ is chloro;
$R^2$ is 3-aminophenyl, B is cyclohexyl, A is $CH_2CH_2$, $Y^0$ is 4-amidinobenzyl, J is hydroxy, and $R^1$ is hydrido;
$R^2$ is 3-aminophenyl, B is oxalan-2-yl, A is $CH_2$, $Y^0$ is 4-amidinobenzyl, J is hydroxy, and $R^1$ is chloro;
$R^2$ is 3-aminophenyl, B is 1-piperidinyl, A is $CH_2CH_2$, $Y^0$ is 4-amidinobenzyl, J is hydroxy, and $R^1$ is chloro;
$R^2$ is 3-aminophenyl, B is 1-pyrrolidinyl, A is $CH_2CH_2CH_2$, $Y^0$ is 4-amidinobenzyl, J is hydroxy, and $R^1$ is chloro;
$R^2$ is 3-amino-5carbomethoxyphenyl, B is cyclobutyl, A is a bond, $Y^0$ is 4-amidinobenzyl, J is hydroxy, and $R^1$ is hydrido;
$R^2$ is 3-amino-5-carboxyphenyl, B is cyclobutyl, A is a bond, $Y^0$ is 4-amidinobenzyl, J is hydroxy, and $R^1$ is hydrido;
$R^2$ is 3,5-diaminophenyl, B is cyclobutyl, A is a bond, $Y^0$ is 4-amidinobenzyl, J is hydroxy, and $R^1$ is hydrido;
$R^2$ is 2-amino-6-carboxy-4-pyridyl, B is cyclobutyl, A is a bond, $Y^0$ is 4-amidinobenzyl, J is hydroxy, and $R^1$ is hydrido;
$R^2$ is 3-amino-5-carbomethoxyphenyl, B is cyclobutyl, A is a bond, $Y^0$ is 4-amidinobenzyl, J is hydroxy, and $R^1$ is chloro;
$R^2$ is 3-amino-5-carboxyphenyl, B is cyclobutyl, A is a bond, $Y^0$ is 4-amidinobenzyl, J is hydroxy, and $R^1$ is chloro;
$R^2$ is 3,5-diaminophenyl, B is cyclopropyl, A is a bond, $Y^0$ is 4-amidinobenzyl, J is hydroxy, and $R^1$ is chloro;
$R^2$ is 3,5-diaminophenyl, B is cyclobutyl, A is a bond, $Y^0$ is 4-amidino-2-fluorobenzyl, J is hydroxy, and $R^1$ is chloro;
$R^2$ is 3,5-diaminophenyl, B is cyclopropyl, A is a bond, $Y^0$ is 4-amidino-2-fluorobenzyl, J is hydroxy, and $R^1$ is chloro;
$R^2$ is 3,5-diaminophenyl, B is cyclobutyl, A is a bond, $Y^0$ is 4-amidinobenzyl, J is hydroxy, and $R^1$ is hydrido;
$R^2$ is 3,5-diaminophenyl, B is cyclobutyl, A is a bond, $Y^0$ is 4-amidino-3-fluorobenzyl, J is hydroxy, and $R^1$ is chloro;
$R^2$ is 3,5-diaminophenyl, B is cyclopentyl, A is a bond, $Y^0$ is 4-amidinobenzyl, J is hydroxy, and $R^1$ is chloro;
$R^2$ is 3-carboxy-5-aminophenyl, B is cyclopropyl, A is a bond, $Y^0$ is 4-amidinobenzyl, J is hydroxy, and $R^1$ is chloro;
$R^2$ is 3-carboxy-5-aminophenyl, B is cyclobutyl, A is a bond, $Y^0$ is 4-amidino-2-fluorobenzyl, J is hydroxy, and $R^1$ is chloro;
$R^2$ is 3-carboxy-5-aminophenyl, B is cyclopropyl, A is a bond, $Y^0$ is 4-amidino-2-fluorobenzyl, J is hydroxy, and $R^1$ is chloro;
$R^2$ is 3-carboxy-5-aminophenyl, B is cyclobutyl, A is a bond, $Y^0$ is 4-amidinobenzyl, J is hydroxy, and $R^1$ is hydrido;

R² is 3-carboxy-5-aminophenyl, B is cyclobutyl, A is a bond, Y⁰ is 4-amidino-3-fluorobenzyl, J is hydroxy, and R¹ is chloro;

R² is 3-carboxy-5-aminophenyl, B is cyclopentyl, A is a bond, Y⁰ is 4-amidinobenzyl, J is hydroxy, and R¹ is chloro;

R² is 3-amino-5-(N-benzylamidocarbonyl)phenyl, B is cyclopropyl, A is a bond, Y⁰ is 4-amidinobenzyl, J is hydroxy, and R¹ is chloro;

R² is 3-amino-5-(N-benzylamidocarbonyl)phenyl, B is cyclobutyl, A is a bond, Y⁰ is 4-amidino-2-fluorobenzyl, J is hydroxy, and R¹ is chloro;

R² is 3-amino-5-(N-benzylamidocarbonyl)phenyl, B is cyclobutyl, A is a bond, Y⁰ is 4-amidinobenzyl, J is hydroxy, and R¹ is chloro;

R² is 3-amino-5-(N-benzylamidocarbonyl)phenyl, B is cyclopropyl, A is a bond, Y⁰ is 4-amidino-2-fluorobenzyl, J is hydroxy, and R¹ is chloro;

R² is 3-amino-5-(N-benzylamidocarbonyl)phenyl, B is cyclobutyl, A is a bond, Y⁰ is 4-amidinobenzyl, J is hydroxy, and R¹ is hydrido;

R² is 3-amino-5-(N-benzylamidocarbonyl)phenyl, B is cyclobutyl, A is a bond, Y⁰ is 4-amidino-3-fluorobenzyl, J is hydroxy, and R¹ is chloro;

R² is 3-amino-5-(N-benzylamidocarbonyl)phenyl, B is cyclopentyl, A is a bond, Y⁰ is 4-amidinobenzyl, J is hydroxy, and R¹ is chloro;

R² is 3-amino-5-(N-(2-chlorobenzyl)amidosulfonyl)phenyl, B is cyclopropyl, A is a bond, Y⁰ is 4-amidinobenzyl, J is hydroxy, and R¹ is chloro;

R² is 3-amino-5-(N-(2-chlorobenzyl)amidosulfonyl)phenyl, B is cyclobutyl, A is a bond, Y⁰ is 4-amidino-2-fluorobenzyl, J is hydroxy, and R¹ is chloro;

R² is 3-amino-5-(N-(2-chlorobenzyl)amidosulfonyl)phenyl, B is cyclobutyl, A is a bond, Y⁰ is 4-amidinobenzyl, J is hydroxy, and R¹ is chloro;

R² is 3-amino-5-(N-(2-chlorobenzyl)amidosulfonyl)phenyl, B is cyclopropyl, A is a bond, Y⁰ is 4-amidino-2-fluorobenzyl, J is hydroxy, and R¹ is chloro;

R² is 3-amino-5-(N-(2-chlorobenzyl)amidosulfonyl)phenyl, B is cyclobutyl, A is a bond, Y⁰ is 4-amidinobenzyl, J is hydroxy, and R¹ is hydrido;

R² is 3-amino-5-(N-(2-chlorobenzyl)amidosulfonyl)phenyl, B is cyclobutyl, A is a bond, Y⁰ is 4-amidino-3-fluorobenzyl, J is hydroxy, and R¹ is chloro;

R² is 3-amino-5-(N-(2-chlorobenzyl)amidosulfonyl)phenyl, B is cyclopentyl, A is a bond, Y⁰ is 4-amidinobenzyl, J is hydroxy, and R¹ is chloro;

R² is 3-amino-5-(N-(2-trifluoromethylbenzyl)amidocarbonyl)-phenyl, B is cyclopropyl, A is a bond, Y⁰ is 4-amidinobenzyl, J is hydroxy, and R¹ is chloro;

R² is 3-amino-5-(N-(2-trifluoromethylbenzyl)amidocarbonyl)-phenyl, B is cyclobutyl, A is a bond, Y⁰ is 4-amidino-2-fluorobenzyl, J is hydroxy, and R¹ is chloro;

R² is 3-amino-5-(N-(2-trifluoromethylbenzyl)amidocarbonyl)-phenyl, B is cyclobutyl, A is a bond, Y⁰ is 4-amidinobenzyl, J is hydroxy, and R¹ is chloro;

R² is 3-amino-5-(N-(2-trifluoromethylbenzyl)amidocarbonyl)-phenyl, B is cyclopropyl, A is a bond, Y⁰ is 4-amidino-2-fluorobenzyl, J is hydroxy, and R¹ is chloro;

R² is 3-amino-5-(N-(2-trifluoromethylbenzyl)amidocarbonyl)-phenyl, B is cyclobutyl, A is a bond, Y⁰ is 4-amidinobenzyl, J is hydroxy, and R¹ is hydrido;

R² is 3-amino-5-(N-(2-trifluoromethylbenzyl)amidocarbonyl)-phenyl, B is cyclobutyl, A is a bond, Y⁰ is 4-amidino-3-fluorobenzyl, J is hydroxy, and R¹ is chloro;

R² is 3-amino-5-(N-(2-trifluoromethylbenzyl)amidocarbonyl)-phenyl, B is cyclopentyl, A is a bond, Y⁰ is 4-amidinobenzyl, J is hydroxy, and R¹ is chloro;

R² is 3-aminophenyl, B is cyclopropyl, A is a bond, Y⁰ is 4-amidinobenzyl, J is fluoro, and R¹ is chloro;

R² is 3-aminophenyl, B is cyclobutyl, A is a bond, Y⁰ is 4-amidino-2-fluorobenzyl, J is fluoro, and R¹ is chloro;

R² is 3-aminophenyl, B is cyclobutyl, A is a bond, Y⁰ is 4-amidinobenzyl, J is fluoro, and R¹ is chloro;

R² is 3-aminophenyl, B is cyclopropyl, A is a bond, Y⁰ is 4-amidino-2-fluorobenzyl, J is fluoro, and R¹ is chloro;

R² is 3-aminophenyl, B is cyclobutyl, A is a bond, Y⁰ is 4-amidinobenzyl, J is fluoro, and R¹ is hydrido;

R² is 3-aminophenyl, B is cyclobutyl, A is a bond, Y⁰ is 4-amidino-3-fluorobenzyl, J is fluoro, and R¹ is chloro;

R² is 3-aminophenyl, B is cyclopentyl, A is a bond, Y⁰ is 4-amidinobenzyl, J is fluoro, and R¹ is chloro;

R² is 5-amino-2-thienyl, B is cyclobutyl, A is a bond, Y⁰ is 4-amidinobenzyl, J is fluoro, and R¹ is chloro;

R² is 3-aminophenyl, B is cyclopropyl, A is CH₂, Y⁰ is 4-amidinobenzyl, J is fluoro, and R¹ is chloro;

R² is 3-aminophenyl, B is 2-(2R)-bicyclo[2.2.1]-heptyl, A is a bond, Y⁰ is 4-amidinobenzyl, J is fluoro, and R¹ is chloro;

R² is 3-aminophenyl, B is cyclopentyl, A is a bond, Y⁰ is 4-amidino-2-fluorobenzyl, J is fluoro, and R¹ is chloro;

R² is 3-aminophenyl, B is cyclohexyl, A is CH₂CH₂, Y⁰ is 4-amidinobenzyl, J is fluoro, and R¹ is hydrido;

R² is 3-aminophenyl, B is oxalan-2-yl, A is CH₂, Y⁰ is 4-amidinobenzyl, J is fluoro, and R¹ is chloro;

R² is 3-aminophenyl, B is 1-piperidinyl, A is CH₂CH₂, Y⁰ is 4-amidinobenzyl, J is fluoro, and R¹ is chloro;

R² is 3-aminophenyl, B is 1-pyrrolidinyl, A is CH₂CH₂CH₂, Y⁰ is 4-amidinobenzyl, J is fluoro, and R¹ is chloro;

R² is 3-amino-5-carbomethoxyphenyl, B is cyclobutyl, A is a bond, Y⁰ is 4-amidinobenzyl, J is fluoro, and R¹ is hydrido;

R² is 3-amino-5-carboxyphenyl, B is cyclobutyl, A is a bond, Y⁰ is 4-amidinobenzyl, J is fluoro, and R¹ is hydrido;

R² is 3,5-diaminophenyl, B is cyclobutyl, A is a bond, Y⁰ is 4-amidinobenzyl, J is fluoro, and R¹ is hydrido;

R² is 2-amino-6-carboxy-4-pyridyl, B is cyclobutyl, A is a bond, Y⁰ is 4-amidinobenzyl, J is fluoro, and R¹ is hydrido;

R² is 3-amino-5-carbomethoxyphenyl, B is cyclobutyl, A is a bond, Y⁰ is 4-amidinobenzyl, J is fluoro, and R¹ is chloro;

R² is 3-amino-5-carboxyphenyl, B is cyclobutyl, A is a bond, Y⁰ is 4-amidinobenzyl, J is fluoro, and R¹ is chloro;

R² is 3,5-diaminophenyl, B is cyclopropyl, A is a bond, Y⁰ is 4-amidinobenzyl, J is fluoro, and R¹ is chloro;

R² is 3,5-diaminophenyl, B is cyclobutyl, A is a bond, Y⁰ is 4-amidino-2-fluorobenzyl, J is fluoro, and R¹ is chloro;

R² is 3,5-diaminophenyl, B is cyclopropyl, A is a bond, Y⁰ is 4-amidino-2-fluorobenzyl, J is fluoro, and R¹ is chloro;

$R^2$ is 3,5-diaminophenyl, B is cyclobutyl, A is a bond, $Y^0$ is 4-amidinobenzyl, J is fluoro, and $R^1$ is hydrido;

$R^2$ is 3,5-diaminophenyl, B is cyclobutyl, A is a bond, $Y^0$ is 4-amidino-3-fluorobenzyl, J is fluoro, and $R^1$ is chloro;

$R^2$ is 3,5-diaminophenyl, B is cyclopentyl, A is a bond, $Y^0$ is 4-amidinobenzyl, J is fluoro, and $R^1$ is chloro;

$R^2$ is 3-carboxy-5-aminophenyl, B is cyclopropyl, A is a bond, $Y^0$ is 4-amidinobenzyl, J is fluoro, and $R^1$ is chloro;

$R^2$ is 3-carboxy-5-aminophenyl, B is cyclobutyl, A is a bond, $Y^0$ is 4-amidino-2-fluorobenzyl, J is fluoro, and $R^1$ is chloro;

$R^2$ is 3-carboxy-5-aminophenyl, B is cyclopropyl, A is a bond, $Y^0$ is 4-amidino-2-fluorobenzyl, J is fluoro, and $R^1$ is chloro;

$R^2$ is 3-carboxy-5-aminophenyl, B is cyclobutyl, A is a bond, $Y^0$ is 4-amidinobenzyl, J is fluoro, and $R^1$ is hydrido;

$R^2$ is 3-carboxy-5-aminophenyl, B is cyclobutyl, A is a bond, $Y^0$ is 4-amidino-3-fluorobenzyl, J is fluoro, and $R^1$ is chloro;

$R^2$ is 3-carboxy-5-aminophenyl, B is cyclopentyl, A is a bond, $Y^0$ is 4-amidinobenzyl, J is fluoro, and $R^1$ is chloro;

$R^2$ is 3-amino-5-(N-benzylamidocarbonyl)phenyl, B is cyclopropyl, A is a bond, $Y^0$ is 4-amidinobenzyl, J is fluoro, and $R^1$ is chloro;

$R^2$ is 3-amino-5-(N-benzylamidocarbonyl)phenyl, B is cyclobutyl, A is a bond, $Y^0$ is 4-amidino-2-fluorobenzyl, J is fluoro, and $R^1$ is chloro;

$R^2$ is 3-amino-5-(N-benzylamidocarbonyl)phenyl, B is cyclobutyl, A is a bond, $Y^0$ is 4-amidinobenzyl, J is fluoro, and $R^1$ is chloro;

$R^2$ is 3-amino-5-(N-benzylamidocarbonyl)phenyl, B is cyclopropyl, A is a bond, $Y^0$ is 4-amidino-2-fluorobenzyl, J is fluoro, and $R^1$ is chloro;

$R^2$ is 3-amino-5-(N-benzylamidocarbonyl)phenyl, B is cyclobutyl, A is a bond, $Y^0$ is 4-amidinobenzyl, J is fluoro, and $R^1$ is hydrido;

$R^2$ is 3-amino-5-(N-benzylamidocarbonyl)phenyl, B is cyclobutyl, A is a bond, $Y^0$ is 4-amidino-3-fluorobenzyl, J is fluoro, and $R^1$ is chloro;

$R^2$ is 3-amino-5-(N-benzylamidocarbonyl)phenyl, B is cyclopentyl, A is a bond, $Y^0$ is 4-amidinobenzyl, J is fluoro, and $R^1$ is chloro;

$R^2$ is 3-amino-5-(N-(2-chlorobenzyl)amidosulfonyl)phenyl, B is cyclopropyl, A is a bond, $Y^0$ is 4-amidinobenzyl, J is fluoro, and $R^1$ is chloro;

$R^2$ is 3-amino-5-(N-(2-chlorobenzyl)amidosulfonyl)phenyl, B is cyclobutyl, A is a bond, $Y^0$ is 4-amidino-2-fluorobenzyl, J is fluoro, and $R^1$ is chloro;

$R^2$ is 3-amino-5-(N-(2-chlorobenzyl)amidosulfonyl)phenyl, B is cyclobutyl, A is a bond, $Y^0$ is 4-amidinobenzyl, J is fluoro, and $R^1$ is chloro;

$R^2$ is 3-amino-5-(N-(2-chlorobenzyl)amidosulfonyl)phenyl, B is cyclopropyl, A is a bond, $Y^0$ is 4-amidino-2-fluorobenzyl, J is fluoro, and $R^1$ is chloro;

$R^2$ is 3-amino-5-(N-(2-chlorobenzyl)amidosulfonyl)phenyl, B is cyclobutyl, A is a bond, $Y^0$ is 4-amidinobenzyl, J is fluoro, and $R^1$ is hydrido;

$R^2$ is 3-amino-5-(N-(2-chlorobenzyl)amidosulfonyl)phenyl, B is cyclobutyl, A is a bond, $Y^0$ is 4-amidino-3-fluorobenzyl, J is fluoro, and $R^1$ is chloro;

$R^2$ is 3-amino-5-(N-(2-chlorobenzyl)amidosulfonyl)phenyl, B is cyclopentyl, A is a bond, $Y^0$ is 4-amidinobenzyl, J is fluoro, and $R^1$ is chloro;

$R^2$ is 3-amino-5-(N-(2-trifluoromethylbenzyl)amidocarbonyl)-phenyl, B is cyclopropyl, A is a bond, $Y^0$ is 4-amidinobenzyl, J is fluoro, and $R^1$ is chloro;

$R^2$ is 3-amino-5-(N-2-trifluoromethylbenzyl)amidocarbonyl)-phenyl, B is cyclobutyl, A is a bond, $Y^0$ is 4-amidino-2-fluorobenzyl, J is fluoro, and $R^1$ is chloro;

$R^2$ is 3-amino-5-(N-(2-trifluoromethylbenzyl)amidocarbonyl)-phenyl, B is cyclobutyl, A is a bond, $Y^0$ is 4-amidinobenzyl, J is fluoro, and $R^1$ is chloro;

$R^2$ is 3-amino-5-(N-(2-trifluoromethylbenzyl)amidocarbonyl)-phenyl, B is cyclopropyl, A is a bond, $Y^0$ is 4-amidino-2-fluorobenzyl, J is fluoro, and $R^1$ is chloro;

$R^2$ is 3-amino-5-(N-2-trifluoromethylbenzyl)amidocarbonyl)-phenyl, B is cyclobutyl, A is a bond, $Y^0$ is 4-amidinobenzyl, J is fluoro, and $R^1$ is hydrido;

$R^2$ is 3-amino-5-(N-(2-trifluoromethylbenzyl)amidocarbonyl)-phenyl, B is cyclobutyl, A is a bond, $Y^0$ is 4-amidino-3-fluorobenzyl, J is fluoro, and $R^1$ is chloro; or $R^2$ is 3-amino-5-(N-(2-trifluoromethylbenzyl)amidocarbonyl)-phenyl, B is cyclopentyl, A is a bond, $Y^0$ is 4-amidinobenzyl, J is fluoro, and $R^1$ is chloro.

6. A composition for inhibiting thrombotic conditions in blood comprising an anticoagulation effective amount of the compound of claim 1 and a pharmaceutically acceptable carrier.

7. A method for inhibiting formation of blood platelet aggregates in blood comprising adding to blood an anticoagulation effective amount of a composition of claim 6.

8. A method for inhibiting thrombus formation in blood comprising adding to blood an anticoagulation effective amount of a composition of claim 6.

9. A method for treating or preventing venuous thromboembolism and pulmonary embolism in a mammal comprising administering to the mammal a therapeutically effective amount of a composition of claim 6.

10. A method for treating or preventing deep vein thrombosis in a mammal comprising administering to the mammal a therapeutically effective amount of a composition of claim 6.

11. A method for treating or preventing cardiogenic thromboembolism in a mammal comprising administering to the mammal a therapeutically effective amount of a composition of claim 6.

12. A method for treating or preventing thromboembolic stroke in humans and other mammals comprising administering to the mammal a therapeutically effective amount of a composition of claim 6.

13. A method for treating or preventing thrombosis associated with cancer and cancer chemotherapy in humans and other mammals comprising administering to the mammal a therapeutically effective amount of a composition of claim 6.

14. The method of claim 11 wherein said cardiogenic thromboembolism is in unstable angina in humans and other mammals.

* * * * *

UNITED STATES PATENT AND TRADEMARK OFFICE
CERTIFICATE OF CORRECTION

PATENT NO.    : 6,852,761 B2
DATED         : February 8, 2005
INVENTOR(S)   : Michael S. South et al.

It is certified that error appears in the above-identified patent and that said Letters Patent is hereby corrected as shown below:

<u>Column 148,</u>
Line 57, "amine, alkexyamino, alkylamino, alkyithie," should read -- amino, alkoyxamino, alkylamino, alkylthio, --.
Line 58, "amidesulfenyl," should read -- amidosulfonyl --.

<u>Column 149,</u>
Line 52, delete "hydrido;"
Line 54, "wherein a ring" should read -- wherein a (a) ring --.
Lines 57, 60 and 63, "positive" should read -- position --.

<u>Column 150,</u>
Line 2, "to the" should read -- to each of the --.
Lines 38 and 46, "3-amino-(N-" should read -- 3-amino-5-(N- --.

<u>Column 151,</u>
Line 22, "3-amino-5-(N-2-" should read -- 3-amino-5-(N-(2- --.

<u>Column 156,</u>
Lines 8 and 20, "3-amino-5-(N-2-" should read -- 3-amino-5-(N-(2- --.

Signed and Sealed this

Twenty-fourth Day of May, 2005

JON W. DUDAS
*Director of the United States Patent and Trademark Office*